(12) United States Patent
Bolli et al.

(10) Patent No.: US 9,493,446 B2
(45) Date of Patent: Nov. 15, 2016

(54) **OREXIN RECEPTOR ANTAGONISTS WHICH ARE [*ORTHO* BI-(HETERO-)ARYL]-[2-(*META* BI-(HETERO-)ARYL)-PYRROLIDIN-1-YL]-METHANONE DERIVATIVES**

(71) Applicant: Actelion Pharmaceuticals Ltd, Allschwil (CH)

(72) Inventors: Martin Bolli, Allschwil (CH); Christoph Boss, Allschwil (CH); Christine Brotschi, Allschwil (CH); Markus Gude, Allschwil (CH); Bibia Heidmann, Allschwil (CH); Thierry Sifferlen, Allschwil (CH); Jodi T. Williams, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/434,997

(22) PCT Filed: Oct. 9, 2013

(86) PCT No.: PCT/IB2013/059233
§ 371 (c)(1),
(2) Date: Apr. 10, 2015

(87) PCT Pub. No.: WO2014/057435
PCT Pub. Date: Apr. 17, 2014

(65) Prior Publication Data
US 2015/0252032 A1    Sep. 10, 2015

(30) Foreign Application Priority Data

Oct. 10, 2012  (EP) .................................. 12188019
Mar. 5, 2013   (EP) .................................. 13157809

(51) Int. Cl.
| C07D 413/14 | (2006.01) |
| C07D 403/04 | (2006.01) |
| C07D 403/14 | (2006.01) |
| C07D 413/04 | (2006.01) |
| C07D 417/14 | (2006.01) |
| C07D 471/04 | (2006.01) |
| C07D 513/04 | (2006.01) |

(52) U.S. Cl.
CPC ............ *C07D 413/14* (2013.01); *C07D 403/04* (2013.01); *C07D 403/14* (2013.01); *C07D 413/04* (2013.01); *C07D 417/14* (2013.01); *C07D 471/04* (2013.01); *C07D 513/04* (2013.01)

(58) Field of Classification Search
CPC ................................................... C07D 207/08
See application file for complete search history.

(56) References Cited

U.S. PATENT DOCUMENTS

| 6,660,759 B1 | 12/2003 | Hattori et al. |
| 7,105,538 B2 | 9/2006 | Hennies et al. |
| 7,763,638 B2 | 7/2010 | Aissaoui et al. |
| 7,994,336 B2 | 8/2011 | Aissaoui et al. |
| 8,063,099 B2 | 11/2011 | Aissaoui et al. |
| 8,106,215 B2 | 1/2012 | Aissaoui et al. |
| 8,133,901 B2 | 3/2012 | Aissaoui et al. |
| 8,236,801 B2 | 8/2012 | Aissaoui et al. |
| 8,236,964 B2 | 8/2012 | Aissaoui et al. |
| 8,288,411 B2 | 10/2012 | Aissaoui et al. |
| 8,288,429 B2 | 10/2012 | Aissaoui et al. |
| 8,288,435 B2 | 10/2012 | Aissaoui et al. |
| 9,150,556 B2 | 10/2015 | Abeywardane et al. |
| 2005/0014765 A1 | 1/2005 | Mailliet et al. |
| 2006/0019975 A1 | 1/2006 | Humphrey et al. |
| 2009/0082394 A1 | 3/2009 | Jenck et al. |
| 2010/0016401 A1 | 1/2010 | Aissaoui et al. |
| 2010/0222328 A1 | 9/2010 | Aissaoui et al. |

(Continued)

FOREIGN PATENT DOCUMENTS

| JP | 2001 247569 | 9/2001 |
| WO | WO 01/96302 | 12/2001 |

(Continued)

OTHER PUBLICATIONS

Lamb, Dec. 3, 2010, Bioorganic & Medicinal Chemistry Letters, vol. 21, p. 2711-2714.*

(Continued)

*Primary Examiner* — Michael Barker
*Assistant Examiner* — Karen Cheng
(74) *Attorney, Agent, or Firm* — Hoxie & Associates LLC

(57) ABSTRACT

The present invention relates to [ortho bi-(hetero-)aryl]-[2-(meta bi-(hetero-)aryl)-pyrrolidin-1-yl]-methanone derivatives of formula (I)

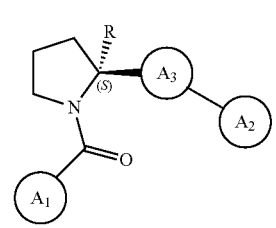

Formula (I)

wherein R, and the rings $A_1$, $A_2$ and $A_3$ are as described in the description, to pharmaceutically acceptable salts thereof, to their preparation, to pharmaceutical compositions containing one or more compounds of formula (I), and to their use as pharmaceuticals, especially to their use as orexin receptor antagonists.

21 Claims, No Drawings

(56) References Cited

U.S. PATENT DOCUMENTS

| | | |
|---|---|---|
| 2010/0234420 A1 | 9/2010 | Jenck et al. |
| 2011/0105491 A1 | 5/2011 | Aissaoui et al. |
| 2011/0212968 A1 | 9/2011 | Aissaoui et al. |
| 2015/0166527 A1 | 6/2015 | Boss et al. |
| 2016/0024064 A1 | 1/2016 | Bolli et al. |

FOREIGN PATENT DOCUMENTS

| | | |
|---|---|---|
| WO | WO 02/44172 | 6/2002 |
| WO | WO 02/089800 | 11/2002 |
| WO | WO 02/090355 | 11/2002 |
| WO | WO 03/002559 | 1/2003 |
| WO | WO 03/002561 | 1/2003 |
| WO | WO 03/032991 | 4/2003 |
| WO | WO 03/041711 | 5/2003 |
| WO | WO 03/051368 | 6/2003 |
| WO | WO 03/051873 | 6/2003 |
| WO | WO 2004/024725 | 3/2004 |
| WO | WO 2004/026866 | 4/2004 |
| WO | WO 2004/041791 | 5/2004 |
| WO | WO 2004/041807 | 5/2004 |
| WO | WO 2004/041816 | 5/2004 |
| WO | WO 2005/044797 | 5/2005 |
| WO | WO 2005/113522 | 12/2005 |
| WO | WO 2005/121131 | 12/2005 |
| WO | WO 2006/123249 | 11/2006 |
| WO | WO 2007/039781 | 4/2007 |
| WO | WO 2008/008517 | 1/2008 |
| WO | WO 2008/020405 | 2/2008 |
| WO | WO 2008/038251 | 4/2008 |
| WO | WO 2008/069997 | 6/2008 |
| WO | WO 2008/087611 | 7/2008 |
| WO | WO 2008/144380 | 11/2008 |
| WO | WO 2008/150364 | 12/2008 |
| WO | WO 2009/003993 | 1/2009 |
| WO | WO 2009/003997 | 1/2009 |
| WO | WO 2009/077990 | 6/2009 |
| WO | WO 2009/124956 | 10/2009 |
| WO | WO 2010/038200 | 4/2010 |
| WO | WO 2010/048012 | 4/2010 |
| WO | WO 2010/060470 | 6/2010 |
| WO | WO 2010/060471 | 6/2010 |
| WO | WO 2010/060472 | 6/2010 |
| WO | WO 2010/063662 | 6/2010 |
| WO | WO 2010/063663 | 6/2010 |
| WO | WO 2010/072722 | 7/2010 |
| WO | WO 2010/114978 | 10/2010 |
| WO | WO 2010/122151 | 10/2010 |
| WO | WO 2010/143116 | 12/2010 |
| WO | WO 2011/050198 | 4/2011 |
| WO | WO 2011/050200 | 4/2011 |
| WO | WO 2011/050202 | 4/2011 |
| WO | WO 2011/090911 | 7/2011 |
| WO | WO 2012/039717 | 3/2012 |

OTHER PUBLICATIONS

Adam et al., "Stress, Eating and the Reward System", Physiology & Behavior, 2007, 91(4) 449-458.

Aston-Jones et al., "Lateral hypothalamic orexin/hypocretin neurons: A role in 3 reward-seeking and addiction", Brain Research, 2009, 1314, p. 74-90.

Berridge et al.,"Hypocretin/orexin in arousal and stress", Brain Research, 2009, 1314, 91-102.

Borgland et al., "Orexin A in the VTA is Critical for the Induction of Synaptic Plasticity and Behavioral Sensitization to Cocaine", Neuron, 2006, 49(4), 589-601.

Boss et al., "Biomedical Application of Orexin/Hypocretin Receptor Ligands in Neuroscience", Journal of Medicinal Chemistry, 2009, 52, 891-903.

Boutrel et al., "Role for hypocretin in mediating stress-induced reinstatement of cocaine-seeking behavior", Proceedings of the National Academy of Sciences, 2005, 102(52), 19168-19173.

Brisbare et al., "Promotion of sleep by targeting the orexin system in rats, dogs and humans", Nature Medicine, 2007, 13, 150-155.

Carter et al., "The brain hypocretins and their receptors: mediators of allostatic Arousal", Current Opinion in Pharmacology, 2009, 9: 39-45.

Chemelli et al., "Narcolepsy in orexin Knockout Mice: Molecular Genetics of Sleep Regulation", Cell Press, 1999, 98, 437-451.

Chrousos et al., "The Concepts of Stress and Stress System Disorders", JAMA 1992, 267(9), 1244-1252.

De Lucca et al., "Nonsymmetric P2/P2' Cyclic Urea HIV Protease Inhibitors. Structure-Activity Relationship, Bioavailability, and Resistance Profile of Monoindazole-Substituted P2 Analogues", Journal of Medicinal Chemistry, 1998, 2411-2423.

Dietrich et al., "Intact learning and memory in rats following treatment with the dual orexin receptor antagonist almorexant", Psychopharmacology, 2010, 212,145-154.

Fendt et al., "The neuroanatomical and neurochemical basis of conditioned fear", Neuroscience Biobehavioral Reviews, 1999, 23, 743-760.

Feng et al., "Changes in brain orexin levels in a rat model of depression induced by neonatal administration of clomipramine", J Psychopharmacol, 2008, 22(7), 784-791.

Furlong et al., "Hypocretin/orexin contributes to the expression of some but not all forms of stress and arousal", European Journal of Neuroscience, 2009, 30(8), 1603-1614.

Gould et al., "Salt Selection for basic drugs", International Journal of Pharmaceutics, 1986, 33, 201-217.

Gozzi et al., "Functional Magnetic Resonance Imaging Reveals Different Neural Substrates for the Effects of Orexin-1 and Orexin-2 Receptor Antagonists", PLoS One 2011, 6(1), e16406.

Greene et al., "Protective Groups in Organic Synthesis", Wiley-Interscience, 1999.

Hollander et al., "Insular hypocretin transmission regulates nicotine reward", Proceedings of the National Academy of Sciences, 2008, 105(49), 19480-19485.

Hutcheson et al., "Orexin-1 receptor antagonist SB-334867 reduces the acquisition and expression of cocaine-conditioned reinforcement and the expression of amphetamine-conditioned reward", Behavioural Pharmacology, 2011, 22(2), 173-181.

International Search Report of International Application No. PCT/IB2013/059233, mailed Feb. 27, 2014, 3 pages.

International Search Report of International Application No. PCT/IB2014/059628, mailed Aug. 25, 2014, 4 pages.

Kang et al., "Amyloid-B Dynamics Are Regulated by Orexin and the Sleep-Wake Cycle", Science Express, 2009, 326(5955), 1005-1007.

Kayaba et al., "Attenuated defense response and low basal blood pressure in orexin knockout mice", American Journal of Physiology—Regulatory Integrative Comparative Physiology, 2003, 285, R581-593.

Koob et al., "Neurobiological mechanisms of addiction: Focus on corticotropin-releasing factor", Current Opinion Investigational Drugs, 2010, 11(1), 63-71.

Lamb et al., Bioorganic &Medicinal Chemistry Letters, 2010, vol. 21, p. 2711-2714.

Langmead et al., "Characterisation of the binding of [$^3$H]-SB-674042, a novel nonpeptide antagonist, to the human orexin-1 receptor", British Journal of Pharmacology, 2004, 141, 340-346.

Lawrence et al., "The orexin system regulates alcohol-seeking in rats", British Journal of Pharmacology, 2006, 148(6), 752-759.

Lesage et al., "Nicotine self-administration in the rat: effects of hypocretin antagonists and changes in hypocretin Mrna", Psychopharmacology, 2010, 209(2), 203-212.

Liu et al., "Insomnia and Hypersomnia Associated with Depressive Phenomenology and Comorbidity in Childhood Depression", Sleep and Childhood Depression, 2007, 30(1), 83-90.

Lucca et al., "NonsymmetricP2/P2' Cyclic Urea HIV Protease Inhibitors. Structure-Activity Relationship, Bioavailability, and Resistance Profile of Monoindazole-Substitutes P2 Analogues", J. Med. Chem., 1998, vol. 41, p. 2411-2423.

Majzoub et al., "Corticotropin-releasing hormone physiology", European Journal of Endocrinology, 2006, 155 (suppl_1) S71-S76.

(56) References Cited

OTHER PUBLICATIONS

Mathes et al., "The biology of binge eating", Appetite, 2009, 52, 545-553.
Moorthy et al., "Photoinduced C-Br Homolysis of 2-Bromobenzophenones and Pschorr Ring Closure of 2-Aroylaryl Radicals to Fluorenones", Journal of Organic Chemistry, 2007, 9786-9.
National Center for Biotechnology Information. PubChem Compound Database; CID=16672186, https://pubchem.ncbi.nlm.nih.gov/compound/16672186 (accessed Mar. 1, 2016).
Nollet et al., "Activation of orexin neurons in dorsomedial/perifornical hypothalamus and antidepressant reversal in a rodent model of depression", NeuroPharmacology, 2011, 61(1-2), 336-46.
Packiarajan et al., "Azetidinyl oxadiazoles as potent mGluR5 positive allosteric modulators", Bioorganic & Medicinal Chemistry Letters, 2012, vol. 22, p. 6469-6474.
Panetta et al., "Disulfide-Functionalized 3-, 4-, 5-, and 6-Substituted 2,2¢-Bipyridines and their Ruthenium Complexes", Journal of Organic Chemistry, 1999, 64(3), 1015-1021.
Powers et al., "Synthesis of methyl-, fluoro-, and chloro-substituted 6-hydroxyisoindolin-1-ones", Tetrahedron Letters, 2009, 1267-1269.
Prud'Homme et al., Nutritional Status Modulates Behavioural and Olfactory Bulb Fos Response to Isoamyl Acetate or Food Odour in Rats: Roles of Orexins and Leptin, Neuroscience, 2009, 162(4), 1287-1298.
Quarta et al., "The orexin-1 receptor antagonist SB-334867 reduces amphetamine-evoked dopamine outflow in the shell of the nucleus accumbens and decreases the expression of amphetamine sensitization", Neurochemistry International, 2009, 56(1), 11-15.
Remington, The Science and Practice of Pharmacy, 21st Edition, Part 5, Pharmaceutical Manufacturing; 2005.
Sakurai et al., "Orexins and Orexin Receptors: A family of Hypothalamic Neuropeptides and G Protein-Coupled Receptors that Regulate Feeding Behavior", Cell Press, 1998, 92, 573-585.
Salomon et al., "Diurnal Variation of Cerebrospinal Fluid Hypocretin-1 (Orexin-A) Levels in Control and Depressed Subjects", Society of Biological Psychiatry, 2003, 54(2), 96-104.
Shippenberg et al., "Recent Advances in Animal Models of Drug Addiction", Neuropsychopharmacalogy, 2002; chapter 97, 1381-1397.
Sharf et al., "Role of orexin/hypocretin in dependence and addiction", Brain Research, 2010, 130-138.
Smith et al., "Orexin / hypocretin signaling at the OX1 receptor regulates cue-elicited cocaine-seeking", Eur Journal Neuroscience, 2009, 30(3), 493-503.
Smith et al., "Orexin/hypocretin is necessary for context-driven cocaine-seeking", Neuropharmacology, 2010, 58(1), 179-184.
Spealman et al, "Pharmacological and Environmental Determinants of Relapse to Cocaine-Seeking Behavior", Pharmacology Biochemistry and Behavior, 1999, 64, 327-336.
Stahl et al., Handbook of Pharmaceutical Salts: Properties, Selection and Use; 2008.
Stickgold et al., "Sleep-dependent memory consolidation", Nature, 2005, 437, 1272-1278.
Sutcliffe et al., "The Hypocretins: Setting the arousal threshold", Nature Reviews Neuroscience, 2002, 3(5), 339-349.
Tsujino et al., "Orexin/Hypocretin: A Neuropeptide at the Interface of Sleep, Energy Homeostasis, and Reward System", Pharmacological Review, 2009, 61(2) 162-176.
Vanderschuren et al., "Sensitization Processes in Drug Addiction", Current Topics in Behavioral Neurosciences, 2009, 3, 179-195.
Vinkers et al., "Translational aspects of pharmacological research into anxiety disorders: The stress-induced hyperthermia (SIH) paradigm", European Journal of Pharmacology, 2008, 585, 407-425.
Winrow et al., "Orexin receptor antagonism prevents transcriptional and behavioral plasticity resulting from stimulant exposure", Neuropharmacology, 2009, 58(1),185-94.
Wouters et al., "Pharmaceutical Salts and Cocrystals", RSC Drug Discovery, 2012.
Zhang W et al., "Multiple components of the defense response depend on orexin: Evidence from orexin knockout mice and orexin neuron-ablated mice", Autonomic Neuroscience, 2006, 126-127, 139-145.

\* cited by examiner

OREXIN RECEPTOR ANTAGONISTS WHICH ARE [*ORTHO* BI-(HETERO-)ARYL]-[2-(*META* BI-(HETERO-)ARYL)-PYRROLIDIN-1-YL]-METHANONE DERIVATIVES

CROSS REFERENCE TO RELATED APPLICATIONS

This application is a U.S. National Phase Application filed under 35 U.S.C. 371 of International Application No. PCT/IB2013/059233, filed on Oct. 9, 2013, which claims the benefit of European Patent Application Nos. 12188019.9, filed on Oct. 10, 2012 and 13157809.8, filed on Mar. 5, 2013, the contents of each of which are herein incorporated by reference in their entirety.

The present invention relates to novel [ortho bi-(hetero-)aryl]-[2-(meta bi-(hetero-)aryl)-pyrrolidin-1-yl]-methanone derivatives and their use as pharmaceuticals. The invention also concerns related aspects including processes for the preparation of the compounds, pharmaceutical compositions containing one or more compounds of formula (I), (II), (III), (IV), (V) or (VI) and especially their use as orexin receptor antagonists.

Orexins (orexin A or OX-A and orexin B or OX-B) are neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexin receptor antagonists are a novel type of nervous system or psychotropic drugs. Their mode of action in animals and humans involves either blockade of both orexin-1 and orexin-2 receptor (dual antagonists), or individual and selective blockade of either the orexin-1 or the orexin-2 receptor (selective antagonists) in the brain. Orexins were initially found to stimulate food consumption in rats suggesting a physiological role for these peptides as mediators in the central feedback mechanism that regulates feeding behaviour (Sakurai T. et al., Cell, 1998, 92, 573-585).

On the other hand, orexin neuropeptides and orexin receptors play an essential and central role in regulating circadian vigilance states. In the brain, orexin neurons collect sensory input about internal and external states and send short intrahypothalamic axonal projections as well as long projections to many other brain regions. The particular distribution of orexin fibers and receptors in basal forebrain, limbic structures and brainstem regions—areas related to the regulation of waking, sleep and emotional reactivity—suggests that orexins exert essential functions as regulators of behavioral arousal; by activating wake-promoting cell firing, orexins contribute to orchestrate all brain arousal systems that regulate circadian activity, energy balance and emotional reactivity. This role opens large therapeutic opportunities for medically addressing numerous mental health disorders possibly relating to orexinergic dysfunctions [see for example: Tsujino N and Sakurai T, "Orexin/hypocretin: a neuropeptide at the interface of sleep, energy homeostasis, and reward systems.", Pharmacol Rev. 2009, 61:162-176; and Carter M E et al., "The brain hypocretins and their receptors: mediators of allostatic arousal.", Curr Op Pharmacol. 2009, 9: 39-45] that are described in the following sections. It was also observed that orexins regulate states of sleep and wakefulness opening potentially novel therapeutic approaches to insomnia and other sleep disorders (Chemelli R. M. et al., Cell, 1999, 98, 437-451).

Human memory is comprised of multiple systems that have different operating principles and different underlying neuronal substrates. The major distinction is between the capacity for conscious, declarative memory and a set of unconscious, non-declarative memory abilities. Declarative memory is further subdivided into semantic and episodic memory. Non-declarative memory is further subdivided into priming and perceptual learning, procedural memory for skills and habits, associative and non-associative learning, and some others. While semantic memory refers to the general knowledge about the world, episodic memory is autobiographical memory of events. Procedural memories refer to the ability to perform skill-based operations, as e.g. motor skills. Long-term memory is established during a multiple stage process through gradual changes involving diverse brain structures, beginning with learning, or memory acquisition, or formation. Subsequently, consolidation of what has been learned may stabilize memories. When long-term memories are retrieved, they may return to a labile state in which original content may be updated, modulated or disrupted. Subsequently, reconsolidation may again stabilize memories. At a late stage, long-term memory may be resistant to disruption. Long-term memory is conceptually and anatomically different from working memory, the latter of which is the capacity to maintain temporarily a limited amount of information in mind. Behavioural research has suggested that the human brain consolidates long-term memory at certain key time intervals. The initial phase of memory consolidation may occur in the first few minutes after we are exposed to a new idea or learning experience. The next, and possibly most important phase, may occur over a longer period of time, such as during sleep; in fact, certain consolidation processes have been suggested to be sleep-dependent [R. Stickgold et al., Sleep-dependent memory consolidation; Nature 2005, 437, 1272-1278]. Learning and memory processes are believed to be fundamentally affected in a variety of neurological and mental disorders, such as e.g. mental retardation, Alzheimer's disease or depression. Indeed, memory loss or impairment of memory acquisition is a significant feature of such diseases, and no effective therapy to prevent this detrimental process has emerged yet.

In addition, both anatomical and functional evidence from in vitro and in vivo studies suggest an important positive interaction of the endogenous orexin system with reward pathways of the brain [Aston-Jones G et al., Brain Res 2010, 1314, 74-90; Sharf R et al., Brain Res 2010, 1314, 130-138]. Selective pharmacological OXR-1 blockade reduced cue- and stress-induced reinstatement of cocaine seeking [Boutrel B, et al., "Role for hypocretin in mediating stress-induced reinstatement of cocaine-seeking behavior." Proc Natl Acad Sci 2005, 102(52), 19168-19173; Smith R J et al., "Orexin/hypocretin signaling at the orexin 1 receptor regulates cue-elicited cocaine-seeking." Eur J Neurosci 2009, 30(3), 493-503; Smith R J et al., "Orexin/hypocretin is necessary for context-driven cocaine-seeking." Neuropharmacology 2010, 58(1), 179-184], cue-induced reinstatement of alcohol seeking [Lawrence A J et al., Br J Pharmacol 2006, 148(6), 752-759] and nicotine self-administration [Hollander J A et al., Proc Natl Acad Sci 2008, 105(49), 19480-19485; LeSage M G et al., Psychopharmacology 2010, 209(2), 203-212]. Orexin-1 receptor antagonism also attenuated the expression of amphetamine- and cocaine-induced CPP [Gozzi A et al., PLoS One 2011, 6(1), e16406; Hutcheson D M et al., Behav Pharmacol 2011, 22(2), 173-181], and reduced the expression or development of locomotor sensitization to amphetamine and cocaine [Borgland S L et al., Neuron 2006, 49(4), 589-601; Quarta D et al., "The orexin-1 receptor antagonist SB-334867 reduces amphetamine-evoked dopamine outflow in the shell of the nucleus accumbens and decreases the expression of amphetamine sensitization." Neurochem Int 2010, 56(1), 11-15].

The effect of a drug to diminish addictions may be modelled in normal or particularly sensitive mammals used as animal models [see for example Spealman et al, Pharmacol. Biochem. Behav. 1999, 64, 327-336; or T. S. Shippenberg, G. F. Koob, "Recent advances in animal models of drug addiction" in Neuropsychopharmacology: The fifth generation of progress; K. L. Davis, D. Charney, J. T. Doyle, C. Nemeroff (eds.) 2002; chapter 97, pages 1381-1397].

Several converging lines of evidence furthermore demonstrate a direct role of the orexin system as modulator of the acute stress response. For instance, stress (i.e. psychological stress or physical stress) is associated with increased arousal and vigilance which in turn is controlled by orexins [Sutcliffe, J G et al., Nat Rev Neurosci 2002, 3(5), 339-349]. Orexin neurons are likely to be involved in the coordinated regulation of behavioral and physiological responses in stressful environments [Y. Kayaba et al., Am. J. Physiol. Regul. Integr. Comp. Physiol. 2003, 285:R581-593]. Hypocretin/orexin contributes to the expression of some but not all forms of stress and arousal [Furlong T M et al., Eur J Neurosci 2009, 30(8), 1603-1614]. Stress response may lead to dramatic, usually time-limited physiological, psychological and behavioural changes that may affect appetite, metabolism and feeding behavior [Chrousos, G P et al., JAMA 1992, 267(9), 1244-1252]. The acute stress response may include behavioural, autonomic and endocrinological changes, such as promoting heightened vigilance, decreased libido, increased heart rate and blood pressure, or a redirection of blood flow to fuel the muscles, heart and the brain [Majzoub, J A et al., European Journal of Endocrinology 2006, 155 (suppl_1) S71-S76].

As outlined above the orexin system regulates homeostatic functions such as sleep-wake cycle, energy balance, emotions and reward. Orexins are also involved in mediating the acute behavioral and autonomous nervous system response to stress [Zhang W et al., "Multiple components of the defense response depend on orexin: evidence from orexin knockout mice and orexin neuron-ablated mice." Auton Neurosci 2006, 126-127, 139-145]. Mood disorders including all types of depression and bipolar disorder are characterized by disturbed "mood" and feelings, as well as by sleeping problems (insomnia as well as hypersomnia), changes in appetite or weight and reduced pleasure and loss of interest in daily or once enjoyed activities [Liu X et al., Sleep 2007, 30(1): 83-90]. Thus, there is a strong rationale that disturbances in the orexin system may contribute to the symptoms of mood disorders. Evidence in humans, for instance, exists that depressed patients show blunted diurnal variation in CSF orexin levels [Salomon R M et al., Biol Psychiatry 2003, 54(2), 96-104]. In rodent models of depression, orexins were also shown to be involved. Pharmacological induction of a depressive behavioral state in rats, for instance, revealed an association with increased hypothalamic orexin levels [Feng P et al., J Psychopharmacol 2008, 22(7): 784-791]. A chronic stress model of depression in mice also demonstrated an association of molecular orexin system disturbances with depressed behavioral states and a reversal of these molecular changes by antidepressant treatment [Nollet et al., NeuroPharm 2011, 61(1-2):336-46].

The orexin system is also involved in stress-related appetitive/reward seeking behaviour (Berridge C W et al., Brain Res 2009, 1314, 91-102). In certain instances, a modulatory effect on stress may be complementary to an effect on appetitive/reward seeking behaviour as such. For instance, an $OX_1$ selective orexin receptor antagonist was able to prevent footshock stress induced reinstatement of cocaine seeking behaviour [Boutrel, B et al., Proc Natl Acad Sci 2005, 102(52), 19168-19173]. In addition, stress is also known to play an integral part in withdrawal which occurs during cessation of drug taking (Koob, G F et al., Curr Opin Investig Drugs 2010, 11(1), 63-71).

Orexins have been found to increase food intake and appetite [Tsujino, N, Sakurai, T, Pharmacol Rev 2009, 61(2) 162-176]. As an additional environmental factor, stress can contribute to binge eating behaviour, and lead to obesity [Adam, T C et al. Physiol Behav 2007, 91(4) 449-458]. Animal models that are clinically relevant models of binge eating in humans are described for example in W. Foulds Mathes et al.; Appetite 2009, 52, 545-553.

A number of recent studies report that orexins may play a role into several other important functions relating to arousal, especially when an organism must respond to unexpected stressors and challenges in the environment [Tsujino N and Sakurai T. Pharmacol Rev. 2009, 61:162-176; Carter M E, Borg J S and deLecea L., Curr Op Pharmacol. 2009, 9: 39-45; C Boss, C Brisbare-Roch, F Jenck, Journal of Medicinal Chemistry 2009, 52: 891-903]. The orexin system interacts with neural networks that regulate emotion, reward and energy homeostasis to maintain proper vigilance states. Dysfunctions in its function may thus relate to many mental health disorders in which vigilance, arousal, wakefulness or attention is disturbed.

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, showed clinical efficacy in humans when tested for the indication primary insomnia. In the rat, the compound has been shown to decrease alertness, characterized by decreases in both active wake and locomotion; and to dose-dependently increase the time spent in both REM and NREM sleep [Brisbare et al., Nature Medicine 2007, 13, 150-155]. The compound further attenuated cardiovascular responses to conditioned fear and novelty exposure in rats [Furlong T M et al., Eur J Neurosci 2009, 30(8), 1603-1614]. It is also active in an animal model of conditioned fear: the rat fear-potentiated startle paradigm (WO2009/047723) which relates to emotional states of fear and anxiety diseases such as anxieties including phobias and post traumatic stress disorders (PTSDs). In addition, intact declarative and non-declarative learning and memory has been demonstrated in rats treated with this compound [WO2007/105177, H Dietrich, F Jenck, Psychopharmacology 2010, 212, 145-154]. Said compound furthermore decreased brain levels of amyloid-beta (Aβ) as well as Aβ plaque deposition after acute sleep restriction in amyloid precursor protein transgenic mice [J E Kang et al., "Amyloid-beta dynamics are regulated by orexin and the sleep-wake cycle.", Science 2009, 326(5955): 1005-1007]. The accumulation of the Aβ in the brain extracellular space is hypothesized to be a critical event in the pathogenesis of Alzheimer's disease. The so-called and generally known "amyloid cascade hypothesis" links Aβ to Alzheimer's disease and, thus, to the cognitive dysfunction, expressed as impairment of learning and memory. The compound has also been shown to induce antidepressant-like activity in a mouse model of depression, when administered chronically [Nollet et al., NeuroPharm 2011, 61(1-2):336-46]. Moreover, the compound has been shown to attenuate the natural activation induced by orexin A in fasted hungry rats exposed to food odors [M J Prud'homme et al., Neuroscience 2009, 162(4), 1287-1298]. The compound also displayed pharmacological activity in a rat model of nicotine self-administration [LeSage M G et al., Psychopharmacology 2010, 209(2), 203-212]. N-Biphenyl-2-yl-1-{[(1-methyl-1H-benzimidazol-2-yl)sulfanyl]acetyl}-L-prolinamide, another dual orexin receptor antagonist, inhibited nicotine-reinstatement for a conditioned reinforcer and reduced behavioral (locomotor sensitization) and molecular (transcriptional responses) changes induced by repeated amphetamine administration in rodents [Winrow et al., Neuropharmacology 2009, 58(1), 185-94].

U.S. Pat. No. 7,105,538 discloses certain [1,3,4]oxadiazol-2,5-diyl compounds including two exemplified [3-phenyl-5-methyl-isoxazol-4-yl]-[2-(5-pyridyl[1,3,4]oxadiazol-2-yl)-pyrrolidin-1-yl]-methanone derivatives (CAS registry no. 1082288-15-0, 1082288-80-9) and their use as antidepressants. The compounds are claimed to inhibit serotonin re-uptake and, thus, to have a pronounced anti-depressive and analgesic effect. It has been found that tested [3-phenyl-5-methyl-isoxazol-4-yl]-[pyrrolidin-1-yl]methanone derivatives showed low or no activity within the limits of detection on the orexin receptors.

WO2006/123249, WO2005/044797, and WO2007/039781 disclose metabotropic glutamate (especially mGluR5) receptor modulators and, thus, to be useful for example for the treatment of anxiety disorders or depression. Some compounds exemplified in WO2007/039781 comprise a 2-substituted pyrrolidine moiety, however, these compounds do not comprise an ortho bi-(hetero-)aryl group corresponding to the present group $A_1$ attached to the carbonyl group of the pyrrolidine-amide. Six example or analogue compounds of WO2007/039781 have been tested for their activity on the orexin receptors and showed low or no activity within the limits of detection.

Orexin receptor antagonists comprising a 2-substituted saturated cyclic amide derivatives (such as 2-substituted pyrrolidine-1-carboxamides) are known for example from WO2008/020405, WO2008/038251, WO2008/081399, WO2008/087611, WO2008/117241, WO2008/139416, WO2009/004584, WO2009/016560, WO2009/016564, WO2009/040730, WO2009/104155, WO2010/004507, WO2010/038200, WO2001/096302, WO2002/044172, WO2002/089800, WO2002/090355, WO2003/002561, WO2003/032991, WO2003/041711, WO2003/051368, WO2003/051873, WO2004/026866, WO2004/041791, WO2004/041807, WO2004/041816, WO2009/003993, WO2009/003997, WO2009/124956, WO2010/060470, WO2010/060471, WO2010/060472, WO2010/063662, WO2010/063663, WO2010/072722, WO2010/122151, and WO2008/150364. WO2003/002559 discloses certain N-aroyl cyclic amine derivatives encompassing pyrrolidine, piperidine and morpholine derivatives as orexin receptor antagonists. Despite the great number of prior art compounds and their high structural variability, all compounds share a common structural feature, i.e. in position 2 of the saturated cyclic amide a linker group such as at least a methylene group (or longer groups such as —CH$_2$—NH—CO—, —CH$_2$—NH—, —CH$_2$—O—, —CH$_2$—S—, etc.) link the cyclic amide to the respective aromatic ring system substituent. A particular 2-substituted pyrrolidine derived compound where the pyrrolidine is linked through a methylene group to an [1,3,4]oxadiazole ring: 1-(5-(2-fluorophenyl)-2-methyl-thiazol-4-yl)-1-[(S)-2-(5-phenyl-[1,3,4] oxadiazol-2-ylmethyl)-pyrrolidin-1-yl)-methanone is exemplified in WO2003/002559 and further characterized in Langmead et. al, Brit. J. Pharmacol. 2004, 141, 340-346 as being highly orexin-1 selective. It has now surprisingly been found that, despite the substantial conformational and, thus, pharmacological changes that may be expected from the removal of a linker between two rigid structural elements, the present compounds, that have an aromatic ring system directly attached to a pyrrolidine amide in position 2, are orexin receptor antagonists which may be active on both orexin receptors.

The present invention, thus, provides novel [ortho bi-(hetero-)aryl]-[2-(meta bi-(hetero-)aryl)-pyrrolidin-1-yl] methanone derivatives of formula (I), (II), (III), (IV), (V) and (VI), which are non-peptide antagonists of human orexin receptors potentially useful in the treatment of disorders relating to orexinergic dysfunctions, comprising especially sleep disorders, anxiety disorders, addiction disorders, cognitive dysfunctions, mood disorders, or appetite disorders; and especially in the treatment of sleep disorders, anxiety disorders, and addiction disorders.

1) A first aspect of the invention relates to compounds of the formula (I),

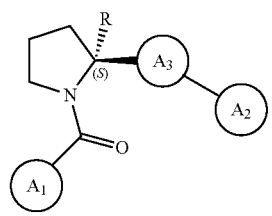

Formula (I)

wherein the carbon atom at position 2 of the pyrrolidine ring is in absolute (S)-configuration;

R represents hydrogen or methyl (in a sub-embodiment, for the compounds of formula (I), R represents especially hydrogen);

ring $A_3$ represents a meta di-substituted 5-membered heteroarylene ring containing one, two or three heteroatoms; wherein at least one of said heteroatoms is nitrogen, and the remaining is/are independently selected from oxygen, sulfur and nitrogen; [wherein it is understood that the two meta-arranged substituents are the pyrrolidine-2-yl group and the substituent $A_2$; and that the ring $A_3$ does not carry any further substituent];

ring $A_2$ represents aryl or 5- to 10-membered heteroaryl; wherein said aryl or 5- to 10-membered heteroaryl is independently unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, hydroxy, $(C_{1-4})$alkoxy-$(C_{1-3})$alkyl, hydroxy-$(C_{1-3})$alkyl, —CO—$(C_{1-4})$alkyl, and $(C_{3-6})$cycloalkyl-oxy-; or ring $A_2$ represents a 2,3-dihydro-benzo[1,4]dioxinyl, a 2,3-dihydro-benzofuranyl, or a benzo[1,3]dioxolyl group optionally di-substituted with fluoro; and ring $A_1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of $A_1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;

and the other of said substituents, if present, is/are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;

provided that ring $A_1$ is not isoxazol-4-yl, substituted in position 5 with $(C_{1-4})$alkyl, attached to the rest of the molecule at position 4, and carrying said further ortho-substitutent in position 3;

with the exception of the compound (1,1'-biphenyl)-2-yl-{(S)-2-[3-(3-pyridinyl)-1H-1,2,4-triazol-5-yl]-1-pyrrolidinyl}-methanone.

The compound (1,1'-biphenyl)-2-yl-{2-[3-(3-pyridinyl)-1H-1,2,4-triazol-5-yl]-1-pyrrolidinyl}-methanone in racemic form (CAS Registry Number: 958700-10-2; PubChem CID 16672186) is known in the literature, however, no pharmaceutical activity of this compound has been reported.

2) A further embodiment of the invention relates to compounds according to embodiment 1), wherein the ring $A_3$ represents a ring

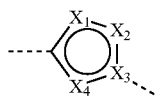

wherein said ring is a meta di-substituted 5-membered heteroarylene ring containing one, two or three heteroatoms at any of the positions $X_1$, $X_2$, $X_3$, and/or $X_4$; wherein at least one of said heteroatoms is nitrogen, and the remaining, if present, is/are independently selected from oxygen, sulfur and nitrogen.

3) A further embodiment of the invention relates to compounds according to embodiment 1), wherein the ring $A_3$ represents a ring

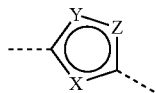

wherein said ring is a meta di-substituted 5-membered heteroarylene ring containing one, two or three heteroatoms at any of the positions X, Y and/or Z; wherein at least one of said heteroatoms is nitrogen, and the remaining, if present, is/are independently selected from oxygen, sulfur and nitrogen.

4) A further embodiment of the invention relates to compounds according to embodiment 1), wherein the ring $A_3$ is a meta di-substituted 5-membered heteroarylene ring selected from the group consisting of oxadiazol-diyl, triazol-diyl, isoxazol-diyl, oxazol-diyl, thiazol-diyl, pyrazol-diyl, imidazol-diyl, isothiazol-diyl, and thiadiazol-diyl.

5) A further embodiment of the invention relates to compounds according to embodiment 1), wherein the ring $A_3$ is a meta di-substituted 5-membered heteroarylene ring selected from the group consisting of oxadiazol-diyl, triazol-diyl, isoxazol-diyl, oxazol-diyl, thiazol-diyl, and thiadiazol-diyl.

6) A further embodiment of the invention relates to compounds according to embodiment 1), wherein the ring $A_3$ is selected from the group consisting of [1,2,4]oxadiazol-3,5-diyl, [1,2,4]triazol-3,5-diyl, [1,2,4]triazol-1,3-diyl, 1H-pyrazol-3,5-diyl, imidazol-2,4-diyl, isoxazol-3,5-diyl, oxazol-2,4-diyl, oxazol-2,5-diyl, thiazol-2,4-diyl, thiazol-2,5-diyl, isothiazol-3,5-diyl, [1,3,4]thiadiazol-2,5-diyl, and [1,3,4]oxadiazol-2,5-diyl (notably [1,2,4]oxadiazol-3,5-diyl or [1,2,4]triazol-3,5-diyl; especially [1,2,4]oxadiazol-3,5-diyl).

7) A further embodiment of the invention relates to compounds according to embodiment 1), wherein the ring $A_3$ is [1,3,4]oxadiazol-2,5-diyl.

8) A further embodiment relates to compounds according to any one of embodiments 1) to 7), or pharmaceutically acceptable salts thereof, for use in the treatment of mental health disorders relating to orexinergic dysfunctions; wherein for the compounds of formula (I) such mental health disorders relating to orexinergic dysfunctions are especially selected from sleep disorders, anxiety disorders, and addiction disorders.

9) A second aspect of the invention relates to novel compounds of the formula (I) which are also compounds of the formula (II):

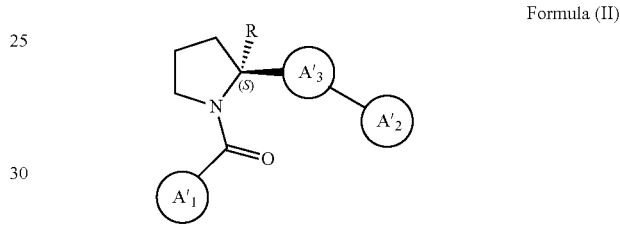

Formula (II)

wherein the carbon atom at position 2 of the pyrrolidine ring is in absolute (S)-configuration;

R represents hydrogen or methyl (in a sub-embodiment, for the compounds of formula (II), R represents especially hydrogen);

ring $A'_3$ represents a meta di-substituted 5-membered heteroarylene ring containing one, two or three heteroatoms; wherein at least one of said heteroatoms is nitrogen, and the remaining is/are independently selected from oxygen, sulfur and nitrogen; provided that said 5-membered heteroarylene ring is not [1,3,4]oxadiazol-2,5-diyl;

[wherein it is understood that the two meta-arranged substituents are the pyrrolidine-2-yl group and the substituent $A'_2$; and that the ring $A'_3$ does not carry any further substituent];

ring $A'_2$ represents aryl or 5- to 10-membered heteroaryl; wherein said aryl or 5- to 10-membered heteroaryl is independently unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, hydroxy, $(C_{1-4})$alkoxy-$(C_{1-3})$alkyl, hydroxy-$(C_{1-3})$alkyl, —CO—$(C_{1-4})$alkyl, and $(C_{3-6})$cycloalkyl-oxy-; or ring $A'_2$ represents a 2,3-dihydro-benzo[1,4]dioxinyl, a 2,3-dihydro-benzofuranyl, or a benzo[1,3]dioxolyl group optionally di-substituted with fluoro; and ring $A'_1$ represents phenyl or 5- or 6-membered heteroaryl, wherein said phenyl or 5- or 6-membered heteroaryl independently is mono-, di-, or tri-substituted; wherein)

one of said substituents is attached in ortho-position to the point of attachment of $A'_1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;

and the other of said substituents, if present, is/are independently selected from the group consisting of $(C_{1-4})$ alkyl, $(C_{1-4})$alkoxy, halogen, cyano, $(C_{1-3})$fluoroalkyl, and $(C_{1-3})$fluoroalkoxy;

provided that ring $A'_1$ is not isoxazol-4-yl, substituted in position 5 with $(C_{1-4})$alkyl, attached to the rest of the molecule at position 4, and carrying said further ortho-substitutent in position 3;

with the exception of the compound (1,1'-biphenyl)-2-yl-{(S)-2-[3-(3-pyridinyl)-1H-1,2,4-triazol-5-yl]-1-pyrrolidinyl}-methanone.

10) A further embodiment of the invention relates to compounds as defined in embodiment 9); wherein in such compounds the ring $A'_3$ represents a ring

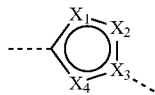

wherein said ring is a meta di-substituted 5-membered heteroarylene ring containing one, two or three heteroatoms at any of the positions $X_1$, $X_2$, $X_3$, and/or $X_4$; wherein at least one of said heteroatoms is nitrogen, and the remaining, if present, is/are independently selected from oxygen, sulfur and nitrogen; provided that said ring is not [1,3,4]oxadiazol-2,5-diyl.

11) A further embodiment of the invention relates to compounds as defined in embodiment 9); wherein in such compounds the ring $A'_3$ represents a ring

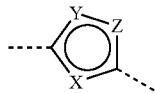

wherein said ring is a meta di-substituted 5-membered heteroarylene ring containing one, two or three heteroatoms at any of the positions X, Y and/or Z; wherein at least one of said heteroatoms is nitrogen, and the remaining, if present, is/are independently selected from oxygen, sulfur and nitrogen; provided that said ring is not [1,3,4]oxadiazol-2,5-diyl.

12) A further embodiment relates to compounds of embodiment 9) wherein the ring $A'_3$ is [1,3,4]thiadiazol-2,5-diyl.

13) A further embodiment relates to compounds of embodiment 9), wherein the ring $A'_3$ is a meta di-substituted 5-membered heteroarylene ring selected from the group consisting of [1,2,4]oxadiazol-3,5-diyl, [1,2,4]triazol-3,5-diyl, [1,2,4]triazol-1,3-diyl, 1H-pyrazol-3,5-diyl, imidazol-2,4-diyl, isoxazol-3,5-diyl, oxazol-2,4-diyl, oxazol-2,5-diyl, thiazol-2,4-diyl, and [1,3,4]thiadiazol-2,5-diyl (notably [1,2,4]oxadiazol-3,5-diyl or [1,2,4]triazol-3,5-diyl; especially [1,2,4]oxadiazol-3,5-diyl).

14) A further embodiment relates to compounds of embodiment 9), wherein the ring $A'_3$ is a meta di-substituted 5-membered heteroarylene ring selected from the group consisting of [1,2,4]oxadiazol-3,5-diyl, [1,2,4]triazol-3,5-diyl, and isoxazol-3,5-diyl (notably [1,2,4]oxadiazol-3,5-diyl or [1,2,4]triazol-3,5-diyl; especially [1,2,4]oxadiazol-3,5-diyl).

15) A further embodiment relates to compounds of formula (I) according to any one of embodiments 1) to 7), or to compounds of formula (II) according to any one of embodiments 9) to 14), wherein ring $A_1$, respectively ring $A'_1$, represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of $A_1/A'_1$ to the rest of the molecule; wherein said substituent is phenyl or 5- or 6-membered heteroaryl; wherein said phenyl or 5- or 6-membered heteroaryl substituent is independently unsubstituted, or mono- or di-substituted, wherein the substituents are independently selected from the group consisting of $(C_{1-4})$alkyl, $(C_{1-4})$alkoxy, and halogen;

and the other of said substituents, if present, is/are independently selected from the group consisting of $(C_{1-4})$ alkyl, $(C_{1-4})$alkoxy, halogen, cyano, $(C_{1-3})$fluoroalkyl, and $(C_{1-3})$fluoroalkoxy;

provided that ring $A_1$, respectively ring $A'_1$, is not isoxazol-4-yl, substituted in position 5 with $(C_{1-4})$alkyl, attached to the rest of the molecule at position 4, and carrying said further ortho-substitutent in position 3.

16) A further embodiment relates to compounds of formula (I) according to any one of embodiments 1) to 7), or to compounds of formula (II) according to any one of embodiments 9) to 14), wherein ring $A_1$, respectively ring $A'_1$, represents 5-membered heteroaryl, wherein the 5-membered heteroaryl is mono- or di-substituted; wherein)

one of said substituents is attached in ortho-position to the point of attachment of $A_1/A'_1$ to the rest of the molecule; wherein said ortho-substituent is phenyl, or 6-membered heteroaryl (especially pyridyl); wherein said phenyl or 6-membered heteroaryl is independently unsubstituted, or mono-, or di-substituted (especially unsubstituted, or mono-substituted), wherein the substituents are independently selected from the group consisting of $(C_{1-4})$alkyl, $(C_{1-4})$alkoxy, halogen, $(C_{1-3})$fluoroalkyl, and $(C_{1-3})$ fluoroalkoxy [wherein said ortho-substituent is especially phenyl which is especially unsubstituted, or mono-substituted with $(C_{1-4})$alkyl, or halogen];

and the other of said substituents, if present, is selected from $(C_{1-4})$alkyl (especially methyl);

provided that ring $A_1$, respectively ring $A'_1$, is not isoxazol-4-yl, substituted in position 5 with $(C_{1-4})$ alkyl, attached to the rest of the molecule at position 4, and carrying said further ortho-substitutent in position 3;

or ring $A_1$, respectively ring $A'_1$, represents phenyl or 6-membered heteroaryl, wherein the phenyl or 6-membered heteroaryl independently is mono-, di-, or tri-substituted; wherein one of said substituents is attached in ortho-position to the point of attachment of $A_1/A'_1$ to the rest of the molecule; wherein said ortho-substituent is phenyl which is unsubstituted, mono-, or di-substituted (especially unsubstituted, or mono-substituted), wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy (especially $(C_{1-4})$alkoxy, and halogen);

or said ortho-substituent is 6-membered heteroaryl (especially pyridyl or pyrimidinyl) which is unsubstituted, mono-, or di-substituted (especially unsubstituted), wherein the substituents are independently selected from the group consisting of $(C_{1-4})$alkyl, $(C_{1-4})$alkoxy, halogen, and $(C_{1-3})$fluoroalkyl (especially $(C_{1-4})$alkyl);

or said ortho-substituent is 5-membered heteroaryl (notably pyrazol-1-yl or [1,2,3]triazol-2-yl) which is unsubstituted, mono-, or di-substituted (especially unsubstituted or mono-substituted), wherein the substituents are independently selected from the group consisting of $(C_{1-4})$alkyl, $(C_{1-4})$alkoxy, halogen, and $(C_{1-3})$fluoroalkyl (especially $(C_{1-4})$alkyl, notably methyl);

and the other of said substituents, if present, is/are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy [especially $(C_{1-4})$alkyl, $(C_{1-4})$alkoxy, and halogen; notably $(C_{1-4})$alkyl and halogen].

17) A further embodiment relates to compounds of formula (I) according to any one of embodiments 1) to 7), or to compounds of formula (II) according to any one of embodiments 9) to 14), wherein ring $A_1$, respectively ring $A'_1$, represents 5-membered heteroaryl, wherein the 5-membered heteroaryl is mono- or di-substituted; wherein)

one of said substituents is attached in ortho-position to the point of attachment of $A_1/A'_1$ to the rest of the molecule; wherein said ortho-substituent is phenyl, or 6-membered heteroaryl (especially pyridyl), wherein said phenyl or 6-membered heteroaryl is independently unsubstituted, mono-, or di-substituted (especially unsubstituted, or mono-substituted), wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy [wherein said ortho-substituent is especially phenyl which is especially unsubstituted, or mono-substituted with $(C_{1-4})$alkyl, or halogen];

and the other of said substituents, if present, is selected from $(C_{1-4})$alkyl (especially methyl);

provided that ring $A_1$, respectively ring $A'_1$, is not isoxazol-4-yl, substituted in position 5 with $(C_{1-4})$alkyl, attached to the rest of the molecule at position 4, and carrying said further ortho-substitutent in position 3;

or ring $A_1$, respectively ring $A'_1$, represents 6-membered heteroaryl, wherein the 6-membered heteroaryl is mono-, or di-substituted; wherein)

one of said substituents is attached in ortho-position to the point of attachment of $A_1/A'_1$ to the rest of the molecule; wherein said ortho-substituent is unsubstituted 5-membered heteroaryl (notably pyrazol-1-yl or [1,2,3]triazol-2-yl); or said ortho-substituent is unsubstituted 6-membered heteroaryl (notably pyridin-2-yl); or said ortho-substituent is phenyl which is unsubstituted, or mono- or di-substituted (especially unsubstituted, or mono-substituted), wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy (especially $(C_{1-4})$alkyl, $(C_{1-4})$alkoxy, and halogen);)

and the other of said substituents, if present, is/are independently selected from the group consisting of $(C_{1-4})$alkyl, $(C_{1-4})$alkoxy, halogen, and $(C_{1-3})$fluoroalkyl (especially $(C_{1-4})$alkyl; notably methyl);

or ring $A_1$, respectively ring $A'_1$, represents phenyl which is mono-, di-, or tri-substituted; wherein one of said substituents is attached in ortho-position to the point of attachment of $A_1/A'_1$ to the rest of the molecule; wherein said ortho-substituent is phenyl which is unsubstituted, mono-, or di-substituted (especially unsubstituted, or mono-substituted), wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy; or said ortho-substituent is 6-membered heteroaryl (especially pyridyl or pyrimidinyl) which is unsubstituted, mono-, or di-substituted (especially unsubstituted or mono-substituted), wherein the substituents are independently selected from the group consisting of $(C_{1-4})$alkyl, $(C_{1-4})$alkoxy, halogen, and $(C_{1-3})$fluoroalkyl (especially $(C_{1-4})$alkyl, $(C_{1-4})$alkoxy); or said ortho-substituent is 5-membered heteroaryl which is unsubstituted, or mono-substituted (especially unsubstituted), wherein the substituents are independently selected from the group consisting of $(C_{1-4})$alkyl, $(C_{1-4})$alkoxy, halogen, and $(C_{1-3})$fluoroalkyl (especially $(C_{1-4})$alkyl, notably methyl);)

and the other of said substituents, if present, is/are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy [especially $(C_{1-4})$alkyl, $(C_{1-4})$alkoxy, and halogen; notably $(C_{1-4})$alkyl and halogen].

18) A further embodiment relates to compounds of formula (I) according to any one of embodiments 1) to 7), or to compounds of formula (II) according to any one of embodiments 9) to 14), wherein ring $A_1$, respectively ring $A'_1$, represents 5-membered heteroaryl, wherein the 5-membered heteroaryl is mono- or di-substituted; wherein one of said substituents is attached in ortho-position to the point of attachment of $A_1/A'_1$ to the rest of the molecule; wherein said ortho-substituent is phenyl which is unsubstituted, or mono-substituted, wherein the substituents are independently selected from the group consisting of $(C_{1-4})$alkyl and halogen;

and the other of said substituents, if present, is independently selected from the group consisting of $(C_{1-4})$alkyl (especially methyl);

provided that ring $A_1$, respectively ring $A'_1$, is not isoxazol-4-yl, substituted in position 5 with $(C_{1-4})$alkyl, attached to the rest of the molecule at position 4, and carrying said further ortho-substitutent in position 3;

or ring $A_1$, respectively ring $A'_1$, represents 6-membered heteroaryl, wherein the 6-membered heteroaryl is mono-, or di-substituted; wherein)

one of said substituents is attached in ortho-position to the point of attachment of $A_1/A'_1$ to the rest of the molecule; wherein said ortho-substituent is unsubstituted 5-membered heteroaryl (notably pyrazol-1-yl or [1,2,3]triazol-2-yl, especially in case $Ar^1$ represents pyridyl); or said ortho-substituent is unsubstituted 6-membered heteroaryl (notably pyridin-2-yl, especially in case Ar¹ represents pyridyl); or said ortho-substituent is phenyl which is unsubstituted, or mono-substituted (especially mono-substituted), wherein the substituents are independently selected from the group consisting of $(C_{1-4})$alkoxy and halogen;

and the other of said substituents, if present, is/are independently selected from the group consisting of $(C_{1-4})$alkyl, (notably methyl);

or ring $A_1$, respectively ring $A'_1$, represents phenyl which is mono-, di-, or tri-substituted; wherein)

one of said substituents is attached in ortho-position to the point of attachment of $A_1/A'_1$ to the rest of the molecule; wherein said ortho-substituent is unsubstituted phenyl; or said ortho-substituent is unsubstituted 6-membered heteroaryl (especially pyridyl or pyrimidinyl);

or said ortho-substituent is 5-membered heteroaryl which is unsubstituted, or mono-substituted, wherein the substituents are independently selected from the group consisting of $(C_{1-4})$alkyl, (notably methyl);

and the other of said substituents, if present, is/are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy [especially $(C_{1-4})$alkyl, $(C_{1-4})$alkoxy, and halogen; notably $(C_{1-4})$alkyl and halogen].

19) A further embodiment relates to compounds of formula (I) according to any one of embodiments 1) to 7) and 15) to 18), or to compounds of formula (II) according to any one of embodiments 9) to 18), wherein the following characteristics are present:

in case ring $A_1$, respectively ring $A'_1$, represents a 5-membered heteroaryl group, such group is an oxazolyl, imidazolyl, or thiazolyl group (especially a thiazolyl group); and/or in case ring $A_1$, respectively ring $A'_1$, represents a 6-membered heteroaryl group, such group is a pyridinyl, pyrazinyl, or pyrimidinyl group (especially a pyridinyl group);

wherein said groups independently are substituted as defined in any one of the preceeding embodiments.

20) A further embodiment relates to compounds of formula (I) according to any one of embodiments 1) to 7) and 15) to 18), or to compounds of formula (II) according to any one of embodiments 9) to 19), wherein the following characteristics are present:

in case said ortho substituent of ring $A_1$, respectively ring $A'_1$, represents a 5-membered heteroaryl group, such group is a triazolyl (especially unsubstituted [1,2,3]triazol-2-yl), a pyrazolyl (especially unsubstituted pyrazol-1-yl, or unsubstituted 2H-pyrazol-3-yl), an oxazolyl (especially unsubstituted oxazol-2-yl), or an oxadiazolyl (especially 3-methyl-[1,2,4]oxadiazol-5-yl); [notably such group is unsubstituted [1,2,3]triazol-2-yl or unsubstituted pyrazol-1-yl]; and/or in case said ortho substituent of ring $A_1$, respectively ring $A'_1$, represents a 6-membered heteroaryl group, such group is a pyridinyl or a pyrimidinyl group (especially 6-methoxy-pyridin-3-yl, pyridin-2-yl, pyridin-3-yl, or pyrimidin-2-yl; notably unsubstituted pyridin-2-yl or unsubstituted pyrimidin-2-yl); and/or in case said ortho substituent of ring $A_1$, respectively ring $A'_1$, represents a phenyl group, such group is an unsubstituted or mono-substituted phenyl group wherein the substituent is selected from the group consisting of $(C_{1-4})$alkyl, $(C_{1-4})$alkoxy, and halogen (especially such group is phenyl, 3-methyl-phenyl, 2-fluorophenyl, 3-fluorophenyl, 4-fluorophenyl, 3-chlorophenyl, 3-methoxyphenyl; notably phenyl);

wherein said groups independently are unsubstituted or substituted as defined in any one of the preceeding embodiments, or as explicitly defined herein.

21) A further embodiment relates to compounds of formula (I) according to any one of embodiments 1) to 7), or to compounds of formula (II) according to any one of embodiments 9) to 14), wherein ring $A_1$, respectively ring $A'_1$, represents a ring

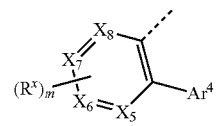

wherein $X_5, X_6, X_7,$ and $X_8$ represent ring carbon atoms; or one of $X_5$ and $X_8$ represents a ring nitrogen atom and the remaining of $X_5, X_6, X_7,$ and $X_8$ represent ring carbon atoms; or $X_5$ and $X_8$ represent ring nitrogen atoms and $X_6$ and $X_7$ represent ring carbon atoms; or $X_5$ and $X_7$ represent ring nitrogen atoms and $X_6$ and $X_8$ represent ring carbon atoms;

$(R^x)_m$ represents one, or two optional substituents [i.e. m represents the integer 0, 1, or 2] independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; and $Ar^4$ represents phenyl or 5- or 6-membered heteroaryl; wherein said phenyl or 5- or 6-membered heteroaryl independently is unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy.

22) A further embodiment relates to compounds of formula (I) according to any one of embodiments 1) to 7), or to compounds of formula (II) according to any one of embodiments 9) to 14), wherein ring $A_1$, respectively ring $A'_1$, represents a ring

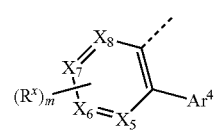

wherein one of $X_5$ and $X_8$ represents a ring nitrogen atom and the remaining of $X_5, X_6, X_7,$ and $X_8$ represent ring carbon atoms; or $X_5$ and $X_8$ represent ring nitrogen atoms and $X_6$ and $X_7$ represent ring carbon atoms; or $X_5$ and $X_7$ represent ring nitrogen atoms and $X_6$ and $X_8$ represent ring carbon atoms;

$(R^x)_m$ represents one, or two optional substituents [i.e. m represents the integer 0, 1, or 2] independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; and $Ar^4$ represents phenyl or 5- or 6-membered heteroaryl; wherein said phenyl or 5- or 6-membered heteroaryl independently is unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy.

23) Another embodiment relates to compounds according to embodiments 21) or 22), wherein $Ar^4$ is selected from the group consisting of unsubstituted or mono-substituted phenyl wherein the substituent is selected from the group consisting of $(C_{1-4})$alkyl, $(C_{1-4})$alkoxy, and halogen (especially such group is phenyl, 3-methyl-phenyl, 2-fluorophenyl, 3-fluorophenyl, 4-fluorophenyl, 3-chlorophenyl, or 3-methoxyphenyl; notably phenyl); triazolyl (especially unsubstituted [1,2,3]triazol-2-yl); pyrazolyl (especially unsubstituted pyrazol-1-yl, or unsubstituted 2H-pyrazol-3-yl); pyridyl (especially unsubstituted pyridin-2-yl); and pyrimidinyl (especially unsubstituted pyrimidin-2-yl); and $(R^x)_m$ represents one or two optional substituents independently selected from $(C_{1-4})$alkyl, $(C_{1-4})$alkoxy, halogen, and $(C_{1-3})$fluoroalkyl.

24) A further embodiment relates to compounds of formula (I) according to any one of embodiments 1) to 7), or to compounds of formula (II) according to any one of embodiments 9) to 14), wherein ring $A_1$, respectively ring $A'_1$, represents a ring

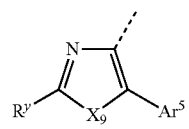

wherein $X_9$ represents O, S, or NH; and
$R^y$ represents hydrogen or $(C_{1-4})$alkyl; and
$Ar^5$ represents phenyl or 6-membered heteroaryl; wherein said phenyl or 6-membered heteroaryl independently is unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy.

25) Another embodiment relates to compounds according to embodiment 24), wherein
$Ar^5$ represents phenyl, wherein said phenyl is unsubstituted, mono-, or di-substituted (especially unsubstituted or mono-substituted), wherein the substituents are independently selected from the group consisting of $(C_{1-4})$alkyl, $(C_{1-4})$alkoxy, and halogen (especially such group is phenyl, 3-methyl-phenyl, 2-fluorophenyl, 3-fluorophenyl, 4-fluorophenyl, 3-chlorophenyl, or 3-methoxyphenyl); and
$R^y$ represents hydrogen or $(C_{1-4})$alkyl (especially hydrogen or methyl).

26) A third aspect of the invention relates to compounds of the formula (I) as defined in embodiment 1) which are also compounds of the formula (III):

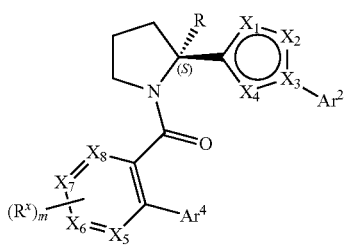

Formula (III)

wherein the carbon atom at position 2 of the pyrrolidine ring is in absolute (S)-configuration;
R represents hydrogen or methyl (in a sub-embodiment, for the compounds of formula (III), R represents especially hydrogen);
wherein the ring

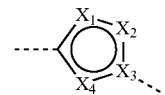

represents a meta di-substituted 5-membered heteroarylene ring containing one, two or three heteroatoms at any of the positions $X_1$, $X_2$, $X_3$, and/or $X_4$; wherein at least one of said heteroatoms is nitrogen, and the remaining, if present, is/are independently selected from oxygen, sulfur and nitrogen;
$X_5$, $X_6$, $X_7$, and $X_8$ represent ring carbon atoms; or one of $X_5$ and $X_8$ represents a ring nitrogen atom and the remaining of $X_5$, $X_6$, $X_7$, and $X_8$ represent ring carbon atoms; or $X_5$ and $X_8$ represent ring nitrogen atoms and $X_6$ and $X_7$ represent ring carbon atoms; or $X_5$ and $X_7$ represent ring nitrogen atoms and $X_6$ and $X_8$ represent ring carbon atoms;
$Ar^2$ represents phenyl or 5- to 10-membered heteroaryl; wherein said phenyl or 5- to 10-membered heteroaryl is independently unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, hydroxy, $(C_{1-4})$alkoxy-$(C_{1-3})$alkyl, hydroxy-$(C_{1-3})$alkyl, —CO—$(C_{1-4})$alkyl, and $(C_{3-6})$cycloalkyl-oxy-; or
$Ar^2$ represents a 2,3-dihydro-benzo[1,4]dioxinyl, a 2,3-dihydro-benzofuranyl, or a benzo[1,3]dioxolyl group optionally di-substituted with fluoro;
$(R^x)_m$ represents one, or two optional substituents [i.e. m represents the integer 0, 1, or 2] independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; and
$Ar^4$ represents phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
with the exception of the compound (1,1'-biphenyl)-2-yl-{(S)-2-[3-(3-pyridinyl)-1H-1,2,4-triazol-5-yl]-1-pyrrolidinyl}-methanone.

27) A fourth aspect of the invention relates to novel compounds of the formula (I) as defined in embodiment 1), which are also compounds of the formula (IV):

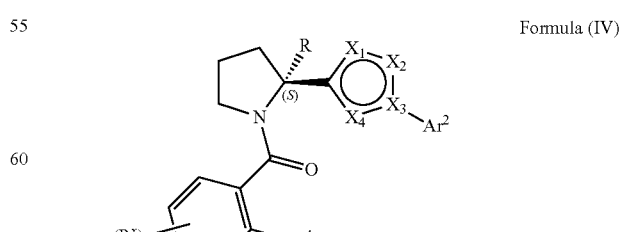

Formula (IV)

wherein the carbon atom at position 2 of the pyrrolidine ring is in absolute (S)-configuration;

wherein
R represents hydrogen or methyl (in a sub-embodiment, for the compounds of formula (IV), R represents especially hydrogen);
the ring

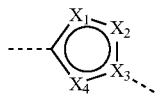

represents a meta di-substituted 5-membered heteroarylene ring containing one, two or three heteroatoms at any of the positions $X_1$, $X_2$, $X_3$, and/or $X_4$; wherein at least one of said heteroatoms is nitrogen, and the remaining, if present, is/are independently selected from oxygen, sulfur and nitrogen [wherein it is understood that the two meta-arranged substituents are the pyrrolidine-2-yl group and the substituent $Ar^2$; and that the above-defined ring does not carry any further substituent];
$Ar^2$ represents phenyl or 5- to 10-membered heteroaryl; wherein said phenyl or 5- to 10-membered heteroaryl is independently unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, hydroxy, $(C_{1-4})$alkoxy-$(C_{1-3})$alkyl, hydroxy-$(C_{1-3})$alkyl, —CO—$(C_{1-4})$alkyl, and $(C_{3-6})$cycloalkyl-oxy-; or
$Ar^2$ represents a 2,3-dihydro-benzo[1,4]dioxinyl, a 2,3-dihydro-benzofuranyl, or a benzo[1,3]dioxolyl group optionally di-substituted with fluoro;
$(R^x)_m$ represents one or two optional substituents [i.e. m represents the integer 0, 1, or 2] independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; and
$Ar^4$ represents phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
with the exception of the compound (1,1'-biphenyl)-2-yl-{(S)-2-[3-(3-pyridinyl)-1H-1,2,4-triazol-5-yl]-1-pyrrolidinyl}-methanone.

28) A further embodiment of the invention relates to compounds of formula (III) according to embodiment 26), or to compounds of formula (IV) according to embodiment 27), wherein the ring

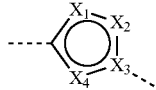

represents a meta di-substituted 5-membered heteroarylene ring selected from the group consisting of oxadiazol-diyl, triazol-diyl, isoxazol-diyl, oxazol-diyl, thiazol-diyl, and thiadiazol-diyl.

29) A further embodiment of the invention relates to compounds of formula (III) according to embodiment 26), or to compounds of formula (IV) according to embodiment 27), wherein the ring

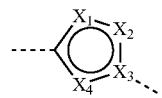

represents a group selected from the group consisting of [1,2,4]oxadiazol-3,5-diyl, [1,2,4]triazol-3,5-diyl, [1,2,4]triazol-1,3-diyl, 1H-pyrazol-3,5-diyl, imidazol-2,4-diyl, isoxazol-3,5-diyl, oxazol-2,4-diyl, oxazol-2,5-diyl, thiazol-2,4-diyl, [1,3,4]thiadiazol-2,5-diyl, and [1,3,4]oxadiazol-2,5-diyl (notably [1,2,4]oxadiazol-3,5-diyl or [1,2,4]triazol-3,5-diyl; especially [1,2,4]oxadiazol-3,5-diyl).

30) A further embodiment of the invention relates to compounds of formula (III) according to embodiment 26), or to compounds of formula (IV) according to embodiment 27), wherein the ring

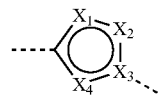

represents a meta di-substituted 5-membered heteroarylene ring independently selected from one, or more (in any combination), or all of the following groups A) to J) [especially said meta di-substituted 5-membered heteroarylene ring is selected from B) or E); notably B)]:

A)

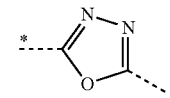

B)

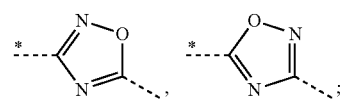

C)

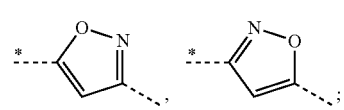

D)

E)

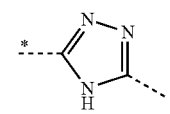

F)

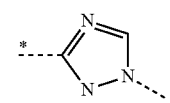

G)

represents a meta di-substituted 5-membered heteroarylene ring independently selected from one, or more (in any combination), or all of the following groups A) to I) [especially said meta di-substituted 5-membered heteroarylene ring is selected from A) or D); notably A)]:

H)

[structure: 1H-pyrazole]

I)

[structure: thiazole]

J)

[structure: 1,3,4-thiadiazole]

wherein the asterisks indicate the bond that is linked to the pyrrolidine moiety of the molecule.

31) A further embodiment of the invention relates to compounds of formula (III) according to embodiment 26), or to compounds of formula (IV) according to embodiment 27), wherein the ring

[structure with $X_1$, $X_2$, $X_3$, $X_4$]

represents a meta di-substituted 5-membered heteroarylene ring containing one, two or three heteroatoms at any of the positions $X_1$, $X_2$, $X_3$, and/or $X_4$; wherein at least one of said heteroatoms is nitrogen, and the remaining, if present, is/are independently selected from oxygen, sulfur and nitrogen; provided that said 5-membered heteroarylene ring is not [1,3,4]oxadiazol-2,5-diyl.

32) A further embodiment of the invention relates to compounds of formula (III) according to embodiment 26), or to compounds of formula (IV) according to embodiment 27), wherein the ring

[structure with $X_1$, $X_2$, $X_3$, $X_4$]

represents a group selected from the group consisting of [1,2,4]oxadiazol-3,5-diyl, [1,2,4]triazol-3,5-diyl, [1,2,4]triazol-1,3-diyl, 1H-pyrazol-3,5-diyl, imidazol-2,4-diyl, isoxazol-3,5-diyl, oxazol-2,4-diyl, oxazol-2,5-diyl, thiazol-2,4-diyl, and [1,3,4]thiadiazol-2,5-diyl (notably [1,2,4]oxadiazol-3,5-diyl or [1,2,4]triazol-3,5-diyl; especially [1,2,4]oxadiazol-3,5-diyl).

33) A further embodiment of the invention relates to compounds of formula (III) according to embodiment 26), or to compounds of formula (IV) according to embodiment 27), wherein the ring

[structure with $X_1$, $X_2$, $X_3$, $X_4$]

represents a meta di-substituted 5-membered heteroarylene ring independently selected from one, or more (in any combination), or all of the following groups A) to I) [especially said meta di-substituted 5-membered heteroarylene ring is selected from A) or D); notably A)]:

A)

[structures: 1,2,4-oxadiazol-3,5-diyl, 1,2,4-oxadiazol-5,3-diyl]

B)

[structures: isoxazoles]

C)

[structures: oxazoles]

D)

[structure: 1,2,4-triazole]

E)

[structures: imidazoles]

F)

[structure: 1,2,4-triazole isomer]

G)

[structure: 1H-pyrazole]

H)

[structure: thiazole]

I)

[structure: 1,3,4-thiadiazole]

wherein the asterisks indicate the bond that is linked to the pyrrolidine moiety of the molecule.

34) A further embodiment of the invention relates to compounds of formula (III) according to embodiment 26), or to compounds of formula (IV) according to embodiment 27), wherein the ring

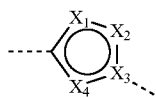

represents a meta di-substituted 5-membered heteroarylene ring independently selected from one, or more (in any combination), or all of the following groups A) to C) [especially said meta di-substituted 5-membered heteroarylene ring is selected from A) or C); notably A)]:

A)

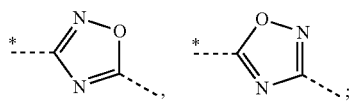

B)

C)

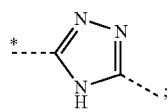

wherein the asterisks indicate the bond that is linked to the pyrrolidine moiety of the molecule.

35) A further embodiment of the invention relates to compounds of formula (III) according to embodiment 26), or to compounds of formula (IV) according to embodiment 27), wherein the ring

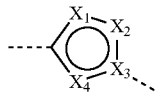

represents a meta di-substituted 5-membered heteroarylene ring independently selected from one, or both of the following groups A) and B) [especially said meta di-substituted 5-membered heteroarylene ring is selected from A)]:

A)

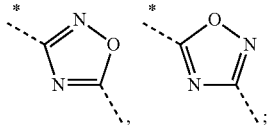

B)

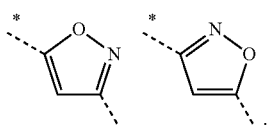

wherein the asterisks indicate the bond that is linked to the pyrrolidine moiety of the molecule.

36) A further embodiment of the invention relates to compounds of formula (III) according to embodiment 26), or to compounds of formula (IV) according to embodiment 27), wherein the ring

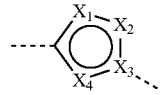

represents

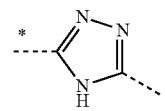

wherein the asterisks indicate the bond that is linked to the pyrrolidine moiety of the molecule.

37) A further embodiment of the invention relates to compounds of formula (III) according to embodiment 26), or to compounds of formula (IV) according to embodiment 27), wherein the ring

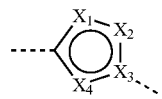

represents

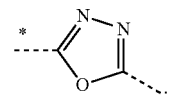

38) A further embodiment relates to compounds of formulae (I), (II), (III), and (IV) according to any one of embodiments 1) to 37), wherein ring $A_2$, respectively ring $A'_2$, respectively $Ar^e$, represents phenyl which is unsubstituted, or mono-, di-, or tri-substituted (especially unsubstituted, or mono- or di-substituted); wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy; hydroxy, $(C_{1-4})$alkoxy-$(C_{1-3})$alkyl, hydroxy-$(C_{1-3})$alkyl, and $(C_{3-6})$cycloalkyl-oxy-; or a 2,3-dihydro-benzo[1,4]dioxinyl, a 2,3-dihydro-benzofuranyl, or a benzo[1,3]dioxolyl group which is optionally di-substituted with fluoro; or 5- or 6-membered heteroaryl; wherein said heteroaryl is independently unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, and $(C_{3-6})$cycloalkyl-oxy-; (especially 6-membered heteroaryl containing one or two ring nitrogen atoms; notably pyridinyl; which is mono- or di-substituted, notably mono-substituted, with said substituents; wherein preferably at least one of said substituents is attached in ortho- or meta-position with respect to the point of attachment of the rest of the molecule); or 8- to 10-membered heteroaryl; wherein said heteroaryl is independently unsubstituted, or mono-, di-, or tri-substituted; wherein the substituents are independently selected from the group consisting of $(C_{1-4})$alkyl, $(C_{1-4})$alkoxy, halogen, $(C_{1-3})$fluoroalkyl, and —CO—$(C_{1-4})$alkyl.

39) A further embodiment relates to compounds of formulae (I), (II), (III), and (IV) according to any one of embodiments 1) to 37), wherein ring $A_2$, respectively ring $A'_2$, respectively $Ar^e$, represents phenyl which is unsubstituted, or mono-, di-, or tri-substituted (notably unsubstituted, or mono- or di-substituted; especially mono- or di-substituted); wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, $(C_{1-3})$fluoroalkoxy; hydroxy, $(C_{1-4})$alkoxy-$(C_{1-3})$alkyl, and hydroxy-$(C_{1-3})$alkyl; or a 2,3-dihydro-benzo[1,4]dioxinyl, a 2,3-dihydro-benzofuranyl, or a benzo[1,3]dioxolyl group which is optionally di-substituted with fluoro; or 6-membered heteroaryl; wherein said heteroaryl is independently unsubstituted, or mono- or di-substituted; wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, $(C_{1-3})$fluoroalkoxy, and $(C_{3-6})$cycloalkyl-oxy-; (notably 6-membered heteroaryl containing one or two ring nitrogen atoms; especially pyridinyl; wherein such 6-membered heteroaryl is mono- or di-substituted, notably mono-substituted; wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, and $(C_{3-6})$cycloalkyl-oxy-; wherein preferably at least one of said substituents is attached in ortho- or meta-position with respect to the point of attachment of the rest of the molecule); or 8- to 10-membered heteroaryl (notably 9-membered heteroaryl containing at least one ring nitrogen atom; especially indolyl, indazolyl, or pyrrolopyridinyl); wherein said heteroaryl is independently unsubstituted, or mono-substituted; wherein the substituent is independently selected from the group consisting of $(C_{1-4})$alkyl, $(C_{1-4})$alkoxy, and —CO—$(C_{1-4})$alkyl.

40) A further embodiment relates to compounds of formulae (I), (II), (III), and (IV) according to any one of embodiments 1) to 37), wherein ring $A_2$, respectively ring $A'_2$, respectively $Ar^2$, represents phenyl which is unsubstituted, or mono-, di-, or tri-substituted (notably unsubstituted, or mono- or di-substituted; especially mono- or di-substituted); wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, and $(C_{1-3})$fluoroalkoxy; or a 2,3-dihydro-benzo[1,4]dioxinyl, a 2,3-dihydro-benzofuranyl, or a benzo[1,3]dioxolyl group; or pyridinyl which is mono-, or di-substituted (especially mono-substituted); wherein the substituents are independently selected from the group consisting of $(C_{1-4})$alkyl, $(C_{1-4})$alkoxy, halogen, $(C_{1-3})$fluoroalkoxy, and $(C_{3-6})$cycloalkyl-oxy- (especially $(C_{1-4})$alkoxy and $(C_{3-6})$cycloalkyl-oxy-); wherein preferably at least one of said substituents is attached in ortho- or meta-position with respect to the point of attachment of the rest of the molecule;

indolyl or pyrrolopyridinyl which are independently unsubstituted, or mono-substituted; wherein the substituent is independently selected from $(C_{1-4})$alkyl;

wherein in a sub-embodiment, ring $A_2$, respectively ring $A'_2$, respectively $Ar^2$, especially represents phenyl which is mono-, di-, or tri-substituted (notably mono- or di-substituted); wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy.

41) A further embodiment relates to compounds of formulae (I), (II), (III), and (IV) according to any one of embodiments 1) to 37), wherein ring $A_2$, respectively ring $A'_2$, respectively $Ar^2$, represents phenyl which is unsubstituted, or mono-, di-, or tri-substituted (notably unsubstituted, or mono- or di-substituted; especially mono- or di-substituted); wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, $(C_{1-3})$fluoroalkoxy; hydroxy, $(C_{1-4})$alkoxy-$(C_{1-3})$alkyl, and hydroxy-$(C_{1-3})$alkyl; or 2,3-dihydro-benzo[1,4]dioxin-5-yl, 2,3-dihydro-benzofuran-7-yl, benzo[1,3]dioxol-4-yl, benzo[1,3]dioxol-5-yl, or 2,2-difluoro-benzo[1,3]dioxol-5-yl; or 5- or 6-membered heteroaryl selected from pyridyl, pyrazolyl, and pyrazinyl; wherein said heteroaryl is independently mono-, or di-substituted (especially mono-substituted); wherein the substituents are independently selected from the group consisting of $(C_{1-4})$alkyl, $(C_{1-3})$alkoxy, halogen, $(C_{1-3})$fluoroalkoxy, and $(C_{3-6})$cycloalkyl-oxy- (especially $(C_{1-4})$alkyl, $(C_{1-4})$alkoxy, and $(C_{3-6})$cycloalkyl-oxy-); wherein preferably at least one of said substituents is attached in ortho- or meta-position with respect to the point of attachment of the rest of the molecule; or 8- to 10-membered heteroaryl selected from indolyl, pyrrolopyridyl, imidazothioazolyl, and indazolyl; wherein said heteroaryl is independently unsubstituted, or mono-substituted; wherein the substituent is independently selected from the group consisting of $(C_{1-4})$alkyl, $(C_{1-4})$alkoxy, and —CO—$(C_{1-4})$alkyl.

42) A further embodiment relates to compounds of formulae (III) and (IV) according to any one of embodiments 26) to 41), wherein one or more of the following characteristics are present:

in case $Ar^4$ represents a 5-membered heteroaryl group, such group is a triazolyl (especially unsubstituted [1,2,3]triazol-2-yl), a pyrazolyl (especially unsubstituted pyrazol-1-yl, or unsubstituted 2H-pyrazol-3-yl), an oxazolyl (especially unsubstituted oxazol-2-yl), or an oxadiazolyl (especially 3-methyl-[1,2,4]oxadiazol-5-yl); [notably such group is unsubstituted [1,2,3]triazol-2-yl or unsubstituted pyrazol-1-yl]; and/or in case $Ar^4$ represents a 6-membered heteroaryl group, such group is a pyridinyl or a pyrimidinyl group (especially 6-methoxy-pyridin-3-yl, pyridin-2-yl, pyridin-3-yl, or pyrimidin-2-yl; notably unsubstituted pyridin-2-yl or unsubstituted pyrimidin-2-yl) and/or in case $Ar^4$ represents a phenyl group, such phenyl group is an unsubstituted or mono-substituted phenyl group wherein the substituent is selected from the group consisting of $(C_{1-4})$alkyl, $(C_{1-4})$alkoxy, and halogen (especially such group is phenyl, 3-methyl-phenyl, 2-fluorophenyl, 3-fluorophenyl, 4-fluorophenyl, 3-chlorophenyl, 3-methoxyphenyl; notably phenyl);

wherein said groups independently are unsubstituted or substituted as defined in any one of the preceeding embodiments, or as explicitly defined herein.

43) Another embodiment relates to compounds of formulae (III) and (IV) according to any one of embodiments 26) to 41), wherein
- $Ar^4$ is selected from the group consisting of unsubstituted triazolyl (especially [1,2,3]triazol-2-yl); unsubstituted pyrazolyl (especially pyrazol-1-yl, or 2H-pyrazol-3-yl); unsubstituted oxazolyl (especially oxazol-2-yl); oxadiazolyl mono-substituted with methyl (especially 3-methyl-[1,2,4]oxadiazol-5-yl); unsubstituted pyridyl (especially pyridin-2-yl); unsubstituted pyrimidinyl (especially pyrimidin-2-yl); and unsubstituted or mono-substituted phenyl wherein the substituent is selected from the group consisting of $(C_{1-4})$alkyl, $(C_{1-4})$alkoxy, and halogen (especially such phenyl group is phenyl, 3-methyl-phenyl, 2-fluorophenyl, 3-fluorophenyl, 4-fluorophenyl, 3-chlorophenyl, or 3-methoxyphenyl; notably phenyl); and
- $(R^x)_m$ represents one or two optional substituents (especially $(R^x)_m$ represents one or two substituents) independently selected from $(C_{1-4})$alkyl, $(C_{1-4})$alkoxy, halogen, cyano, $(C_{1-3})$fluoroalkyl, and $(C_{1-3})$fluoroalkoxy.

44) A further embodiment relates to compounds of formulae (III) and (IV) according to any one of embodiments 26) to 41), wherein
- $Ar^4$ represents a 5-membered heteroaryl group, selected from the group consisting of a triazolyl (especially unsubstituted [1,2,3]triazol-2-yl), a pyrazolyl (especially unsubstituted pyrazol-1-yl, or unsubstituted 2H-pyrazol-3-yl), an oxazolyl (especially unsubstituted oxazol-2-yl), and an oxadiazolyl group (especially 3-methyl-[1,2,4]oxadiazol-5-yl); [notably $Ar^4$ represents unsubstituted [1,2,3]triazol-2-yl or unsubstituted pyrazol-1-yl]; wherein said groups independently are unsubstituted or substituted as defined in any one of the preceeding embodiments, or as explicitly defined herein; and
- $(R^x)_m$ represents one or two optional substituents (especially $(R^x)_m$ represents one or two substituents) independently selected from $(C_{1-4})$alkyl, $(C_{1-4})$alkoxy, halogen, cyano, $(C_{1-3})$fluoroalkyl, and $(C_{1-3})$fluoroalkoxy (in particular: methyl, methoxy, fluoro, chloro, cyano, trifluoromethyl, and trifluoromethoxy).

45) Another embodiment relates to compounds of formulae (III) and (IV) according to any one of embodiments 26) to 41), wherein
- $Ar^4$ represents unsubstituted triazolyl (especially unsubstituted [1,2,3]triazol-2-yl); or unsubstituted pyrimidinyl (especially unsubstituted pyrimidin-2-yl); and
- $(R^x)_m$ represents one or two substituents independently selected from $(C_{1-4})$alkyl, $(C_{1-4})$alkoxy, halogen, cyano, $(C_{1-3})$fluoroalkyl, and $(C_{1-3})$fluoroalkoxy (in particular: methyl, methoxy, fluoro, chloro, cyano, trifluoromethyl, and trifluoromethoxy).

46) A further embodiment relates to compounds of formulae (III) and (IV) according to any one of embodiments 26) to 41), wherein
- $Ar^4$ represents unsubstituted [1,2,3]triazol-2-yl; and
- $(R^x)_m$ represents one or two substituents independently selected from $(C_{1-4})$alkyl, $(C_{1-4})$alkoxy, halogen, cyano, $(C_{1-3})$fluoroalkyl, and $(C_{1-3})$fluoroalkoxy (in particular: methyl, methoxy, fluoro, chloro, cyano, trifluoromethyl, and trifluoromethoxy).

47) A further embodiment relates to compounds of formulae (I), (II), (III), or (IV) according to any one of embodiments 1) to 41), wherein
i): the ring $A_1$,
ii): respectively, the ring $A'_1$,
iii): respectively, (mutatis mutandis) the group

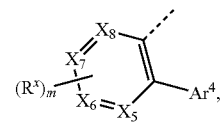

and iv): respectively, (mutatis mutandis) the group

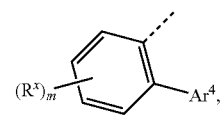

is a group independently selected from one, or more (in any combination), or all of the following groups A) to C) [i.e. the group iii) being selected from groups A) or B); the group iv) being selected from groups A)]:

A) substituted phenyl groups selected from the groups:

A1)

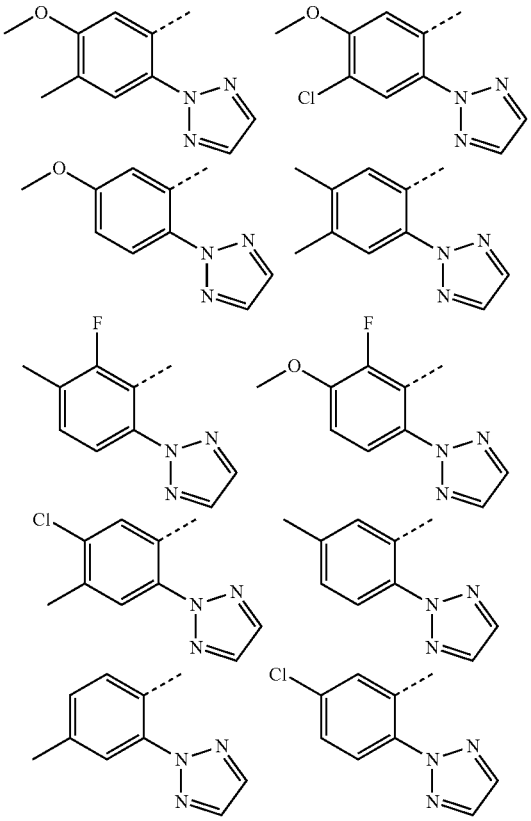

A2)
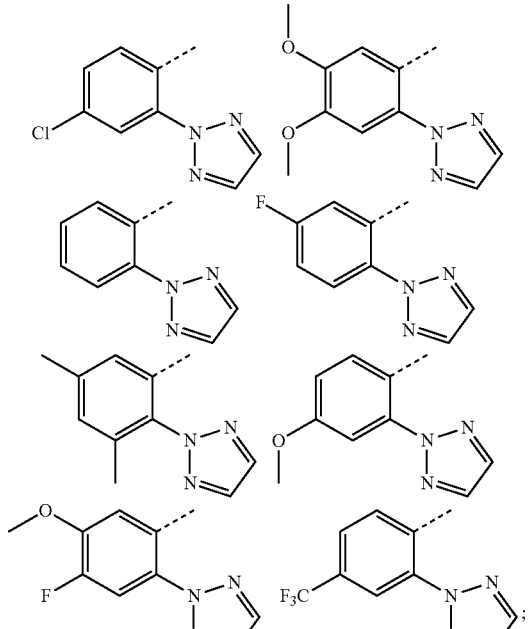
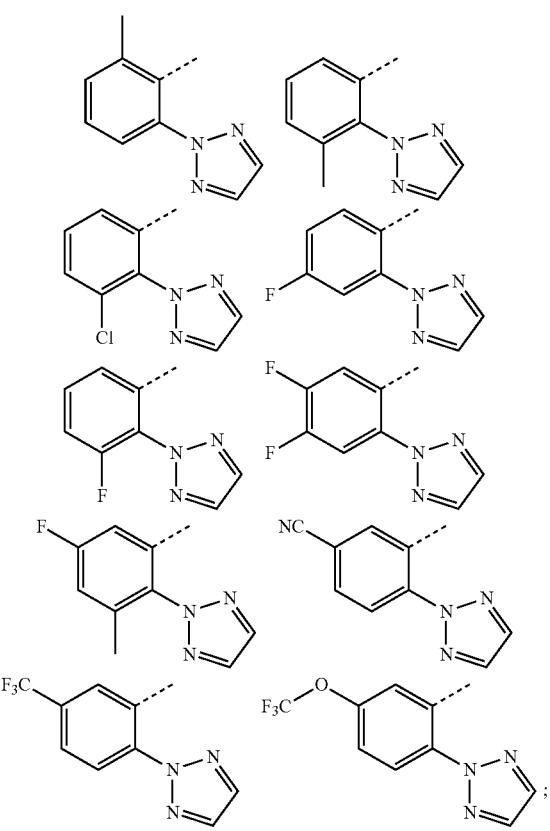
A3)
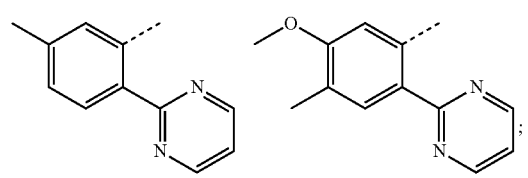
A4)
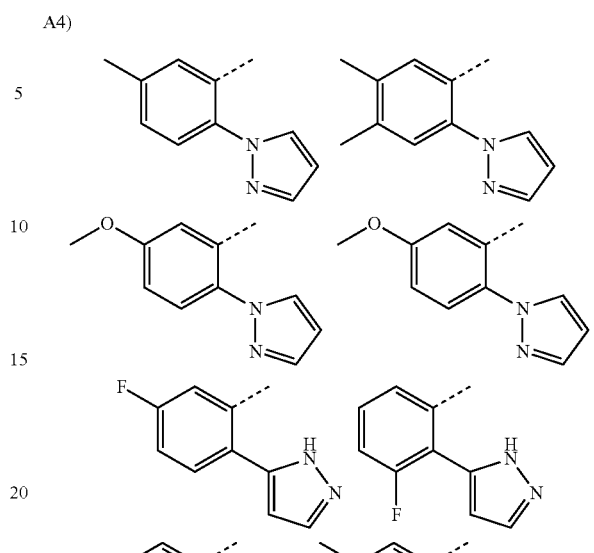
A5)
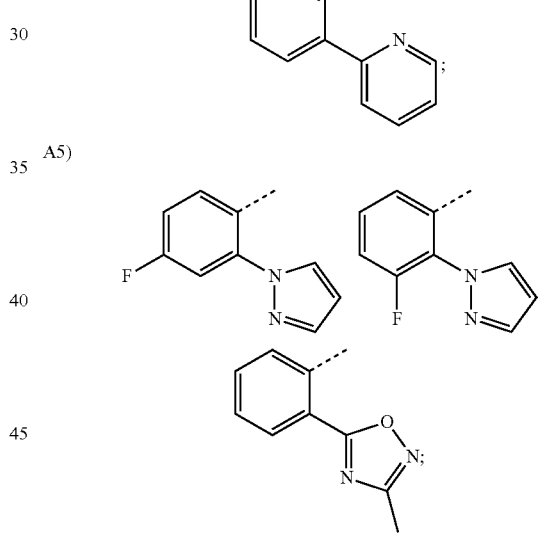
A6)
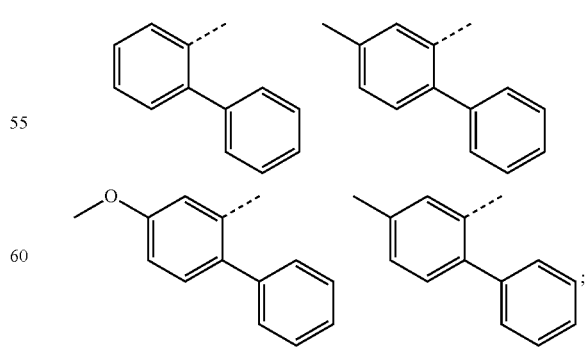
B) substituted 6-membered heteroaryl groups selected from the groups:

B1)
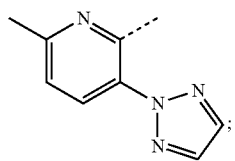

B2)
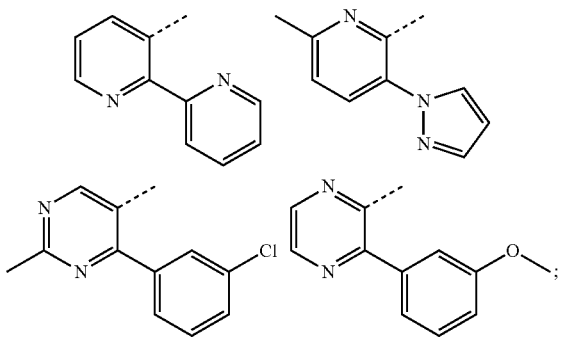

C) substituted 5-membered heteroaryl groups selected from the groups:

C1)
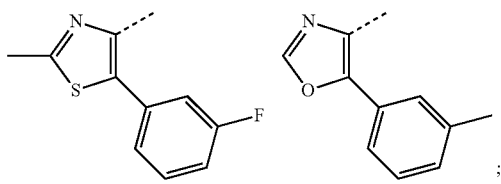

C2)
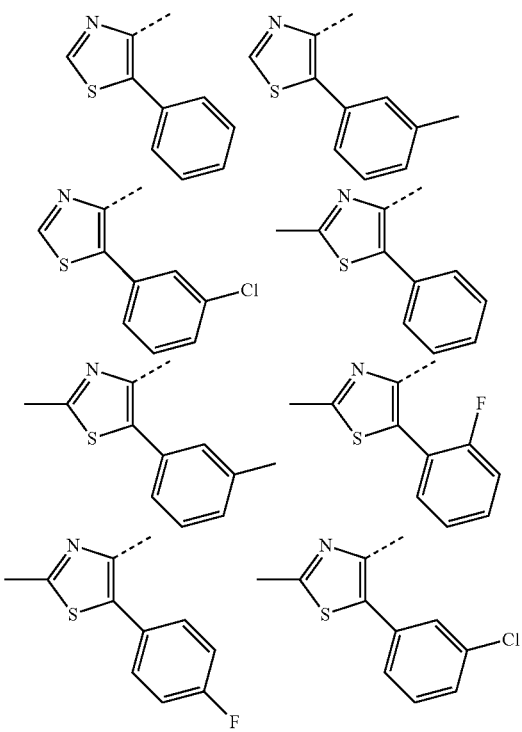

-continued
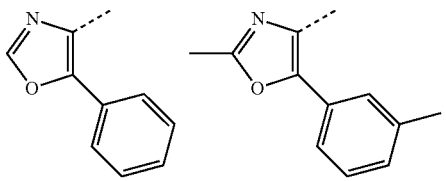

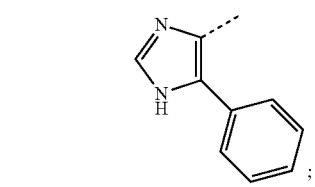

wherein each of the groups A) to C) and their respective subgroups [especially group A1)] forms a particular sub-embodiment.

48) A further embodiment relates to compounds of formula (IV) according to any one of embodiments 27) to 41), wherein the group

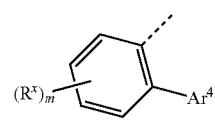

is a group independently selected from one, or more (in any combination), or all of the following groups A), B), C) and/or D):

A)
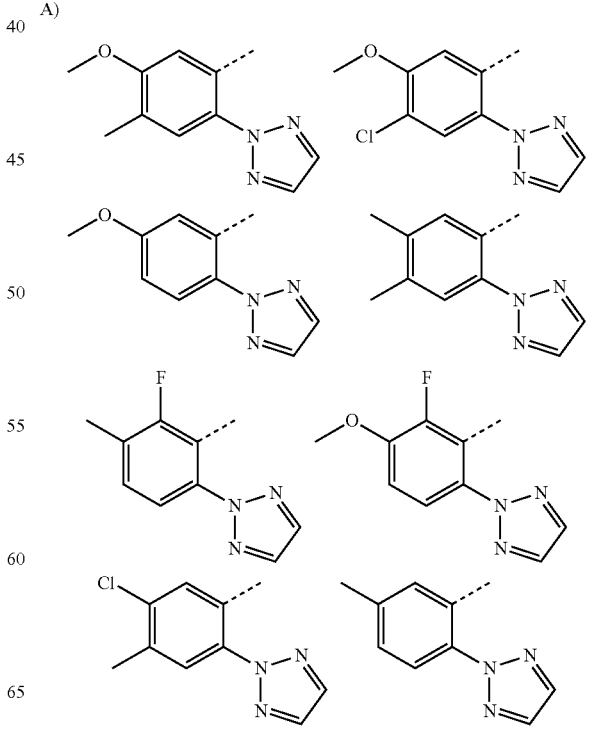

-continued

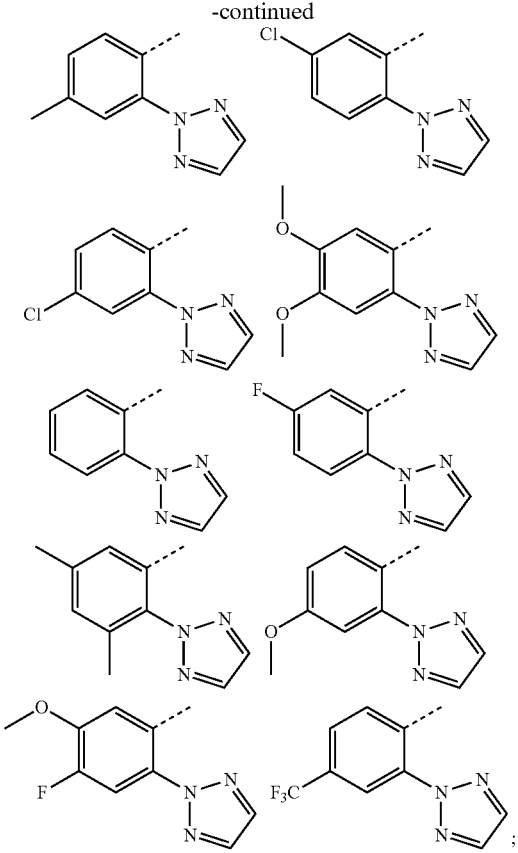

B)

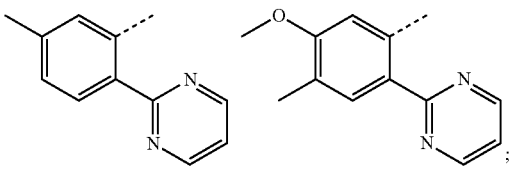

C)

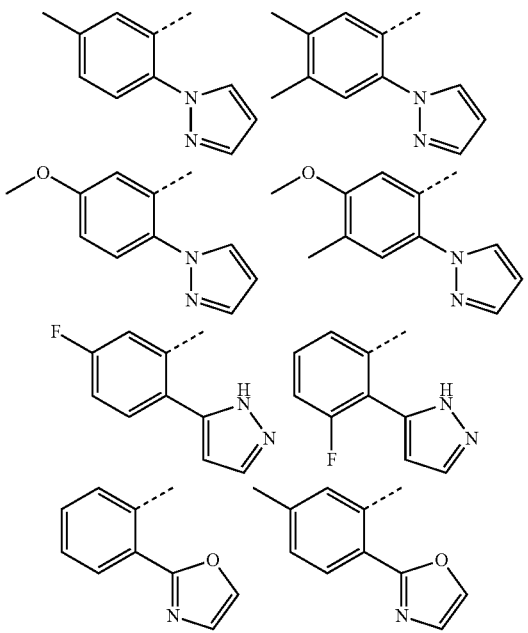

-continued

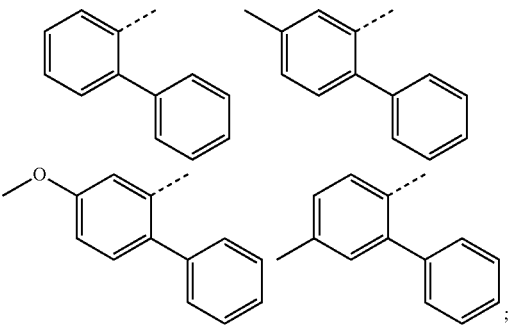

D)

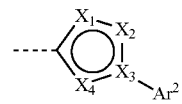

wherein each of the groups A), B), C) and D) forms a particular sub-embodiment [and said group is especially selected from groups A) and B); notably from A1)].

49) A further embodiment relates to compounds of formulae (I), (II), (III), or (IV) according to any one of embodiments 1) to 48), wherein i): the group $A_3$-$A_2$, ii): respectively, the group $A'_3$-$A'_2$, iii): and, respectively, the group

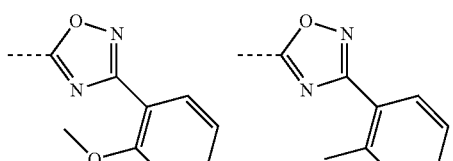

represents a group independently selected from one, or more (in any combination), or all of the following groups A) to H) [especially from A) and/or B); and/or from F)]:

A): [1,2,4]oxadiazol-3,5-diyl groups selected from the groups:

A1)

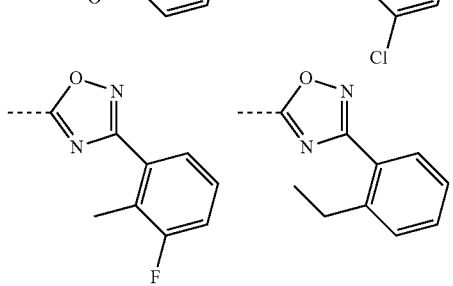

-continued
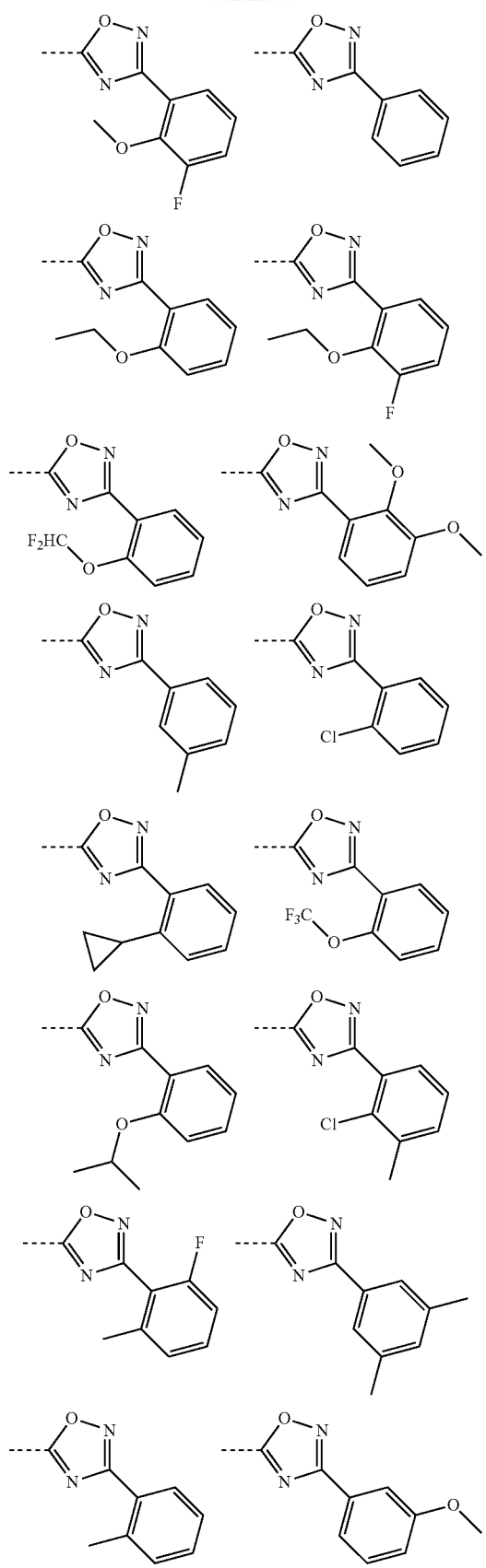
-continued
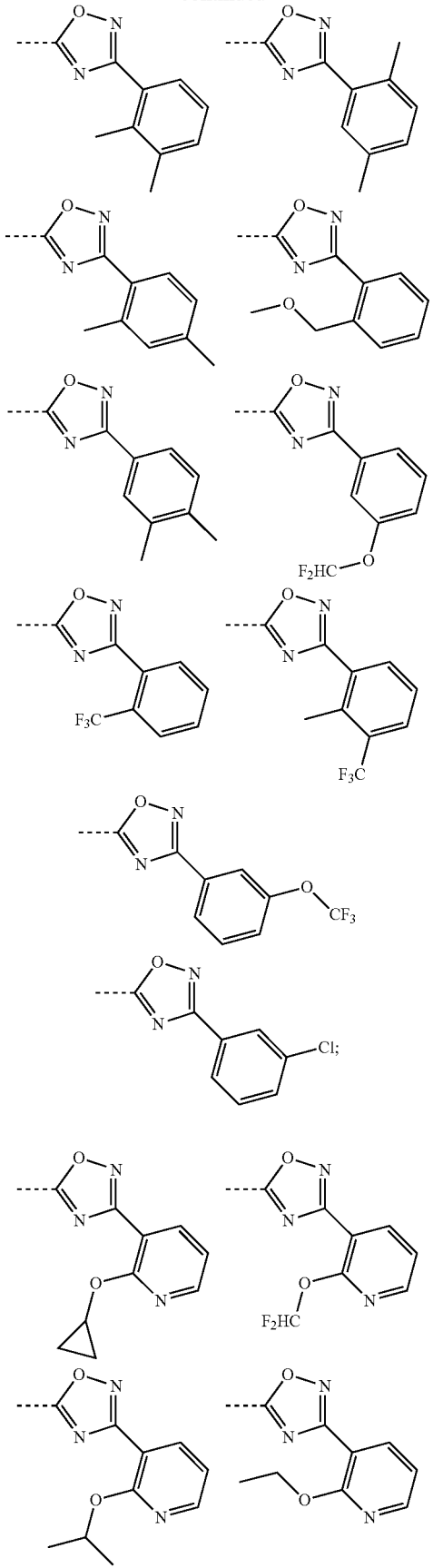
A2)

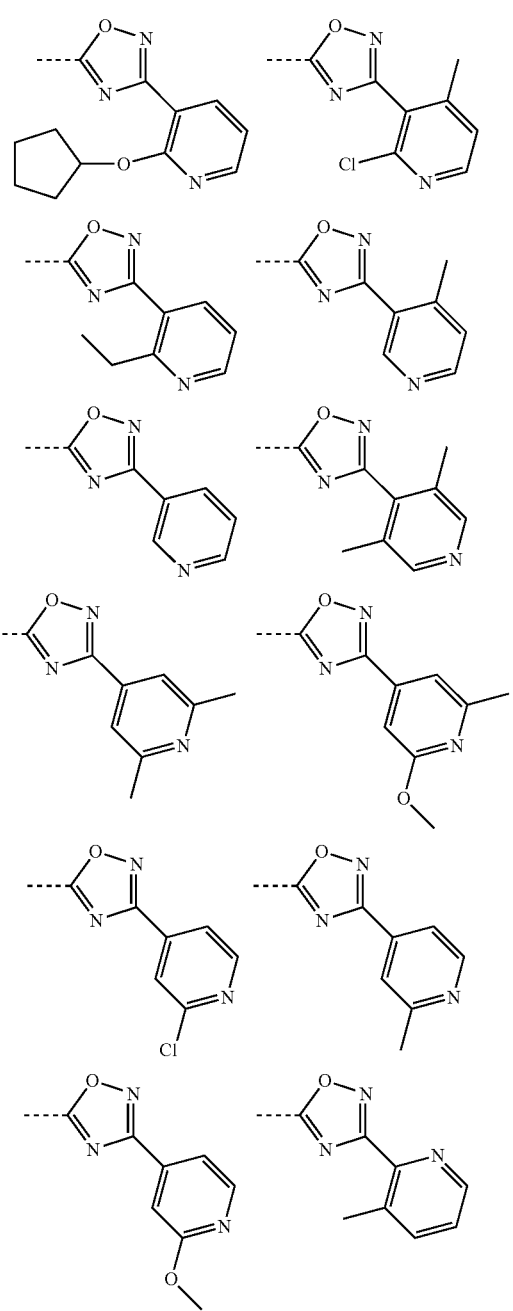
A3)
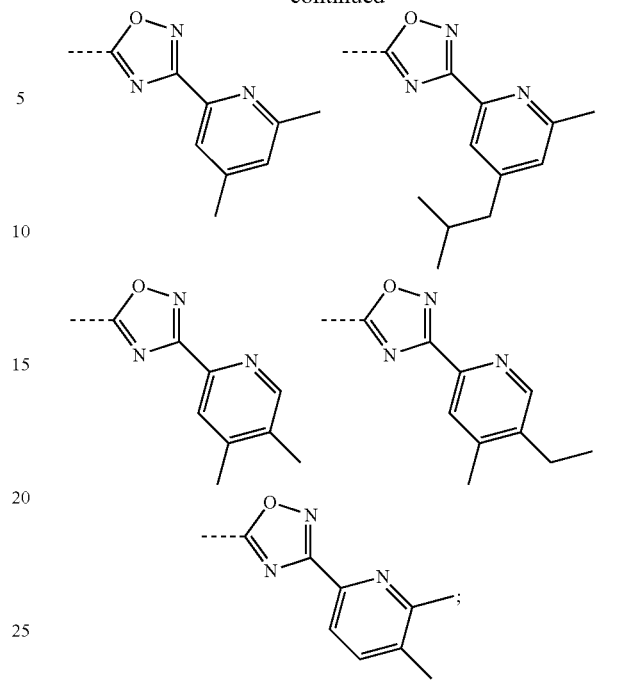
A4)
A5)
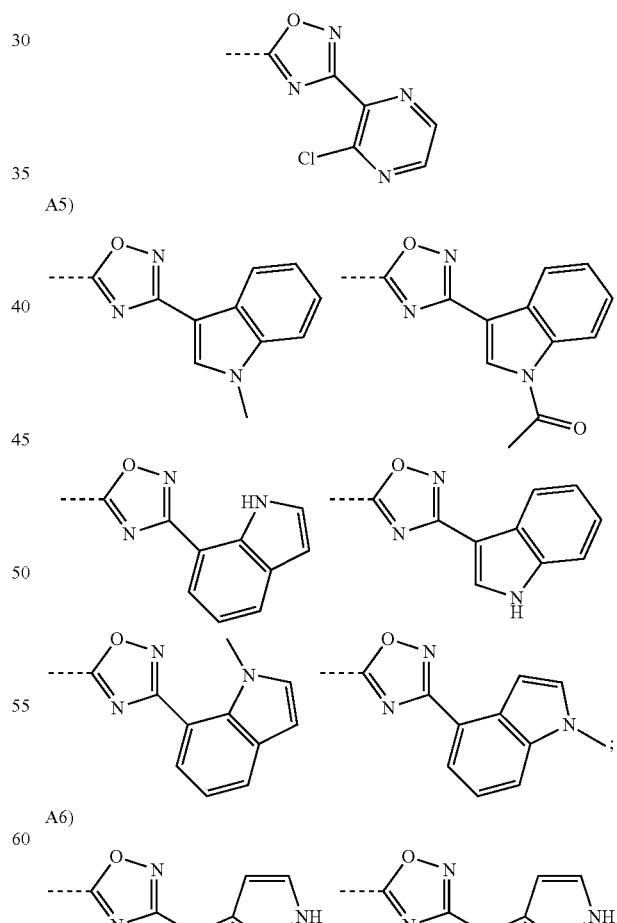
A6)
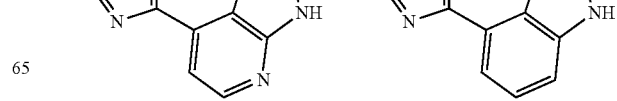

-continued
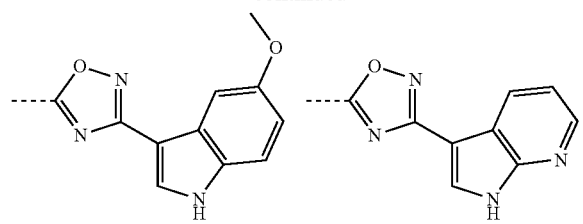
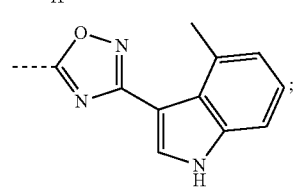
A7)
A8)
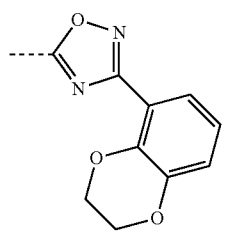
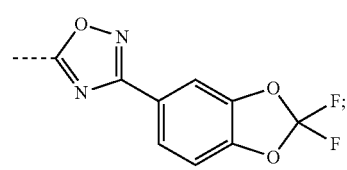
B): [1,2,4]oxadiazol-3,5-diyl groups selected from the groups:
B1)
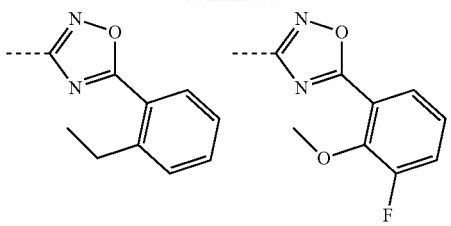
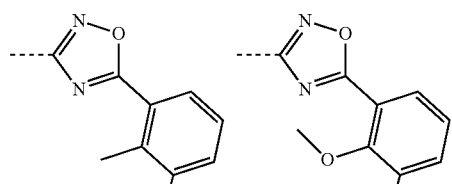
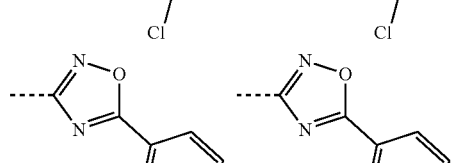
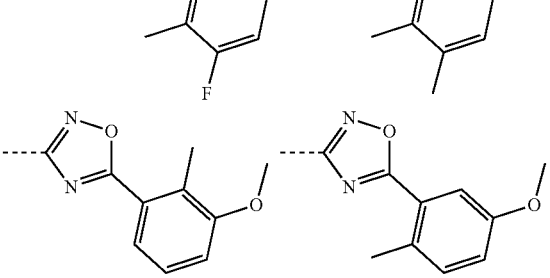
-continued
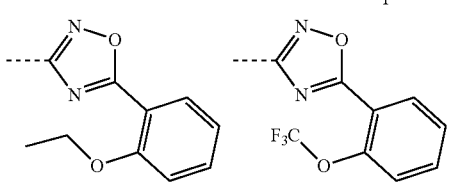
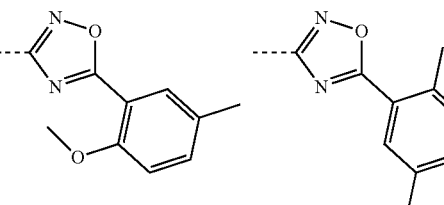
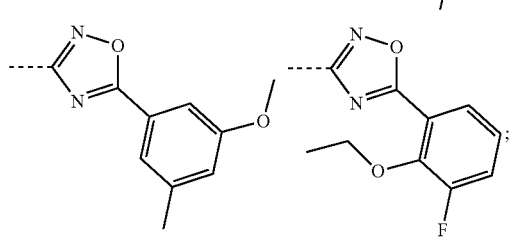
B2)
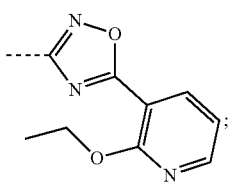
B3)
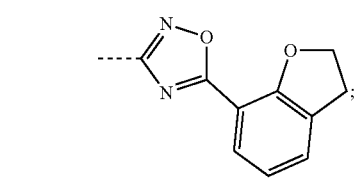
C): oxazol-2,4-diyl groups selected from:
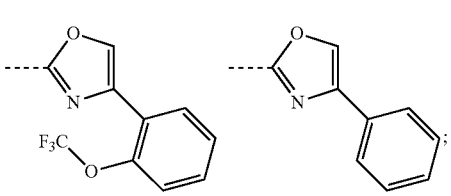

D): oxazol-2,5-diyl groups selected from:
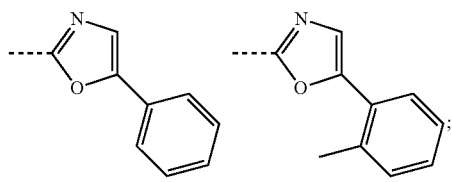
E): isoxazol-3,5-diyl groups selected from the groups:
E1)
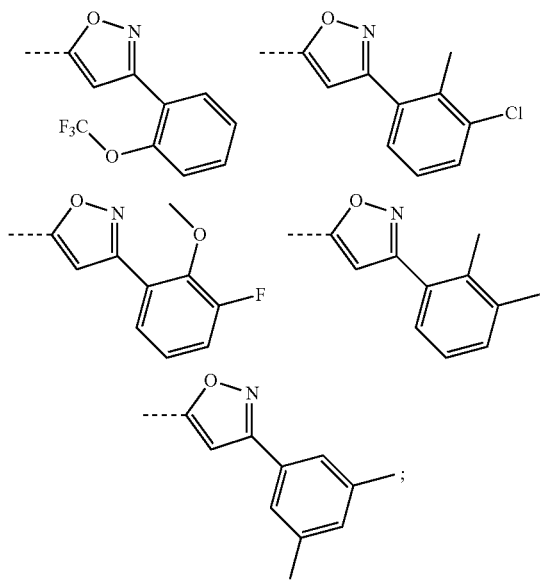
E2)
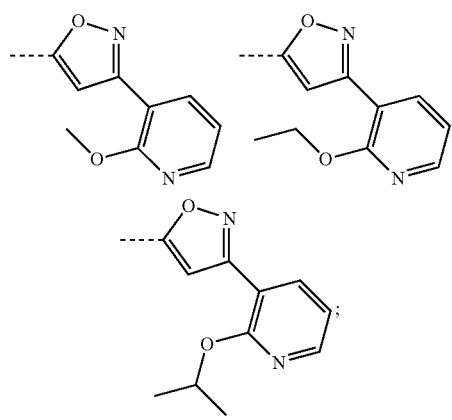
E3)
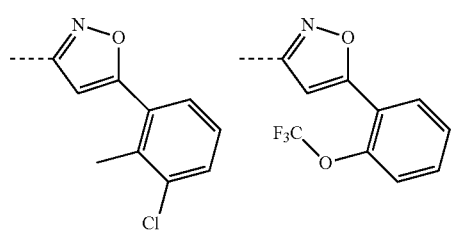
-continued
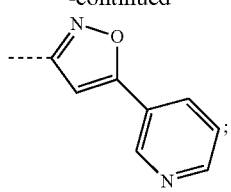
F): [1,2,4]triazol-3,5-diyl groups selected from the groups:
F1)
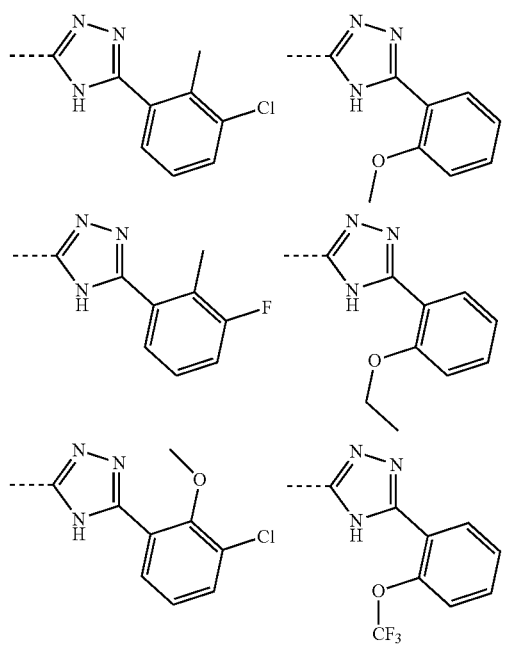
F2)
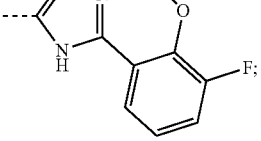
F3)
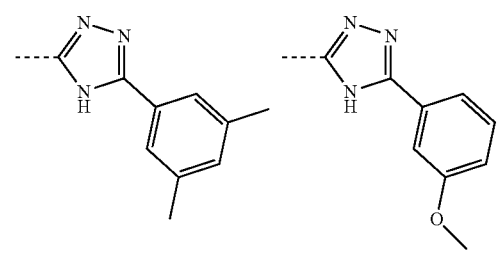

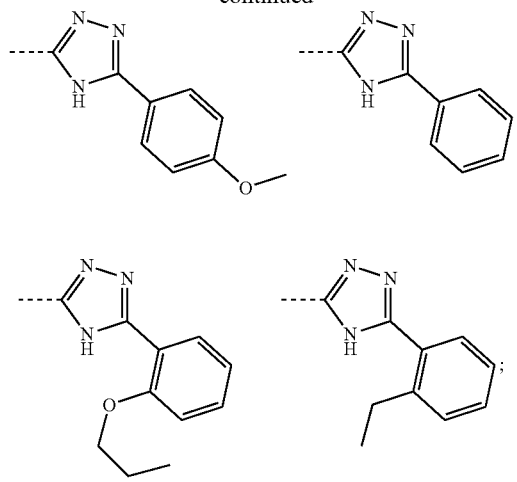

G): imidazol-2,4-diyl groups selected from the groups:

G1)

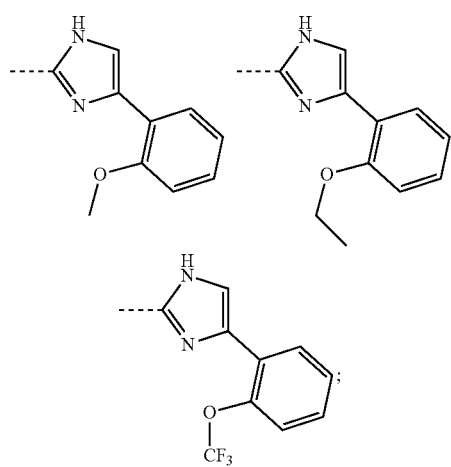

G2)

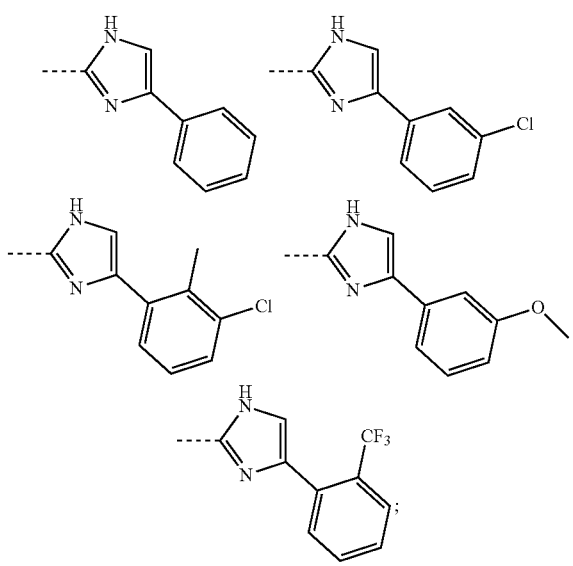

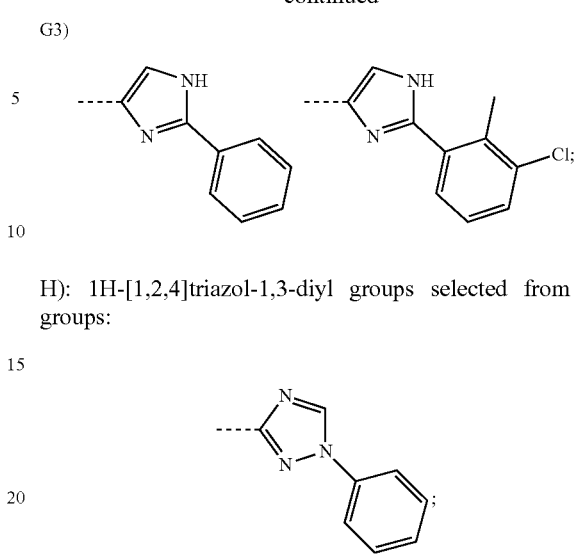

G3)

H): 1H-[1,2,4]triazol-1,3-diyl groups selected from the groups:

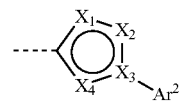

wherein each of the groups A) to H) [notably the groups A) and B)] and their respective subgroups [notably the subgroups A1) and B1)] forms a particular sub-embodiment.

50) A further embodiment relates to compounds of formulae (I), (II), (III), or (IV) according to any one of embodiments 1) to 48), wherein i): the group $A_3$-$A_2$, ii): respectively, the group $A'_3$-$A'_2$, iii): and, respectively, the group

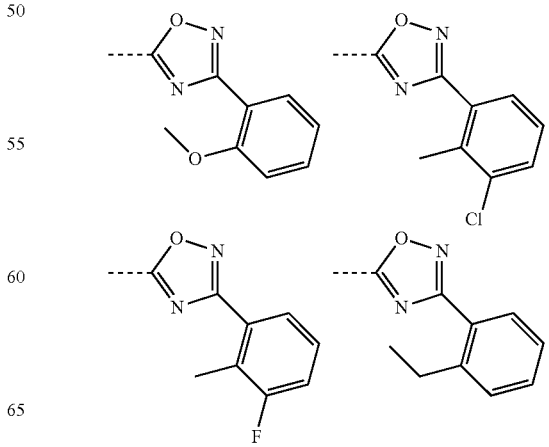

represents a group independently selected from one, or more (in any combination), or all of the following groups A) to E):

A): [1,2,4]oxadiazol-3,5-diyl groups selected from the groups:

A1)

-continued
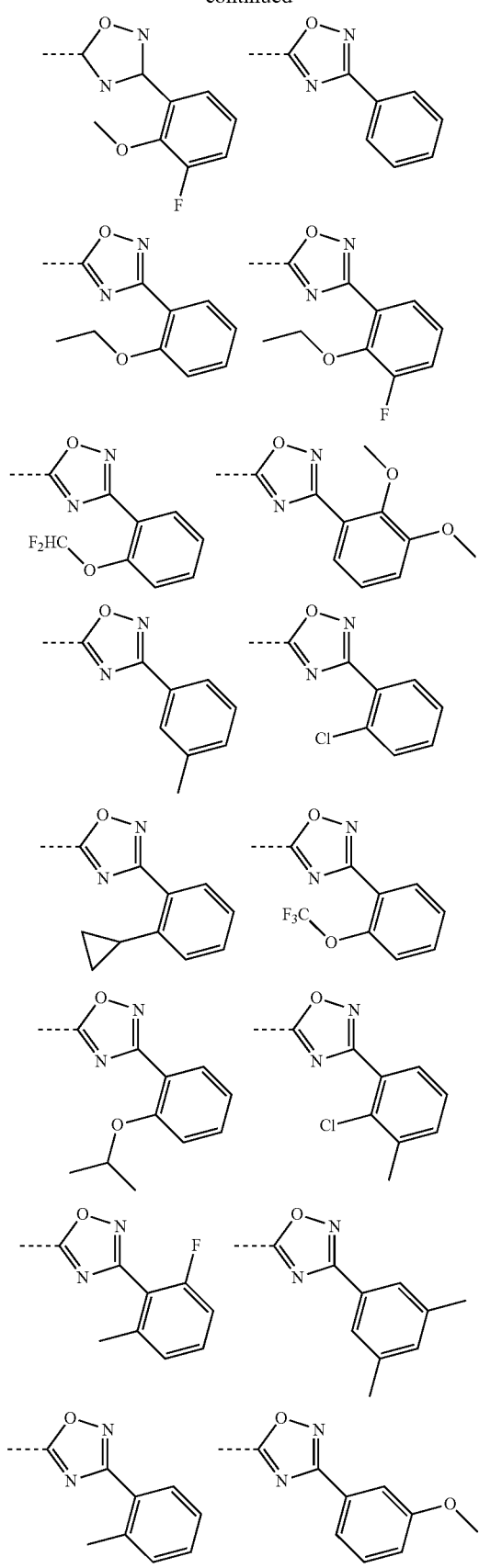
-continued
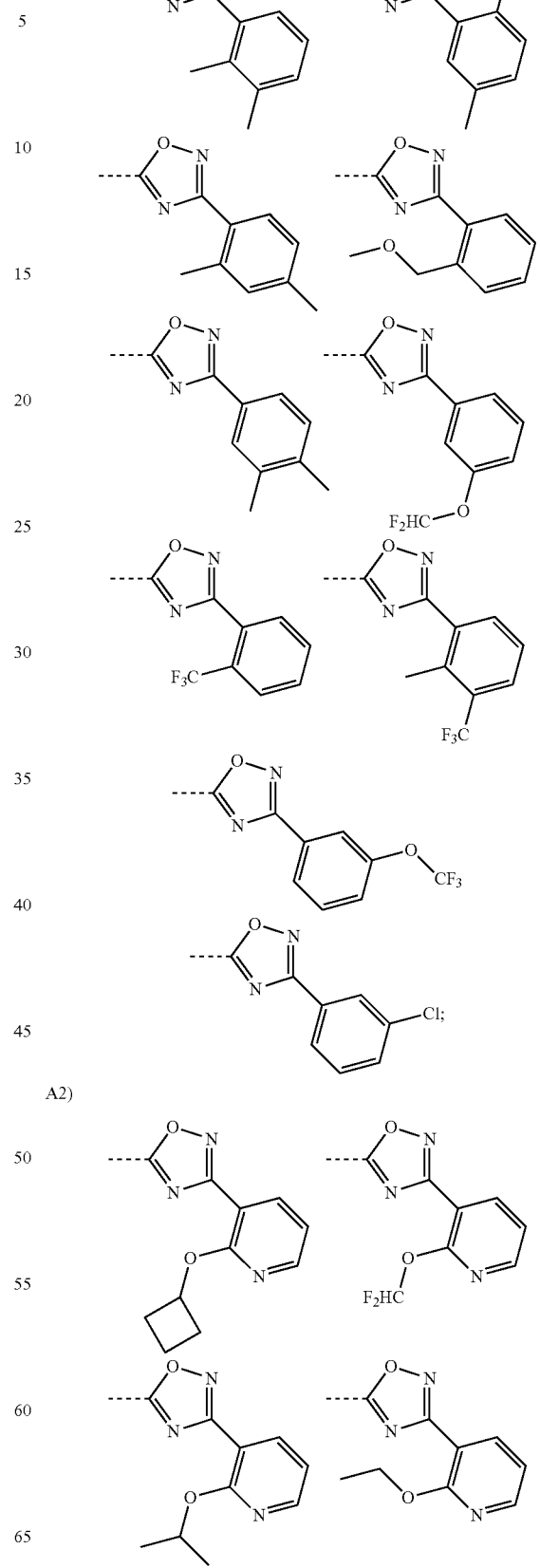
A2)

-continued
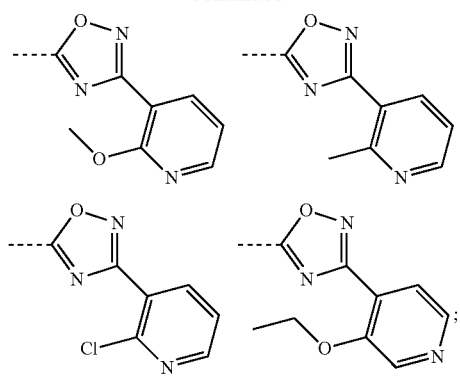
A3)
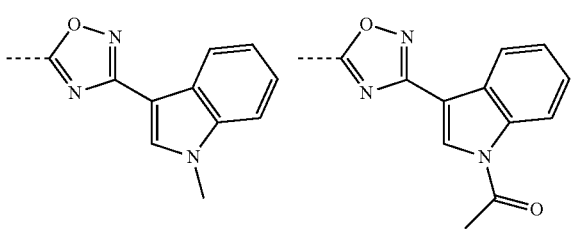
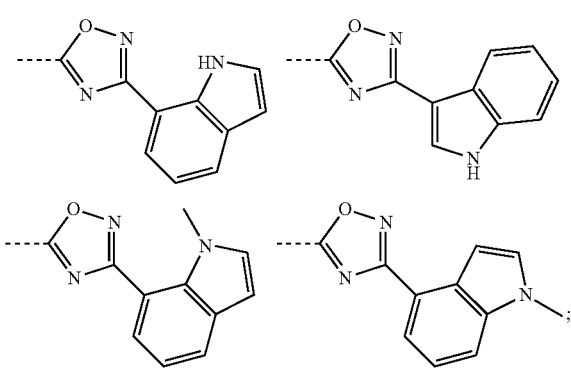
A4)
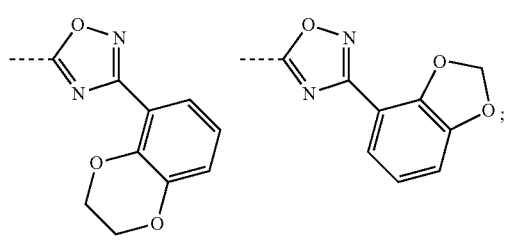
B): [1,2,4]oxadiazol-3,5-diyl groups selected from the groups:
B1)
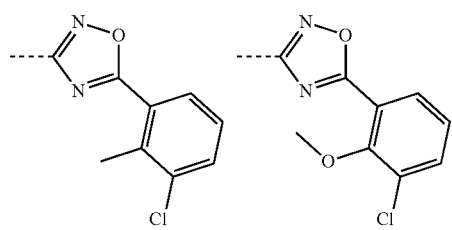
-continued
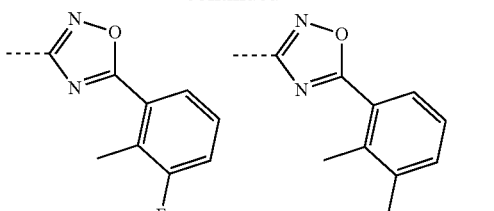
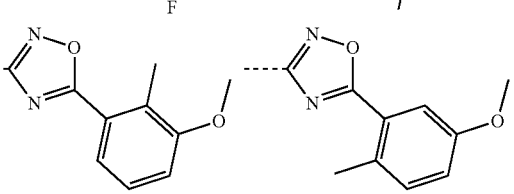
B2)
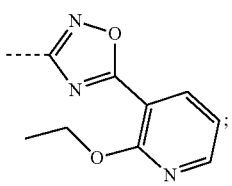
B3)
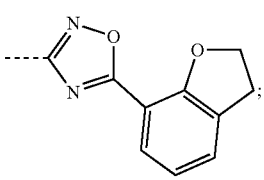

C): isoxazol-3,5-diyl groups selected from the groups:

C1)

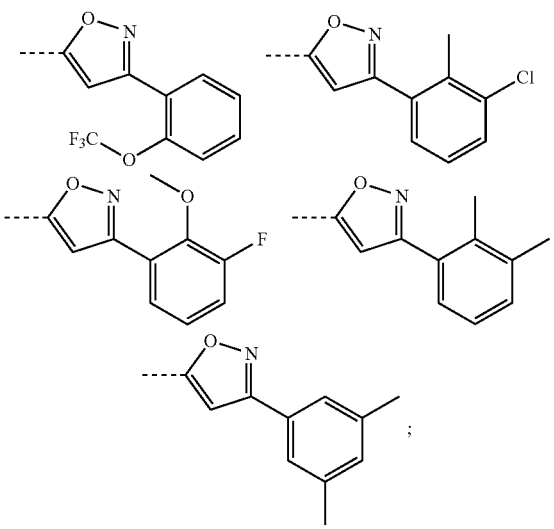

C2)

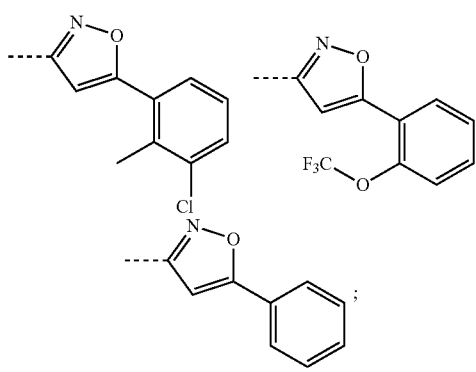

D): [1,2,4]triazol-3,5-diyl groups selected from the groups:

D1)

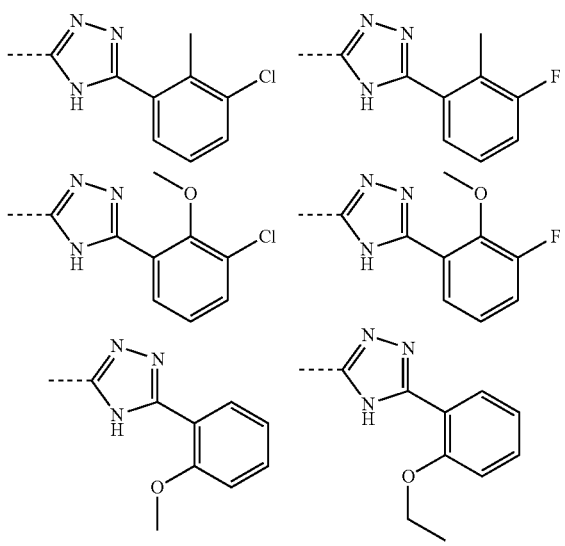

-continued

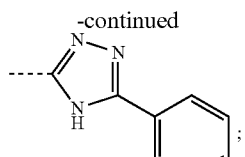

D2)

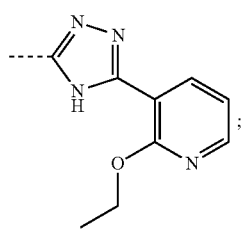

E): imidazol-2,4-diyl groups selected from the groups:

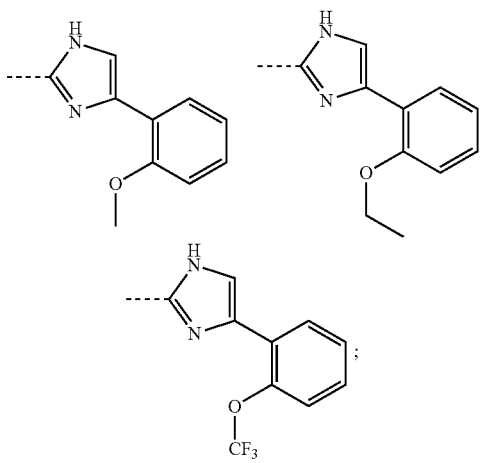

wherein each of the groups A) to E) and their respective subgroups forms a particular sub-embodiment [and said groups are especially selected from groups A), B), C), and D); notably from the groups A) and B); in particular from A1) and B1)].

51) The invention, thus, relates to compounds of the formula (I) as defined in embodiment 1), compounds of the formula (II) as defined in embodiment 9), compounds of the formula (III) as defined in embodiment 26), compounds of the formula (IV) as defined in embodiment 27); or to such compounds further limited by the characteristics of any one of embodiments 2) to 50), under consideration of their respective dependencies; to pharmaceutically acceptable salts thereof; and to the use of such compounds as medicaments especially in the treatment of mental health disorders relating to orexinergic dysfunctions, which disorders are as defined below and which are especially selected from sleep disorders, anxiety disorders, addiction disorders, cognitive dysfunctions, mood disorders, or appetite disorders. Especially the following embodiments relating to the compounds of formulae (I), (II), (III), and (IV) are thus possible and intended and herewith specifically disclosed in individualized form:

1, 4+1, 6+1, 17+1, 17+4+1, 17+6+1, 18+1, 18+4+1, 18+6+1, 19+1, 19+4+1, 19+6+1, 19+17+1, 19+17+4+1, 19+17+6+1,

19+18+1, 19+18+4+1, 19+18+6+1, 20+1, 20+4+1, 20+6+1, 20+17+1, 20+17+4+1, 20+17+6+1, 20+18+1, 20+18+4+1, 20+18+6+1, 20+19+1, 20+19+4+1, 20+19+6+1, 20+19+17+1, 20+19+17+4+1, 20+19+17+6+1, 20+19+18+1, 20+19+18+4+1, 20+19+18+6+1, 24+1, 24+4+1, 24+6+1, 25+24+1, 25+24+4+1, 25+24+6+1, 40+1, 40+4+1, 40+6+1, 40+17+1, 40+17+4+1, 40+17+6+1, 40+18+1, 40+18+4+1, 40+18+6+1, 40+19+1, 40+19+4+1, 40+19+6+1, 40+19+17+1, 40+19+17+4+1, 40+19+17+6+1, 40+19+18+1, 40+19+18+4+1, 40+19+18+6+1, 40+20+1, 40+20+4+1, 40+20+6+1, 40+20+17+1, 40+20+17+4+1, 40+20+17+6+1, 40+20+18+1, 40+20+18+4+1, 40+20+18+6+1, 40+20+19+1, 40+20+19+4+1, 40+20+19+6+1, 40+20+19+17+1, 40+20+19+17+4+1, 40+20+19+17+6+1, 40+20+19+18+1, 40+20+19+18+4+1, 40+20+19+18+6+1, 41+1, 41+4+1, 41+6+1, 41+17+1, 41+17+4+1, 41+17+6+1, 41+18+1, 41+18+4+1, 41+18+6+1, 41+19+1, 41+19+4+1, 41+19+6+1, 41+19+17+1, 41+19+17+4+1, 41+19+17+6+1, 41+19+18+1, 41+19+18+4+1, 41+19+18+6+1, 41+20+1, 41+20+4+1, 41+20+6+1, 41+20+17+1, 41+20+17+4+1, 41+20+17+6+1, 41+20+18+1, 41+20+18+4+1, 41+20+18+6+1, 41+20+19+1, 41+20+19+4+1, 41+20+19+6+1, 41+20+19+17+1, 41+20+19+17+4+1, 41+20+19+17+6+1, 41+20+19+18+1, 41+20+19+18+4+1, 41+20+19+18+6+1; 47+1, 47+4+1, 47+6+1, 47+40+1, 47+41+1, 47+40+4+1, 47+40+6+1, 47+41+4+1, 47+41+6+1;

9, 13+9, 14+9, 17+9, 17+13+9, 17+14+9, 17+40+9, 17+40+13+9, 17+40+14+9, 17+41+9, 17+41+13+9, 17+41+14+9, 17+49+9, 18+9, 18+13+9, 18+14+9, 18+40+9, 18+40+13+9, 18+40+14+9, 18+41+9, 18+41+13+9, 18+41+14+9, 18+49+9, 19+9, 19+13+9, 19+14+9, 19+17+9, 19+17+13+9, 19+17+14+9, 19+17+40+9, 19+17+40+13+9, 19+17+40+14+9, 19+17+41+9, 19+17+41+13+9, 19+17+41+14+9, 19+17+49+9, 19+18+9, 19+18+13+9, 19+18+14+9, 19+18+40+9, 19+18+40+13+9, 19+18+40+14+9, 19+18+41+9, 19+18+41+13+9, 19+18+41+14+9, 19+18+49+9, 19+40+9, 19+40+13+9, 19+40+14+9, 19+41+9, 19+41+13+9, 19+41+14+9, 19+49+9, 20+9, 20+13+9, 20+14+9, 20+17+9, 20+17+13+9, 20+17+14+9, 20+17+40+9, 20+17+40+13+9, 20+17+40+14+9, 20+17+41+9, 20+17+41+13+9, 20+17+41+14+9, 20+17+49+9, 20+18+9, 20+18+13+9, 20+18+14+9, 20+18+40+9, 20+18+40+13+9, 20+18+40+14+9, 20+18+41+9, 20+18+41+13+9, 20+18+41+14+9, 20+18+49+9, 20+19+9, 20+19+13+9, 20+19+14+9, 20+19+17+9, 20+19+17+13+9, 20+19+17+14+9, 20+19+17+40+9, 20+19+17+40+13+9, 20+19+17+40+14+9, 20+19+17+41+9, 20+19+17+41+13+9, 20+19+17+41+14+9, 20+19+17+49+9, 20+19+18+9, 20+19+18+13+9, 20+19+18+14+9, 20+19+18+40+9, 20+19+18+40+13+9, 20+19+18+40+14+9, 20+19+18+41+9, 20+19+18+41+13+9, 20+19+18+41+14+9, 20+19+18+49+9, 20+19+40+9, 20+19+40+13+9, 20+19+40+14+9, 20+19+41+9, 20+19+41+13+9, 20+19+41+14+9, 20+19+49+9, 20+40+9, 20+40+13+9, 20+40+14+9, 20+41+9, 20+41+13+9, 20+41+14+9, 20+49+9, 24+9, 24+13+9, 24+14+9, 24+40+9, 24+40+13+9, 24+40+14+9, 24+41+9, 24+41+13+9, 24+41+14+9, 24+49+9, 25+24+9, 25+24+13+9, 25+24+14+9, 25+24+40+9, 25+24+40+13+9, 25+24+40+14+9, 25+24+41+9, 25+24+41+13+9, 25+24+41+14+9, 25+24+49+9, 40+9, 40+13+9, 40+14+9, 41+9, 41+13+9, 41+14+9, 49+9, 49+17+9, 49+18+9, 49+17+19+9, 49+18+19+9, 49+17+20+9, 49+18+20+9, 49+17+19+20+9, 49+18+19+20+9, 49+24+9, 49+25+24+9, 49+47+9;

27, 28+27, 30+27, 32+27, 34+27, 35+27, 36+27, 40+27, 40+28+27, 40+30+27, 40+32+27, 40+34+27, 40+35+27, 40+36+27, 41+27, 41+28+27, 41+30+27, 41+32+27, 41+34+27, 41+35+27, 41+36+27, 42+27, 42+28+27, 42+30+27, 42+32+27, 42+34+27, 42+35+27, 42+36+27, 42+40+27, 42+40+28+27, 42+40+30+27, 42+40+32+27, 42+40+34+27, 42+40+35+27, 42+40+36+27, 42+41+27, 42+41+28+27, 42+41+30+27, 42+41+32+27, 42+41+34+27, 42+41+35+27, 42+41+36+27, 43+27, 43+28+27, 43+30+27, 43+32+27, 43+34+27, 43+35+27, 43+36+27, 43+40+27, 43+40+28+27, 43+40+30+27, 43+40+32+27, 43+40+34+27, 43+40+35+27, 43+40+36+27, 43+41+27, 43+41+28+27, 43+41+30+27, 43+41+32+27, 43+41+34+27, 43+41+35+27, 43+41+36+27, 46+27, 46+28+27, 46+30+27, 46+32+27, 46+34+27, 46+36+27, 46+37+27, 46+40+27, 46+40+28+27, 46+40+30+27, 46+40+32+27, 46+40+34+27, 46+40+35+27, 46+40+36+27, 46+41+27, 46+41+28+27, 46+41+30+27, 46+41+32+27, 46+41+34+27, 46+41+35+27, 46+41+36+27, 47+27, 47+28+27, 47+30+27, 47+32+27, 47+33+27, 47+34+27, 47+35+27, 47+35+27, 47+36+27, 47+40+27, 47+40+28+27, 47+40+30+27, 47+40+32+27, 47+40+34+27, 47+40+35+27, 47+40+36+27, 47+41+27, 47+41+28+27, 47+41+30+27, 47+41+32+27, 47+41+34+27, 47+41+35+27, 47+41+36+27, 48+27, 48+28+27, 48+30+27, 48+32+27, 48+33+27, 48+34+27, 48+35+27, 48+36+27, 48+40+27, 48+40+28+27, 48+40+30+27, 48+40+32+27, 48+40+34+27, 48+40+35+27, 48+40+36+27, 48+41+27, 48+41+28+27, 48+41+30+27, 48+41+32+27, 48+41+34+27, 48+41+35+27, 48+41+36+27, 49+27, 49+42+27, 49+43+27, 49+44+27, 49+45+27, 49+46+27, 49+47+27, 49+48+27, 50+27, 50+42+27, 50+43+27, 50+44+27, 50+45+27, 50+46+27, 50+47+27, 50+48+27.

In the list above, the numbers refer to the embodiments according to their numbering provided hereinabove whereas "+" indicates the dependency from another embodiment. The different individualized embodiments are separated by commas. In other words, "41+28+27" for example refers to embodiment 41) depending on embodiment 28), depending on embodiment 27), i.e. embodiment "41+28+27" corresponds to the compounds of embodiment 27) further limited by the features of the embodiments 28) and 41).

52) A further aspect of the invention relates to compounds of the formula (I) according to embodiment 1), which are also compounds of the compounds of the formula (V); wherein the absolute configuration is as depicted in formula (V):

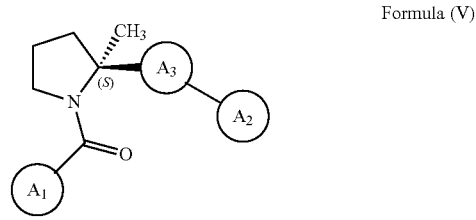

Formula (V)

wherein the carbon atom at position 2 of the pyrrolidine ring is in absolute (S)-configuration;

ring $A_3$ represents a meta di-substituted 5-membered heteroarylene ring containing one, two or three heteroatoms; wherein at least one of said heteroatoms is nitrogen, and the remaining is/are independently selected from oxygen, sulfur and nitrogen; [wherein it is understood that the two meta-arranged substituents are the pyrrolidine-2-yl group and the substituent $A_2$; and that the ring $A_3$ does not carry any further substituent];

ring $A_2$ represents aryl or 5- to 10-membered heteroaryl; wherein said aryl or 5- to 10-membered heteroaryl is independently unsubstituted, or mono-, di-, or tri-substituted;

wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, hydroxy, $(C_{1-4})$alkoxy-$(C_{1-3})$alkyl, hydroxy-$(C_{1-3})$alkyl, —CO—$(C_{1-4})$alkyl, and $(C_{3-6})$cycloalkyl-oxy-; or ring $A_2$ represents a 2,3-dihydro-benzo[1,4]dioxinyl, a 2,3-dihydro-benzofuranyl, or a benzo[1,3]dioxolyl group optionally di-substituted with fluoro; and ring $A_1$ represents phenyl or 5- or 6-membered heteroaryl, wherein said phenyl or 5- or 6-membered heteroaryl independently is mono-, di-, or tri-substituted; wherein
one of said substituents is attached in ortho-position to the point of attachment of $A_1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
and the other of said substituents, if present, is/are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
provided that ring $A_1$ is not isoxazol-4-yl, substituted in position 5 with $(C_{1-4})$alkyl, attached to the rest of the molecule at position 4, and carrying said further ortho-substitutent in position 3;

wherein the characteristics disclosed in embodiments 2) to 50) above are intended to apply mutatis mutandis also to the compounds formula (V) according to embodiment 52); wherein especially the following embodiments are thus possible and intended and herewith specifically disclosed in individualized form: 52, 4+52, 6+52, 17+52, 17+4+52, 17+6+52, 18+52, 18+4+52, 18+6+52, 19+52, 19+4+52, 19+6+52, 19+17+52, 19+17+4+52, 19+17+6+52, 19+18+52, 19+18+4+52, 19+18+6+52, 20+52, 20+4+52, 20+6+52, 20+17+52, 20+17+4+52, 20+17+6+52, 20+18+52, 20+18+4+52, 20+18+6+52, 20+19+52, 20+19+4+52, 20+19+6+52, 20+19+17+52, 20+19+17+4+52, 20+19+17+6+52, 20+19+18+52, 20+19+18+4+52, 20+19+18+6+52, 24+52, 24+4+52, 24+6+52, 25+24+52, 25+24+4+52, 25+24+6+52, 40+52, 40+4+52, 40+6+52, 40+17+52, 40+17+4+52, 40+17+6+52, 40+18+52, 40+18+4+52, 40+18+6+52, 40+19+52, 40+19+4+52, 40+19+6+52, 40+19+17+52, 40+19+17+4+52, 40+19+17+6+52, 40+19+18+52, 40+19+18+4+52, 40+19+18+6+52, 40+20+52, 40+20+4+52, 40+20+6+52, 40+20+17+52, 40+20+17+4+52, 40+20+17+6+52, 40+20+18+52, 40+20+18+4+52, 40+20+18+6+52, 40+20+19+52, 40+20+19+4+52, 40+20+19+6+52, 40+20+19+17+52, 40+20+19+17+4+52, 40+20+19+17+6+52, 40+20+19+18+52, 40+20+19+18+4+52, 40+20+19+18+6+52, 41+52, 41+4+52, 41+6+52, 41+17+52, 41+17+4+52, 41+17+6+52, 41+18+52, 41+18+4+52, 41+18+6+52, 41+19+52, 41+19+4+52, 41+19+6+52, 41+19+17+52, 41+19+17+4+52, 41+19+17+6+52, 41+19+18+52, 41+19+18+4+52, 41+19+18+6+52, 41+20+52, 41+20+4+52, 41+20+6+52, 41+20+17+52, 41+20+17+4+52, 41+20+17+6+52, 41+20+18+52, 41+20+18+4+52, 41+20+18+6+52, 41+20+19+52, 41+20+19+4+52, 41+20+19+6+52, 41+20+19+17+52, 41+20+19+17+4+52, 41+20+19+17+6+52, 41+20+19+18+52, 41+20+19+18+4+52, 41+20+19+18+6+1; 47+52, 47+4+52, 47+6+52, 47+40+52, 47+41+52, 47+41+4+52, 47+40+6+52, 47+41+4+52, 47+41+6+52.

In the list above, the numbers refer to the embodiments according to their numbering provided hereinabove whereas "+" indicates the dependency from another embodiment.

The different individualized embodiments are separated by commas. In other words, "41+17+52" for example refers to embodiment 41) depending on embodiment 17), depending on embodiment 52), i.e. embodiment "41+17+53" corresponds to the compounds of embodiment 52) further limited by the features of the embodiments 17) and 41).

53) A further aspect of the invention relates to compounds of the formula (IV) according to embodiment 27), which are also compounds of the formula (VI); wherein the absolute configuration is as depicted in formula (VI):

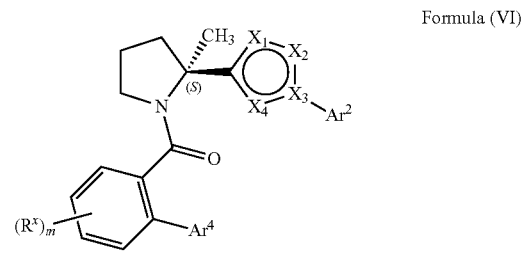

Formula (VI)

wherein the carbon atom at position 2 of the pyrrolidine ring is in absolute (S)-configuration;
wherein the ring

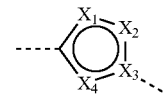

represents a meta di-substituted 5-membered heteroarylene ring containing one, two or three heteroatoms at any of the positions $X_1$, $X_2$, $X_3$, and/or $X_4$; wherein at least one of said heteroatoms is nitrogen, and the remaining, if present, is/are independently selected from oxygen, sulfur and nitrogen [wherein it is understood that the two meta-arranged substituents are the pyrrolidine-2-yl group and the substituent $Ar^2$; and that the above-defined ring does not carry any further substituent];

$Ar^2$ represents phenyl or 5- to 10-membered heteroaryl; wherein said phenyl or 5- to 10-membered heteroaryl is independently unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, hydroxy, $(C_{1-4})$alkoxy-$(C_{1-3})$alkyl, hydroxy-$(C_{1-3})$alkyl, —CO—$(C_{1-4})$alkyl, and $(C_{3-6})$cycloalkyl-oxy-; or $Ar^2$ represents a 2,3-dihydro-benzo[1,4]dioxinyl, a 2,3-dihydro-benzofuranyl, or a benzo[1,3]dioxolyl group optionally di-substituted with fluoro;

$(R^x)_m$ represents one, or two optional substituents [i.e. m represents the integer 0, 1, or 2] independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; and $Ar^4$ represents phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;

wherein the characteristics disclosed in embodiments 28) to 50) are intended to apply mutatis mutandis also to the compounds formula (VI) according to embodiment 53);

wherein especially the following embodiments are thus possible and intended and herewith specifically disclosed in individualized form: 53, 28+53, 30+53, 32+53, 34+53, 36+53, 37+53, 40+53, 40+28+53, 40+30+53, 40+32+53, 40+34+53, 40+36+53, 40+37+53, 41+53, 41+28+53, 41+30+53, 41+32+53, 41+34+53, 41+36+53, 41+37+53, 42+53, 42+28+53, 42+30+53, 42+32+53, 42+34+53, 42+36+53, 42+37+53, 42+40+53, 42+40+28+53, 42+40+30+53, 42+40+32+53, 42+40+34+53, 42+40+36+53, 42+40+37+53, 42+41+53, 42+41+28+53, 42+41+30+53, 42+41+32+53, 42+41+34+53, 42+41+36+53, 42+41+37+53, 43+53, 43+28+53, 43+30+53, 43+32+53, 43+34+53, 43+36+53, 43+37+53, 43+40+53, 43+40+28+53, 43+40+30+53, 43+40+32+53, 43+40+34+53, 43+40+36+53, 43+40+37+53, 43+41+53, 43+41+28+53, 43+41+30+53, 43+41+32+53, 43+41+34+53, 43+41+36+53, 43+41+37+53, 46+53, 46+28+53, 46+30+53, 46+32+53, 46+34+53, 46+36+53, 46+37+53, 46+40+53, 46+40+28+53, 46+40+30+53, 46+40+32+53, 46+40+34+53, 46+40+36+53, 46+40+37+53, 46+41+53, 46+41+28+53, 46+41+30+53, 46+41+32+53, 46+41+34+53, 46+41+36+53, 46+41+37+53, 47+53, 47+28+53, 47+30+53, 47+32+53, 47+33+53, 47+34+53, 47+35+53, 47+36+53, 47+37+53, 47+40+53, 47+40+28+53, 47+40+30+53, 47+40+32+53, 47+40+34+53, 47+40+36+53, 47+40+37+53, 47+41+53, 47+41+28+53, 47+41+30+53, 47+41+32+53, 47+41+34+53, 47+41+36+53, 47+41+37+53, 48+53, 48+28+53, 48+30+53, 48+32+53, 48+33+53, 48+34+53, 48+35+53, 48+36+53, 48+37+53, 48+40+53, 48+40+28+53, 48+40+30+53, 48+40+32+53, 48+40+34+53, 48+40+36+53, 48+40+37+53, 48+41+53, 48+41+28+53, 48+41+30+53, 48+41+32+53, 48+41+34+53, 48+41+36+53, 48+41+37+53, 49+53, 49+42+53, 49+43+53, 49+44+53, 49+45+53, 49+46+53, 49+47+53, 49+48+53, 50+53, 50+42+53, 50+43+53, 50+44+53, 50+45+53, 50+46+53, 50+47+53, 50+48+53.

In the list above, the numbers refer to the embodiments according to their numbering provided hereinabove whereas "+" indicates the dependency from another embodiment. The different individualized embodiments are separated by commas. In other words, "41+28+53" for example refers to embodiment 41) depending on embodiment 28), depending on embodiment 53), i.e. embodiment "41+28+53" corresponds to the compounds of embodiment 53) further limited by the features of the embodiments 28) and 41).

54) A further embodiment relates to compounds of formula (VI) according to embodiment 53), wherein the group

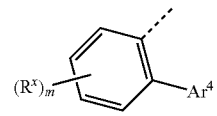

is a group selected from the following groups:

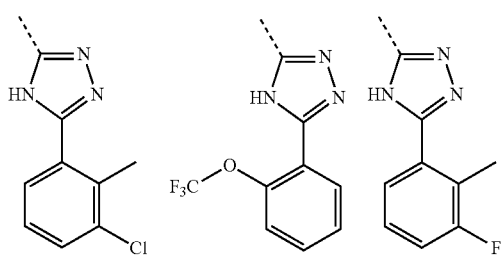

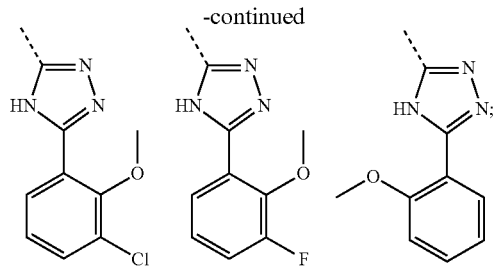

and the group

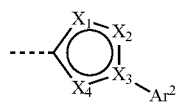

is as defined in embodiments 49) or 50); wherein, in a sub-embodiment, particular groups are independently selected from the following groups:

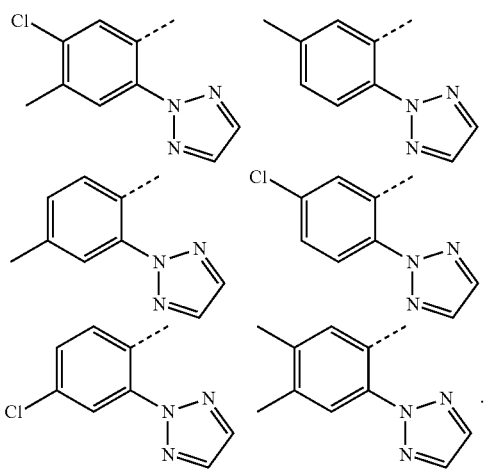

55) Particular compounds according to embodiment 1) are selected from the group consisting of:
{(S)-2-[3-(2-Cyclopropyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(1H-Indol-3-yl)-[1,2,4]oxadiazol-5-yl]-pyrrolidin-1-yl}-(5-methyl-2-[1,2,3]triazol-2-yl-phenyl)-methanone;
(5-Methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
{(S)-2-[3-(3-Chloro-2-methyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Ethyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(3-Fluoro-2-methoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(2,3-Dihydro-benzo[1,4]dioxin-5-yl)-[1,2,4]oxadiazol-5-yl]-pyrrolidin-1-yl}-(5-methyl-2-[1,2,3]triazol-2-yl- phenyl)-methanone;

{(S)-2-[3-(2-Ethoxy-phenyl)-[1,2,4]oxadiazol-5-yl]-pyrrolidin-1-yl}-(5-methyl-2-[1,2,3]triazol-2-yl-phenyl)-methanone;

{(S)-2-[3-(2-Ethoxy-pyridin-3-yl)-[1,2,4]oxadiazol-5-yl]-pyrrolidin-1-yl}-(5-methyl-2-[1,2,3]triazol-2-yl-phenyl)-methanone;

{(S)-2-[3-(1H-Indol-7-yl)-[1,2,4]oxadiazol-5-yl]-pyrrolidin-1-yl}-(5-methyl-2-[1,2,3]triazol-2-yl-phenyl)-methanone;

{(S)-2-[3-(1-Methyl-1H-pyrrolo[2,3-b]pyridin-3-yl)-[1,2,4]oxadiazol-5-yl]-pyrrolidin-1-yl}-(5-methyl-2-[1,2,3]triazol-2-yl-phenyl)-methanone;

{(S)-2-[3-(2-Ethoxy-3-fluoro-phenyl)-[1,2,4]oxadiazol-5-yl]-pyrrolidin-1-yl}-(5-methyl-2-[1,2,3]triazol-2-yl-phenyl)-methanone;

{(S)-2-[3-(1-Methyl-1H-indol-3-yl)-[1,2,4]oxadiazol-5-yl]-pyrrolidin-1-yl}-(5-methyl-2-[1,2,3]triazol-2-yl-phenyl)-methanone;

{(S)-2-[3-(2-Isopropoxy-pyridin-3-yl)-[1,2,4]oxadiazol-5-yl]-pyrrolidin-1-yl}-(5-methyl-2-[1,2,3]triazol-2-yl-phenyl)-methanone;

1-(3-{5-[(S)-1-(5-Methyl-2-[1,2,3]triazol-2-yl-benzoyl)-pyrrolidin-2-yl]-[1,2,4]oxadiazol-3-yl}-indol-1-yl)-ethanone;

{(S)-2-[3-(3-Chloro-2-methyl-phenyl)-[1,2,4]oxadiazol-5-yl]-pyrrolidin-1-yl}-(4-methyl-biphenyl-2-yl)-methanone;

{(S)-2-[3-(3-Chloro-2-methyl-phenyl)-[1,2,4]oxadiazol-5-yl]-pyrrolidin-1-yl}-(4,5-dimethyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(4-methoxy-biphenyl-2-yl)-methanone;

{(S)-2-[3-(3-Chloro-2-methyl-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-methyl-2-oxazol-2-yl-phenyl)-methanone;

(4-Methyl-biphenyl-2-yl)-{(S)-2-[3-(2-trifluoromethoxy-phenyl)-[1,2,4]oxadiazol-5-yl]-pyrrolidin-1-yl}-methanone;

(5-Methyl-2-pyrazol-1-yl-phenyl)-{(S)-2-[3-(2-trifluoromethoxy-phenyl)-[1,2,4]oxadiazol-5-yl]-pyrrolidin-1-yl}-methanone;

(5-Methyl-2-pyridin-2-yl-phenyl)-{(S)-2-[3-(2-trifluoromethoxy-phenyl)-[1,2,4]oxadiazol-5-yl]-pyrrolidin-1-yl}-methanone;

(5-Chloro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(2-Fluoro-3-methyl-6-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4,5-Dimethyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4-Methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(5-Methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4-Methoxy-biphenyl-2-yl)-{(S)-2-[3-(2-trifluoromethoxy-phenyl)-[1,2,4]oxadiazol-5-yl]-pyrrolidin-1-yl}-methanone;

(5-Methoxy-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4,5-Dimethyl-2-pyrazol-1-yl-phenyl)-{(S)-2-[3-(2-trifluoromethoxy-phenyl)-[1,2,4]oxadiazol-5-yl]-pyrrolidin-1-yl}-methanone;

[3-Fluoro-2-(2H-pyrazol-3-yl)-phenyl]-{(S)-2-[3-(2-trifluoromethoxy-phenyl)-[1,2,4]oxadiazol-5-yl]-pyrrolidin-1-yl}-methanone;

(5-Methyl-2-oxazol-2-yl-phenyl)-{(S)-2-[3-(2-trifluoromethoxy-phenyl)-[1,2,4]oxadiazol-5-yl]-pyrrolidin-1-yl}-methanone;

{(S)-2-[3-(2-Difluoromethoxy-phenyl)-[1,2,4]oxadiazol-5-yl]-pyrrolidin-1-yl}-(4,5-dimethyl-2-[1,2,3]triazol-2-yl-phenyl)-methanone;

{(S)-2-[3-(2-Difluoromethoxy-phenyl)-[1,2,4]oxadiazol-5-yl]-pyrrolidin-1-yl}-(5-methoxy-4-methyl-2-[1,2,3]triazol-2-yl-phenyl)-methanone;

(4,5-Dimethyl-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(5-methoxy-4-methyl-2-[1,2,3]triazol-2-yl-phenyl)-methanone;

(5-Chloro-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

(4,5-Dimethyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-pyridin-3-yl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(2-Ethoxy-pyridin-3-yl)-[1,2,4]oxadiazol-5-yl]-pyrrolidin-1-yl}-(5-methyl-2-pyridin-2-yl-phenyl)-methanone;

{(S)-2-[3-(2-Ethoxy-pyridin-3-yl)-[1,2,4]oxadiazol-5-yl]-pyrrolidin-1-yl}-(5-methyl-2-oxazol-2-yl-phenyl)-methanone;

(4,5-Dimethyl-2-[1,2,3]triazol-2-yl-phenyl)-{(S)-2-[3-(2-methoxy-phenyl)-[1,2,4]oxadiazol-5-yl]-pyrrolidin-1-yl}-methanone;

(4,5-Dimethyl-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

(5-Chloro-2-[1,2,3]triazol-2-yl-phenyl)-{(S)-2-[3-(2-ethoxy-phenyl)-[1,2,4]oxadiazol-5-yl]-pyrrolidin-1-yl}-methanone;

{(S)-2-[3-(2-Ethoxy-phenyl)-[1,2,4]oxadiazol-5-yl]-pyrrolidin-1-yl}-(4-methyl-2-[1,2,3]triazol-2-yl-phenyl)-methanone;

(4,5-Dimethyl-2-[1,2,3]triazol-2-yl-phenyl)-{(S)-2-[3-(2-ethoxy-phenyl)-[1,2,4]oxadiazol-5-yl]-pyrrolidin-1-yl}-methanone;

{(S)-2-[3-(2-Ethoxy-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(2-Ethoxy-phenyl)-[1,2,4]oxadiazol-5-yl]-pyrrolidin-1-yl}-(5-methoxy-2-[1,2,3]triazol-2-yl-phenyl)-methanone;

(5-Methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

{(S)-2-[5-(2-Ethoxy-phenyl)-[1,2,4]oxadiazol-3-yl]-pyrrolidin-1-yl}-(5-methyl-2-[1,2,3]triazol-2-yl-phenyl)-methanone;

(5-Methoxy-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

{(S)-2-[5-(2-Ethoxy-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(2-Ethoxy-pyridin-3-yl)-[1,2,4]oxadiazol-3-yl]-pyrrolidin-1-yl}-(5-methoxy-4-methyl-2-[1,2,3]triazol-2-yl-phenyl)- methanone;

{(S)-2-[5-(3-Chloro-2-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2-Ethoxy-3-fluoro-phenyl)-[1,2,4]oxadiazol-3-yl]-pyrrolidin-1-yl}-(5-methyl-2-[1,2,3]triazol-2-yl-phenyl)-methanone;

{(S)-2-[5-(3-Chloro-2-methyl-phenyl)-[1,2,4]oxadiazol-3-yl]-pyrrolidin-1-yl}-(5-methoxy-4-methyl-2-[1,2,3]triazol-2-yl-phenyl)- methanone;

{(S)-2-[5-(3-Chloro-2-methyl-phenyl)-[1,2,4]oxadiazol-3-yl]-pyrrolidin-1-yl}-(4,5-dimethyl-2-[1,2,3]triazol-2-yl-phenyl)-methanone;

{(S)-2-[5-(2-Ethoxy-3-fluoro-phenyl)-[1,2,4]oxadiazol-3-yl]-pyrrolidin-1-yl}-(5-methoxy-4-methyl-2-[1,2,3]triazol-2-yl-phenyl)- methanone;

(4,5-Dimethyl-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

{(S)-2-[5-(2-Ethoxy-3-fluoro-phenyl)-[1,2,4]oxadiazol-3-yl]-pyrrolidin-1-yl}-(5-methoxy-2-[1,2,3]triazol-2-yl-phenyl)-methanone;

(5-Chloro-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

{(S)-2-[5-(2-Ethoxy-3-fluoro-phenyl)-[1,2,4]oxadiazol-3-yl]-pyrrolidin-1-yl}-(4-methyl-2-[1,2,3]triazol-2-yl-phenyl)-methanone;

(4-Chloro-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

{(S)-2-[5-(2-Ethoxy-pyridin-3-yl)-[1,2,4]oxadiazol-3-yl]-pyrrolidin-1-yl}-(5-methyl-2-[1,2,3]triazol-2-yl-phenyl)-methanone;

(4,5-Dimethyl-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(3-Fluoro-2-methoxy-phenyl)-[1,2,4]oxadiazol-3-yl]-pyrrolidin-1-yl}-(5-methyl-2-[1,2,3]triazol-2-yl-phenyl)-methanone;

{(S)-2-[5-(3-Fluoro-2-methoxy-phenyl)-[1,2,4]oxadiazol-3-yl]-pyrrolidin-1-yl}-(4-methyl-2-[1,2,3]triazol-2-yl-phenyl)-methanone;

(4,5-Dimethyl-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

{(S)-2-[5-(3-Fluoro-2-methoxy-phenyl)-[1,2,4]oxadiazol-3-yl]-pyrrolidin-1-yl}-(5-methoxy-4-methyl-2-[1,2,3]triazol-2-yl-phenyl)- methanone;

(5-Chloro-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

{(S)-2-[3-(3-Chloro-2-methyl-phenyl)-isoxazol-5-yl]-pyrrolidin-1-yl}-(5-methyl-2-[1,2,3]triazol-2-yl-phenyl)-methanone;

(5-Methyl-2-[1,2,3]triazol-2-yl-phenyl)-{(S)-2-[3-(2-trifluoromethoxy-phenyl)-isoxazol-5-yl]-pyrrolidin-1-yl}-methanone;

(5-Methyl-2-[1,2,3]triazol-2-yl-phenyl)-{(S)-2-[4-(2-trifluoromethoxy-phenyl)-oxazol-2-yl]-pyrrolidin-1-yl}-methanone;

{(S)-2-[5-(3-Chloro-2-methyl-phenyl)-[1,3,4]oxadiazol-2-yl]-pyrrolidin-1-yl}-(4,5-dimethyl-2-[1,2,3]triazol-2-yl-phenyl)-methanone;

(4-Chloro-5-methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-3-fluoro-phenyl)-[1,2,4]oxadiazol-5-yl]-pyrrolidin-1-yl}-(4-methyl-2-[1,2,3]triazol-2-yl-phenyl)-methanone;

(4,5-Dimethyl-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone;

{(S)-2-[3-(2-Ethoxy-3-fluoro-phenyl)-[1,2,4]oxadiazol-5-yl]-pyrrolidin-1-yl}-(5-methoxy-4-methyl-2-[1,2,3]triazol-2-yl-phenyl)- methanone;

{(S)-2-[3-(3-Chloro-2-methyl-phenyl)-[1,2,4]oxadiazol-5-yl]-pyrrolidin-1-yl}-(5-chloro-4-methyl-2-[1,2,3]triazol-2-yl-phenyl)- methanone;

(4-Chloro-5-methoxy-2-[1,2,3]triazol-2-yl-phenyl)-{(S)-2-[5-(3-chloro-2-methyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(3-Chloro-2-methyl-phenyl)-[1,2,4]oxadiazol-3-yl]-pyrrolidin-1-yl}-(5-chloro-4-methyl-2-[1,2,3]triazol-2-yl-phenyl)- methanone;

(4-Methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(4-Chloro-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

{(S)-2-[5-(2-Ethoxy-phenyl)-4H-[1,2,4]triazol-3-yl]-pyrrolidin-1-yl}-(5-methyl-2-[1,2,3]triazol-2-yl-phenyl)-methanone;

{(S)-2-[5-(3-Fluoro-2-methoxy-phenyl)-4H-[1,2,4]triazol-3-yl]-pyrrolidin-1-yl}-(5-methyl-2-[1,2,3]triazol-2-yl-phenyl)- methanone;

{(S)-2-[5-(2-Ethyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2-Ethyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(2-ethyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2-ethyl-phenyl)-[1,2,4]oxadiazol-3-yl]-pyrrolidin-1-yl}-methanone;

{(S)-2-[5-(2,3-Dimethyl-phenyl)-[1,2,4]oxadiazol-3-yl]-pyrrolidin-1-yl}-(4,5-dimethyl-2-[1,2,3]triazol-2-yl-phenyl)-methanone;

(4,5-Dimethyl-2-[1,2,3]triazol-2-yl-phenyl)-{(S)-2-[5-(2-ethyl-phenyl)-[1,2,4]oxadiazol-3-yl]-pyrrolidin-1-yl}-methanone;

{(S)-2-[5-(2,3-Dimethyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(2-Ethyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(2,5-Dimethyl-phenyl)-[1,2,4]oxadiazol-3-yl]-pyrrolidin-1-yl}-(5-methoxy-4-methyl-2-[1,2,3]triazol-2-yl-phenyl)-methanone;

(4-Chloro-5-methoxy-2-[1,2,3]triazol-2-yl-phenyl)-{(S)-2-[5-(2,3-dimethyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2-ethyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2,5-dimethyl-phenyl)-[1,2,4]oxadiazol-3-yl]-pyrrolidin-1-yl}-methanone;

{(S)-2-[5-(3-Methoxy-5-methyl-phenyl)-[1,2,4]oxadiazol-3-yl]-pyrrolidin-1-yl}-(5-methyl-2-[1,2,3]triazol-2-yl-phenyl)-methanone;

(4,5-Dimethyl-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

{(S)-2-[5-(3-Methoxy-5-methyl-phenyl)-[1,2,4]oxadiazol-3-yl]-pyrrolidin-1-yl}-(5-methoxy-4-methyl-2-[1,2,3]triazol-2-yl- phenyl)-methanone;

(4-Chloro-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(2-Ethoxy-pyridin-3-yl)-[1,2,4]oxadiazol-3l1]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(4-chloro-5-methoxy-2-[1,2,3]triazol-2-yl- phenyl)-methanone;

{(S)-2-[5-(3-Chloro-2-methoxy-phenyl)-[1,2,4]oxadiazol-3-yl]-pyrrolidin-1-yl}-(5-methoxy-4-methyl-2-[1,2,3]triazol-2-yl- phenyl)-methanone;

{(S)-2-[5-(3-Chloro-2-methoxy-phenyl)-[1,2,4]oxadiazol-3-yl]-pyrrolidin-1-yl}-(4-chloro-2-[1,2,3]triazol-2-yl-phenyl)-methanone;

(4-Chloro-5-methoxy-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(5-methyl-2-[1,2,3]triazol-2-yl-phenyl)-methanone;

(4-Chloro-5-methoxy-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(4-methyl-2-[1,2,3]triazol-2-yl-phenyl)-methanone;

{(S)-2-[5-(3-Chloro-2-methoxy-phenyl)-[1,2,4]oxadiazol-3-yl]-pyrrolidin-1-yl}-(4,5-dimethyl-2-[1,2,3]triazol-2-yl-phenyl)-methanone;

(4,5-Dimethyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(5-Methoxy-4-methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(4-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(4-Chloro-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(4-Chloro-5-methoxy-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(2-methoxy-phenyl)-4H-[1,2,4]triazol-3-yl]-pyrrolidin-1-yl}-methanone;

(4-Chloro-5-methoxy-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(4,5-Dimethyl-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(4-Chloro-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(4-Chloro-5-methoxy-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone;

{(S)-2-[5-(2-Ethoxy-pyridin-3-yl)-4H-[1,2,4]triazol-3-yl]-pyrrolidin-1-yl}-(5-methoxy-4-methyl-2-[1,2,3]triazol-2-yl- phenyl)-methanone;

(4,5-Dimethyl-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone;

(4-Chloro-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(2-ethoxy-pyridin-3-yl)-4H-[1,2,4]triazol-3-yl]-pyrrolidin-1- yl}-methanone;

{(S)-2-[5-(3-Chloro-2-methoxy-phenyl)-4H-[1,2,4]triazol-3-yl]-pyrrolidin-1-yl}-(4-chloro-5-methoxy-2-[1,2,3]triazol-2-yl- phenyl)-methanone;
{(S)-2-[5-(3-Chloro-2-methoxy-phenyl)-4H-[1,2,4]triazol-3-yl]-pyrrolidin-1-yl}-(4,5-dimethyl-2-[1,2,3]triazol-2-yl-phenyl)- methanone;
(5-Chloro-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
(5-Chloro-4-methyl-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone;
(5-Chloro-4-methyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;
(5-Chloro-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;
(5-Chloro-4-methyl-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;
(5-Chloro-4-methyl-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;
{(S)-2-[5-(2-Methoxy-phenyl)-1H-imidazol-2-yl]-pyrrolidin-1-yl}-(5-methyl-2-[1,2,3]triazol-2-yl-phenyl)-methanone;
{(S)-2-[5-(2-Ethoxy-phenyl)-1H-imidazol-2-yl]-pyrrolidin-1-yl}-(5-methyl-2-[1,2,3]triazol-2-yl-phenyl)-methanone;
(5-Methyl-2-[1,2,3]triazol-2-yl-phenyl)-{(S)-2-[5-(2-trifluoromethoxy-phenyl)-1H-imidazol-2-yl]-pyrrolidin-1-yl}-methanone;
(4-Methyl-2-[1,2,3]triazol-2-yl-phenyl)-{(S)-2-[5-(2-trifluoromethoxy-phenyl)-1H-imidazol-2-yl]-pyrrolidin-1-yl}-methanone;
{(S)-2-[5-(2-Ethoxy-phenyl)-1H-imidazol-2-yl]-pyrrolidin-1-yl}-(4-methyl-2-[1,2,3]triazol-2-yl-phenyl)-methanone;
{(S)-2-[5-(3-Chloro-2-methyl-phenyl)-isoxazol-3-yl]-pyrrolidin-1-yl}-(5-methyl-2-[1,2,3]triazol-2-yl-phenyl)-methanone;
{(S)-2-[5-(3-Chloro-2-methyl-phenyl)-isoxazol-3-yl]-pyrrolidin-1-yl}-(5-methoxy-4-methyl-2-[1,2,3]triazol-2-yl-phenyl)-methanone;
(5-Methyl-2-[1,2,3]triazol-2-yl-phenyl)-{(S)-2-[5-(2-trifluoromethoxy-phenyl)-isoxazol-3-yl]-pyrrolidin-1-yl}-methanone;
(4-Methyl-2-[1,2,3]triazol-2-yl-phenyl)-{(S)-2-[5-(2-trifluoromethoxy-phenyl)-isoxazol-3-yl]-pyrrolidin-1-yl}-methanone; and
(5-Methoxy-4-methyl-2-[1,2,3]triazol-2-yl-phenyl)-{(S)-2-[5-(2-trifluoromethoxy-phenyl)-isoxazol-3-yl]-pyrrolidin-1-yl}-methanone.

In a sub-embodiment of embodiment 55), particular compounds according to embodiment 1) are
(5-Methoxy-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;
(5-Methoxy-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; and
{(S)-2-[3-(3-Chloro-2-methyl-phenyl)-[1,2,4]oxadiazol-5-yl]-pyrrolidin-1-yl}-(4,5-dimethyl-2-[1,2,3]triazol-2-yl-phenyl)-methanone.

In a further sub-embodiment of embodiment 55), another particular compound according to embodiment 1) is
(4-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone.

56) In addition to the above-listed compounds, further compounds according to embodiment 1) are selected from the group consisting of:
(5-Methyl-2-[1,2,3]triazol-2-yl-phenyl)-[(3)-2-(3-phenyl-[1,2,4]oxadiazol-5-yl)-pyrrolidin-1-yl]-methanone;
(5-Methyl-2-[1,2,3]triazol-2-yl-phenyl)-[(3)-2-(3-m-tolyl-[1,2,4]oxadiazol-5-yl)-pyrrolidin-1-yl]-methanone;
{(S)-2-[3-(3-Methoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Methoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(3,5-Dimethyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(2,3-Dimethyl-phenyl)-[1,2,4]oxadiazol-5-yl]-pyrrolidin-1-yl}-(5-methyl-2-[1,2,3]triazol-2-yl-phenyl)-methanone;
(5-Methyl-2-[1,2,3]triazol-2-yl-phenyl)-[(3)-2-(3-o-tolyl-[1,2,4]oxadiazol-5-yl)-pyrrolidin-1-yl]-methanone;
{(S)-2-[3-(3-Chloro-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Chloro-phenyl)-[1,2,4]oxadiazol-5-yl]-pyrrolidin-1-yl}-(5-methyl-2-[1,2,3]triazol-2-yl-phenyl)-methanone;
{(S)-2-[3-(3-Fluoro-2-methyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Chloro-3-methyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Chloro-pyridin-3-yl)-[1,2,4]oxadiazol-5-yl]-pyrrolidin-1-yl}-(5-methyl-2-[1,2,3]triazol-2-yl-phenyl)-methanone;
(5-Methyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone;
{(S)-2-[3-(2-Difluoromethoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(3-Difluoromethoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Methoxymethyl-phenyl)-[1,2,4]oxadiazol-5-yl]-pyrrolidin-1-yl}-(5-methyl-2-[1,2,3]triazol-2-yl-phenyl)-methanone;
[(S)-2-(3-Benzo[1,3]dioxol-4-yl-[1,2,4]oxadiazol-5-yl)-pyrrolidin-1-yl]-(5-methyl-2-[1,2,3]triazol-2-yl-phenyl)-methanone;
(5-Methyl-2-[1,2,3]triazol-2-yl-phenyl)-{(S)-2-[3-(2-methyl-3-trifluoromethyl-phenyl)-[1,2,4]oxadiazol-5-yl]-pyrrolidin-1-yl}-methanone;
{(S)-2-[3-(3-Ethoxy-pyridin-4-yl)-[1,2,4]oxadiazol-5-yl]-pyrrolidin-1-yl}-(5-methyl-2-[1,2,3]triazol-2-yl-phenyl)-methanone;
{(S)-2-[3-(2,3-Dimethoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(1-Methyl-1H-indol-4-yl)-[1,2,4]oxadiazol-5-yl]-pyrrolidin-1-yl}-(5-methyl-2-[1,2,3]triazol-2-yl-phenyl)-methanone;

{(S)-2-[3-(2-Fluoro-6-methyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(1-Methyl-1H-indol-7-yl)-[1,2,4]oxadiazol-5-yl]-pyrrolidin-1-yl}-(5-methyl-2-[1,2,3]triazol-2-yl-phenyl)-methanone;

{(S)-2-[3-(2-Methyl-pyridin-3-yl)-[1,2,4]oxadiazol-5-yl]-pyrrolidin-1-yl}-(5-methyl-2-[1,2,3]triazol-2-yl-phenyl)-methanone;

{(S)-2-[3-(2-Difluoromethoxy-pyridin-3-yl)-[1,2,4]oxadiazol-5-yl]-pyrrolidin-1-yl}-(5-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-chloro-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(2-fluoro-3-methyl-6-[1,2,3]triazol-2-yl-phenyl)- methanone;

Biphenyl-2-yl-{(S)-2-[3-(3-chloro-2-methyl-phenyl)-[1,2,4]oxadiazol-5-yl]-pyrrolidin-1-yl}-methanone;

{(S)-2-[3-(3-Chloro-2-methyl-phenyl)-[1,2,4]oxadiazol-5-yl]-pyrrolidin-1-yl}-(5-methyl-2-pyrazol-1-yl-phenyl)-methanone;

{(S)-2-[3-(3-Chloro-2-methyl-phenyl)-[1,2,4]oxadiazol-5-yl]-pyrrolidin-1-yl}-(5-methyl-2-pyridin-2-yl-phenyl)-methanone;

{(S)-2-[3-(3-Chloro-2-methyl-phenyl)-[1,2,4]oxadiazol-5-yl]-pyrrolidin-1-yl}-(2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(4-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-methoxy-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-fluoro-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-methoxy-4-methyl-2-pyrazol-1-yl-phenyl)-methanone;

{(S)-2-[3-(3-Chloro-2-methyl-phenyl)-[1,2,4]oxadiazol-5-yl]-pyrrolidin-1-yl}-(5-methoxy-2-pyrazol-1-yl-phenyl)-methanone;

{(S)-2-[3-(3-Chloro-2-methyl-phenyl)-[1,2,4]oxadiazol-5-yl]-pyrrolidin-1-yl}-(4,5-dimethyl-2-pyrazol-1-yl-phenyl)-methanone;

{(S)-2-[3-(3-Chloro-2-methyl-phenyl)-[1,2,4]oxadiazol-5-yl]-pyrrolidin-1-yl}-[5-fluoro-2-(2H-pyrazol-3-yl)-phenyl]-methanone;

{(S)-2-[3-(3-Chloro-2-methyl-phenyl)-[1,2,4]oxadiazol-5-yl]-pyrrolidin-1-yl}-[3-fluoro-2-(2H-pyrazol-3-yl)-phenyl]-methanone;

{(S)-2-[3-(3-Chloro-2-methyl-phenyl)-[1,2,4]oxadiazol-5-yl]-pyrrolidin-1-yl}-(4-methoxy-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(3,5-dimethyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(2-oxazol-2-yl-phenyl)-methanone;

{(S)-2-[3-(3-Chloro-2-methyl-phenyl)-[1,2,4]oxadiazol-5-yl]-pyrrolidin-1-yl}-(4-chloro-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(4-fluoro-5-methoxy-2-[1,2,3]triazol-2-yl-phenyl)- methanone;

{(S)-2-[3-(3-Chloro-2-methyl-phenyl)-[1,2,4]oxadiazol-5-yl]-pyrrolidin-1-yl}-(4,5-dimethoxy-2-[1,2,3]triazol-2-yl-phenyl)-methanone;

Biphenyl-2-yl-{(S)-2-[3-(2-trifluoromethoxy-phenyl)-[1,2,4]oxadiazol-5-yl]-pyrrolidin-1-yl}-methanone;

(5-m-Tolyl-oxazol-4-yl)-{(S)-2-[3-(2-trifluoromethoxy-phenyl)-[1,2,4]oxadiazol-5-yl]-pyrrolidin-1-yl}-methanone;

(2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(5-Fluoro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(5-Methoxy-4-methyl-2-pyrazol-1-yl-phenyl)-{(S)-2-[3-(2-trifluoromethoxy-phenyl)-[1,2,4]oxadiazol-5-yl]-pyrrolidin-1-yl}-methanone;

[5-Fluoro-2-(2H-pyrazol-3-yl)-phenyl]-{(S)-2-[3-(2-trifluoromethoxy-phenyl)-[1,2,4]oxadiazol-5-yl]-pyrrolidin-1-yl}-methanone;

(3,5-Dimethyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(2-Oxazol-2-yl-phenyl)-{(S)-2-[3-(2-trifluoromethoxy-phenyl)-[1,2,4]oxadiazol-5-yl]-pyrrolidin-1-yl}-methanone;

(4-Chloro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4,5-Dimethyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone;

(5-Methoxy-4-methyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone;

(5-Chloro-2-[1,2,3]triazol-2-yl-phenyl)-{(S)-2-[3-(2-difluoromethoxy-phenyl)-[1,2,4]oxadiazol-5-yl]-pyrrolidin-1-yl}-methanone;

{(S)-2-[3-(2-Difluoromethoxy-phenyl)-[1,2,4]oxadiazol-5-yl]-pyrrolidin-1-yl}-(4-methyl-2-[1,2,3]triazol-2-yl-phenyl)-methanone;

{(S)-2-[3-(2-Difluoromethoxy-phenyl)-[1,2,4]oxadiazol-5-yl]-pyrrolidin-1-yl}-[3-fluoro-2-(2H-pyrazol-3-yl)-phenyl]-methanone;

{(S)-2-[3-(2-Difluoromethoxy-phenyl)-[1,2,4]oxadiazol-5-yl]-pyrrolidin-1-yl}-(5-methyl-2-pyridin-2-yl-phenyl)-methanone;

(3,5-Dimethyl-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(2-[1,2,3]triazol-2-yl-phenyl)-methanone;

(5-Chloro-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(4-methyl-2-[1,2,3]triazol-2-yl-phenyl)-methanone;

{(S)-2-[3-(3-Fluoro-2-methoxy-phenyl)-[1,2,4]oxadiazol-5-yl]-pyrrolidin-1-yl}-(5-methoxy-2-[1,2,3]triazol-2-yl-phenyl)-methanone;

{(S)-2-[3-(3-Fluoro-2-methoxy-phenyl)-[1,2,4]oxadiazol-5-yl]-pyrrolidin-1-yl}-(5-fluoro-2-[1,2,3]triazol-2-yl-phenyl)-methanone;

{(S)-2-[3-(3-Fluoro-2-methoxy-phenyl)-[1,2,4]oxadiazol-5-yl]-pyrrolidin-1-yl}-[3-fluoro-2-(2H-pyrazol-3-yl)-phenyl]-methanone;

{(S)-2-[3-(3-Fluoro-2-methoxy-phenyl)-[1,2,4]oxadiazol-5-yl]-pyrrolidin-1-yl}-(5-methyl-2-pyridin-2-yl-phenyl)-methanone;

(4-Chloro-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(2-[1,2,3]triazol-2-yl-4-trifluoromethyl-phenyl)-methanone;

{(S)-2-[3-(3-Fluoro-2-methoxy-phenyl)-[1,2,4]oxadiazol-5-yl]-pyrrolidin-1-yl}-(4-fluoro-5-methoxy-2-[1,2,3]triazol-2-yl-phenyl)-methanone;

(4,5-Dimethoxy-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

(3,5-Dimethyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-pyridin-3-yl)-[1,2,4]oxadiazol-5-yl]-pyrrolidin-1-yl}-(4-methyl-2-[1,2,3]triazol-2-yl-phenyl)-methanone;

{(S)-2-[3-(2-Ethoxy-pyridin-3-yl)-[1,2,4]oxadiazol-5-yl]-pyrrolidin-1-yl}-(6-methyl-3-[1,2,3]triazol-2-yl-pyridin-2-yl)-methanone;

{(S)-2-[3-(2-Ethoxy-pyridin-3-yl)-[1,2,4]oxadiazol-5-yl]-pyrrolidin-1-yl}-[3-fluoro-2-(2H-pyrazol-3-yl)-phenyl]-methanone;

{(S)-2-[3-(2-Ethoxy-pyridin-3-yl)-[1,2,4]oxadiazol-5-yl]-pyrrolidin-1-yl}-(5-methoxy-2-[1,2,3]triazol-2-yl-phenyl)-methanone;

(4-Chloro-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-pyridin-3-yl)-[1,2,4]oxadiazol-5-yl]-pyrrolidin-1-yl}-(4-fluoro-5-methoxy-2-[1,2,3]triazol-2-yl-phenyl)-methanone;

(5-Methoxy-4-methyl-2-[1,2,3]triazol-2-yl-phenyl)-{(S)-2-[3-(2-methoxy-phenyl)-[1,2,4]oxadiazol-5-yl]-pyrrolidin-1-yl}-methanone;

{(S)-2-[3-(2-Chloro-phenyl)-[1,2,4]oxadiazol-5-yl]-pyrrolidin-1-yl}-(4,5-dimethyl-2-[1,2,3]triazol-2-yl-phenyl)-methanone;

{(S)-2-[3-(2-Chloro-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(2-[1,2,3]triazol-2-yl-phenyl)-methanone;

(5-Chloro-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

{(S)-2-[3-(3-Fluoro-2-methyl-phenyl)-[1,2,4]oxadiazol-5-yl]-pyrrolidin-1-yl}-(4-methyl-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(5-methoxy-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(5-fluoro-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-[3-fluoro-2-(2H-pyrazol-3-yl)-phenyl]-methanone;

{(S)-2-[3-(2-Ethoxy-phenyl)-[1,2,4]oxadiazol-5-yl]-pyrrolidin-1-yl}-[3-fluoro-2-(2H-pyrazol-3-yl)-phenyl]-methanone;

{(S)-2-[3-(3,4-Dimethyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(2,4-Dimethyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(2,5-Dimethyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-methoxy-4-methyl-2-pyrimidin-2-yl-phenyl)-methanone;

(5-Methyl-2-[1,2,3]triazol-2-yl-phenyl)-{(S)-2-[3-(3-trifluoromethoxy-phenyl)-[1,2,4]oxadiazol-5-yl]-pyrrolidin-1-yl}-methanone;

{(S)-2-[3-(3-Chloro-2-methyl-phenyl)-[1,2,4]oxadiazol-5-yl]-pyrrolidin-1-yl}-(5-methyl-2-pyrimidin-2-yl-phenyl)-methanone;

{(S)-2-[5-(2,3-Dihydro-benzofuran-7-yl)-[1,2,4]oxadiazol-3-yl]-pyrrolidin-1-yl}-(5-methyl-2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(3-Chloro-2-methyl-phenyl)-[1,2,4]oxadiazol-3-yl]-pyrrolidin-1-yl}-(4-fluoro-5-methoxy-2-[1,2,3]triazol-2-yl-phenyl)-methanone;

{(S)-2-[5-(2-Ethoxy-3-fluoro-phenyl)-[1,2,4]oxadiazol-3-yl]-pyrrolidin-1-yl}-(4-fluoro-5-methoxy-2-[1,2,3]triazol-2-yl-phenyl)-methanone;

{(S)-2-[5-(2-Ethoxy-pyridin-3-yl)-[1,2,4]oxadiazol-3-yl]-pyrrolidin-1-yl}-(4-fluoro-5-methoxy-2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(2-[1,2,3]triazol-2-yl-phenyl)-methanone;

{(S)-2-[5-(3-Fluoro-2-methoxy-phenyl)-[1,2,4]oxadiazol-3-yl]-pyrrolidin-1-yl}-(2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

{(S)-2-[3-(2,3-Dimethyl-phenyl)-isoxazol-5-yl]-pyrrolidin-1-yl}-(5-methyl-2-[1,2,3]triazol-2-yl-phenyl)-methanone;

{(S)-2-[3-(3,5-Dimethyl-phenyl)-isoxazol-5-yl]-pyrrolidin-1-yl}-(5-methyl-2-[1,2,3]triazol-2-yl-phenyl)-methanone;

{(S)-2-[3-(2-Methoxy-pyridin-3-yl)-isoxazol-5-yl]-pyrrolidin-1-yl}-(5-methyl-2-[1,2,3]triazol-2-yl-phenyl)-methanone;

{(S)-2-[3-(2-Ethoxy-pyridin-3-yl)-isoxazol-5-yl]-pyrrolidin-1-yl}-(5-methyl-2-[1,2,3]triazol-2-yl-phenyl)-methanone;

{(S)-2-[3-(3-Fluoro-2-methoxy-phenyl)-isoxazol-5-yl]-pyrrolidin-1-yl}-(5-methyl-2-[1,2,3]triazol-2-yl-phenyl)-methanone;

{(S)-2-[5-(3-Chloro-2-methyl-phenyl)-[1,3,4]oxadiazol-2-yl]-pyrrolidin-1-yl}-(5-methyl-2-[1,2,3]triazol-2-yl-phenyl)-methanone;

[5-(3-Fluoro-phenyl)-2-methyl-thiazol-4-yl]-{(S)-2-[5-(2-trifluoromethoxy-phenyl)-[1,3,4]oxadiazol-2-yl]-pyrrolidin-1-yl}-methanone;

{(S)-2-[5-(3-Chloro-2-methyl-phenyl)-[1,3,4]oxadiazol-2-yl]-pyrrolidin-1-yl}-(5-methoxy-4-methyl-2-[1,2,3]triazol-2-yl-phenyl)- methanone;

(4-Chloro-5-methoxy-2-[1,2,3]triazol-2-yl-phenyl)-{(S)-2-[5-(3-chloro-2-methyl-phenyl)-[1,3,4]oxadiazol-2-yl]-pyrrolidin-1-yl}-methanone;

(4-Chloro-5-methoxy-2-[1,2,3]triazol-2-yl-phenyl)-{(S)-2-[3-(3-chloro-2-methyl-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(5-methoxy-4-methyl-2-pyrimidin-2-yl-phenyl)-methanone;

{(S)-2-[3-(2-Ethoxy-pyridin-3-yl)-[1,2,4]oxadiazol-5-yl]-pyrrolidin-1-yl}-(5-methoxy-4-methyl-2-pyrimidin-2-yl-phenyl)-methanone;

(4-Fluoro-5-methoxy-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

{(S)-2-[5-(3-Fluoro-2-methoxy-phenyl)-[1,2,4]oxadiazol-3-yl]-pyrrolidin-1-yl}-(4-fluoro-5-methoxy-2-[1,2,3]triazol-2-yl- phenyl)-methanone;

(4-Chloro-5-methoxy-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(5-Chloro-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(4-Chloro-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

(5-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

{(S)-2-[5-(3-Chloro-2-methyl-phenyl)-4H-[1,2,4]triazol-3-yl]-pyrrolidin-1-yl}-(5-methyl-2-[1,2,3]triazol-2-yl-phenyl)- methanone;

{(S)-2-[5-(3-Fluoro-2-methyl-phenyl)-4H-[1,2,4]triazol-3-yl]-pyrrolidin-1-yl}-(5-methyl-2-[1,2,3]triazol-2-yl-phenyl)- methanone;

{(S)-2-[5-(2-Ethoxy-pyridin-3-yl)-4H-[1,2,4]triazol-3-yl]-pyrrolidin-1-yl}-(5-methyl-2-[1,2,3]triazol-2-yl-phenyl)-methanone;

{(S)-2-[5-(2,3-Dimethyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2,5-Dimethyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2,3-Dimethyl-phenyl)-[1,2,4]oxadiazol-3-yl]-pyrrolidin-1-yl}-(4-methyl-2-[1,2,3]triazol-2-yl-phenyl)-methanone;

{(S)-2-[5-(2,5-Dimethyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(2,3-dimethyl-phenyl)-[1,2,4]oxadiazol-3-yl]-pyrrolidin-1-yl}-methanone;

(5-Chloro-2-[1,2,3]triazol-2-yl-phenyl)-{(S)-2-[5-(2,5-dimethyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2,3-dimethyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2,5-dimethyl-phenyl)-[1,2,4]oxadiazol-3-yl]-pyrrolidin-1-yl}-methanone;

{(S)-2-[5-(2,5-Dimethyl-phenyl)-[1,2,4]oxadiazol-3-yl]-pyrrolidin-1-yl}-(4,5-dimethyl-2-[1,2,3]triazol-2-yl-phenyl)-methanone;

{(S)-2-[5-(5-Methoxy-2-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2-Methoxy-5-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(5-Methoxy-2-methyl-phenyl)-[1,2,4]oxadiazol-3-yl]-pyrrolidin-1-yl}-(4-methyl-2-[1,2,3]triazol-2-yl-phenyl)-methanone;

{(S)-2-[5-(2-Methoxy-5-methyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

(5-Chloro-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone;

(5-Chloro-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

{(S)-2-[5-(5-Methoxy-2-methyl-phenyl)-[1,2,4]oxadiazol-3-yl]-pyrrolidin-1-yl}-(5-methoxy-4-methyl-2-[1,2,3]triazol-2-yl- phenyl)-methanone;

{(S)-2-[5-(2-Methoxy-5-methyl-phenyl)-[1,2,4]oxadiazol-3-yl]-pyrrolidin-1-yl}-(5-methoxy-4-methyl-2-[1,2,3]triazol-2-yl- phenyl)-methanone;

(4-Chloro-5-methoxy-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(5-chloro-2-[1,2,3]triazol-2-yl-phenyl)-methanone;

{(S)-2-[5-(3-Methoxy-2-methyl-phenyl)-[1,2,4]oxadiazol-3-yl]-pyrrolidin-1-yl}-(5-methoxy-4-methyl-2-[1,2,3]triazol-2-yl- phenyl)-methanone;

{(S)-2-[5-(3-Methoxy-2-methyl-phenyl)-[1,2,4]oxadiazol-3-yl]-pyrrolidin-1-yl}-(5-methyl-2-[1,2,3]triazol-2-yl-phenyl)-methanone;
(2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;
(5-Chloro-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;
(4-Chloro-5-methoxy-2-[1,2,3]triazol-2-yl-phenyl)-{(S)-2-[5-(2-methoxy-phenyl)-4H-[1,2,4]triazol-3-yl]-pyrrolidin-1-yl}-methanone;
(5-Methoxy-4-methyl-2-[1,2,3]triazol-2-yl-phenyl)-{(S)-2-[5-(2-methoxy-phenyl)-4H-[1,2,4]triazol-3-yl]-pyrrolidin-1-yl}-methanone;
(4-Chloro-2-[1,2,3]triazol-2-yl-phenyl)-{(S)-2-[5-(2-methoxy-phenyl)-4H-[1,2,4]triazol-3-yl]-pyrrolidin-1-yl}-methanone;
{(S)-2-[5-(3-Fluoro-2-methoxy-phenyl)-4H-[1,2,4]triazol-3-yl]-pyrrolidin-1-yl}-(5-methoxy-4-methyl-2-[1,2,3]triazol-2-yl- phenyl)-methanone;
{(S)-2-[5-(3-Fluoro-2-methoxy-phenyl)-4H-[1,2,4]triazol-3-yl]-pyrrolidin-1-yl}-(4-methyl-2-[1,2,3]triazol-2-yl-phenyl)- methanone;
{(S)-2-[5-(3-Chloro-2-methoxy-phenyl)-4H-[1,2,4]triazol-3-yl]-pyrrolidin-1-yl}-(5-methyl-2-[1,2,3]triazol-2-yl-phenyl)- methanone;
{(S)-2-[5-(3-Chloro-2-methoxy-phenyl)-4H-[1,2,4]triazol-3-yl]-pyrrolidin-1-yl}-(4-methyl-2-[1,2,3]triazol-2-yl-phenyl)- methanone;
{(S)-2-[5-(3-Chloro-2-methoxy-phenyl)-4H-[1,2,4]triazol-3-yl]-pyrrolidin-1-yl}-(5-methoxy-4-methyl-2-[1,2,3]triazol-2-yl-phenyl)-methanone;
{(S)-2-[5-(4-Chloro-6-methoxy-pyridin-2-yl)-[1,2,4]oxadiazol-3-yl]-pyrrolidin-1-yl}-(5-methyl-2-[1,2,3]triazol-2-yl-phenyl)- methanone;
{(S)-2-[5-(3-Methoxy-phenyl)-1H-imidazol-2-yl]-pyrrolidin-1-yl}-(5-methyl-2-[1,2,3]triazol-2-yl-phenyl)-methanone;
(5-Methyl-2-[1,2,3]triazol-2-yl-phenyl)-[(3)-2-(5-phenyl-isoxazol-3-yl)-pyrrolidin-1-yl]-methanone;
(5-Methoxy-4-methyl-2-[1,2,3]triazol-2-yl-phenyl)-[(3)-2-(5-phenyl-isoxazol-3-yl)-pyrrolidin-1-yl]-methanone; and
(4-Chloro-5-methoxy-2-[1,2,3]triazol-2-yl-phenyl)-{(S)-2-[5-(2-trifluoromethoxy-phenyl)-isoxazol-3-yl]-pyrrolidin-1-yl}-methanone.

57) In addition to the above-listed compounds, further compounds according to embodiment 1) are selected from the group consisting of:
{(S)-2-[3-(2-Cyclobutoxy-pyridin-3-yl)-[1,2,4]oxadiazol-5-yl]-pyrrolidin-1-yl}-(5-methyl-2-[1,2,3]triazol-2-yl-phenyl)-methanone;
(2-Fluoro-3-methoxy-6-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
{(S)-2-[5-(2-Methoxy-phenyl)-4H-[1,2,4]triazol-3-yl]-pyrrolidin-1-yl}-(5-methyl-2-[1,2,3]triazol-2-yl-phenyl)-methanone;
(4,5-Dimethyl-2-[1,2,3]triazol-2-yl-phenyl)-{(S)-2-[5-(2-methoxy-phenyl)-4H-[1,2,4]triazol-3-yl]-pyrrolidin-1-yl}-methanone;
{(S)-2-[5-(2-Methoxy-phenyl)-4H-[1,2,4]triazol-3-yl]-pyrrolidin-1-yl}-(4-methyl-2-[1,2,3]triazol-2-yl-phenyl)-methanone; and
(5-Methyl-2-[1,2,3]triazol-2-yl-phenyl)-[(3)-2-(1-phenyl-1H-[1,2,4]triazol-3-yl)-pyrrolidin-111]-methanone.

58) In addition to the above-listed compounds, further compounds according to embodiment 1) are selected from the group consisting of:
(5-Methyl-2-[1,2,3]triazol-2-yl-phenyl)-{(3)-2-methyl-2-[5-(2-trifluoromethoxy-phenyl)-4H-[1,2,4]triazol-3-yl]-pyrrolidin-1-yl}-methanone;
4-Methyl-2-[1,2,3]triazol-2-yl-phenyl)-{(3)-2-methyl-2-[5-(2-trifluoromethoxy-phenyl)-4H-[1,2,4]triazol-3-yl]-pyrrolidin-1-yl}-methanone;
(4-Chloro-2-[1,2,3]triazol-2-yl-phenyl)-{(3)-2-methyl-2-[5-(2-trifluoromethoxy-phenyl)-4H-[1,2,4]triazol-3-yl]-pyrrolidin-1-yl}-methanone;
(5-Chloro-4-methyl-2-[1,2,3]triazol-2-yl-phenyl)-{(3)-2-methyl-2-[5-(2-trifluoromethoxy-phenyl)-4H-[1,2,4]triazol-3-yl]-pyrrolidin-1-yl}-methanone;
(4,5-Dimethyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;
(5-Chloro-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;
{(S)-2-[5-(3-Chloro-2-methyl-phenyl)-4H-[1,2,4]triazol-3-yl]-2-methyl-pyrrolidin-1-yl}-(4-methyl-2-[1,2,3]triazol-2-yl- phenyl)-methanone;
{(S)-2-[5-(3-Chloro-2-methyl-phenyl)-4H-[1,2,4]triazol-3-yl]-2-methyl-pyrrolidin-1-yl}-(5-chloro-4-methyl-2-[1,2,3]triazol-2-yl-phenyl)-methanone;
{(S)-2-[5-(3-Chloro-2-methyl-phenyl)-4H-[1,2,4]triazol-3-yl]-2-methyl-pyrrolidin-1-yl}-(4,5-dimethyl-2-[1,2,3]triazol-2- yl-phenyl)-methanone; and
{(S)-2-[5-(3-Chloro-2-methyl-phenyl)-4H-[1,2,4]triazol-3-yl]-2-methyl-pyrrolidin-1-yl}-(4-chloro-2-[1,2,3]triazol-2-yl- phenyl)-methanone;
{(S)-2-[5-(3-Chloro-2-methyl-phenyl)-4H-[1,2,4]triazol-3-yl]-2-methyl-pyrrolidin-1-yl}-(5-chloro-2-[1,2,3]triazol-2-yl- phenyl)-methanone;
(5-Methyl-biphenyl-2-yl)-{(S)-2-methyl-2-[5-(2-trifluoromethoxy-phenyl)-4H-[1,2,4]triazol-3-yl]-pyrrolidin-1-yl}-methanone; and
(4-Methyl-biphenyl-2-yl)-{(S)-2-methyl-2-[5-(2-trifluoromethoxy-phenyl)-4H-[1,2,4]triazol-3-yl]-pyrrolidin-1-yl}-methanone.

In a sub-embodiment of embodiment 58), a particular compound according to embodiment 1) is (4-Chloro-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone.

The compounds of formulae (I), (II), (III), (IV), (V) and (VI) contain at least one stereogenic center which is situated in position 2 of the pyrrolidine moiety. It is understood that the absolute configuration of said chiral center is as depicted in formulae (I), (II), (III), (IV), (V) and (VI), i.e. it is in absolute (S) configuration. In addition, the compounds of formula (I) and (II) may contain one or more further stereogenic or asymmetric centers, such as one or more asymmetric carbon atoms. The compounds of formulae (I), (II), (III), (IV), (V) and (VI) may thus be present as mixtures of stereoisomers or preferably as pure stereoisomers. Mixtures of stereoisomers may be separated in a manner known to a person skilled in the art.

In some instances, the compounds of formulae (I), (II), (III), (IV), (V) and (VI) may contain tautomeric forms. Such tautomeric forms are encompassed in the scope of the present invention. For example, in case the present compounds contain heteroaromatic aromatic rings containing unsubstituted ring nitrogen atoms having a free valency such as imidazol-2,4-diyl, or [1,2,4]-triazol-3,5-diyl, such rings may be present in tautomeric forms. For example, the group imidazol-2,4-diyl represents the tautomeric forms 1H-imidazol-2,4-diyl and 3H-imidazol-2,4-diyl; and the group [1,2,4]triazol-3,5-diyl represents the tautomeric forms 1H-[1,2,4]triazol-3,5-diyl, 2H-[1,2,4]triazol-3,5-diyl and 4H-[1,2,4]triazol-3,5-diyl.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formulae (I), (II), (III), (IV), (V) and (VI) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formulae (I), (II), (III), (IV), (V) and (VI) are not isotopically labelled, or they are labelled only with one or more deuterium atoms. In a sub-embodiment, the compounds of formulae (I), (II), (III), (IV), (V) and (VI) are not isotopically labelled at all. Isotopically labelled compounds of formulae (I), (II), (III), (IV), (V) and (VI) may be prepared in analogy to the methods described hereinafter, but using the appropriate isotopic variation of suitable reagents or starting materials.

In this patent application, a dotted line shows the point of attachment of the radical drawn. For example, the radical drawn below

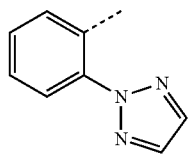

2-(2-triazolyl)-phenyl group.

Where the plural form is used for compounds, salts, pharmaceutical compositions, diseases and the like, this is intended to mean also a single compound, salt, or the like.

Any reference to compounds of formulae (I), (II), (III), (IV), (V) and (VI) as defined in any one of embodiments 1) to 58) is to be understood as referring also to the salts (and especially the pharmaceutically acceptable salts) of such compounds, as appropriate and expedient.

The term "pharmaceutically acceptable salts" refers to non-toxic, inorg. or organic acid and/or base addition salts. Reference can be made to "Salt selection for basic drugs", *Int. J. Pharm.* (1986), 33, 201-217.

Definitions provided herein are intended to apply uniformly to the compounds of formulae (I), (II), (III), (IV), (V) and (VI) as defined in any one of embodiments 1) to 53), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine.

The term "alkyl", used alone or in combination, refers to a saturated straight or branched chain alkyl group containing one to six carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl.

The term "cycloalkyl", used alone or in combination, refers to a saturated cyclic alkyl group containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl and cyclohexyl. Preferred is cyclopropyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy.

The term "aryl" refers to a naphthyl or, preferably, to a phenyl group; wherein said group is unsubstituted or substituted as explicitly defined.

Particular examples of the ring $A_1$, respectively the ring $A'_1$, representing a phenyl group wherein said phenyl is mono-, di-, or tri-substituted; wherein one of said substituents is attached in ortho-position to the point of attachment of ring $A_1$, respectively the ring $A'_1$, to the rest of the molecule, are such that the other of said substituents, if present, is/are independently selected from the group consisting of $(C_{1-4})$alkyl, $(C_{1-4})$alkoxy, and halogen (especially methyl, methoxy and halogen). Likewise, in the group

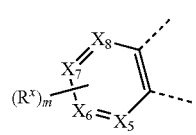

wherein X$_5$ to X$_8$ represent ring carbon atoms; respectively in the group

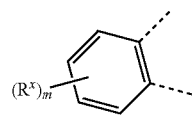

the group (R$^x$)$_m$ represents one or two optional substituents independently selected from (C$_{1-4}$)alkyl, (C$_{1-4}$)alkoxy, and halogen (especially methyl, methoxy and halogen). Particular examples of the above mentioned phenyl groups are 1,2-phenylene, 4-methyl-1,2-phenylene, 5-methyl-1,2-phenylene, 4,5-dimethyl-1,2-phenylene, 3,5-dimethyl-1,2-phenylene, 3-methyl-1,2-phenylene, 6-methyl-1,2-phenylene, 5-fluoro-1,2-phenylene, 3-fluoro-1,2-phenylene, 4-fluoro-1,2-phenylene, 4,5-difluoro-1,2-phenylene, 5-chloro-1,2-phenylene, 4-chloro-1,2-phenylene, 3-chloro-1,2-phenylene, 5-cyano-1,2-phenylene, 5-methoxy-1,2-phenylene, 4-methoxy-1,2-phenylene, 4,5-dimethoxy-1,2-phenylene, 4-methyl-5-methoxy-1,2-phenylene, 4-chloro-5-methoxy-1,2-phenylene, 5-chloro-4-methyl-1,2-phenylene, 5-trifluoromethyl-1,2-phenylene, 4-trifluoromethoxy-1,2-phenylene, 5-trifluoromethoxy-1,2-phenylene, 6-fluoro-5-methyl-1,2-phenylene, 5-fluoro-3-methyl-1,2-phenylene, 4-fluoro-5-methoxy-1,2-phenylene, and 6-fluoro-5-methoxy-1,2-phenylene; wherein in the above groups the carbonyl group is attached in position 1.

Particular examples of the ring A$_2$, respectively the ring A'$_2$, respectively Ar$^2$; representing an aryl group are especially phenyl groups which are unsubstituted, or mono-, di-, or tri-substituted; wherein the substituents are independently selected from the group consisting of (C$_{1-4}$)alkyl, (C$_{1-4}$)alkoxy, (C$_{3-6}$)cycloalkyl, halogen, (C$_{1-3}$)fluoroalkyl, (C$_{1-3}$)fluoroalkoxy; hydroxy, (C$_{1-4}$)alkoxy-(C$_{1-3}$)alkyl, and hydroxy-(C$_{1-3}$)alkyl; [notably from (C$_{1-4}$)alkyl, (C$_{1-4}$)alkoxy, (C$_{3-6}$)cycloalkyl, halogen, (C$_{1-3}$)fluoroalkyl, and (C$_{1-3}$)fluoroalkoxy; especially from methyl, methoxy, cyclopropyl, halogen, trifluoromethyl, and trifluoromethoxy]. Particular examples are phenyl, 2-methyl-phenyl, 2-ethyl-phenyl, 3-methyl-phenyl, 2,3-dimethyl-phenyl, 2,4-dimethyl-phenyl, 2,5-dimethyl-phenyl, 3,4-dimethyl-phenyl, 3,5-dimethyl-phenyl, 2-methoxy-phenyl, 3-methoxy-phenyl, 2-ethoxy-phenyl, 2-isopropoxy-phenyl, 2,3-dimethoxy-phenyl, 2-methoxymethyl-phenyl, 3-methoxy-2-methyl-phenyl, 3-methoxy-6-methyl-phenyl, 2-methoxy-5-methyl-phenyl, 3-methoxy-5-methyl-phenyl, 3-fluoro-2-methyl-phenyl, 2-fluoro-6-methyl-phenyl, 3-fluoro-2-methoxy-phenyl, 3-fluoro-2-ethoxy-phenyl, 2-chloro-phenyl, 3-chloro-phenyl, 3-chloro-2-methyl-phenyl, 2-chloro-3-methyl-phenyl, 2-trifluoromethyl-phenyl, 2-methyl-3-trifluoromethyl-phenyl, 2-trifluoromethoxy-phenyl, 3-trifluoromethoxy-phenyl, 2-difluoromethoxy-phenyl, 3-difluoromethoxy-phenyl, and 2-cyclopropyl-phenyl.

Examples of the particular phenyl groups which are ortho substituents of ring A$_1$, respectively ring A'$_1$, (in particular: groups Ar$^4$ and Ar$^5$) are unsubstituted or mono-substituted phenyl groups wherein the substituent is selected from the group consisting of (C$_{1-4}$)alkyl, (C$_{1-4}$)alkoxy, and halogen (especially methyl, methoxy and halogen); such as especially phenyl, 3-methyl-phenyl, 2-fluorophenyl, 3-fluorophenyl, 4-fluorophenyl, 3-chlorophenyl, and 3-methoxyphenyl.

The term "heteroaryl", if not explicitly stated otherwise, refers to a 5- to 10-membered monocyclic or bicyclic aromatic ring containing 1 to a maximum of 3 heteroatoms independently selected from oxygen, nitrogen and sulfur. Examples of such heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, and triazolyl; 6-membered monocyclic heteroaryl such as pyridyl, pyrimidyl, pyridazinyl, and pyrazinyl; and 8- to 10-membered bicyclic heteroaryl such as indolyl, isoindolyl, benzofuranyl, isobenzofuranyl, benzothiophenyl, indazolyl, benzimidazolyl, benzoxazolyl (or benzooxazolyl), benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, pyrrolo[3,2-d]pyrimidinyl, pyrrolo[2,3-d]pyrimidinyl, 4H-furo[3,2-b]pyrrolyl, pyrrolo[2,1-b]thiazolyl, and imidazo[2,1-b]thiazolyl.

Examples of the particular 5- or 6-membered heteroaryl groups which are further substituted in ortho position as used for the ring A$_1$, respectively ring A'$_1$, are the above mentioned 5- or 6-membered heteroaryl groups, notably oxazolyl (in particular oxazol-4,5-diyl, 2-methyl-oxazol-4,5-diyl), thiazolyl (in particular thiazol-4,5-diyl, 2-methyl-thiazol-4,5-diyl), imidazolyl (in particular imidazol-4,5-diyl), pyridyl (in particular pyridin-2,3-diyl, 6-methyl-pyridin-2,3-diyl), pyrimidyl (in particular pyrimidin-4,5-diyl, 2-methyl-pyrimidin-4,5-diyl), and pyrazinyl (in particular pyrazin-2,3-diyl). These groups are at least monosubstituted in ortho position, and preferably carry no further substituent or one further substitutent as explicitly defined. In particular such optional further substituent is (C$_{1-4}$)alkyl, notably methyl. The above groups are preferably attached to the rest of the molecule (i.e. the carbonyl group) in position 4 of oxazolyl, imidazolyl, or thiazolyl groups, in position 2 or 3 of pyridyl or pyrazinyl groups, or in position 5 of pyrimidinyl groups. In a sub-embodiment, examples of such groups are thiazol-4,5-diyl, 2-methyl-thiazol-4,5-diyl, oxazol-4,5-diyl, 2-methyl-oxzol-4,5-diyl, imidazol-4,5-diyl, pyrimidin-4,5-diyl, 2-methyl-pyrimidin-4,5-diyl, pyridin-2,3-diyl and 6-methyl-pyridin-2,3-diyl. Likewise, particular examples of the group

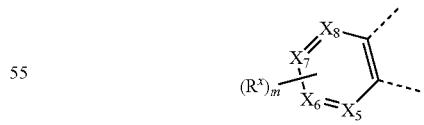

wherein at least one of X$_5$ to X$_7$ is nitrogen are pyrimidin-4,5-diyl, 2-methyl-pyrimidin-4,5-diyl, pyridin-2,3-diyl and 6-methyl-pyridin-2,3-diyl.

Particular examples of the ring A$_2$, respectively the ring A'$_2$, respectively Ar$^2$; representing a 5- to 10-membered heteroaryl are especially 5- to 10-membered heteroaryl groups which are unsubstituted, or mono-substituted; wherein the substituent is selected from the group consisting of (C$_{1-4}$)alkyl, (C$_{1-4}$)alkoxy, (C$_{3-6}$)cycloalkyl, halogen, ($C_{1-3}$)fluoroalkyl, ($C_{1-3}$)fluoroalkoxy, —CO—($C_{1-4}$)alkyl, and ($C_{3-6}$)cycloalkyl-oxy-[notably from ($C_{1-4}$)alkyl, ($C_{1-4}$) alkoxy, halogen, ($C_{1-3}$)fluoroalkoxy, —CO—($C_{1-4}$)alkyl, and ($C_{3-6}$)cycloalkyl-oxy-]. Particular examples of such heteroaryl groups are 6-membered heteroaryl groups, such as pyrazinyl, pyrimidyl and notably pyridyl groups, which groups are unsubstituted, or mono-substituted; wherein the substituent is selected from the group consisting of ($C_{1-4}$) alkyl, ($C_{1-4}$)alkoxy, halogen, ($C_{1-3}$)fluoroalkoxy, and ($C_{3-6}$) cycloalkyl-oxy- (especially methyl, methoxy, ethoxy, isopropoxy, halogen, difluoromethoxy, and cyclobutyloxy); such as especially 2-(cyclobutyl-oxy)-pyridin-3-yl, 2-difluoromethoxy-pyridin-3-yl, 2-isopropoxy-pyridin-3-yl, 2-ethoxy-pyridin-3-yl, 3-ethoxy-pyridin-4-yl, 6-ethoxy-pyridin-3-yl, 2-methoxy-pyridin-3-yl, 6-methoxy-pyridin-3-yl, 6-isopropoxy-pyridin-3-yl, 2-methyl-pyridin-3-yl, and 2-chloro-pyridin-3-yl. Further particular examples of such heteroaryl groups are 8- to 10-membered heteroaryl groups, such as imidazothiazolyl, indazolyl, pyrrolopyridyl (especially 1H-pyrrolo[2,3-b]pyridinyl) and notably indolyl groups which are groups are unsubstituted, or mono-substituted; wherein the substituent is selected from the group consisting of ($C_{1-4}$)alkyl, ($C_{1-4}$)alkoxy, and —CO—($C_{1-4}$) alkyl (especially methyl, methoxy, and acetyl); such as especially indol-3-yl, 1-methyl-indol-3-yl, 4-methyl-indol-3-yl, 1-acetyl-indol-3-yl, indol-4-yl, 1-methyl-indol-4-yl, indol-7-yl, 1-methyl-indol-7-yl, 5-methoxy-indol-3-yl, 1H-pyrrolo[2,3-b]pyridin-3-yl, 1-methyl-1H-pyrrolo[2,3-b]pyridin-3-yl, and 1H-pyrrolo[2,3-b]pyridin-4-yl.

Examples of the particular 5- or 6-membered heteroaryl groups which are ortho substituents of ring $A_1$, respectively ring $A'_1$, (in particular: groups $Ar^4$) are the above mentioned 5- or 6-membered heteroaryl groups, notably oxazolyl, isoxazolyl, oxadiazolyl, thienyl, thiazolyl, isothiazolyl, thiadiazolyl, imidazolyl, pyrazolyl, triazolyl, pyridyl, pyrimidyl, and pyrazinyl. The above mentioned groups are preferably unsubstituted or may be substituted as explicitly defined. Preferred examples are triazolyl (notably unsubstituted [1,2,3]triazol-2-yl), pyrazolyl (notably unsubstituted pyrazol-1-yl, or unsubstituted 2H-pyrazol-3-yl), oxazolyl (notably unsubstituted oxazol-2-yl), oxadiazolyl (notably 3-methyl-[1,2,4]oxadiazol-5-yl); pyridinyl (notably unsubstituted pyridin-2-yl), and pyrimidinyl (notably unsubstituted pyrimidin-2-yl) [notably unsubstituted [1,2,3]triazol-2-yl, unsubstituted pyrazol-1-yl, and unsubstituted pyrimidin-2-yl].

In benzo[1,3]dioxolyl groups which are optionally di-substituted with fluoro, such fluoro substituents are preferably attached to the methylene group of the dioxole ring. An example of such group is 2,2-difluoro-benzo[1,3]dioxol-5-yl.

The compounds of compounds of formulae (I), (II), (III), (IV), (V) and (VI) as defined in any one of embodiments 1) to 58) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject in need thereof a pharmaceutically active amount of a compounds of formulae (I), (II), (III), (IV), (V) and (VI) as defined in any one of embodiments 1) to 58).

In a preferred embodiment of the invention, the administered amount of such a compound of formulae (I), (II), (III), (IV), (V) and (VI) as defined in any one of embodiments 1) to 58) is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as being useful for the prevention or treatment of certain diseases, such compounds are likewise suitable for use in the preparation of a medicament for the prevention or treatment of said diseases.

The compounds of formulae (I), (II), (III), (IV), (V) and (VI) as defined in any one of embodiments 1) to 58) are useful for the prevention or treatment of disorders relating to orexinergic dysfunctions.

Such disorders relating to orexinergic dysfunctions are diseases or disorders where an antagonist of a human orexin receptor is required, notably mental health disorders relating to orexinergic dysfunctions. The above mentioned disorders may in particular be defined as comprising sleep disorders, anxiety disorders, addiction disorders, cognitive dysfunctions, mood disorders, and appetite disorders. In one sub-embodiment, the above mentioned disorders comprise especially sleep disorders, anxiety disorders, addiction disorders, cognitive dysfunctions, and appetite disorders. In another sub-embodiment, the above mentioned disorders comprise especially sleep disorders, anxiety disorders, and addiction disorders. In yet another sub-embodiment, the above mentioned disorders comprise especially sleep disorders.

In addition, further disorders relating to orexinergic dysfunctions are selected from treating, controlling, ameliorating or reducing the risk of epilepsy, including absence epilepsy; treating or controlling pain, including neuropathic pain; treating or controlling Parkinson's disease; treating or controlling psychosis including acute mania and bipolar disorder; treating or controlling stroke, particularly ischemic or haemorrhagic stroke; blocking an emetic response i.e. nausea and vomiting; and treating or controlling agitation, in isolation or co-morbid with another medical condition.

In another embodiment, further disorders relating to orexinergic dysfunctions are selected from schizoaffective disorders; dissociative disorders including multiple personality syndromes and psychogenic amnesias; sexual and reproductive dysfunction; psychosexual dysfunction and addiction; increased anaesthetic risk; anaesthetic responsiveness; hypothalamic-adrenal dysfunctions; all types of amnesia; severe mental retardation; dyskinesias and muscular diseases; muscle spasticity; tremors; movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; seizure disorders; complex partial and generalized seizures; Lennox-Gastaut syndrome; migraine and headache; anaesthesia and analgesia; enhanced or exaggerated sensitivity to pain such as hyperalgesia, causalgia, and allodynia; acute pain; burn pain; atypical facial pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; all types of cerebrovascular disorders including subarachnoid haemorrhage, and vascular dementia; chronic renal failure and other renal diseases; gout; kidney cancer; and urinary incontinence.

In another embodiment, a further disorder relating to orexinergic dysfunctions is sundowning (or sundown syndrome).

Anxiety disorders can be distinguished by the primary object or specificity of threat, ranging from rather diffuse as in generalized anxiety disorder, to circumscribed as encountered in phobic anxieties (PHOBs) or post-traumatic stress disorders (PTSDs). Anxiety disorders may, thus, be defined as comprising generalized anxiety disorders (GAD), obsessive compulsive disorders (OCDs), acute stress disorders, posttraumatic stress disorders (PTSDs), panic anxiety disorders (PADs) including panic attacks, phobic anxieties (PHOBs), specific phobia, social phobia (social anxiety disorder), avoidance, somatoform disorders including hypochondriasis, separation anxiety disorder, anxiety disorders due to a general medical condition, and substance induced anxiety disorders. In a sub-embodiment, particular examples of circumscribed threat induced anxiety disorders are phobic anxieties or post-traumatic stress disorders. Anxiety disorders especially include post-traumatic stress disorders, obsessive compulsive disorders, panic attacks, phobic anxieties, and avoidance.

Addiction disorders may be defined as addictions to one or more rewarding stimuli, notably to one rewarding stimulus. Such rewarding stimuli may be of either natural or synthetic origin. Examples of such rewarding stimuli are substances/drugs {of either natural or synthetic origin; such as cocaine, amphetamines, opiates [of natural or (semi-)synthetic origin such as morphine or heroin], *cannabis*, ethanol, mescaline, nicotine, and the like}, which substances/drugs may be consumed alone or in combination; or other rewarding stimuli {of either natural origin (such as food, sweet, fat, or sex, and the like), or synthetic origin [such as gambling, or internet/IT (such as immoderate gaming, or inappropriate involvement in online social networking sites or blogging), and the like]}. In a sub-embodiment, addiction disorders relating to psychoactive substance use, abuse, seeking and reinstatement are defined as all types of psychological or physical addictions and their related tolerance and dependence components. Substance-related addiction disorders especially include substance use disorders such as substance dependence, substance craving and substance abuse; substance-induced disorders such as substance intoxication, substance withdrawal, and substance-induced delirium. The expression "prevention or treatment of addictions" (i.e. preventive or curative treatment of patients who have been diagnosed as having an addiction, or as being at risk of developing addictions) refers to diminishing addictions, notably diminishing the onset of addictions, to weakening their maintenance, to facilitating withdrawal, to facilitating abstinence, or to attenuating, decreasing or preventing the occurrence of reinstatement of addiction (especially to diminishing the onset of addictions, to facilitating withdrawal, or to attenuating, decreasing or preventing the occurrence of reinstatement of addiction).

Mood disorders include major depressive episode, manic episode, mixed episode and hypomanic episode; depressive disorders including major depressive disorder, dysthymic disorders; bipolar disorders including bipolar I disorder, bipolar II disorder (recurrent major depressive episodes with hypomanic episodes), cyclothymic disorder; mood disorders including mood disorder due to a general medical condition (including the subtypes with depressive features, with major depressive-like episode, with manic features, and with mixed features), substance-induced mood disorder (including the subtypes with depressive features, with manic features, and with mixed features). Such mood disorders are especially major depressive episode, major depressive disorder, mood disorder due to a general medical condition; and substance-induced mood disorder.

Appetite disorders comprise eating disorders and drinking disorders. Eating disorders may be defined as comprising eating disorders associated with excessive food intake and complications associated therewith; anorexias; compulsive eating disorders; obesity (due to any cause, whether genetic or environmental); obesity-related disorders including overeating and obesity observed in Type 2 (non-insulin-dependent) diabetes patients; bulimias including bulimia nervosa; cachexia; and binge eating disorder. Particular eating disorders comprise metabolic dysfunction; dysregulated appetite control; compulsive obesities; bulimia or anorexia nervosa. In a sub-embodiment, eating disorders may be defined as especially comprising anorexia nervosa, bulimia, cachexia, binge eating disorder, or compulsive obesities. Drinking disorders include polydipsias in psychiatric disorders and all other types of excessive fluid intake. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance.

Cognitive dysfunctions include deficits in attention, learning and especially memory functions occurring transiently or chronically in psychiatric, neurologic, neurodegenerative, cardiovascular and immune disorders, and also occurring transiently or chronically in the normal, healthy, young, adult, or especially aging population. Cognitive dysfunctions especially relate to the enhancement or maintenance of memory in patients who have been diagnosed as having, or being at risk of developing, diseases or disorders in which diminished memory (notably declarative or procedural) is a symptom [in particular dementias such as frontotemporal dementia, or dementia with Lewy bodies, or (especially) Alzheimer's disease]. Especially, the term "prevention or treatment of cognitive dysfunctions" relates to the enhancement or maintenance of memory in patients who have a clinical manifestation of a cognitive dysfunction, especially expressed as a deficit of declarative memory, linked to dementias such as frontotemporal dementia, or dementia with Lewy bodies, or (especially) Alzheimer's disease. Furthermore, the term "prevention or treatment of cognitive dysfunctions" also relates to improving memory consolidation in any of the above mentioned patient populations.

Sleep disorders comprise dyssomnias, parasomnias, sleep disorders associated with a general medical condition and substance-induced sleep disorders. In particular, dyssomnias include intrinsic sleep disorders (especially insomnias, breathing-related sleep disorders, periodic limb movement disorder, and restless leg syndrome), extrinsic sleep disorders, and circadian-rythm sleep disorders. Dyssomnias notably include insomnia, primary insomnia, idiopathic insomnia, insomnias associated with depression, emotional/mood disorders, aging, Alzheimer's disease or cognitive impairment; REM sleep interruptions; breathing-related sleep disorders; sleep apnea; periodic limb movement disorder (nocturnal myoclonus), restless leg syndrome, circadian rhythm sleep disorder; shift work sleep disorder; and jet-lag syndrome. Parasomnias include arousal disorders and sleep-wake transition disorders; notably parasomnias include nightmare disorder, sleep terror disorder, and sleepwalking disorder. Sleep disorders associated with a general medical condition are in particular sleep disorders associated with diseases such as mental disorders, neurological disorders, neuropathic pain, and heart and lung diseases. Substance-induced sleep disorders include especially the subtypes insomnia type, parasomnia type and mixed type, and notably include conditions due to drugs which cause reductions in REM sleep as a side effect. Sleep disorders especially include all types of insomnias, sleep-related dystonias; restless leg syndrome; sleep apneas; jet-lag syndrome; shift work sleep disorder, delayed or advanced sleep phase syndrome, or insomnias related to psychiatric disorders. In addition, sleep disorders further include sleep disorders associated with aging; intermittent treatment of chronic insomnia; situational transient insomnia (new environment, noise) or short-term insomnia due to stress; grief; pain or illness.

In the context of the present invention, it is to be understood that, in case certain environmental conditions such as stress or fear (wherein stress may be of social origin (e.g. social stress) or of physical origin (e.g. physical stress), including stress caused by fear) facilitate or precipitate any of the disorders or diseases as defined before, the present compounds may be particularly useful for the treatment of such environmentally conditioned disorder or disease.

Preparation of Compounds of Formulae (I), (II), (III) (IV), (V) and (VI):

The present compounds can be prepared by well known literature methods, by the methods given below, by the methods given in the experimental part or by analogous methods. Optimum reaction conditions may vary with the particular reactants or solvents used, but such conditions can be determined by a person skilled in the art by routine optimisation procedures. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. In some cases the order of carrying out the following reaction schemes, and/or reaction steps, may be varied to facilitate the reaction or to avoid unwanted reaction products. In the general sequence of reactions outlined below, the generic groups R, $A_1$, $A_2$, and $A_3$ are as defined for formula (I). In some instances the generic groups $A_1$, $A_2$, and $A_3$ may be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into pharmaceutically acceptable salts thereof in a manner known per se. Compounds are synthesized as their S-enantiomers from commercially available proline, 2-methyl-proline, or derivatives thereof.

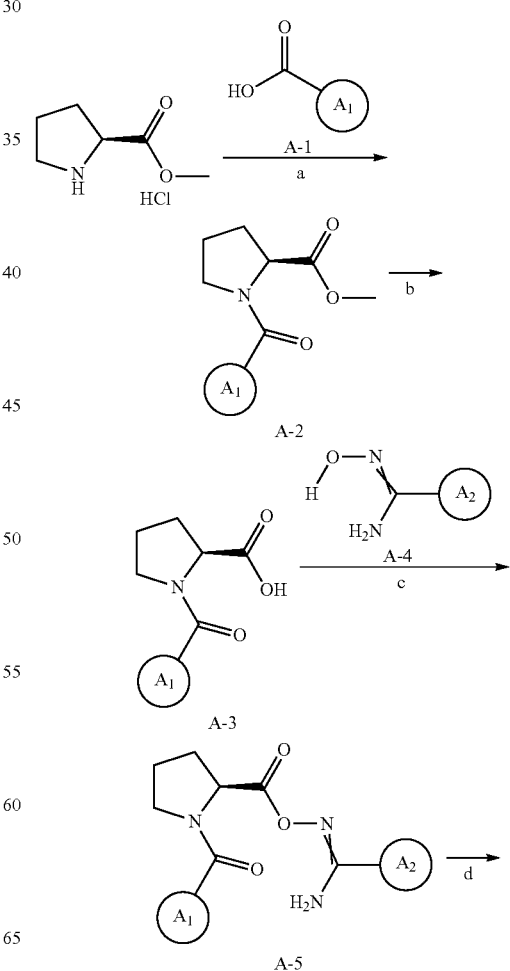

Reaction Scheme A

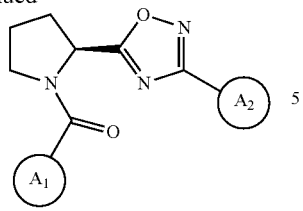

In case A₃ is a [1,2,4]oxadiazol-3,5-diyl-, compounds of formula (I) may in general be prepared as illustrated in Reaction Scheme A and B. Compounds of structure A-1 can be coupled with commercially available L-proline methyl ester HCl using standard amide coupling conditions such as EDC/HOBt, HOAt/DCC, TBTU, HATU or PyBOP in the presence of a base such as DIPEA or Et₃N at rt in a suitable solvent such as DCM, DMF, MeCN or mixtures thereof (Step a, Reaction Scheme A). Saponification of the ester function of compounds of structure A-2 using methods known in the art such as treatment with base such as NaOH in a solvent or a solvent mixture such as EtOH/water or THF may afford the desired carboxylic acids of structure A-3 (Step b, Reaction Scheme A). Compounds of structure A-3 may be converted in a two step procedure to compounds of formula (I). First, coupling of a compound of structure A-3 with hydroxyamidine A-4 in the presence of coupling reagents such as EDC/HOBT, PyBOP, HATU, TBTU in the presence of a base such as DIPEA or Et₃N at rt in a suitable solvent such as DCM, DMF or mixture thereof to give intermediate acyl hydroxyamidines of structure A-5 (Step c, Reaction Scheme A). Second, the cyclization of compounds of structure A-5 in solvents such as dioxane or xylene may be achieved thermally in a temperature range from 60-100° C. for hours to days to obtain compounds of formula (I) (Step d, Reaction Scheme A).

Carboxylic acids A-1 are well known in the art and can be especially prepared following the procedures reported in WO2008069997, WO2008008517, WO2010048012, WO2010063662, WO2010063663, WO2011050198, WO2011050200 and WO2011050202. In addition, they may be prepared in analogy to the methods given in the experimental part.

Commercially available nitrile-derivatives may be reacted with hydroxylamine under neutral or basic conditions such as NEt₃, DIPEA, sodium carbonate, sodium hydrogencarbonate, sodium hydroxide, potassium tert-butoxide and the like in a suitable solvent (methanol, ethanol, etc) to obtain hydroxyamidine A-4. The reaction typically proceeds by allowing the reaction temperature to go from rt to a range of 65-80° C., for about 30 min to several days (see WO 2006/12349, Lucca et al J. Med. Chem. 1998, 2411-2423).

Reaction Scheme B

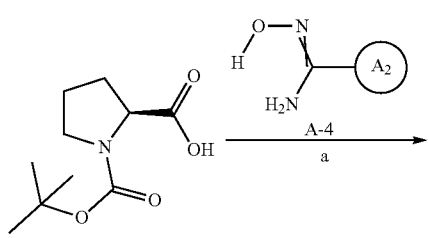

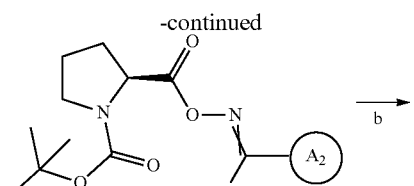

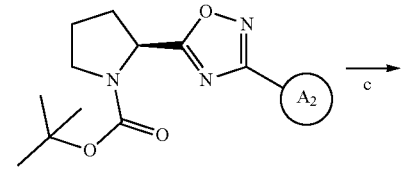

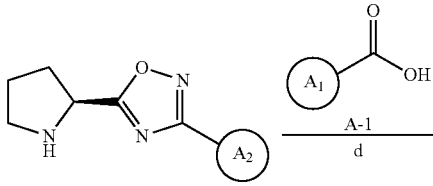

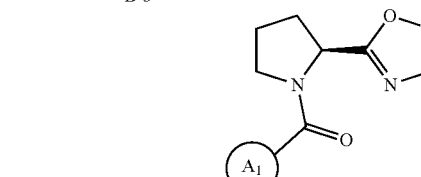

Compounds of formula (I), wherein A₃ is a [1,2,4]oxadiazol-3,5-diyl-, can alternatively be prepared as outlined in Reaction Scheme B. The commercially available Boc-L-proline may be coupled with hydroxyamidines of structure A-4 to obtain acyl-hydroxyamidines of structure B-1 (Step a, Reaction Scheme B). The coupling reaction may be promoted by coupling reagents outlined in Step c, Reaction Scheme A. Cyclization is performed as outlined in Step d, Reaction Scheme A, leading to compounds of structure B-2 (Step b, Reaction Scheme B). Boc-deprotection of compounds of structure B-2 by using standard methods such as treatment with 4N HCl in dioxane or with TFA leads to compounds of structure B-3 (Step c, Reaction Scheme B). Reaction of compounds of B-3 with acids of structure A-1 in the presence of coupling reagents, base and solvents as outlined in Step a, Reaction Scheme A furnishes compounds of formula (I) (Step d, Reaction Scheme B).

Reaction Scheme C

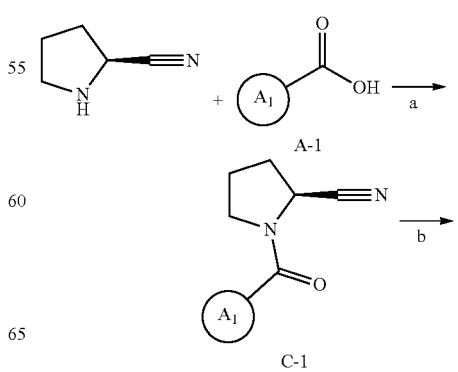

-continued

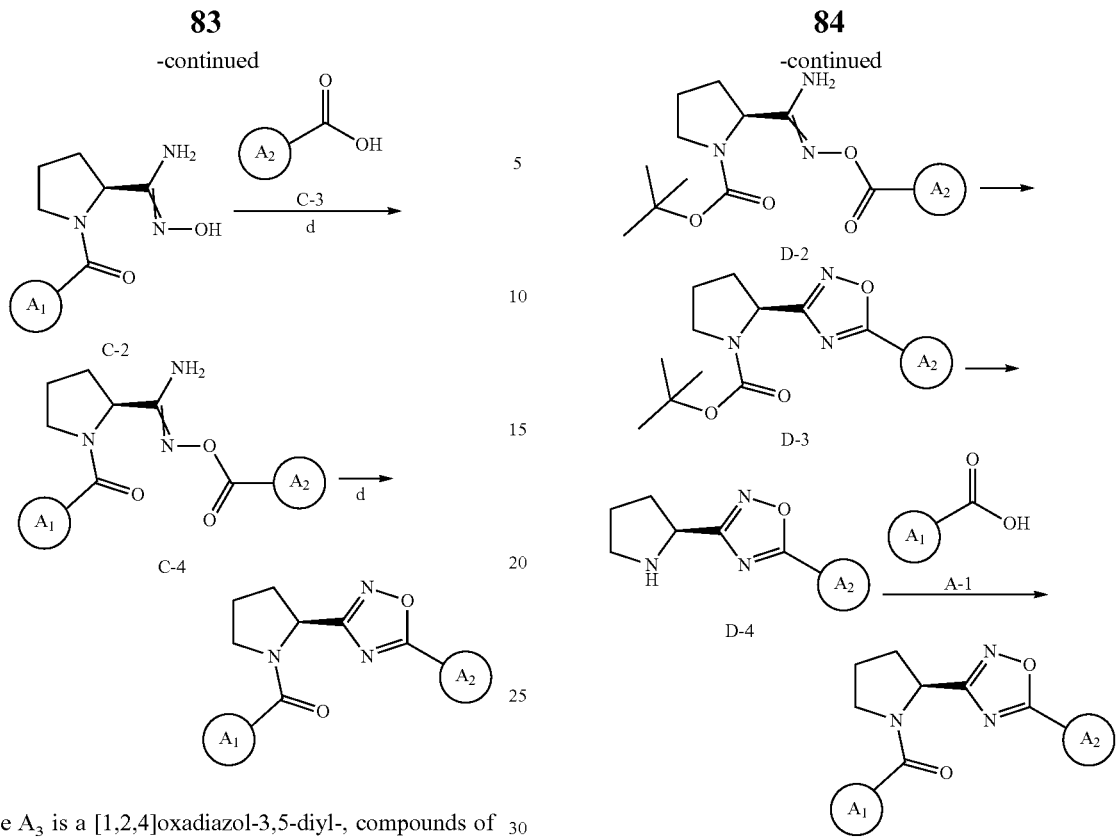

In case A₃ is a [1,2,4]oxadiazol-3,5-diyl-, compounds of formula (I) may in general be prepared as illustrated in Reaction Schemes C and D.

In Reaction Scheme C, the synthesis starts with the coupling of commercially available (S)-pyrrolidine-2-carbonitrile and carboxylic acids of structure A-1, in the presence of coupling reagents, base and solvents as mentioned in Step a, Reaction Scheme A. The intermediates C-1 are converted to hydroxyamidines of structure C-2 in the presence of hydroxylamine, base such as NaHCO₃ in solvents such as MeOH. The acyl-hydroxyamidine intermediates of structure C-4 can be synthesized by reacting compounds of structure C-2 with commercially available carboxylic acids C-3, in the presence of coupling reagents, base and solvents such as mentioned in Step c, Reaction Scheme A. The cyclization of compounds of structure C-4 can be achieved thermally as mentioned in Step d, Reaction Scheme A, to yield compounds of formula (I).

Reaction Scheme D

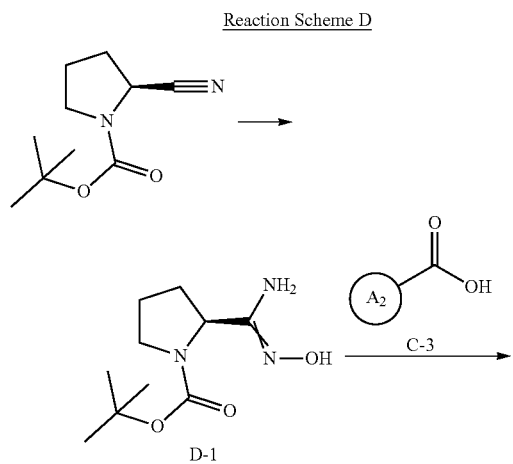

Compounds of formula (I), wherein A₃ is a [1,2,4]oxadiazol-3,5-diyl-, can alternatively be prepared as outlined in Reaction Scheme D.

The commercially available (S)-1-Boc-pyrrolidine-2-carbonitrile can be converted to hydroxyamidine of structure D-1, using methods described in Step b, Reaction Scheme C. The acyl-hydroxyamidines of structure D-2 can be synthesized from coupling compounds of structure D-1 with compounds of structure C-3 as depicted in Step c, Reaction Scheme A. The cyclization of compounds of structure D-2 can be achieved thermally as mentioned in Step d, Reaction Scheme A to yield compounds of structure D-3. Boc-deprotection using standard methods as mentioned in Step c, Scheme B lead to compounds D-4. Reaction of amines D-4 with carboxylic acids of structure A-1, in the presence of coupling reagents, base and solvents as outlined in Step a, Reaction Scheme A furnishes compounds of formula (I).

In case A₃ is an isoxazol-3,5-diyl-, compounds of formula (I) may in general be prepared as illustrated in Reaction Scheme E (Step a to d).

The commercially available Boc-L-prolinal was converted to the alkyne-derivative E-1 using methods described in patent WO2010/114978. Isoxazoles E-3 can be synthesized by click chemistry of alkynes E-1 with oximes E-2 in the presence of chloramine T trihydrate in solvents such as MeOH at elevated temperature of about 70° C. (Step b, Reaction Scheme E). Oximes of structure E-2 can be synthesized from the corresponding aldehyde in the presence of hydroxylamine HCl and NaOAc in solvents such as MeOH. Boc-deprotection using standard methods such as mentioned in Step c, Scheme B lead to compounds of structure E-4. Reaction of amines E-4 with acid A-1, in the presence of coupling reagents, base and solvents as outlined in, Step a, Reaction Scheme A furnishes compounds of formula (I).

Reaction Scheme E

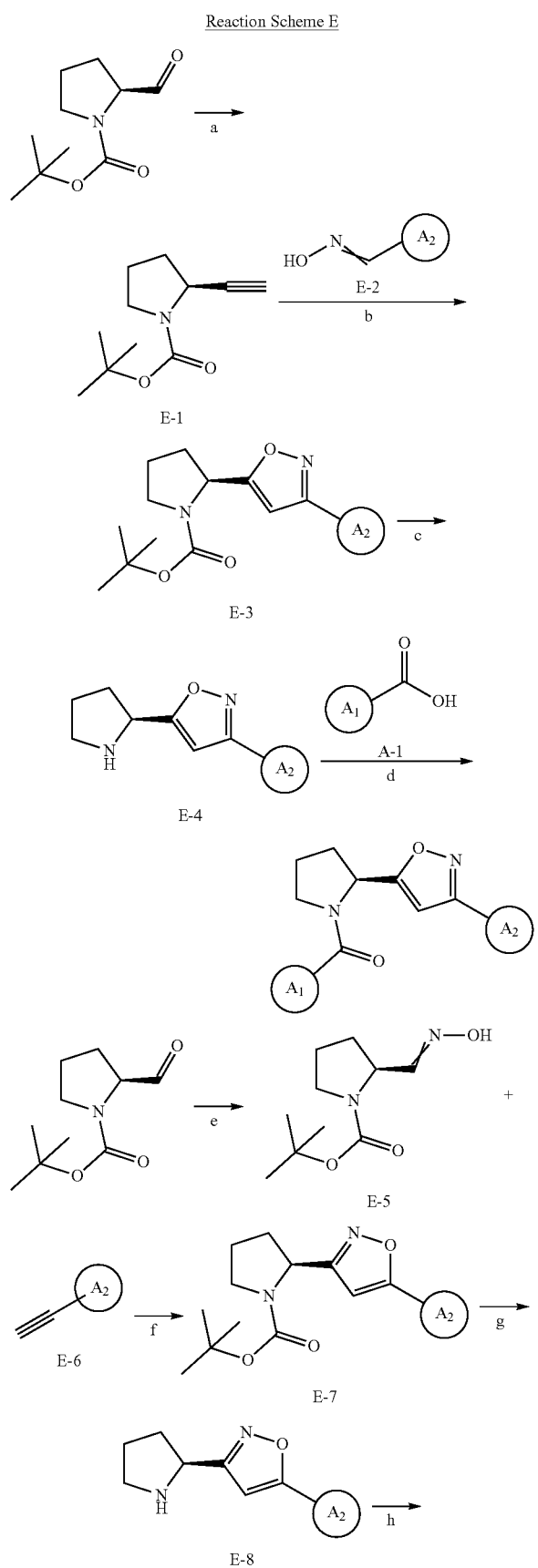

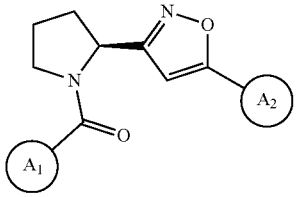

Alternatively, in case $A_3$ is an isoxazol-3,5-diyl-, compounds of formula (I) may in general be prepared as illustrated in Reaction Scheme E (Step e to h). The commercially available Boc-L-prolinal was converted to the oxime E-5 using hydroxylamine HCl and NaOAc in solvents such as MeOH. Isoxazoles E-7 can be synthesized by click chemistry of alkynes E-6 with oximes E-5 in the presence of chloramine T trihydrate in solvents such as MeOH at elevated temperature of about 70° C. (Step f, Reaction Scheme E). Boc-deprotection using standard methods such as mentioned in Step c, Scheme B lead to compounds of structure E-8. Reaction of amines E-8 with acid A-1, in the presence of coupling reagents, base and solvents as outlined in Step a, Reaction Scheme A furnishes compounds of formula (I).

In case $A_3$ is a [1,3,4]-oxadioxazol-2,5-diyl- compounds of formula (I) may in general be prepared as illustrated in Reaction Schemes F and G.

The commercially available Boc-L-proline can be coupled with hydrazides of structure F-1, either commercially available or synthesized from commercially available carboxylic acid or esters according to procedures known by persons skilled in the art to yield derivatives F-2. Cyclization to 1,3,4,dioxazoles can be achieved in presence of Burgess' reagent, in a solvent such as dioxane at elevated temperatures of 110-120° C. under microwave irradiation for several minutes up to hours. Boc-deprotection using standard methods such as mentioned in Step c, Scheme B leads to compounds of structure F-4. Amide coupling of amine F-4 with acids of A-1, in the presence of coupling reagents, base and solvents as outlined in Step d, Reaction Scheme B furnishes compounds of formula (I).

Reaction Scheme F

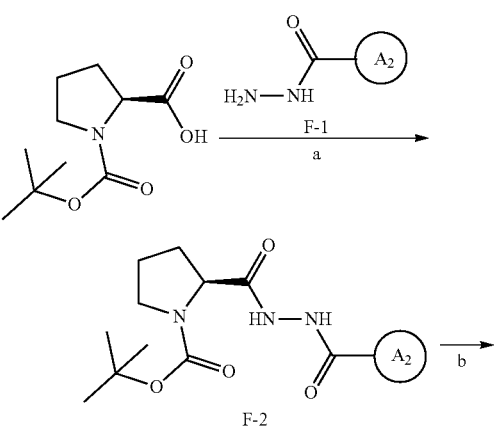

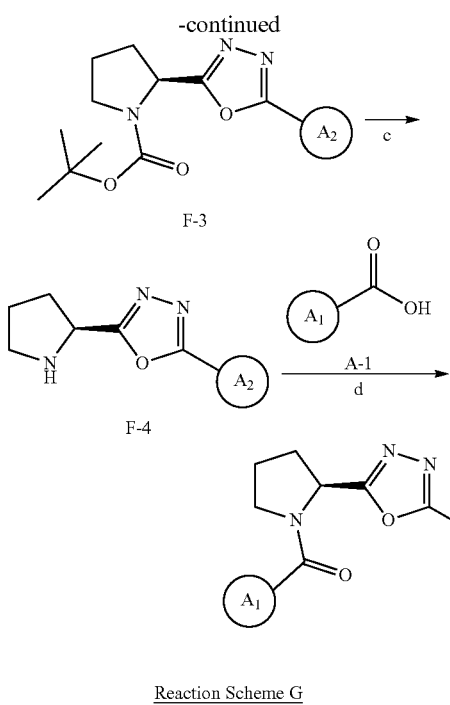

Reaction Scheme G

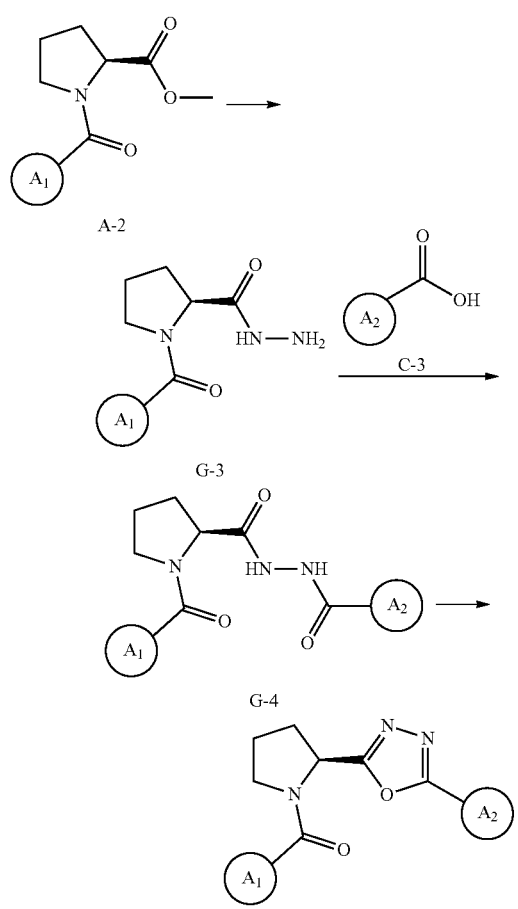

Compounds of formula (I), wherein $A_3$ is a [1,3,4]-oxadioxazol-2,5-diyl-, can alternatively be prepared as outlined in Reaction Scheme G.

Methylesters of structure A-2 (see Scheme A) can be converted to hydrazides of structure G-3, using an excess of hydrazine in the presence or absence of coupling reagents such as TBTU or DMAP and base such as DIPEA in solvents such as DMF at rt.

Intermediates of structure G-4 can be synthesized by reacting compounds of structure G-3 with carboxylic acids C-3 in the presence of coupling reagents, base and solvents such as mentioned in Step c, Reaction Scheme A. Cyclization to a compound of formula (I) can be achieved in presence of Burgess' reagent, in solvents such as dioxane at elevated temperatures of about 120° C. under microwave irradiation for several minutes up to hours.

Reaction Scheme H

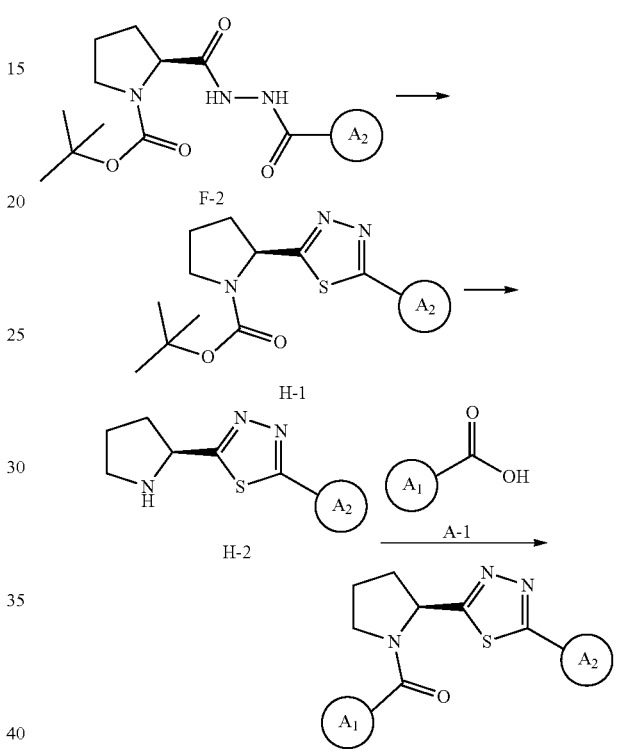

In case $A_3$ is a [1,3,4]-thiadiazol-2,5-diyl-, compounds of formula (I) may in general be prepared as illustrated in Reaction Scheme H.

Intermediates of structure F-2 can be converted to thiadiazoles of structure H-1 in the presence of Lawesson's reagent in solvents such as dioxane at elevated temperature of about 120° C.

Boc-deprotection using standard methods such as mentioned in Step c, Scheme B leads to compounds H-2. Reaction of amines of structure H-2 with carboxylic acids of structure A-1, in the presence of coupling reagents, base and solvents as outlined in Step d, Reaction Scheme B furnishes compounds of formula (I).

Reaction Scheme I

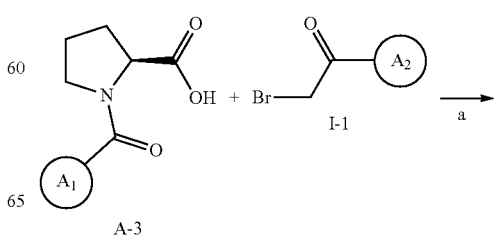

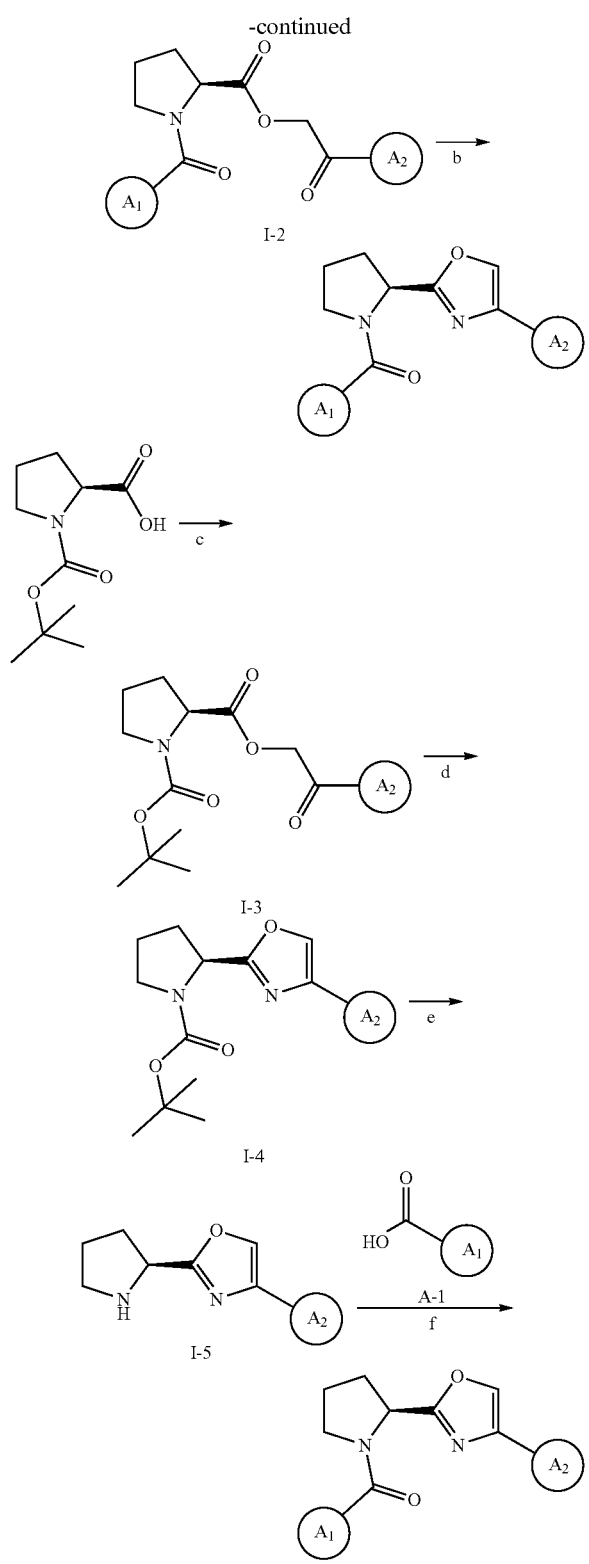

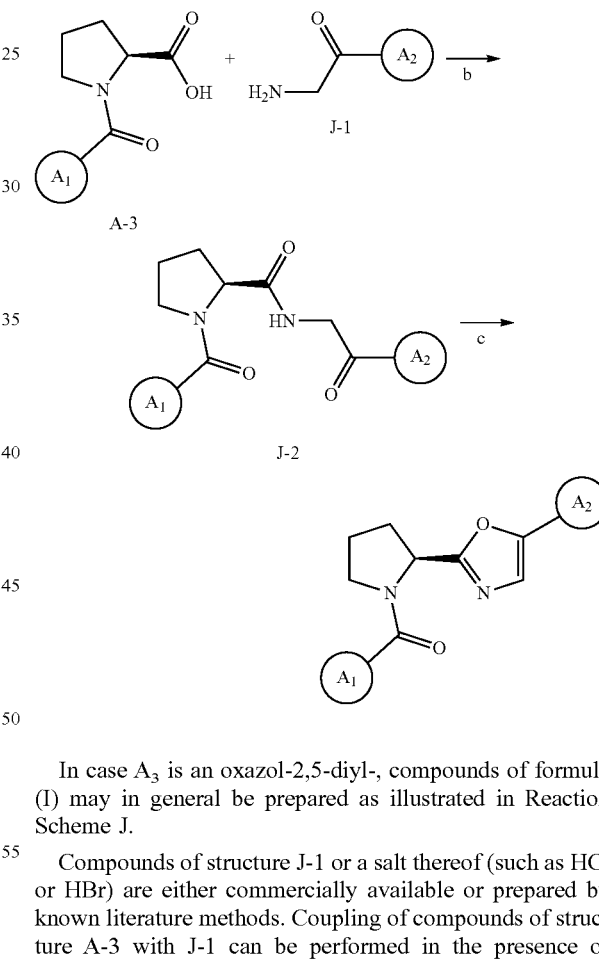

or elevated temperature. Cyclization can be achieved in the presence of acetamide and catalytic amounts of $BF_3.Et_2O$ in solvents or solvent mixtures such as diethylether and/or o-xylene at elevated temperature of about 120-140° C. to yield compounds of formula (I).

Alternatively, Boc-L-proline can react with compounds of structure I-1 to form compounds of structure I-3 under basic conditions such as $K_2CO_3$ in solvents such as DMF at ambient or elevated temperature. Cyclization can be performed as outlined in Step b, Reaction Scheme I, or in presence of ammonium acetate in acetic acid at elevated temperature (see U.S. Pat. No. 6,660,759, 2003), leading to compounds of structure I-4. Boc-deprotection using standard methods such as mentioned in Step c, Scheme B leads to compounds of structure I-5. Amide coupling of amines of structure I-5 with acids of structure A-1, in the presence of coupling reagents, base and solvents as outlined in Step d, Reaction Scheme B furnishes compounds of formula (I).

In case $A_3$ is an oxazol-2,4-diyl-, compounds of formula (I) may in general be prepared as illustrated in Reaction Scheme I, in analogy to WO 2003/002559.

Compounds of structure I-1 are either commercially available or prepared by known literature methods from the corresponding methyl-ketone-analog. Compounds of structure I-2 can be synthesized from A-3 and I-1 in the presence of base such as $K_2CO_3$, in solvents such as DMF at ambient In case $A_3$ is an oxazol-2,5-diyl-, compounds of formula (I) may in general be prepared as illustrated in Reaction Scheme J.

Compounds of structure J-1 or a salt thereof (such as HCl or HBr) are either commercially available or prepared by known literature methods. Coupling of compounds of structure A-3 with J-1 can be performed in the presence of coupling reagents, base and solvents such as mentioned in Step c, Reaction Scheme A. Intermediate J-2 can be cyclized to compounds of formula (I) in the presence of polyphosphoric acid at elevated temperature of about 150° C. adapted from the procedure described in WO2003/002559 or by using trifluoromethanesulfonic anhydride in the presence of pyridine in DCM at ambient temperature (see US 2006-19975).

Reaction Scheme K

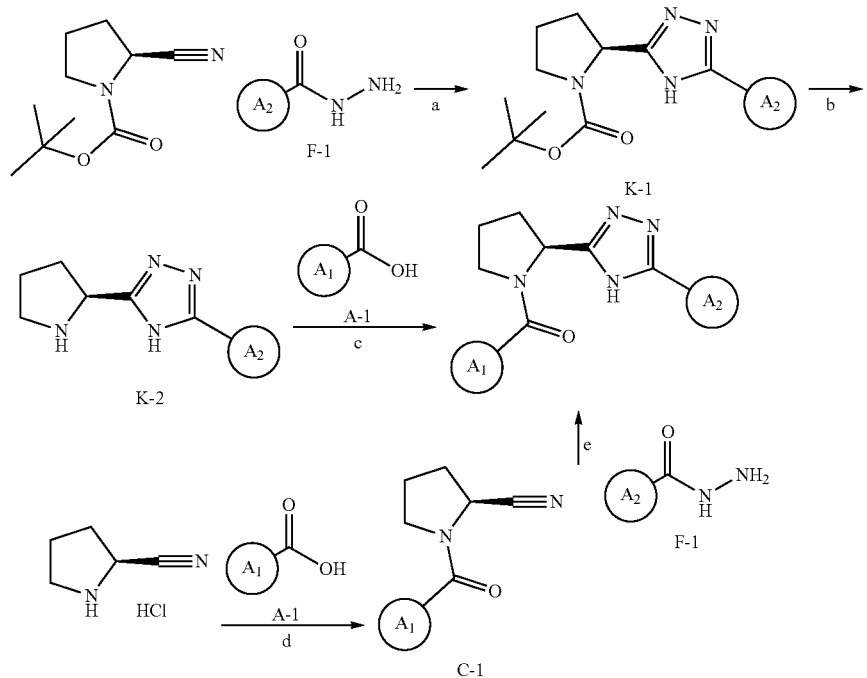

In case $A_3$ is a [1,2,4]triazol-3,5-diyl-, compounds of formula (I) may in general be prepared as illustrated in Reaction Scheme K.

Compounds of structure K-1 can be synthesized from (S)-1-Boc-pyrrolidine-2-carbonitrile and hydrazides of structure F-1 in presence of a base such as $K_2CO_3$ in a solvent such as n-butanol at elevated temperature of about 125° C. or under microwave irradiation at a temperature of about 150° C. Boc-deprotection using standard methods such as mentioned in Step c, Scheme B leads to compounds of structure K-2. Amide coupling of amines of structure K-2 with acids of structure A-1, in the presence of coupling reagents, base and solvents as outlined in Step d, Reaction Scheme B furnishes compounds of formula (I).

Alternatively, the commercially available (S)-pyrrolidine-2-carbonitrile HCl can be coupled with carboxylic acids of structure A-1 to intermediate C-1, in the presence of coupling reagents, base and solvents as outlined in Step a, Reaction Scheme A. Reaction of nitriles of structure C-1 with hydrazides of structure F-1 in the presence of base such as $K_2CO_3$ in solvent such as n-BuOH at elevated temperature of about 160° C. in presence or absence of microwave irradiation furnishes compounds of formula (I).

Reaction Scheme L

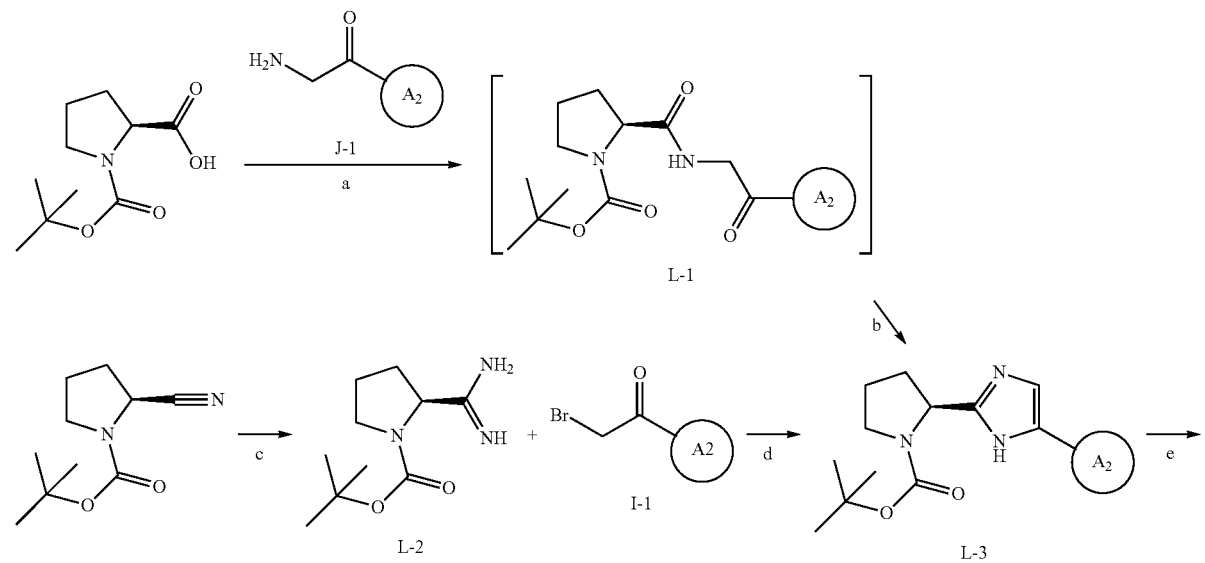

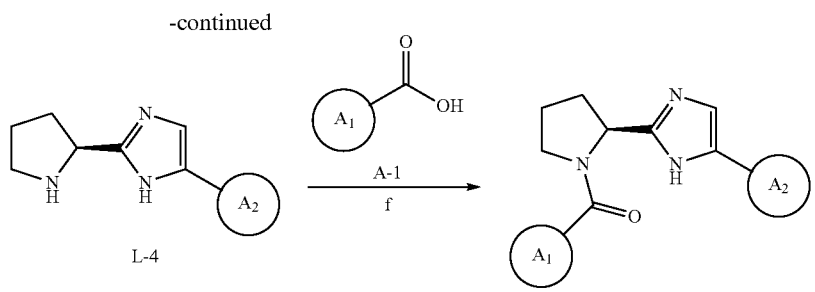

In case A₃ is a 1H-imidazol-2,5-diyl-, compounds of formula (I) may in general be prepared as illustrated in Reaction Scheme L.

Synthesis can be performed in accordance to published methods (WO2008/144380 for Step a and b). The commercially available Boc-L-proline can be coupled with compounds of structure J-1 in the presence of coupling reagents, base and solvents as outlined in Step d, Reaction Scheme B furnishes intermediates of structure L-1, which may undergo cyclization to compounds of structure L-3, in the presence of ammonium acetate in solvents such as acetic acid or mixture of acetic acid and xylene at elevated temperatures of about 110° C. Boc-deprotection using standard methods such as mentioned in Step c, Scheme B leads to compounds of structure L-4. Amide coupling of amines of structure L-4 with carboxylic acids of structure A-1, in the presence of coupling reagents, base and solvents as outlined in Step d, Reaction Scheme B furnishes compounds of formula (I).

Alternatively, the commercially available (S)-1-Boc-pyrrolidine-2-carbonitrile can be converted to the amidine L-2 in the presence of a base such as NaOMe and ammonium bromide in solvents such as MeOH at ambient temperature. In a two step reaction compounds of structure L-2 can react with compounds of structure I-1 to compounds of structure L-3, in presence of a base such as K₂CO₃, in solvents such as DMF at ambient temperature. Following Step e and f, as mentioned above, leads to compounds of formula (I).

Reaction Scheme M

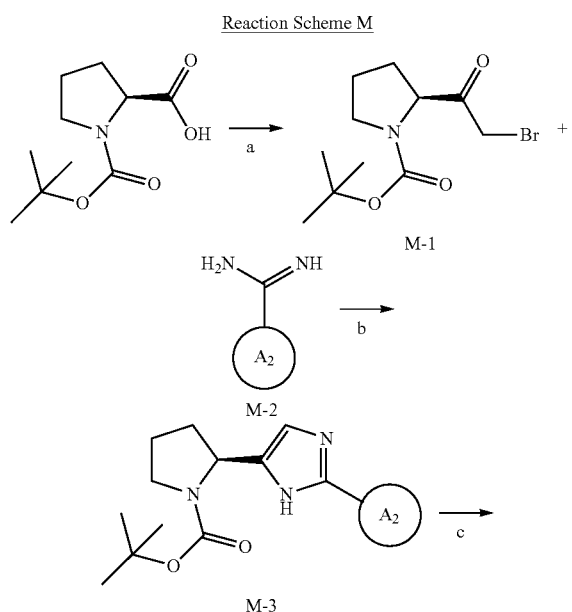

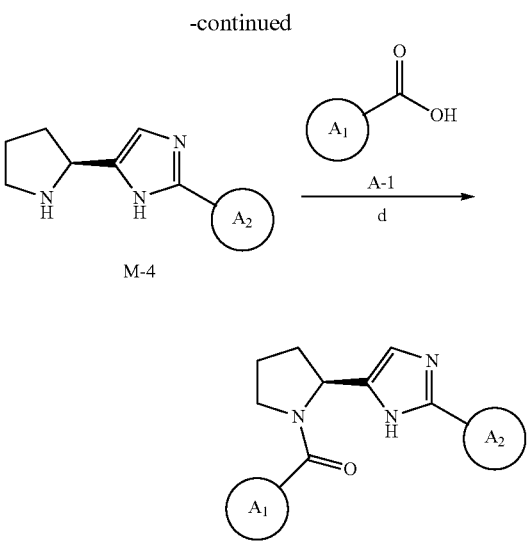

In case A₃ is a 1H-imidazol-2,5-diyl-, compounds of formula (I) may in general be prepared as illustrated in Reaction Scheme M.

Compounds of structure M-1 are prepared by known literature methods (US 2008-300279, WO2012/39717) from the corresponding commercially available Boc-L-proline. In a two step reaction, compounds of structure M-1 can react with amidine of structure M-2 to compounds of structure M-3, in presence of a base such as K₂CO₃, in solvents such as DMF at ambient temperature. Boc-deprotection using standard methods such as mentioned in Step c, Scheme B leads to compounds of structure M-4. Amide coupling of amines of structure M-4 with carboxylic acids of structure A-1, in the presence of coupling reagents, base and solvents as outlined in Step d, Reaction Scheme B furnishes compounds of formula (I).

Reaction Scheme N

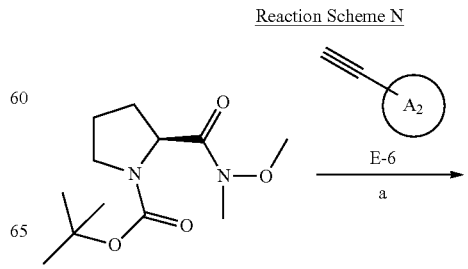

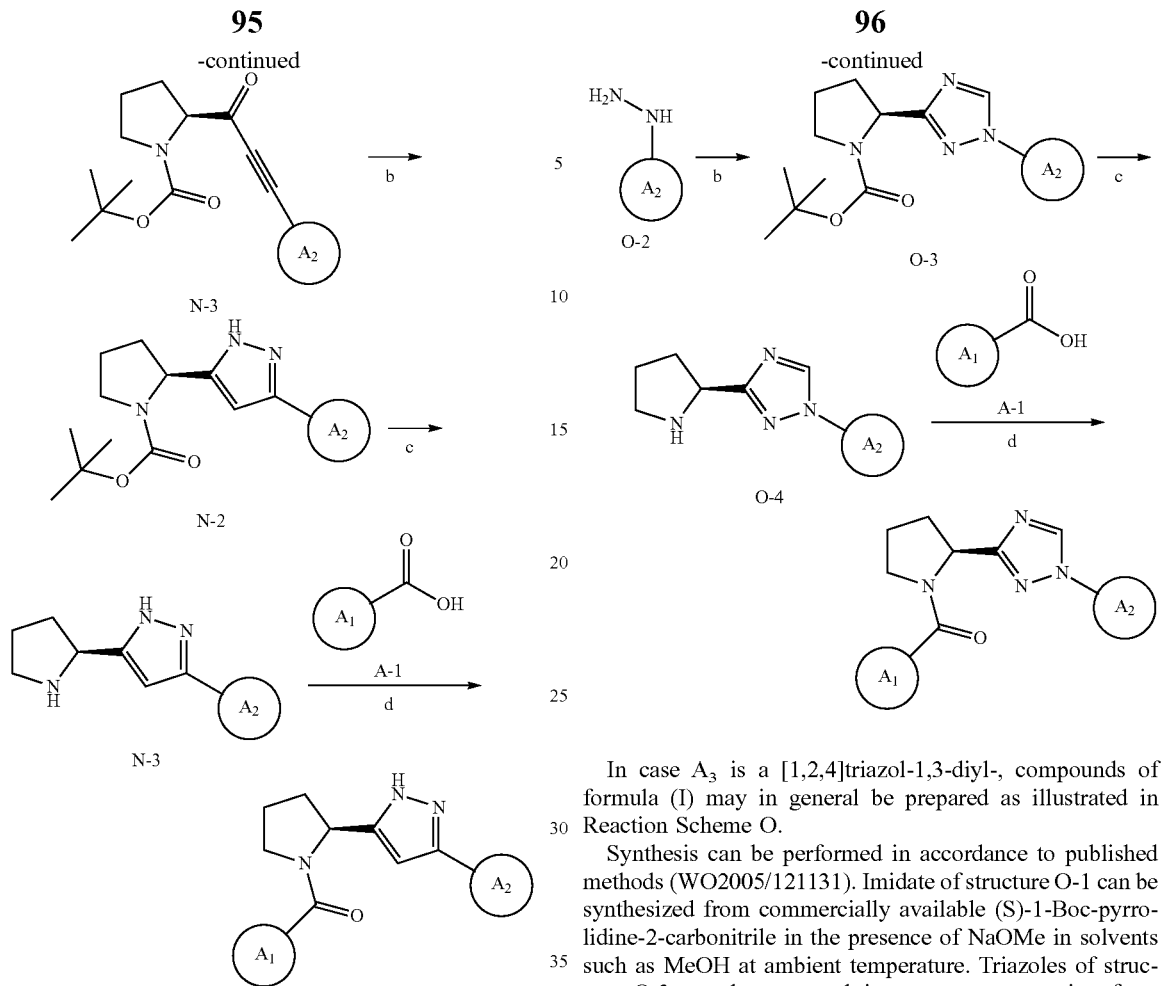

In case $A_3$ is a 1H-pyrazol-3,5-diyl-, compounds of formula (I) may in general be prepared as illustrated in Reaction Scheme N.

Synthesis can be performed in accordance to published methods (WO2008/144380). Commercially available N-Boc-L-proline N'-methoxy-N'-methylamide can be converted to alkyne N-1 in the presence of alkyne E-6 and ethylmagnesium bromide in THF at 0° C. to rt. Pyrazoles of structure N-2 can be synthesized from compounds of structure N-1 in the presence of hydrazine, in solvents such as EtOH at elevated temperature of about 80° C. Boc-deprotection using standard methods such as mentioned in Step c, Scheme B leads to compounds of structure N-3. Amide coupling of amines of structure N-3 with carboxylic acids of structure A-1, in the presence of coupling reagents, base and solvents as outlined in Step d, Reaction Scheme B furnishes compounds of formula (I).

In case $A_3$ is a [1,2,4]triazol-1,3-diyl-, compounds of formula (I) may in general be prepared as illustrated in Reaction Scheme O.

Synthesis can be performed in accordance to published methods (WO2005/121131). Imidate of structure O-1 can be synthesized from commercially available (S)-1-Boc-pyrrolidine-2-carbonitrile in the presence of NaOMe in solvents such as MeOH at ambient temperature. Triazoles of structure O-3 can be prepared in a two step reaction from compound of structure O-1 and hydrazine of structure O-2 in the presence of base such as trietyhlamine in solvent such as MeOH at rt for hours or several days and subsequent addition of triethyl orthoformate in pyridine and heating to 120° for several hours. Boc-deprotection using standard methods such as mentioned in Step c, Scheme B leads to compounds of structure O-4. Amide coupling of amines of structure O-3 with carboxylic acids of structure A-1, in the presence of coupling reagents, base and solvents as outlined in Step d, Reaction Scheme B furnishes compounds of formula (I).

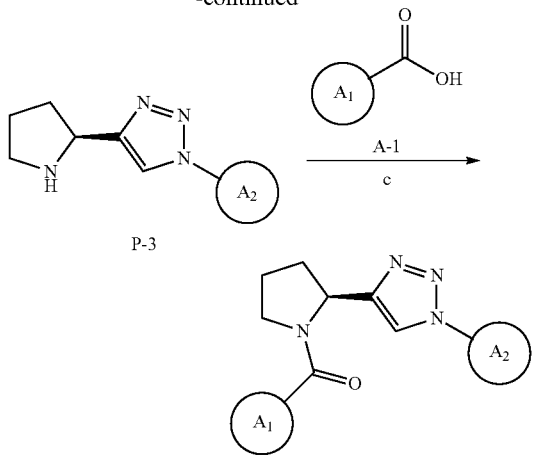

In case A₃ is a [1,2,3]-triazol-1,4-diyl-, compounds of formula (I) may in general be prepared in accordance to published methods (WO2005/121131), as illustrated in Reaction Scheme P; see experimental part for details.

be coupled with hydroxyamidines of structure A-4 to obtain acyl-hydroxyamidines of structure Q-2 (Step b, Reaction Scheme Q). The coupling reaction may be promoted by coupling reagents outlined in Step c, Reaction Scheme A. Cyclization is performed as outlined in Step d, Reaction Scheme A, leading to compounds of structure Q-3 (Step c, Reaction Scheme Q). Boc-deprotection of compounds of structure Q-3 by using standard methods such as treatment with 4N HCl in dioxane or with TFA leads to compounds of structure Q-4 (Step d, Reaction Scheme Q). Reaction of compounds of Q-4 with acids of structure A-1 in the presence of coupling reagents, base and solvents as outlined in Step a, Reaction Scheme A furnishes compounds of formula (I) (Step e, Reaction Scheme Q).

Alternatively, compounds of structure A-1 can be converted into the corresponding acid chloride (using standard reagents such as thionylchloride) which then react with the commercially available 2-methyl-L-proline HCl in presence of base such as TEA in solvents such as DCM, pyridine or mixtures thereof to compounds of structure Q-5. Compounds of structure Q-5 may be converted in a two step procedure to compounds of formula (I). First, coupling of a compound of structure Q-5 with hydroxyamidine A-4 in the Reaction Scheme Q

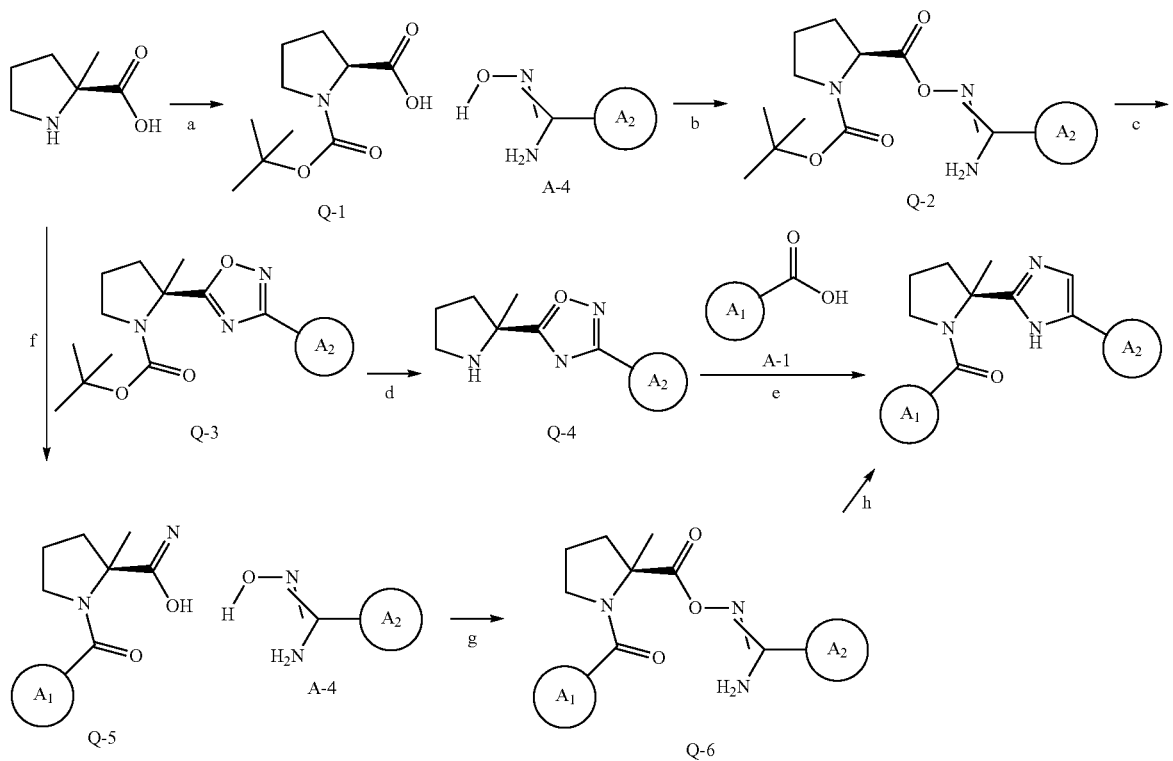

Compounds of formula (I), wherein R is methyl can be prepared from commercially available 2-methyl-proline or derivatives thereof in analogy to the methods given above. For example when A₃ is a [1,2,4]oxadiazol-3,5-diyl-, compounds of formula (I) may be prepared as outlined in Reaction Scheme Q. The commercially available 2-methyl-L-proline HCl can be Boc-protected with Boc₂O in the presence of TEA, DIPEA or Na₂CO₃ in solvents such as MeCN, DCM, THF and H₂O or mixtures thereof at rt within hours to days. The obtained compound of structure Q-1 may presence of coupling reagents such as EDC/HOBT, PyBOP, HATU, TBTU in the presence of a base such as DIPEA or TEA at rt in a suitable solvent such as DCM, DMF or mixture thereof to give intermediate acyl hydroxyamidines of structure Q-6 (Step g, Reaction SchemeQ). Second, the cyclization of compounds of structure Q-6 in solvents such as dioxane, xylene and pyridine or mixtures thereof may be achieved thermally in a temperature range from 60-100° C. for hours to days to obtain compounds of formula (I) (Step h, Reaction Scheme Q).

Reaction Scheme R

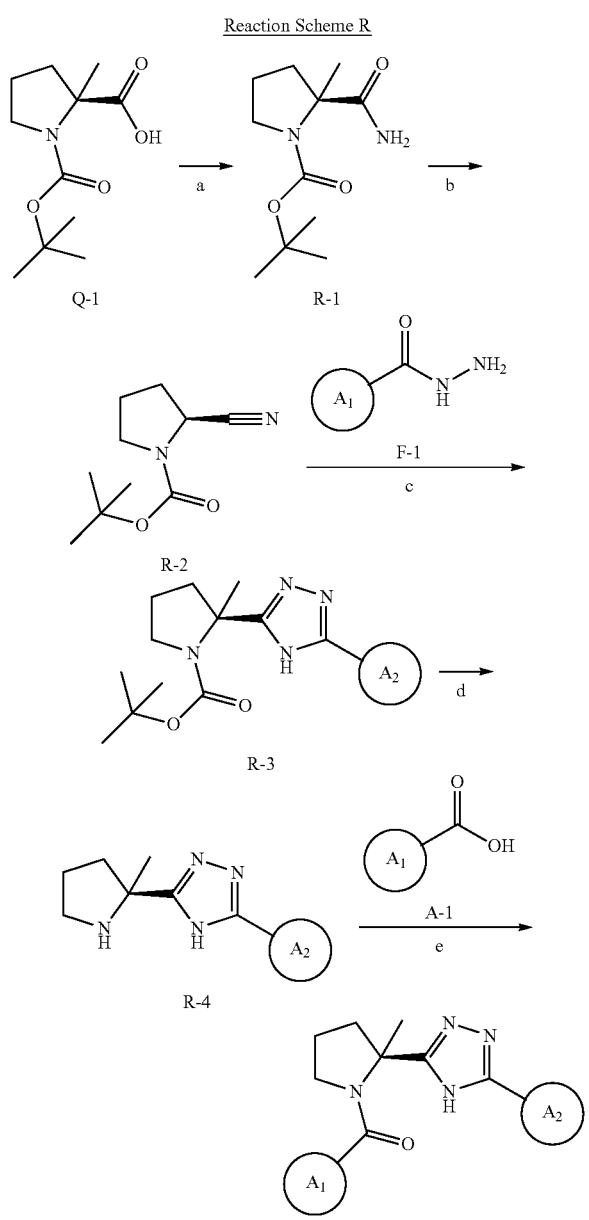

Compounds of formula (I), wherein R is methyl and $A_3$ is a [1,2,4]triazol-3,5-diyl- group, can for example be prepared as outlined in Reaction Scheme R. Compounds of structure R-1 can be synthesized from Q-1 by activation of ethyl chloroformate in the presence of base such as TEA or DIPEA in THF at around 0° C., followed by the addition of ammonia (Step a, Scheme R) at 0° C. to rt. Reduction of compound R-1 to nitrile of structure R-2 may be performed with trifluoroacetic anhydride in presence of base such as TEA in solvents such as DCM at temperature of about 0° C. to rt (Step b, Scheme R). Compounds of structure R-4 can be synthesized from nitrile R-2 and hydazides of structure F-1 in presence of a base such as $K_2CO_3$ in a solvent such as n-butanol at elevated temperature of about 125° C. for days or under microwave irradiation at a temperature of about 150° C. (Step c, Scheme R). Boc-deprotection using standard methods such as mentioned in Step c, Scheme B leads to compounds of structure R-4. Amide coupling of amines of structure R-4 with acids of structure A-1, in the presence of coupling reagents, base and solvents as outlined in Step d, Reaction Scheme B furnishes the compounds of formula (I).

EXPERIMENTAL PART

I. Chemistry

All temperatures are stated in ° C. Commercially available starting materials were used as received without further purification. Unless otherwise specified, all reactions were carried out under an atmosphere of nitrogen or argon. Compounds were purified by flash column chromatography on silica gel or by preparative HPLC. Compounds described in the invention are characterized by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.

LC-MS with Acidic Conditions
Method A:
Agilent 1100 series with mass spectrometry detection (MS: Finnigan single quadrupole). Column: Zorbax SB-aq (3.5 μm, 4.6×50 mm). Conditions: MeCN [eluent A]; water+ 0.04% TFA [eluent B]. Gradient: 95% B→5% B over 1.5 min (flow: 4.5 mL/min). Detection: UV/Vis+MS.

Method B:
Agilent 1100 series with mass spectrometry detection (MS: Finnigan single quadrupole). Column: Waters XBridge C18 (2.5 μm, 4.6×30 mm). Conditions: MeCN [eluent A]; water+0.04% TFA [eluent B]. Gradient: 95% B→5% B over 1.5 min (flow: 4.5 mL/min). Detection: UV/Vis+MS.

LC-MS with Basic Conditions
Method C:
Agilent 1100 series with mass spectrometry detection (MS: Finnigan single quadrupole). Column: Zorbax Extend C18 (5 μm, 4.6×50 mm). Conditions: MeCN [eluent A]; 13 mmol/L $NH_3$ in water [eluent B]. Gradient: 95% B→5% B over 1.5 min (flow: 4.5 mL/min). Detection: UV/Vis+MS.

Method D:
Agilent 1100 series with mass spectrometry detection (MS: Finnigan single quadrupole). Column: Waters XBridge C18 (5 μm, 4.6×50 mm). Conditions: MeCN [eluent A]; 13 mmol/L $NH_3$ in water [eluent B]. Gradient: 95% B→5% B over 1.5 min (flow: 4.5 mL/min). Detection: UV/Vis+MS.

Preparative HPLC with Acidic Conditions
Method E:
Column: Waters XBridge (10 μm, 75×30 mm). Conditions: MeCN [eluent A]; water+0.5% HCOOH [eluent B]; Gradient: 90% B→5% B over 6.4 min (flow: 75 mL/min). Detection: UV/Vis+MS.

Method F:
Column: Waters Atlantis (10 μm, 75×30 mm). Conditions: MeCN [eluent A]; water+0.5% HCOOH [eluent B]; Gradient: 90% B→5% B over 6.4 min (flow: 75 mL/min). Detection: UV/Vis+MS.

Preparative HPLC with Basic Conditions
Method G:
Column: Waters XBridge (10 μm, 75×30 mm). Conditions: MeCN [eluent A]; water+0.5% $NH_4OH$ (25% aq.) [eluent B]; Gradient: 90% B→5% B over 6.5 min (flow: 75 mL/min). Detection: UV/Vis+MS Abbreviations (as Used Hereinbefore or Hereinafter):
aq. aqueous
atm atmosphere BSA bovine serum albumin
Boc butyloxycarbonyl
Boc$_2$O di-tert-butyl dicarbonate
Burgess reagent methyl N-(triethylammoniumsulfonyl)carbamate
CDI carbonyl diimidazole
Chloramine T trihydrate N-chloro-p-toluenesulfonamide sodium salt
d days
dba dibenzylidene acetone
DCC dicyclohexyl carbodiimide
DCM dichloromethane
DIPEA diisopropyl-ethylamine, Hünig's base, ethyl-diisopropylamine
DMAP 4-dimethylaminopyridne
DMCDA trans-N,N'-dimethylcyclohexane-1,2-diamine
DME 1,2-dimethoxyethane
DMF dimethylformamide
DMSO dimethylsulfoxide
EDC N-(3-dimethylaminopropyl)-N'-ethyl-carbodiimide
eq. equivalent(s)
Et ethyl
EtOAc ethyl acetate
Ex. example(s)
FC flash chromatography
GM general method
h hour(s)
hex hexane
hept heptane
HOBt 1-hydroxybenzotriazole
HPLC high performance liquid chromatography
KO$^t$Bu potassium tert-butoxide
Lawesson's reagent 2,4-bis(4-methoxyphenyl)-1,3,2,4-dithiadiphosphetane-2,4-dithione
LC-MS liquid chromatography mass spectrometry
Me methyl
MeCN acetonitrile
MeOH methanol
min minute(s)
NaOAc sodium acetate
OAc acetate
org. organic
Pd(dppf)Cl$_2$.DCM [1,1'-bis(diphenylphosphino)-ferrocene] dichloropalladium (II) complex with dichloromethane
Pd(PPh$_3$)$_4$ tetrakis(triphenylphosphine)palladium
Pd(PPh$_3$)$_2$Cl$_2$ bis(triphenylphosphine)palladiumchloride
Ph phenyl
PPh$_3$ triphenyl phosphine
prep. preparative
PyBOP benzotriazol-1-yl-oxy-tris-pyrrolidino-phosphonium-hexafluoro-phosphate
rt room temperature
rxn reaction
s second(s)
sat. saturated
SM starting material
TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
t$_R$ retention time Synthesis of Intermediate A-1

Compounds of structure A-1 were prepared in analogy to the procedure described in WO2008/069997. The addition of DMCDA is optional, but may alter the yield.

2-Fluoro-3-methyl-6-(2H-1,2,3-triazol-2-yl)benzoic acid (A-1-1)

Cs$_2$CO$_3$ (6.98 g, 21.4 mmol) was added portionwise to a rt solution of 2-fluoro-6-iodo-3-methyl-benzoic acid (3.0 g, 10.7 mmol) in DMF (15 mL) followed by 1H-1,2,3-triazole (1.24 mL, 21.4 mmol) and Cu(I)I (103 mg, 0.54 mmol) and the resulting blue suspension was stirred at 80° C. overnight. The rxn mixture was quenched with 2M aq. HCl and filtered through a celite plug before being extracted with DCM (3×). The combined org. layers were dried (Na$_2$SO$_4$), filtered and evaporated in vacuo to give the crude product that was purified by prep. HPLC (method E) to give the title compound A-1-1 as a pale yellow solid. LC-MS B: t$_R$=0.55 min; [M+H]$^+$=222.01.

Listed in Table 1 below are o-triazolocarboxylic or o-pyrazolocarboxylic acids of structure A-1, unless otherwise stated, prepared from the corresponding commercially available iodo-carboxylic acid according to the above procedure (see A-1-1), using 1H-1,2,3-triazole or 1H-pyrazole accordingly.

TABLE 1

| A-1 | Name | t$_R$ [min]; LC-MS Method | MS-data m/z [M + H]$^+$ |
|---|---|---|---|
| A-1-2 | 5-Methyl-2-(2H-1,2,3-triazol-2-yl)benzoic acid | 0.53; B | 204.13 |
| A-1-3 | 4-Methyl-2-(2H-1,2,3-triazol-2-yl)benzoic acid | 0.53; B | 204.23 |
| A-1-4 | 2-(2H-1,2,3-Triazol-2-yl)benzoic acid | 0.55; A | 190.08 |
| A-1-5 | 5-Chloro-2-(2H-1,2,3-triazol-2-yl)benzoic acid | 0.66; A | ($^{35}$Cl) 224.3 |
| A-1-6 | 4,5-Dimethyl-2-(2H-1,2,3-triazol-2-yl)benzoic acid | 0.59; B | 218.09 |
| A-1-7 | 5-Fluoro-2-(2H-1,2,3-triazol-2-yl)benzoic acid | 0.49; B | 208.32 |
| A-1-8[#] | 4-Fluoro-2-(2H-1,2,3-triazol-2-yl)benzoic acid | 0.51; B | 208.16 |
| A-1-9 | 2-Fluoro-3-methoxy-6-(2H-1,2,3-triazol-2-yl)benzoic acid | 0.48; B | 238.01 |
| A-1-10 | 5-Methoxy-2-(2H-1,2,3-triazol-2-yl)benzoic acid | 0.49; B | 220.19 |
| A-1-11[#‡] | 5-Methoxy-4-methyl-2-(2H-1,2,3-triazol-2-yl)benzoic acid | 0.68; A | 234.05 |
| A-1-12 | 4,5-Dimethoxy-2-(2H-1,2,3-triazol-2-yl)benzoic acid | 0.46; B | 250.03 |
| A-1-13[#] | 5-Methoxy-4-methyl-2-(1H-pyrazol-1-yl)benzoic acid | 0.58; B | 233.17 |
| A-1-14 | 6-Methyl-3-(2H-1,2,3-triazol-2-yl)picolinic acid | 0.30; B | 205.35 |
| A-1-15[#] | 3-Fluoro-2-(2H-1,2,3-triazol-2-yl)benzoic acid | 0.56; A | 208.08 |

TABLE 1-continued

| A-1 | Name | $t_R$ [min]; LC-MS Method | MS-data m/z [M + H]$^+$ |
|---|---|---|---|
| A-1-16 | 4-Chloro-2-(2H-1,2,3-triazol-2-yl)benzoic acid | 0.66; A | ($^{35}$Cl) 224.10 |
| A-1-17#‡ | 3,5-Dimethyl-2-(2H-1,2,3-triazol-2-yl)benzoic acid | 0.66; A | 218.10 |
| A-1-18 | 2-Methyl-6-(2H-1,2,3-triazol-2-yl)benzoic acid | 0.51; B | 204.22 |
| A-1-19 | 5-Cyano-2-(2H-1,2,3-triazol-2-yl)benzoic acid | 0.46; B | No ionization |
| A-1-20# | 4-Methoxy-2-(2H-1,2,3-triazol-2-yl)benzoic acid | 0.60; A | 220.05 |
| A-1-21 | 2-(2H-1,2,3-triazol-2-yl)-5-(trifluoromethyl)benzoic acid | 0.64; B | No ionization |
| A-1-22# | 2-(2H-1,2,3-triazol-2-yl)-4-(trifluoromethyl)benzoic acid | 0.72; A | No ionization |
| A-1-23 | 2-(2H-1,2,3-triazol-2-yl)-5-(trifluoromethoxy)benzoic acid | 0.66; B | 273.71 |
| A-1-24# | 4,5-Difluoro-2-(2H-1,2,3-triazol-2-yl)benzoic acid | 0.56; B | No ionization |
| A-1-25 | 4,5-Dimethyl-2-(1H-pyrazol-1-yl)benzoic acid | 0.59; B | 217.18 |
| A-1-26#‡ | 4-Fluoro-5-methoxy-2-(2H-1,2,3-triazol-2-yl)benzoic acid | 0.64; A | 238.1 |
| A-1-27 | 3,4-Dimethyl-2-(2H-1,2,3-triazol-2-yl)benzoic acid | 0.65; A | 218.23 |
| A-1-28 | 5-Methyl-2-(1H-pyrazol-1-yl)benzoic acid | 0.52; B | 203.22 |
| A-1-29# | 5-Methoxy-2-(1H-pyrazol-1-yl)benzoic acid | 0.49; B | 219.18 |
| A-1-30# | 3-Fluoro-2-(1H-pyrazol-1-yl)benzoic acid | 0.47; A | 207.19 |
| A-1-31 | 6-Methyl-3-(1H-pyrazol-1-yl)picolinic acid | 0.26; B | No ionization |
| A-1-32# | 4-Fluoro-2-(1H-pyrazol-1-yl)benzoic acid | 0.50; B | 207.20 |
| A-1-33#‡ | 5-Fluoro-3-methyl-2-(2H-1,2,3-triazol-2-yl)benzoic acid | 0.62; A | 222.15 |
| A-1-59#‡ | 4-Chloro-5-methoxy-2-(2H-1,2,3-triazol-2-yl)benzoic acid | 0.70; A | ($^{35}$Cl) 254.01 |
| A-1-61# | 3-Chloro-2-(2H-1,2,3-triazol-2-yl)benzoic acid | 0.61; A | No ionization |

Prepared from the corresponding o-bromo-carboxylic acid
‡Corresponding o-bromo-carboxylic acid was synthesized according to below mentioned procedures.

Synthesis of 2-bromo-substituted benzoic acids were performed in analogy to described methods (Tetrahedron Letters, 2009, 1267-1269, J. Org. Chem, 2007, 9786-9).

2-Bromo-5-methoxy-4-methyl-benzoic acid

Br$_2$ (0.74 mL, 14.4 mmol) was added to a rt suspension of 3-methoxy-4-methylbenzoic acid (2.00 g, 12 mmol) in acetic acid (15 mL) and water (15 mL), then the mixture was heated to 60° C. for 2 h. The mixture was allowed to reach rt and the solids were filtered off and rinsed with cold water (40 mL) to yield 2-bromo-5-methoxy-4-methylbenzoic acid as a white solid which was used further without purification. LC-MS A: $t_R$=0.76 min, [M+H]$^+$=no ionization. $^1$H NMR (DMSO) $\delta_H$: 7.49 (s, 1H), 7.29 (s, 1H), 3.82 (s, 3H), 2.17 (s, 3H).

2-Bromo-4-fluoro-5-methoxy-benzoic acid

The title compound was prepared from 4-fluoro-3-methoxybenzoic acid in analogy to the above described method. LC-MS A: $t_R$=0.72 min, [M+H]$^+$=no ionization. $^1$H NMR (DMSO) $\delta_H$: 13.52 (bs, 1H), 7.77 (dd, 1H), 7.44 (dd, 1H), 4.01 (s, 3H).

2-Bromo-3,5-dimethyl-benzoic acid

The title compound was prepared from 3,5-dimethyl-benzoic acid in analogy to the above described method. LC-MS A: $t_R$=0.75 min, [M+H]$^+$=no ionization. $^1$H NMR (DMSO) $\delta_H$: 7.56 (s, 1H), 7.28 (m, 2H), 2.36 (s, 3H), 2.27 (s, 3H).

2-Bromo-4-chloro-5-methoxybenzoic acid

The title compound was prepared from 4-chloro-3-methoxybenzoic acid in analogy to the above described method. LC-MS A: $t_R$=0.77 min, [M+H]$^+$=no ionization. $^1$H NMR (DMSO) $\delta_H$: 13.60 (bs, 1H), 7.82 (s, 1H), 7.47 (s, 1H), 3.91 (s, 3H).

2-Bromo-5-fluoro-3-methylbenzoic acid

Synthesis was performed in analogy to methods described in WO2011/90911: A solution of 2,3-dibromo-5-fluorotoluene (1.0 g, 3.73 mmol) in THF (32 mL) was cooled to −30° C. (dry-ice/acetone) and isopropylmagnesium chloride solution (2.0M in THF, 2.5 mL) was added. During the addition the rxn mixture was allowed to reach −12° C., but was cooled down after the addition to −40° C. and stirred at this temperature for 45 min before the rxn mixture warmed to −15° C. After 4 h at this temperature, a pellet of dry ice was added (gas evolution) and the rxn mixture was allowed to reach rt overnight. The rxn mixture was basified with 1M aq. NaOH to pH 14 and washed with EtOAc (2×). These combined org. layers did not contain any product and were discarded. The aq. layer was acidified with 2N aq. HCl to pH 1 and extracted with EtOAc (2×). The combined org. layers were dried (MgSO$_4$), filtered and concentrated under reduced pressure to yield the title compound as a white solid which was used in the next step without further purification.

3-Methyl-2-(2H-1,2,3-triazol-2-yl)benzoic acid (A-1-34)

Step A:
K$_2$CO$_3$ (8.18 g, 59.2 mmol) was added to a rt solution of 2-fluoro-3-methylbenzonitrile (4.0 g, 29.6 mmol) and 1H-1,2,3-triazole (1.72 mL, 29.6 mmol) in DMF (80 mL) and the resulting suspension was heated to 120° C. for 4 h. The mixture was allowed to reach rt, water was added and the rxn mixture was extracted with EtOAc (3×). The combined org. extracts were washed with brine, dried (Na$_2$SO$_4$), filtered, evaporated in vacuo and purified by FC (hex/EtOAc 2:1 to 1:1) to give 3-methyl-2-(2H-1,2,3-triazol-2-yl)benzonitrile as a white solid. LC-MS B: t$_R$=0.62 min; [M+H]$^+$=185.16.

Step B:

4N aq. NaOH (10 mL, 40.2 mmol) was added to a rt solution of 3-methyl-2-(2H-1,2,3-triazol-2-yl)benzonitrile (1.48 g, 8.04 mmol) in MeOH (15 mL) and the resulting mixture was heated to 90° C. for 50 h. After the rxn mixture reached rt, water was added and the org. solvent was removed in vacuo. The residue was extracted with EtOAc (2×) and the combined org. layers were washed with 1M aq. HCl and brine, dried (Na$_2$SO$_4$), filtered and evaporated in vacuo. To remove the residual side product, the crude product was re-dissolved in 2N aq. NaOH and washed with EtOAc (2×). The aq. layer was acidified with 2N aq. HCl and extracted with EtOAc (3×). The combined acidic org. extracts were washed with brine, dried (Na$_2$SO$_4$), filtered and evaporated in vacuo to give the title compound A-1-34 that was used further without purification. LC-MS B: t$_R$=0.50 min; [M+H]$^+$=186.17.

4-Methyl-[1,1'-biphenyl]-2-carboxylic acid (A-1-35)

Step A:

H$_2$SO$_4$ 95-98% (2.54 mL, 0.048 mol) was added to a solution of 2-iodo-5-methylbenzoic acid (25.0 g, 0.095 mol) in MeOH (220 mL) and refluxed for 20 h. The rxn mixture was cooled with an ice bath, and 1N aq. NaOH was added dropwise until pH 8 was reached. The org. solvent was removed in vacuo and the aq. layer was extracted with DCM (2×). The combined org. extracts were washed with sat. aq. NaHCO$_3$ (1×) and H$_2$O (1×), dried (Na$_2$SO$_4$), filtered and concentrated in vacuo to give methyl 2-iodo-5-methylbenzoate as a pale yellow liquid which was used in the next step without further purification. LC-MS A: t$_R$=0.87 min; [M+H]$^+$=259.22.

Step B:

Pd(PPh$_3$)$_4$ (523 mg, 0.45 mmol) was added to a rt solution of methyl 2-iodo-5-methylbenzoate in toluene (23 mL). After the solution was stirred for 10 min, a solution of phenylboronic acid (1.24 g, 9.96 mmol) in EtOH (10 mL) was added, followed by 2M aq. Na$_2$CO$_3$ (21 mL). The mixture was vigorously stirred and heated to reflux for 24 h. The rxn mixture was allowed to reach rt, then Et$_2$O was added and the org. layer was separated and concentrated in vacuo. Purification by FC (Biotage SP1: EtOAc/hept eluting with a gradient of 0-10% EtOAc) was performed to give methyl 4-methyl-[1,1'-biphenyl]-2-carboxylate as a colorless oil. LC-MS A: t$_R$=0.94 min; [M+H]$^+$=227.16.

Step C:

32% aq. NaOH (74 mL) was added to a rt solution of methyl 4-methyl-[1,1-biphenyl]-2-carboxylate (15.5 g, 0.068 mol) in MeOH (124 mL). The rxn mixture was stirred at 65° C. for 2 h, then the org. solvent was evaporated, water added, and the aq. layer acidified with conc. HCl. The mixture was stirred at rt for 30 min, and the precipitate was filtered off to give the title compound A-1-35 as a white solid. LC-MS D: t$_R$=0.55 min; [M+H]$^+$=211.27.

2-(Oxazol-2-yl)benzoic acid (A-1-36)

Step A:

Pd(PPh$_3$)$_2$Cl$_2$ (34 mg, 0.05 mmol) was added to a degassed rt solution of methyl 2-iodobenzoate (250 mg, 0.95 mmol) and 2-(tri-n-butylstannyl)oxazole (0.25 mL, 1.14 mmol) in DMF (3 mL). The rxn mixture was irradiated in the microwave at 130° C. for 25 min (with cooling function). The rxn mixture was diluted with DCM and sat. aq. NaHCO$_3$. The org. layer was separated and the aq. layer was extracted with DCM (3×). The combined org. layers were dried (MgSO$_4$), filtered and concentrated in vacuo. Purification by FC (hex/EtOAc 2:3) yielded methyl 2-(oxazol-2-yl)benzoate as a beige solid. LC-MS A: t$_R$=0.70 min; [M+H]$^+$=204.12.

Step B:

Methyl 2-(oxazol-2-yl)benzoate (314 mg, 0.39 mmol) was suspended in MeOH (1 mL) and THF (1 mL), then treated with 1N aq. NaOH (0.9 mL). The solution was stirred at rt for 6 h, then the rxn mixture was concentrated, diluted with DCM and acidified with 1N HCl to pH 1. The org. layer was separated and the aq. layer was extracted with DCM (2×). The combined org. layers were washed with brine (1×), dried (MgSO$_4$), filtered and concentrated to yield the title compound A-1-36 as a white solid that was used in the next step without purification. LC-MS A: t$_R$=0.57 min; [M+H]$^+$=190.14.

5-Methyl-2-(oxazol-2-yl)benzoic acid (A-1-37)

Step A:

Pd(PPh$_3$)$_2$Cl$_2$ (34 mg, 0.05 mmol) was added to a rt solution of 2-iodo-5-methylbenzoic acid methyl ester (263 mg, 0.95 mmol) and 2-(tri-n-butylstannyl)oxazole (0.25 mL, 1.14 mmol) in degassed DMF (3 mL). The rxn mixture was irradiated in the microwave at 125° C. for 25 min (with cooling function). The rxn mixture was diluted with DCM and sat. aq. NaHCO$_3$. The org. layer was separated and the aq. layer was extracted with DCM (3×). The combined org. layer were dried (MgSO$_4$), filtered, concentrated in vacuo and purified by FC (hex/EtOAc 2:3) to yield methyl 5-methyl-2-(oxazol-2-yl)benzoate as a beige solid. LC-MS A: t$_R$=0.76 min; [M+H]$^+$=218.17.

Step B:

2N aq. NaOH (0.9 mL) was added to a rt solution of methyl 5-methyl-2-(oxazol-2-yl)benzoate (157 mg, 0.72 mmol) in MeOH (2.5 mL). The rxn mixture was stirred at rt for 2 h, then another 0.5 mL of 2N aq. NaOH was added and stirred at rt for 18 h. The rxn mixture was concentrated, then diluted with DCM and acidified with 1N HCl to pH 1. The org. layer was separated and the aq. layer was extracted with DCM (2×). The combined org. layers were washed with brine (1×), dried (MgSO$_4$), filtered and concentrated to yield the title compound A-1-37 as white crystals. LC-MS A: t$_R$=0.64 min; [M+H]$^+$=204.20.

5-Methyl-2-(pyridin-2-yl)benzoic acid (A-1-38)

Step A:

Pd(PPh$_3$)$_4$ (1.59 g, 1.38 mmol) was added to a rt solution of 2-iodo-5-methylbenzoic acid methyl ester (3.80 g, 13.77 mmol), CuI (0.52 g, 2.75 mmol), CsF (4.22 g, 27.53 mmol), 2-tributylstannylpyridine (5.96 g, 20.65 mmol) in DMF (60 mL). The resulting suspension was stirred at 90° C. overnight. The obtained rxn mixture was diluted with EtOAc and filtered through a short pad of celite, then a solution of sat. aq. NaHCO$_3$ was added to the filtrate and the aq. layer extracted with EtOAc (3×). The combined org. layers were washed with H$_2$O and brine, dried (Na$_2$SO$_4$), filtered and concentrated under reduced pressure. Purification by FC (EtOAc/hept 1:4 to 3:7) yielded methyl 5-methyl-2-(pyridin-2-yl)benzoate as a brown oil. LC-MS B: t$_R$=0.67 min, [M+H]$^+$=228.07.

Step B:

1M aq. NaOH (23.2 mL) was added to a solution of methyl 5-methyl-2-(pyridin-2-yl)benzoate (11.62 mmol) in MeOH (15 mL) and THF (17 mL), and the resulting mixture was stirred at rt overnight. The volatiles were evaporated under reduced pressure and the remaining aq. layer was acidified with 2M HCl to pH 1 and extracted with DCM (3×). The combined org. layers were dried ($Na_2SO_4$), filtered and concentrated under reduced pressure to give the title compound A-1-38 as a pale brown foam. LC-MS B: $t_R$=0.39 min, $[M+H]^+$=214.25.

4-Methoxy-[1,1'-biphenyl]-2-carboxylic acid (A-1-39)

Step A:

$Pd(PPh_3)_4$ (1.06 g, 0.92 mmol) was added to a rt solution of methyl-2-bromo-5-methoxybenzoate (2.26 g, 9.2 mmol), phenylboronic acid (1.68 g, 13.8 mmol), $K_2CO_3$ (2.54 g, 18.4 mmol), toluene (12 mL) and MeOH (10 mL), and the yellow suspension was heated to 80° C. overnight. After the rxn mixture reached rt, water was added until all solids were dissolved. The org. layer was separated and the aq. layer was extracted with EtOAc (3×). The combined org. layers were dried ($Na_2SO_4$), filtered and concentrated under reduced pressure. Purification by FC (Biotage SP1: EtOAc/hex 1:9 to 3:7) yielded methyl 4-methoxy-[1,1'-biphenyl]-2-carboxylate as a colorless oil. LC-MS B: $t_R$=0.85 min, $[M+H]^+$=241.58.

Step B:

To a solution of methyl 4-methoxy-[1,1'-biphenyl]-2-carboxylate (2.22 g, 9.18 mmol) in THF (20 mL) 1N aq. NaOH (20 mL) was added and the resulting rxn mixture was stirred at 65° C. overnight. The org. solvent was evaporated and the residue was diluted with DCM and acidified with 2N aq. HCl to pH 1. The org. layer was separated and the aq. layer was extracted with DCM (3×). The combined org. layers were washed with brine, dried ($MgSO_4$), filtered and concentrated under reduced pressure to give title compound A-1-39 as an off-white solid. LC-MS B: $t_R$=0.70 min, $[M+H]^+$=229.04.

5-Fluoro-2-(1H-pyrazol-5-yl)benzoic acid (A-1-40)

Step A:

A flask was charged with methyl 2-bromo-5-fluorobenzoate (1.0 g, 4.3 mmol), 1H-pyrazole-5-boronic acid (554 mg, 4.7 mmol), DME (15.3 mL) and a solution of $NaHCO_3$ (721 mg, 8.6 mmol) in $H_2O$ (3 mL). The flask was evacuated and backfilled with $N_2$ several times, then $Pd(PPh_3)_4$ (236 mg, 0.204 mmol) was added and refluxed overnight. The rxn mixture was allowed to cool to rt, and the solid was filtered off and rinsed with EtOAc. The filtrate was washed with water (1×), dried ($MgSO_4$), filtered and concentrated under reduced pressure. Purification by FC (Biotage SP1: EtOAc/hex eluting with a gradient of 0-30% EtOAc) yielded 5-fluoro-2-(1H-pyrazol-5-yl)benzoate as a colorless oil. LC-MS B: $t_R$=0.59 min, $[M+H]^+$=221.07.

Step B:

2M aq. NaOH (1.33 mL) was added to a rt solution of 5-fluoro-2-(1H-pyrazol-5-yl)benzoate (237 mg, 1.08 mmol) in MeOH (4 mL) and the mixture was stirred at rt for 2 h. The rxn mixture was concentrated, diluted with DCM and acidified with 1N aq. HCl to pH 1. Part of the product precipitated and was filtered off. The remaining filtrate was extracted with DCM (2×), the combined org. layers were dried ($MgSO_4$) and concentrated together with the solids to obtain the title compound A-1-40 as a white solid. LC-MS B: $t_R$=0.48 min, $[M+H]^+$=207.09.

3-Fluoro-2-(1H-pyrazol-5-yl)benzoic acid (A-1-41)

Step A:

A solution of $NaHCO_3$ (2.0 g, 23.9 mmol) in $H_2O$ (8.5 mL) was added to a rt solution of 2-bromo-3-fluorobenzonitrile (2.84 g, 14.2 mmol), 1H-pyrazole-5-boronic acid (2.25 g, 19.1 mmol) in DME (40 mL) The flask was evacuated and backfilled with $N_2$ several times, then $Pd(PPh_3)_4$ (1.3 g, 1.14 mmol) was added and refluxed overnight. The rxn mixture was allowed to cool to rt, and the solid was filtered off and rinsed with EtOAc. The layers were separated and the aq. layer was extracted with EtOAc (1×), dried ($MgSO_4$), filtered and concentrated under reduced pressure. Purification by FC (Biotage SP1: EtOAc/hex eluting with a gradient of 0-30% EtOAc) yielded 3-fluoro-2-(1H-pyrrol-2-yl)benzonitrile as a white solid. LC-MS B: $t_R$=0.54 min, $[M+H]^+$=188.17.

Step B:

4M aq. NaOH (5.6 mL) was added to a rt solution of 3-fluoro-2-(1H-pyrrol-2-yl)benzonitrile (995 mg, 5.32 mmol) in MeOH (10 mL) and the resulting suspension was refluxed for 2 days. The rxn mixture was allowed to reach rt and acidified with 4N aq. HCl to pH 1 and extracted with EtOAc (2×). The combined org. layers were dried ($MgSO_4$), filtered and concentrated under reduced pressure to yield the title compound A-1-41 as a crude white solid which was used as such. LC-MS B: $t_R$=0.47 min, $[M+H]^+$=207.10.

5-Methoxy-4-methyl-2-(pyrimidin-2-yl)benzoic acid (A-1-56)

Step A was performed in analogy to a described method (J. Org. Chem, 2007, 9786-9).

Step A:

$Br_2$ (1.11 mL, 21.7 mmol) was added to a rt suspension of 3-methoxy-4-methylbenzoic acid (3.00 g, 18.1 mmol) in a mixture of acetic acid (23 mL) and water (23 mL) and the mixture was heated to 60° C. for 2 h. The mixture was allowed to reach rt and the solids were filtered and rinsed with water to yield 2-bromo-5-methoxy-4-methylbenzoic acid as a white solid which was used as such in the next step. LC-MS A: $t_R$=0.76 min, no ionization.

Step B:

$H_2SO_4$ (0.5 mL, 9.3 mmol) was added to a suspension of 2-bromo-5-methoxy-4-methylbenzoic acid (4.07 g, 16.6 mmol) in MeOH (40 mL) and the resulting rxn mixture was heated to 70° C. overnight. The rxn mixture was cooled to 0° C. and basified with 1M aq. NaOH (10 mL) to pH 11. The rxn mixture was extracted with DCM and the combined org. layers were dried ($MgSO_4$), filtered and concentrated in vacuo to yield methyl 2-bromo-5-methoxy-4-methylbenzoate as a yellow solid that was used as such in the next step without purification. LC-MS A: $t_R$=0.90 min, $[M+H]^+$=258.91.

Step C:

$Pd(PPh_3)_4$ (416 mg, 0.36 mmol) was added to a rt solution of 2-tributylstannylpyrimidine (1.40 g, 3.6 mmol) and methyl 2-bromo-5-methoxy-4-methylbenzoate (1.03 g, 3.96 mmol) in degassed DME (7 mL) and the resulting mixture was irradiated in the microwave at 160° C. for 1 h. To the rxn mixture was added $Pd(PPh_3)_4$ (315 mg, 0.27 mmol) and irradiation was continued at 160° C. for another 2 h. The rxn mixture was diluted with EtOAc and $H_2O$, filtered over celite, the org. layer was separated and the aq. layer was re-extracted with EtOAc. The combined org. extracts were dried (MgSO$_4$), filtered, concentrated in vacuo and purified by FC (Biotage SP1: EtOAc/hex 1:9 to 3:7) to yield methyl 5-methoxy-4-methyl-2-(pyrimidin-2-yl)benzoate as a brown solid which was used without further purification. LC-MS A: $t_R$=0.75 min, [M+H]$^+$=258.99.

Step D:

1M aq. NaOH (4 mL) was added to a rt suspension of methyl 5-methoxy-4-methyl-2-(pyrimidin-2-yl)benzoate (503 mg, 1.95 mmol) in MeOH (5 mL) and THF (5 mL) and stirred at rt for 2 days. The residue was acidified with 25% aq. HCl, washed with DCM and concentrated in vacuo to yield the title compound A-1-56 as a off-white solid as its HCl-salt. LC-MS A: $t_R$=0.63 min, [M+H]$^+$=245.06.

5-Chloro-4-methyl-2-(2H-1,2,3-triazol-2-yl)benzoic acid (A-1-58)

Cs$_2$CO$_3$ (742 mg, 2.28 mmol) was added portionwise to a rt solution of 2-bromo-5-chloro-4-methyl-benzoic acid methyl ester (300 mg, 1.14 mmol) in DMF (3 mL) followed by 1H-1,2,3-triazole (0.1 mL, 1.71 mmol), Cu(I)I (13 mg, 0.068 mmol) and DMCDA (40 uL, 0.23 mmol). The resulting suspension was stirred at 120° C. for 4 h. The rxn mixture was quenched with 2M aq. HCl and extracted with EtOAc (3×). The combined org. layers were dried (Na$_2$SO$_4$), filtered and evaporated in vacuo to obtain the crude product that was purified by prep. HPLC (method E) to give the title compound A-1-58 as a pale yellow solid. LC-MS A: $t_R$=0.72 min; [M+H]$^+$=238.01.

5-Methyl-[1,1'-biphenyl]-2-carboxylic acid (A-1-66)

Pd(PPh$_3$)$_4$ (0.40 g, 0.34 mmol) was added to a rt solution of 2-iodo-4-methylbenzoic acid (3.00 g, 11.4 mmol) and phenylboronic acid (1.41 g, 11.6 mmol) in 2M aq. NaHCO$_3$ (30 mL), toluene (30 mL) and isopropanol (30 mL). The rxn mixture was heated to 80° C. overnight. The rxn mixture was diluted with EtOAc, acidified with 1 N aq. HCl to pH 1 and extracted with EtOAc (2×). The combined org. layers were dried (MgSO$_4$), filtered and concentrated. The crude was purified by prep. HPLC (Method G) to yield the title compound as a beige solid. LC-MS A: $t_R$=0.81 min; [M+H+MeCN]$^+$=254.12.

Carboxylic acids from Table 2 are either commercially available or fully described in the literature.

TABLE 2

| A-1 | Name of Carboxylic Acid | Literature Procedure or Commercial Availability |
| --- | --- | --- |
| A-1-42 | 5-(m-Tolyl)oxazole-4-carboxylic acid | WO200977990 WO2010143116 |
| A-1-43 | 5-(3-Chlorophenyl)thiazole-4-carboxylic acid | WO200916560 |
| A-1-44 | 5-(3-Fluorophenyl)-2-methylthiazole-4-carboxylic acid | WO200838251 |
| A-1-45 | 5-(4-Fluorophenyl)-2-methylthiazole-4-carboxylic acid | WO200838251 |
| A-1-46 | 5-(2-Fluorophenyl)-2-methylthiazole-4-carboxylic acid | WO200838251 |
| A-1-47 | 4-(Phenyl)-1H-imidazole-5-carboxylic acid | US2005-14765 or commercially available |
| A-1-48 | 3-(3-Methoxyphenyl)pyrazine-2-carboxylic acid | WO201044054 WO201038200 |
| A-1-49 | 2-Methyl-4-(3-Chloro-phenyl)-pyrimidine-5-carboxylic acid | WO201044054 page140 |
| A-1-50 | 2-(3-Methyl-1,2,4-oxadiazol-5-yl)benzoic acid | commercially available |
| A-1-51 | [2,2'-Bipyridine]-3-carboxylic acid | J. Org. Chem., 1999, 1015-1021 or commercially available |
| A-1-52 | [1,1'-Biphenyl]-2-carboxylic acid | commercially available |
| A-1-53 | 2-Methyl-5-(m-tolyl)oxazole-4-carboxylic acid | WO20104507 WO200977990 |
| A-1-54 | 2-Methyl-5-(m-tolyl)thiazole-4-carboxylic acid | WO200881399 WO200865626 |
| A-1-55 | 5-Methyl-2-(pyrimidin-2-yl)benzoic acid | commercially available |
| A-1-57 | 5-(3-Chlorophenyl)-2-methylthiazole-4-carboxylic acid | WO200838251 |
| A-1-60 | 3-(2-Chlorophenyl)-5-methylisoxazole-4-carboxylic acid | commercially available |
| A-1-62 | 2-Methyl-5-phenyl-thiazole-4-carboxylic acid | commercially available |
| A-1-63 | 5-Phenyl-1,3-thiazole-4-carboxylic acid | commercially available |
| A-1-64 | 5-Phenyl-1,3-oxazole-4-carboxylic acid | commercially available |
| A-1-65 | 5-(m-Tolyl)thiazole-4-carboxylic acid | WO 2010044054 |

Synthesis of Intermediate A-2

(S)-Methyl 1-(5-methyl-2-(2H-1,2,3-triazol-2-yl)benzoyl)pyrrolidine-2-carboxylate (A-2-1)

TBTU (7.1 g, 22.1 mmol) was added to a rt solution of 5-methyl-2-(2H-1,2,3-triazol-2-yl)benzoic acid A-1-3 (3.0 g, 14.8 mmol) and DIPEA (10.1 mL, 59.1 mmol) in DCM (30 mL), and after stirring for 10 min, amine L-proline methylester HCl (3.19 g, 15.4 mmol) was added and stirred at rt for 18 h. The rxn mixture was diluted with DCM and water, the org. layer was separated and the aq. layer was extracted with DCM (2×). The combined org. extracts were washed with brine, dried (MgSO$_4$), filtered and the solvent removed under reduced pressure to give the crude product that was purified by FC (EtOAc/hept 7:3) to give the title compound A-2-1 as a white solid. LC-MS A: $t_R$=0.75 min; [M+H]$^+$=315.29.

(S)-Methyl 1-(4-methyl-2-(2H-1,2,3-triazol-2-yl)benzoyl)pyrrolidine-2-carboxylate (A-2-2)

TBTU (4.17 g, 13.0 mmol) was added to a rt solution of 4-methyl-2-(2H-1,2,3-triazol-2-yl)benzoic acid A-1-4 (2.20 g, 10.8 mmol) and DIPEA (7.41 mL, 43.3 mmol) in DCM (50 mL), and after stirring for 5 min, amine L-proline methyl ester HCl (1.83 g, 10.8 mmol) was added and stirred at rt for 48 h. The rxn mixture was diluted with DCM and washed with sat. aq. NaHCO$_3$. The aq. layer was re-extracted with DCM (1×) and the combined org. extracts were dried (MgSO$_4$), filtered and the solvent was removed under reduced pressure to give the title compound A-2-2 as an orange oil which was used further without purification. LC-MS A: $t_R$=0.66 min; [M+H]$^+$=315.07.

Synthesis of Intermediate A-3

(S)-1-(5-Methyl-2-(2H-1,2,3-triazol-2-yl)benzoyl)pyrrolidine-2-carboxylic acid (A-3-1)

2N aq. NaOH (6.3 mL) was added to a rt solution of (S)-methyl 1-(5-methyl-2-(2H-1,2,3-triazol-2-yl)benzoyl)pyrrolidine-2-carboxylate A-2-1 (2.2 g, 7.0 mmol) in MeOH (9 mL) and THF (9 mL). The mixture was stirred at rt for 2 h, then the org. solvents were removed in vacuo and the residue was acidified with 1N aq. HCl. The aq. layer was extracted with DCM (3×), the combined org. layers washed with brine, dried (MgSO$_4$), filtered and concentrated in vacuo to give the title compound A-3-1 as a white solid that was used further without purification. LC-MS A: $t_R$=0.66 min; [M+H]$^+$=301.28.

(S)-1-(4-Methyl-2-(2H-1,2,3-triazol-2-yl)benzoyl)pyrrolidine-2-carboxylic acid (A-3-2)

1M aq. NaOH (50 mL) was added to a rt solution of (S)-methyl 1-(4-methyl-2-(2H-1,2,3-triazol-2-yl)benzoyl)pyrrolidine-2-carboxylate A-2-2 (5.79 g, 18.4 mmol) in MeOH (30 mL) and THF (30 mL). The rxn mixture was stirred at rt for 2 h, then the org. solvents were removed in vacuo and the residue was acidified with 1M aq. HCl. The aq. layer was extracted with DCM (2×), the combined org. layers washed with brine, dried (MgSO$_4$), filtered and concentrated in vacuo to give the title compound A-3-2 as a white foam that was used further without purification. LC-MS A: $t_R$=0.58 min; [M+H]$^+$=301.05.

Synthesis of Intermediate A-4

General Method A for the Synthesis of Hydroxyamidines (A-4)

To a solution of nitrile-derivative (1.0 eq.) in MeOH (0.5 M), hydroxylamine HCl (1.1 to 3.0 eq.) and NaHCO$_3$ (1.1 to 3.0 eq.) was added at rt. The resulting suspension was stirred at a given temperature and time (see Table 3). The mixture was concentrated in vacuo, then EtOAc was added to the remaining residue and the org. layer was washed with brine (1×), dried (MgSO$_4$), filtered and concentrated to yield hydroxyamidine A-4.

General Method B for the Synthesis of Hydroxyamidines (A-4)

Hydroxylamine HCl (1.0 eq.) was added to a rt solution of nitrile-derivative (1 eq.) and 1M aq. NaOH (1 eq.) in EtOH (1 M). The resulting suspension was stirred at a given temperature and time (see Table 3). The org. solvent was concentrated in vacuo and the remaining residue was extracted with DCM (3×). The combined org. layers were dried (MgSO$_4$), filtered and concentrated to yield hydroxyamidine A-4.

General Method C for the Synthesis of Hydroxyamidines (A-4)

To a solution of hydroxylamine HCl (1.1 to 3 eq.) and NaHCO$_3$ (1.1 to 3 eq.) in water (2M), nitrile-derivative and EtOH (2M) was added at rt and stirred at a given temperature and time (see Table 3). The org. solvent was concentrated in vacuo and the remaining residue was extracted with DCM (3×). The combined org. layers were dried (MgSO$_4$), filtered and concentrated to yield hydroxyamidine A-4.

General Method D for the Synthesis of Hydroxyamidines (A-4)

To a solution of nitrile-derivative (1 eq.) in MeOH (0.5 M), hydroxylamine HCl (1.1 to 3.0 eq.) and NEt$_3$ (1.1 to 3.0 eq.) was added at rt. The resulting mixture was stirred at a given temperature and time (see Table 3). The mixture was concentrated in vacuo, then to the remaining residue EtOAc was added and the org. layer was washed with brine (1×), dried (MgSO$_4$), filtered and concentrated to yield hydroxyamidine A-4.

General Method E for the Synthesis of Hydroxyamidines (A-4)

To a solution of KOtBu (1.1-3.0 eq.) in MeOH (1M), hydroxylamine HCl (1.1 to 3.0 eq.) was added. After stirring for 30 min at rt, nitrile-derivative was added and the mixture was stirred at a given temperature and time (see Table 3). The org. solvent was concentrated in vacuo and the remaining residue was extracted with DCM (3×). The combined org. layers were dried (MgSO$_4$), filtered and concentrated to yield hydroxyamidine A-4.

Listed in Table 3 below are hydroxylamidines of type A-4, prepared from either commercially available nitrile-derivates or synthesized according to described methods.

TABLE 3

| A-4 | Hydroxyamidine | SM | GM | T [° C.] time [h] | $t_R$ [min] LC/MS-Method | MS-data m/z [M + H]$^+$ |
|---|---|---|---|---|---|---|
| A-4-1 | N-Hydroxy-3-methyl-benzamidine | | B | 80 5.5 | 0.39 A | 151.08 |
| A-4-2 | N-Hydroxy-3-methoxy-benzamidine | | A | 65 18 | 0.37 A | 167.14 |
| A-4-3 | N-Hydroxy-nicotinamidine | | A | 80 18 | 0.17 A | 138.2 |
| A-4-4 | N-Hydroxy-4-methyl-benzamidine | | A | 75 18 | 0.39 A | 151.21 |

TABLE 3-continued

| A-4 | Hydroxyamidine | SM | GM | T [° C.] time [h] | $t_R$ [min] LC/MS-Method | MS-data m/z [M + H]$^+$ |
|---|---|---|---|---|---|---|
| A-4-5 | 2-Cyclopropyl-N-hydroxy-benzamidine | 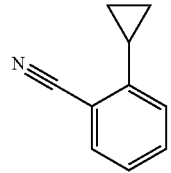 | A | 60 18 | 0.34 A | 177.21 |
| A-4-6 | N-Hydroxy-2-methoxy-benzamidine | 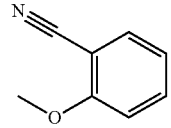 | A | 80 48 | 0.36 A | 167.05 |
| A-4-7 | N-Hydroxy-2-methoxy-nicotinamidine | 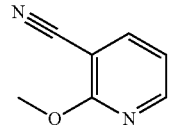 | A | 80 5 | 0.17 B | 167.99 |
| A-4-8 | N-Hydroxy-3,4-dimethyl-benzamidine | 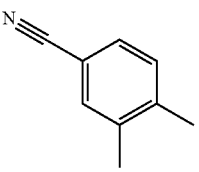 | A | 60 18 | 0.38 B | 165.05 |
| A-4-9 | 3,5-Difluoro-N-hydroxy-benzamidine | 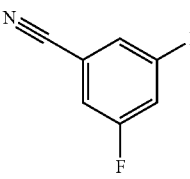 | A | 60 18 | 0.26 B | 172.95 |
| A-4-10 | 2,3-Difluoro-N-hydroxy-benzamidine | 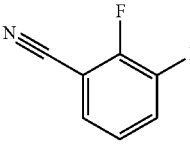 | A | 60 18 | 0.22 B | 172.96 |
| A-4-11 | N-Hydroxy-2,4-dimethyl-benzamidine | 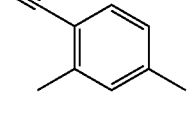 | A | 70 96 | 0.35 B | 165.23 |
| A-4-12 | N-Hydroxy-3,5-dimethyl-benzamidine | 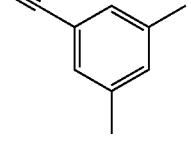 | A | 80 5 | 0.38 B | 165.02 |
| A-4-13 | N-Hydroxy-4,6-dimethyl-pyridine-2-carboxamidine | 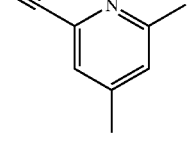 | A | 80 3 | 0.38 A | 166.14 |

TABLE 3-continued

| A-4 | Hydroxyamidine | SM | GM | T [° C.] time [h] | $t_R$ [min] LC/MS- Method | MS-data m/z [M + H]$^+$ |
|---|---|---|---|---|---|---|
| A-4-14 | N-Hydroxy-2,3-dimethyl-benzamidine | | A | 85 72 | 0.41 A | 165.18 |
| A-4-15 | N-Hydroxy-4-methyl-pyridine-2-carboxamidine | | A | 80 0.25 | 0.32 A | 152.2 |
| A-4-16 | 3-Fluoro-N-hydroxy-benzamidine | | A | 80 1.5 | 0.3 A | 155.17 |
| A-4-17 | N-Hydroxy-1H-indole-3-carboxamidine | | A | 60 72 | 0.42 A | 176.19 |
| A-4-18 | N-Hydroxy-3-methyl-pyridine-2-carboxamidine | | A | 80 18 | 0.18 A | 152.22 |
| A-4-19 | N-Hydroxy-2-methyl-benzamidine | | A | 85 48 | 0.3 A | 151.23 |
| A-4-20 | N-Hydroxy-2,5-dimethyl-benzamidine | | A | 85 96 | 0.43 A | 165.07 |
| A-4-21 | N-Hydroxy-2-trifluoromethoxy-benzamidine | | A | 85 6 | 0.39 A | 221.03 |
| A-4-22 | 3-Chloro-N-hydroxy-benzamidine | | C | rt 48 | 0.3 B | ($^{35}$Cl) 170.98 |
| A-4-23 | 2,2-Difluoro-N-hydroxy-benzo[1,3]dioxole-5-carboxamidine | | C | rt 48 | 0.38 B | 217.13 |
| A-4-24 | 3,4-Difluoro-N-hydroxy-benzamidine | | C | rt 18 | 0.27 B | 172.08 |

TABLE 3-continued

| A-4 | Hydroxyamidine | SM | GM | T [° C.] time [h] | $t_R$ [min] LC/MS- Method | MS-data m/z [M + H]$^+$ |
|---|---|---|---|---|---|---|
| A-4-25 | 2-Chloro-N-hydroxy-benzamidine | | C | 80 / 24 | 0.21 / B | ($^{35}$Cl) 170.97 |
| A-4-26 | N-Hydroxy-benzo[1,3]dioxole-5-carboxamidine | | C | 80 / 24 | 0.24 / B | 181.25 |
| A-4-27 | 3-Chloro-N-hydroxy-2-methyl-benzamidine | | A | 80 / 24 | 0.35 / B | ($^{35}$Cl) 185.22 |
| A-4-28 | 2-Chloro-N-hydroxy-6-methyl-benzamidine | | C | 80 / 48 | 0.27 / B | ($^{35}$Cl) 185.22 |
| A-4-29 | 2-Ethyl-N-hydroxy-benzamidine | | C | 80 / 48 | 0.3 / B | 165.07 |
| A-4-30 | 3-Fluoro-N-hydroxy-2-methyl-benzamidine | | C | 80 / 24 | 0.27 / B | 169.04 |
| A-4-31 | 2-Chloro-N-hydroxy-3-methyl-benzamidine | | C | 80 / 24 | 0.31 / B | ($^{35}$Cl) 185.22 |
| A-4-32 | 2-Chloro-N-hydroxy-nicotinamidine | | A | rt / 48 | 0.12 / B | ($^{35}$Cl) 171.97 |
| A-4-33 | N-Hydroxy-2-trifluoromethyl-benzamidine | | A | 85 / 18 | 0.32 / A | 205.18 |
| A-4-34 | 3-Chloro-N-hydroxy-pyrazine-2-carboxamidine | | A | rt / 48 | 0.22 / A | ($^{35}$Cl) 172.87 |

TABLE 3-continued

| A-4 | Hydroxyamidine | SM | GM | T [° C.] time [h] | $t_R$ [min] LC/MS-Method | MS-data m/z [M + H]+ |
|---|---|---|---|---|---|---|
| A-4-35 | 2,N-Dihydroxy-benzamidine | | A | 70 24 | 0.17 B | 153.16 |
| A-4-36 | N-Hydroxy-2-methoxy-isonicotinamidine | | A | rt 18 | 0.19 B | 168.07 |
| A-4-37 | 2-Difluoromethoxy-N-hydroxy-benzamidine | | A | 70 18 | 0.26 B | 203.22 |
| A-4-38 | 3-Fluoro-N-hydroxy-2-methoxy-benzamidine | | A | 70 18 | 0.26 B | 185.26 |
| A-4-39 | 2-Fluoro-N-hydroxy-3-methoxy-benzamidine | | A | 70 5 | 0.24 B | 185.27 |
| A-4-40 | 2-Chloro-N-hydroxy-4-methyl-nicotinamidine | | A | 70 48 | 0.13 B | ($^{35}$Cl) 186.21 |
| A-4-41 | N-Hydroxy-3,5-dimethyl-isonicotinamidine | | A | 70 48 | 0.1 B | 166.13 |
| A-4-42 | N-Hydroxy-2,3-dihydro-benzo[1,4]dioxine-5-carboxamidine | | A | 70 18 | 0.28 B | 195.25 |
| A-4-43 | N-Hydroxy-1H-indole-4-carboxamidine | | A | 70 18 | 0.19 B | 176.3 |

TABLE 3-continued

| A-4 | Hydroxyamidine | SM | GM | T [° C.] time [h] | $t_R$ [min] LC/MS- Method | MS-data m/z [M + H]+ |
|---|---|---|---|---|---|---|
| A-4-44 | 2-Ethoxy-N-hydroxy-benzamidine | 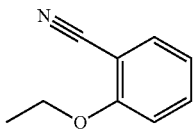 | A | 70 18 | 0.33 B | 181.32 |
| A-4-45 | 2-Ethoxy-N-hydroxy-nicotinamidine | 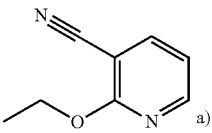 a) | A | 70 6 | 0.27 B | 182.18 |
| A-4-46 | N-Hydroxy-5-methoxy-1H-indole-3-carboxamidine | 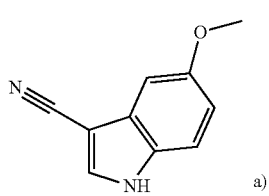 a) | A | 60 36 | 0.46 A | 206.23 |
| A-4-47 | 3-Difluoromethoxy-N-hydroxy-benzamidine | 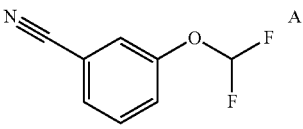 | A | 70 1 | 0.31 B | 203.1 |
| A-4-48 | N-Hydroxy-2-methoxymethyl-benzamidine | 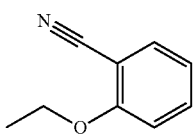 | A | 65 18 | 0.24 B | 181.21 |
| A-4-49 | N-Hydroxy-2-propoxy-benzamidine | 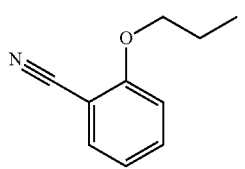 | A | 80 18 | 0.48 A | 195.17 |
| A-4-50 | N-Hydroxy-1H-indole-7-carboxamidine | 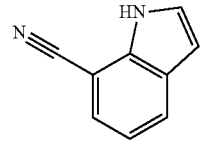 | A | 80 18 | 0.4 A | 176.2 |
| A-4-51 | N-Hydroxy-3,5-dimethoxy-benzamidine | 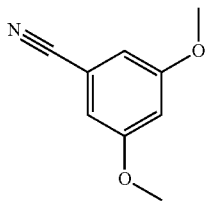 | A | 60 2 | 0.44 A | 197.26 |
| A-4-52 | 2-Cyclobutoxy-N-hydroxy-nicotinamidine | 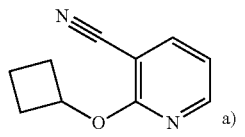 a) | A | 70 6 | 0.39 B | 208.13 |

TABLE 3-continued

| A-4 | Hydroxyamidine | SM | GM | T [° C.] time [h] | $t_R$ [min] LC/MS- Method | MS-data m/z $[M + H]^+$ |
|---|---|---|---|---|---|---|
| A-4-53 | 2-Cyclopentyloxy-N-hydroxy-nicotinamidine | | A | 70 6 | 0.43 B | 222.11 |
| A-4-54 | 3-(N-Hydroxycarbamimidoyl)-pyrrolo[2,3-b]pyridine-1-carboxylic acid tert-butyl ester | | A | 70 3 | 0.43 B | 277.04 |
| A-4-55 | N-Hydroxy-1-methyl-1H-pyrrolo[2,3-b]pyridine-3-carboxamidine | | A | 70 4 | 0.26 B | 191.18 |
| A-4-56 | N-Hydroxy-benzo[1,3]dioxole-4-carboxamidine | | A | 80 5 | 0.37 A | 181.15 |
| A-4-57 | 2-Ethyl-N-hydroxy-nicotinamidine | | A | 70 72 | 0.1 B | 165.99 |
| A-4-58 | N-Hydroxy-2-trifluoromethyl-benzamidine | | A | 70 3 | 0.41 B | 219.07 |
| A-4-59 | 3-Ethoxy-N-hydroxy-isonicotinamidine | | A | 80 18 | 0.27 A | 182.18 |
| A-4-60 | 2-Ethoxy-3-fluoro-N-hydroxy-benzamidine | | A | 70 18 | 0.36 B | 199.16 |
| A-4-61 | N-Hydroxy-1-methyl-1H-indole-3-carboxamidine | | A | 80 18 | 0.47 A | 190.29 |

TABLE 3-continued

| A-4 | Hydroxyamidine | SM | GM | T [° C.] time [h] | $t_R$ [min] LC/MS-Method | MS-data m/z [M + H]+ |
|---|---|---|---|---|---|---|
| A-4-62 | N-Hydroxy-4-methyl-nicotinamidine | | A | 80 25 | 0.17 A | 152.18 |
| A-4-63 | N-Hydroxy-2,3-dimethoxy-benzamidine | | A | 60 18 | 0.29 B | 197.17 |
| A-4-64 | N-Hydroxy-1-methyl-1H-pyrazole-4-carboxamidine | | C | rt 18 | 0.44 A | 142.02 |
| A-4-65 | 5-Ethyl-N-hydroxy-4-methyl-pyridine-2-carboxamidine | | D | 75 6 | 0.54 A | 180.01 |
| A-4-66 | N-Hydroxy-4,5-dimethyl-pyridine-2-carboxamidine | | D | 75 18 | 0.48 A | 166.05 |
| A-4-67 | N-Hydroxy-5,6-dimethyl-pyridine-2-carboxamidine | | D | 75 48 | 0.49 A | 166.03 |
| A-4-68 | 4,N-Dihydroxy-2-methoxy-benzamidine | | E | 65 18 | 0.41 A | 183.05 |
| A-4-69 | N-Hydroxy-2,6-dimethyl-isonicotinamidine | | E | 60 15 | 0.12 B | 166.04 |
| A-4-70 | N-Hydroxy-2-methoxy-6-methyl-isonicotinamidine | | E | 65 18 | 0.43 A | 181.96 |

TABLE 3-continued

| A-4 | Hydroxyamidine | SM | GM | T [° C.] time [h] | $t_R$ [min] LC/MS-Method | MS-data m/z [M + H]+ |
|---|---|---|---|---|---|---|
| A-4-71 | N-Hydroxy-6-isobutyl-4-methyl-pyridine-2-carboxamidine | | E | 60 18 | 0.63 A | 208.29 |
| A-4-72 | N-Hydroxy-2-methyl-isonicotinamidine | | A | 60 18 | 0.11 B | 152.06 |
| A-4-73 | 2-6-Difluoro-N-hydroxy-5-methoxy-benzamidine | | A | 60 18 | 0.24 B | 203.11 |
| A-4-74 | 2-Chloro-N-hydroxy-3-methoxy-benzamidine | | A | 60 18 | 0.27 B | ($^{35}$Cl) 201.10 |
| A-4-75 | 2-Isopropoxy-N-hydroxy-nicotinamidine | | A | 65 18 | 0.35 B | 196.17 |
| A-4-76 | 2-Fluoro-N-hydroxy-6-methoxy-benzamidine | | A | 65 18 | 0.22 B | 185.16 |
| A-4-77 | 2-Chloro-N-hydroxy-isonicotinamidine | | A | 65 18 | 0.21 B | ($^{35}$Cl) 171.88 |
| A-4-78 | N-Hydroxy-1-methyl-1H-indole-4-carboxamidine | | A | 65 18 | 0.32 B | 190.19 |
| A-4-79 | N-Hydroxy-1H-pyrrolo[2,3-b]pyridine-4-carboxamidine | | A | 65 18 | 0.13 B | 177.21 |

TABLE 3-continued

| A-4 | Hydroxyamidine | SM | GM | T [° C.] time [h] | $t_R$ [min] LC/MS-Method | MS-data m/z [M + H]⁺ |
|---|---|---|---|---|---|---|
| A-4-80 | 2-Fluoro-N-hydroxy-6-methyl-benzamidine | | A | 70 18 | 0.21 B | 168.96 |
| A-4-81 | N-Hydroxy-1-methyl-1H-indole-7-carboxamidine | | A | 70 18 | 0.34 B | 190.18 |
| A-4-82 | N-Hydroxy-2-methyl-nicotinamidine | | A | 60 18 | 0.10 B | 152.2 |
| A-4-83 | N,2-Dihydroxy nicotinamidine | | A | 60 4 | 0.10 B | 154.03 |
| A-4-84 | N-Hydroxy-3-trifluoromethoxy-benzamidine | | A | 70 2 | 0.49 A | 221.16 |
| A-4-85 | N-Hydroxy-3,4-dimethoxy-benzamidine | | A | 60 2 | 0.39 A | 197.27 | a) Nitriles, which are not commercially available, are synthesized according to procedures described below.

Synthesis of Nitriles

5-Methoxy-1H-indole-3-carbonitrile

NaOAc (3.51 g, 42.8 mmol) was added to a rt solution of 5-methoxyindole-3-carboxaldehyde (3.0 g, 17.1 mmol), hydroxylamine HCl (2.98 g, 42.8 mmol) in AcOH (20 mL) and the resulting mixture was stirred for 1.5 h, then acetic anhydride (16.2 mL, 171 mmol) was added and the rxn mixture was heated to 115° C. for 30 min. After the rxn mixture reached rt, it was poured into ice-water and extracted with EtOAc (4×). The combined org. layers were washed with brine, dried (MgSO₄), decolorized with charcoal, filtered and the solvent was removed under reduced pressure. The crude was purified by FC (EtOAc/hex 3:1) to yield 5-methoxy-1H-indole-3-carbonitrile as a yellow solid. LC-MS B: $t_R$=0.71 min; [M+H]⁺=no ionization. ¹H NMR (CDCl₃) $\delta_H$: 8.67 (m, 1H), 7.70 (d, J=2.9 Hz, 1H), 7.37 (d, J=8.9 Hz, 1H), 7.21 (s, 1H), 7.00 (m, 1H), 3.91 (s, 3H).

2-Cyclobutoxynicotinonitrile

NaH 60% dispersion in mineral oil (100 mg, 2.5 mmol) was added to a rt solution of cyclobutanol (0.125 mL, 1.6 mmol) in DMF (1.5 mL). After stirring for 1 h, 3-cyano-2-fluoropyridine (150 mg, 1.23 mmol) was added and the brown suspension was stirred at rt for 1 h. The rxn mixture was quenched with water and extracted with DCM (2×). The combined org. layers were dried (MgSO₄), filtered and concentrated in vacuo to yield 2-cyclobutoxynicotinonitrile as an orange oil. LC-MS B: $t_R$=0.76 min; [M+H]⁺=175.21. ¹H NMR (DMSO) $\delta_H$: 8.43 (m, 1H), 8.26 (dd, J₁=7.6 Hz, J₂=1.9 Hz, 1H), 7.17 (dd, J₁=7.6 Hz, J₂=5.0 Hz, 1H), 5.25 (m, 1H), 2.43 (m, 2H), 2.13 (m, 2H), 1.82 (m, 1H), 1.66 (m, 1H).

2-(Cyclopentyloxy)nicotinonitrile

The title compound was prepared from 3-cyano-2-fluoropyridine and cyclopentanol in analogy to the procedure described for 2-cyclobutoxynicotinonitrile. LC-MS B:

$t_R$=0.81 min; [M+H]$^+$=no ionization. $^1$H NMR (DMSO) δ: 8.46 (dd, J$_1$=5.0 Hz, J$_2$=1.9 Hz, 1H), 8.24 (dd, J$_1$=7.6 Hz, J$_2$=1.9 Hz, 1H), 7.15 (dd, J$_1$=7.6 Hz, J$_2$=5.0 Hz, 1H), 5.50 (m, 1H), 1.97 (m, 2H), 1.68 (m, 6H)

tert-Butyl
3-cyano-1H-pyrrolo[2,3-b]pyridine-1-carboxylate

Step A:
Hydroxylamine HCl (264 mg, 3.8 mmol) was added to a rt solution of 7-azaindole-3-carboxaldehyde (500 mg, 3.42 mmol) in pyridine (1 mL) and the resulting yellow solution was stirred for 1 h before acetic anhydride (0.63 mL, 6.56 mmol) was added and heated to 110° C. for 30 min. The rxn mixture was cooled to rt, EtOAc was added and the org. layer was washed with sat. aq. NaHCO$_3$. The aq. layer was re-extracted with EtOAc, and the combined org. layers were dried (MgSO$_4$), filtered and concentrated in vacuo to yield 1H-pyrrolo[2,3-b]pyridine-3-carbonitrile as an off-white solid which was used in the next step without further purification.
Step B:
NaH 60% dispersion in mineral oil (115 mg, 2.88 mmol) was added to a rt solution of 1H-pyrrolo[2,3-b]pyridine-3-carbonitrile (275 mg, 1.92 mmol) in DMF (10 mL) and after stirring for 5 min at rt, di-tert-butyldicarbonate (629 mg, 2.88 mmol) was added at rt and stirring was continued for 1 h. The rxn mixture was quenched with water and extracted with EtOAc (2×). The combined org. layers were concentrated in vacuo to yield the title compound as a yellow solid. LC-MS B: $t_R$=0.73 min; [M+H]$^+$=244.05.

1-Methyl-1H-pyrrolo[2,3-b]pyridine-3-carbonitrile

NaH 60% dispersion in mineral oil (115 mg, 2.88 mmol) was added to a rt solution of 1H-pyrrolo[2,3-b]pyridine-3-carbonitrile (275 mg, 1.92 mmol) in DMF (10 mL) and the resulting mixture was stirred for 5 min before MeI (0.18 mL, 2.88 mmol) was added and stirring was continued for 1 h. The rxn mixture was quenched with water, extracted with EtOAc (2×) and the combined org. layers were dried (MgSO$_4$) and concentrated in vacuo to yield the title compound as a yellow solid. LC-MS B: $t_R$=0.51 min; [M+H]$^+$=158.05.

3-Ethoxyisonicotinonitrile

Sodium ethoxide (53 mg, 0.743 mmol) was added to a 0° C. solution of 3-chloro-4-cyanopyridine (100 mg, 0.72 mmol) in DMF (1 mL). The mixture was stirred at 0° C. for 30 min and at rt for 2 h, then the mixture was concentrated in vacuo. To the residue Et$_2$O was added and the salts were filtered off. The filtrate was concentrated in vacuo to yield the title compound as a white solid. LC-MS A: $t_R$=0.67 min; [M($^{35}$Cl)+H]$^+$=149.06.

2-Ethoxy-3-fluorobenzonitrile

NaH 60% dispersion in mineral oil (575 mg, 14.4 mmol) was added to a rt solution of EtOH (1.0 mL, 17.1 mmol) in DMF (6.0 mL). After stirring for 40 min at rt, the solution was cooled to 0° C., 2,3-difluorobenzonitrile (1.59 mL, 14.4 mmol) was added dropwise and stirring was continued for 1 h at rt. The rxn mixture was quenched with water and extracted with DCM (2×). The combined org. layers were dried (MgSO$_4$), filtered and concentrated in vacuo to yield 2-ethoxy-3-fluorobenzonitrile as an orange oil. LC-MS B: $t_R$=0.74 min; [M+H]$^+$=no ionization. $^1$H NMR (CDCl$_3$) δ$_H$: 7.66 (m, 2H), 7.27 (m, 1H), 4.32 (q, 2H), 1.35 (t, 3H).

1-Methyl-1H-indole-3-carbonitrile

The title compound was prepared from 1-methylindole-3-carboxaldehyde in analogy to the procedure described for 5-methoxy-1H-indole-3-carbonitrile. LC-MS A: $t_R$=0.78 min; [M+H]$^+$=157.16.

Synthesis of Intermediate B-2

(S)-2-[3-(3-Chloro-2-methylphenyl)-[1,2,4]oxadiazol-5-yl]-pyrrolidine-1-carboxylic acid tert-butyl ester (B-2-1)

Step A:
PyBOP (9.89 g, 19.0 mmol) was added to a 0° C. solution of Boc-L-proline (3.40 g, 15.8 mmol), hydroxyamidine A-4-27 (2.92 g, 15.8 mmol) and DIPEA (8.12 mL, 47.4 mmol) in DCM (50 mL). The resulting mixture was stirred at rt for 3 h, then concentrated in vacuo to yield (S)-tert-butyl 2-((((amino(3-chloro-2-methylphenyl)methylene)amino)oxy)carbonyl)pyrrolidine-1-carboxylate B-1-1 that was used further without purification.
Step B:
The crude B-1-1 was taken up in dioxane (50 mL) and refluxed (75° C.) for 2 days. The rxn mixture was concentrated and purified by FC (Biotage SP1: EtOAc/hex 3:7) to give the title compound B-2-1 as a yellow oil. LC-MS B: $t_R$=1.02 min; [M($^{35}$Cl)+H]$^+$=363.98.

Listed in Table 4 below are compounds of structure B-2, prepared from the commercially available Boc-L-proline and the corresponding hydroxyamidine according to the above procedure (see B-2-1).

TABLE 4

| B-2 | SM A-4 | Name | $t_R$ [min] LC/MS-Method | MS-data m/z [M + H]$^+$ |
|---|---|---|---|---|
| B-2-2 | A-4-21 | (S)-2-[3-(2-Trifluoromethoxy-phenyl)-[1,2,4]oxadiazol-5-yl]-pyrrolidine-1-carboxylic acid tert-butyl ester | 0.96 B | 400.06 |
| B-2-3 | A-4-33 | (S)-2-[3-(2-Trifluoromethyl-phenyl)-[1,2,4]oxadiazol-5-yl]-pyrrolidine-1-carboxylic acid tert-butyl ester | 0.92 B | 383.97 |
| B-2-4 | A-4-37 | (S)-2-[3-(2-Difluoromethoxy-phenyl)-[1,2,4]oxadiazol-5-yl]-pyrrolidine-1-carboxylic acid tert-butyl ester | 0.89 B | 381.98 |
| B-2-5 | A-4-38 | (S)-2-[3-(3-Fluoro-2-methoxy-phenyl)-[1,2,4]oxadiazol-5-yl]-pyrrolidine-1-carboxylic acid tert-butyl ester | 0.98 B | 364.05 |
| B-2-6 | A-4-45 | (S)-2-[3-(2-Ethoxy-pyridin-3-yl)-[1,2,4]oxadiazol-5-yl]-pyrrolidine-1-carboxylic acid tert-butyl ester | 0.86 B | 361.05 |

TABLE 4-continued

| B-2 | SM A-4 | Name | $t_R$ [min] LC/MS-Method | MS-data m/z [M + H]$^+$ |
|---|---|---|---|---|
| B-2-11 | A-4-60 | (S)-2-[3-(2-Ethoxy-3-fluoro-phenyl)-[1,2,4]oxadiazol-5-yl]-pyrrolidine-1-carboxylic acid tert-butyl ester | 0.98 A | 378.08 |
| B-2-12 | A-4-84 | (S)-2-[3-(3-Trifluoromethoxy-phenyl)-[1,2,4]oxadiazol-5-yl]-pyrrolidine-1-carboxylic acid tert-butyl ester | 1.02 A | 400.10 |

(S)-2-[3-(2-Methoxy-phenyl)-[1,2,4]oxadiazol-5-yl]-pyrrolidine-1-carboxylic acid tert-butyl ester (B-2-7)

Step A:

TBTU (6.49 g, 20.2 mmol) was added to a rt solution of (S)-1-(tert-butoxycarbonyl)pyrrolidine-2-carboxylic acid (2.90 g, 13.5 mmol) and DIPEA (7 mL, 40.9 mmol) in DCM (32 mL) and stirred for 15 min before hydroxyamidine A-4-6 (2.46 g, 14.8 mmol) was added. After stirring for 1 h, the mixture was diluted with DCM and water. The layers were separated and the aq. layer was extracted with DCM (2×). The combined org. layers were washed with brine, dried (MgSO$_4$), filtered and concentrated in vacuo to obtain (S)-tert-butyl 2-((((amino(2-methoxyphenyl)methylene)amino)oxy)carbonyl)pyrrolidine-1-carboxylate (B-1-7) as an oil which was used further without purification.

Step B:

The crude B-1-7 was taken up in dioxane (85 mL) and refluxed (90° C.) for 2 days. The rxn mixture was concentrated and purified by FC (EtOAc/hept 2:3) to give the title compound B-2-7 as a yellow oil. LC-MS A: $t_R$=0.88 min; [M+H]$^+$=346.05.

Listed in Table 5 below are compounds of structure B-2, prepared from the commercially available (S)-1-(tert-butoxycarbonyl)pyrrolidine-2-carboxylic acid and the corresponding hydroxyamidine according to the above procedure (see B-2-7).

TABLE 5

| B-2 | Hydroxy amidine A-4 | Name | $t_R$ [min] LC/MS-Method | MS-data m/z [M + H]$^+$ |
|---|---|---|---|---|
| B-2-8 | A-4-25 | (S)-2-[3-(2-Chloro-phenyl)-[1,2,4]oxadiazol-5-yl]-pyrrolidine-1-carboxylic acid tert-butyl ester | 0.94 A | ($^{35}$Cl) 350.00 |
| B-2-9 | A-4-30 | (S)-2-[3-(3-Fluoro-2-methyl-phenyl)-[1,2,4]oxadiazol-5-yl]-pyrrolidine-1-carboxylic acid tert-butyl ester | 0.97 A | 348.11 |
| B-2-10 | A-4-44 | (S)-2-[3-(2-Ethoxy-phenyl)-[1,2,4]oxadiazol-5-yl]-pyrrolidine-1-carboxylic acid tert-butyl ester | 0.93 A | 360.06 |

Synthesis of Intermediate B-3

3-(3-Chloro-2-methyl-phenyl)-5-(S)-pyrrolidin-2-yl-[1,2,4]oxadiazole (B-3-1)

TFA (4.88 mL, 63.8 mmol) was added to a 0° C. solution of B-2-1 (1.85 g, 5.08 mmol) in DCM (70 mL). The resulting rxn mixture was warmed to rt and stirred overnight. The volatiles were removed under reduced pressure, the residue diluted with DCM and basified with 1N aq. NaOH. The org. layer was separated and the aq. layer extracted with DCM (2×). The combined org. layers were dried (MgSO$_4$), filtered and concentrated in vacuo to give title compound B-3-1 as a brown oil which was used further without purification. LC-MS B: $t_R$=0.54 min; [M($^{35}$Cl)+H]$^+$=264.11.

Listed in Table 6 below are compounds of structure B-3, prepared according to the above procedure (see B-3-1).

TABLE 6

| B-3 | B-2 | Name | $t_R$ [min] LC/MS-Method | MS-data m/z [M + H]$^+$ |
|---|---|---|---|---|
| B-3-2 | B-2-2 | 5-(S)-Pyrrolidin-2-yl-3-(2-trifluoromethoxy-phenyl)-[1,2,4]oxadiazole | 0.52 B | 300.08 |
| B-3-3 | B-2-3 | 5-(S)-Pyrrolidin-2-yl-3-(2-trifluoromethyl-phenyl)-[1,2,4]oxadiazole | 0.50 B | 284.02 |
| B-3-4 | B-2-4 | 3-(2-Difluoromethoxy-phenyl)-5-(S)-pyrrolidin-2-yl-[1,2,4]oxadiazole | 0.48 B | 282.02 |
| B-3-5 | B-2-5 | 3-(3-Fluoro-2-methoxy-phenyl)-5-(S)-pyrrolidin-2-yl-[1,2,4]oxadiazole | 0.45 B | 264.04 |
| B-3-6 | B-2-6 | 2-Ethoxy-3-((S)-5-pyrrolidin-2-yl-[1,2,4]oxadiazol-3-yl)-pyridine | 0.43 B | 261.60 |
| B-3-11 | B-2-11 | 3-(2-Ethoxy-3-fluoro-phenyl)-5-(S)-pyrrolidin-2-yl-[1,2,4]oxadiazole | 0.61 A | 278.10 |
| B-3-12 | B-2-12 | 5-(S)-Pyrrolidin-2-yl-3-(3-trifluoromethoxy-phenyl)-[1,2,4]oxadiazole | 0.64 A | 300.13 |

3-(2-Methoxy-phenyl)-5-(S)-pyrrolidin-2-yl-[1,2,4]oxadiazole (B-3-7)

4N HCl in dioxane (22 mL, 88 mmol) was added to a 0° C. solution of (S)-tert-butyl 2-(3-(2-methoxyphenyl)-1,2,4-oxadiazol-5-yl)pyrrolidine-1-carboxylate (3.76 g, 10.9 mmol) in DCM (40 mL). The resulting mixture was allowed to warm to rt and stirred at rt for 2 h, then poured into an ice-cooled solution of 4M aq. NaOH (20 mL) and extracted with DCM (2×). The combined org. extracts were washed with brine, dried (MgSO$_4$), filtered and concentrated in vacuo to obtain the title compound B-3-7 as a yellow oil that was used further without purification. LC-MS A: $t_R$=0.53 min; [M+H]$^+$=246.05.

Listed in Table 7 below are compounds of structure B-3, prepared according to the above procedure (see B-3-7).

TABLE 7

| B-3 | SM (B-2) | Name | $t_R$ [min] LC/MS-Method | MS-data m/z [M + H]⁺ |
|---|---|---|---|---|
| B-3-8 | B-2-8 | 3-(2-Chloro-phenyl)-5-(S)-pyrrolidin-2-yl-[1,2,4]oxadiazole | 0.56 A | (³⁵Cl) 250.01 |
| B-3-9 | B-2-9 | 3-(3-Fluoro-2-methyl-phenyl)-5-(S)-pyrrolidin-2-yl-[1,2,4]oxadiazole | 0.61 A | 248.05 |
| B-3-10 | B-2-10 | 3-(2-Ethoxy-phenyl)-5-(S)-pyrrolidin-2-yl-[1,2,4]oxadiazole | 0.58 A | 260.08 |

Synthesis of Intermediate C-1

(S)-1-(5-Methyl-2-[1,2,3]triazol-2-yl-benzoyl)-pyrrolidine-2-carbonitrile (C-1-1)

TBTU (2.03 g, 6.34 mmol) was added to a rt solution of carboxylic acid A-1-2 (1.07 g, 5.28 mmol) and DIPEA (2.71 mL, 15.8 mmol) in DCM (40 mL) and stirred for 5 min, before (S)-pyrrolidine-2-carbonitrile (700 mg, 5.28 mmol) was added. The resulting mixture was stirred at rt for 18 h, then the mixture was diluted with DCM and the org. layer was washed with water. The aq. layer was re-extracted with DCM (2×) and the combined org. layers were dried (MgSO₄), filtered and concentrated in vacuo to give the crude product that was purified by FC (Biotage SP1: EtOAc/hex 3:7 to 1:1) to give the title compound C-1-1 as a white solid. LC-MS A: $t_R$=0.74 min; [M+H]⁺=282.12.

Listed in Table 8 below are compounds of structure C-1, prepared according to the above procedure (see C-1-1).

TABLE 8

| C-1 | SM (A-1) | Name | $t_R$ [min] LC/MS-Method | MS-data m/z [M + H]⁺ |
|---|---|---|---|---|
| C-1-2 | A-1-11 | (S)-1-(5-Methoxy-4-methyl-2-[1,2,3]triazol-2-yl-benzoyl)-pyrrolidine-2-carbonitrile | 0.78 A | 312.05 |
| C-1-3 | A-1-6 | (S)-1-(4,5-Dimethyl-2-[1,2,3]triazol-2-yl-benzoyl)-pyrrolidine-2-carbonitrile | 0.78 A | 296.09 |

Synthesis of Intermediate C-2

(S)—N—Hydroxy-1-(5-methyl-2-[1,2,3]triazol-2-yl-benzoyl)-pyrrolidine-2-carboxamidine (C-2-1)

Hydroxylamine HCl (25 mg, 0.36 mmol) was added to a rt solution of C-1-1 (50 mg, 0.18 mmol) and NaHCO₃ (30 mg, 0.36 mmol) in MeOH (1.2 mL) and the mixture was stirred at rt for 1 h. After the solvent was removed in vacuo, the residue was taken up in EtOAc and brine. The layers were separated and the org. layer was dried (MgSO₄), filtered and concentrated in vacuo to afford the title compound C-2-1 as a yellow paste. LC-MS A: $t_R$=0.56 min; [M+H]⁺=315.15. Listed in Table 9 below are compounds of structure C-2, prepared according to the above procedure (see C-2-1).

TABLE 9

| C-2 | SM (C-1) | Name | $t_R$ [min] LC/MS-Method | MS-data m/z [M + H]⁺ |
|---|---|---|---|---|
| C-2-2 | C-1-2 | (S)-N-Hydroxy-1-(5-methoxy-4-methyl-2-[1,2,3]triazol-2-yl-benzoyl)-pyrrolidine-2-carboxamidine | 0.60 A | 345.03 |
| C-2-3 | C-1-3 | (S)-1-(4,5-Dimethyl-2-[1,2,3]triazol-2-yl-benzoyl)-N-hydroxy-pyrrolidine-2-carboxamidine | 0.60 A | 329.1 |

Synthesis of Intermediate D-1

(S)-2-(N-Hydroxycarbamimidoyl)-pyrrolidine-1-carboxylic acid tert-butyl ester (D-1)

Hydroxylamine HCl (429 mg, 6.11 mmol) was added to a rt solution of (S)-1-Boc-pyrrolidine-2-carbonitrile (800 mg, 4.08 mmol), and NaHCO₃ (514 mg, 6.11 mmol) in MeOH (10 mL). The resulting suspension was stirred at 60° C. for 1.5 h, then filtered (washed with MeOH) and concentrated in vacuo to yield the title compound D-1 as a white solid that was used further without purification. LC-MS B: $t_R$=0.36 min; [M+H]⁺=230.11.

Synthesis of Intermediate D-3

(S)-2-[5-(3-Chloro-2-methyl-phenyl)-[1,2,4]oxadiazol-3-yl]-pyrrolidine-1-carboxylic acid tert-butyl ester (D-3-1)

Step A:

PyBOP (10.16 g, 19.5 mmol) was added to a 0° C. solution of D-1 (4.10 g, 17.9 mmol), 3-chloro-2-methylbenzoic acid (2.77 g, 16.2 mmol) and DIPEA (8.34 mL, 48.7 mmol) in DCM (50 mL). The cooling bath was removed and the mixture was stirred at rt for 2 h, then the mixture was concentrated in vacuo to give (S)-tert-butyl 2-(N'-hydroxycarbamimidoyl) pyrrolidine-1-carboxylate D-2-1 that was used further without purification. LC-MS B: $t_R$=0.88 min; [M(³⁵Cl)+H]⁺=382.14.

Step B:

The crude D-2-1 was dissolved in dioxane (30 mL) and the resulting solution was stirred at 90° C. overnight. The mixture was concentrated in vacuo, diluted with EtOAc and washed with sat. aq. NaHCO₃ (2×). The org. layer was dried (MgSO₄), filtered and concentrated in vacuo to give crude product that was purified by FC (Biotage SP1: EtOAc/hex 1:9 to 1:4) to give the title compound D-3-1 as a yellow oil. LC-MS A: $t_R$=1.01 min; [M(³⁵Cl)+H]⁺=364.14.

Listed in Table 10 below are compounds of structure D-3, prepared according to the above procedure (see D-3-1).

TABLE 10

| D-3 | SM | Name | $t_R$ [min] LC/MS-Method | MS-data m/z [M + H]$^+$ |
|---|---|---|---|---|
| D-3-2 | | (S)-2-[5-(2-Trifluoromethoxy-phenyl)-[1,2,4]oxadiazol-3-yl]-pyrrolidine-1-carboxylic acid tert-butyl ester | 0.99 A | 400.12 |
| D-3-3 | | (S)-2-[5-(2-Ethoxy-3-fluoro-phenyl)-[1,2,4]oxadiazol-3-yl]-pyrrolidine-1-carboxylic acid tert-butyl ester | 0.97 A | 378.18 |
| D-3-4 | | (S)-2-[5-(2-Ethoxy-pyridin-3-yl)-[1,2,4]oxadiazol-3-yl]-pyrrolidine-1-carboxylic acid tert-butyl ester | 0.93 A | 361.2 |
| D-3-5 | | (S)-2-[5-(3-Fluoro-2-methyl-phenyl)-[1,2,4]oxadiazol-3-yl]-pyrrolidine-1-carboxylic acid tert-butyl ester | 0.98 A | 348.11 |
| D-3-6 | | (S)-2-[5-(3-Fluoro-2-methoxy-phenyl)-[1,2,4]oxadiazol-3-yl]-pyrrolidine-1-carboxylic acid tert-butyl ester | 0.94 A | 264.09 |
| D-3-7 | | (S)-2-[5-(2,3-Dimethyl-phenyl)-[1,2,4]oxadiazol-3-yl]-pyrrolidine-1-carboxylic acid tert-butyl ester | 0.99 A | 344.13 |
| D-3-8 | | (S)-2-[5-(2-Ethyl-phenyl)-[1,2,4]oxadiazol-3-yl]-pyrrolidine-1-carboxylic acid tert-butyl ester | 1.00 A | 344.14 |
| D-3-9 | | (S)-2-[5-(2,5-Dimethyl-phenyl)-[1,2,4]oxadiazol-3-yl]-pyrrolidine-1-carboxylic acid tert-butyl ester | 1.00 A | 344.14 |

TABLE 10-continued

| D-3 | SM | Name | $t_R$ [min] LC/MS-Method | MS-data m/z [M + H]$^+$ |
|---|---|---|---|---|
| D-3-10 | | (S)-2-[5-(3-Methyl-5-methoxy-phenyl)-[1,2,4]oxadiazol-3-yl]-pyrrolidine-1-carboxylic acid tert-butyl ester | 0.97 A | 360.11 |
| D-3-11 | | (S)-2-[5-(2-Methyl-5-methoxy-phenyl)-[1,2,4]oxadiazol-3-yl]-pyrrolidine-1-carboxylic acid tert-butyl ester | 0.98 A | 360.13 |
| D-3-12 | | (S)-2-[5-(3-Methyl-6-methoxy-phenyl)-[1,2,4]oxadiazol-3-yl]-pyrrolidine-1-carboxylic acid tert-butyl ester | 0.94 A | 360.1 |
| D-3-13 | | (S)-2-[5-(3-Chloro-2-methoxy-phenyl)-[1,2,4]oxadiazol-3-yl]-pyrrolidine-1-carboxylic acid tert-butyl ester | 0.97 A | 380.04 |
| D-3-14 | | (S)-2-[5-(2-Methyl-3-methoxy-phenyl)-[1,2,4]oxadiazol-3-yl]-pyrrolidine-1-carboxylic acid tert-butyl ester | 0.98 A | 360.12 |

Synthesis of Intermediate D-4

5-(3-Chloro-2-methyl-phenyl)-3-(S)-pyrrolidin-2-yl-[1,2,4]oxadiazole (D-4-1)

TFA (10 mL, 131 mmol) was added to a rt solution of D-3-1 (3.68 g, 10.1 mmol) in DCM (50 mL) and the resulting mixture was stirred for 1 h. The volatiles were removed in vacuo and the residue was dissolved in EtOAc and basified with 1M aq. NaOH. The org. layer was separated and the aq. layer extracted with EtOAc (1×). The combined org. extracts were concentrated in vacuo to give the title compound D-4-1 as a red oil that was used further without purification. LC-MS A: $t_R$=0.61 min; [M($^{35}$Cl)+H]$^+$=264.22.

Listed in Table 11 below are compounds of structure D-4, prepared according to the above procedure (see D-4-1).

TABLE 11

| D-4 | SM (D-3) | Name | $t_R$ [min] LC/MS-Method | MS-data m/z [M + H]$^+$ |
|---|---|---|---|---|
| D-4-2 | D-3-2 | 3-(S)-Pyrrolidin-2-yl-5-(2-trifluoromethoxy-phenyl)-[1,2,4]oxadiazole | 0.63 A | 300.11 |
| D-4-3 | D-3-3 | 5-(2-Ethoxy-3-fluoro-phenyl)-3-(S)-pyrrolidin-2-yl-[1,2,4]oxadiazole | 0.59 A | 278.24 |
| D-4-4 | D-3-4 | 2-Ethoxy-3-((S)-3-pyrrolidin-2-yl-[1,2,4]oxadiazol-5-yl)-pyridine | 0.53 A | 261.23 |
| D-4-5 | D-3-5 | 5-(3-Fluoro-2-methyl-phenyl)-3-(S)-pyrrolidin-2-yl-[1,2,4]oxadiazole | 0.59 A | 248.09 |

TABLE 11-continued

| D-4 | SM (D-3) | Name | $t_R$ [min] LC/MS-Method | MS-data m/z [M + H]$^+$ |
|---|---|---|---|---|
| D-4-6 | D-3-6 | 5-(3-Fluoro-2-methoxy-phenyl)-3-(S)-pyrrolidin-2-yl-[1,2,4]oxadiazole | 0.56 A | 264.08 |
| D-4-7 | D-3-7 | 5-(2,3-Dimethyl-phenyl)-3-(S)-pyrrolidin-2-yl-[1,2,4]oxadiazole | 0.61 A | 244.10 |
| D-4-8 | D-3-8 | 5-(2-Ethyl-phenyl)-3-(S)-pyrrolidin-2-yl-[1,2,4]oxadiazole | 0.60 A | 244.11 |
| D-4-9 | D-3-9 | 5-(2,5-Dimethyl-phenyl)-3-(S)-pyrrolidin-2-yl-[1,2,4]oxadiazole | 0.60 A | 244.11 |
| D-4-10 | D-3-10 | 5-(3-Methoxy-5-methyl-phenyl)-3-(S)-pyrrolidin-2-yl-[1,2,4]oxadiazole | 0.60 A | 260.11 |
| D-4-11 | D-3-11 | 5-(5-Methoxy-2-methyl-phenyl)-3-(S)-pyrrolidin-2-yl-[1,2,4]oxadiazole | 0.60 A | 260.10 |
| D-4-12 | D-3-12 | 5-(2-Methoxy-5-methyl-phenyl)-3-(S)-pyrrolidin-2-yl-[1,2,4]oxadiazole | 0.58 A | 260.10 |
| D-4-13 | D-3-13 | 5-(3-Chloro-2-methoxy-phenyl)-3-(S)-pyrrolidin-2-yl-[1,2,4]oxadiazole | 0.59 A | 280.05 |
| D-4-14 | D-3-14 | 5-(3-Methoxy-2-methyl-phenyl)-3-(S)-pyrrolidin-2-yl-[1,2,4]oxadiazole | 0.60 A | 260.10 |

Synthesis of Intermediate E-1

(S)-2-Ethynyl-pyrrolidine-1-carboxylic acid tert-butyl ester (E-1)

Dimethyl(1-diazo-2-oxopropyl)phosphonate (2.30 g, 12 mmol) was added to a rt solution of Boc-L-prolinal (1.88 mL, 10 mmol) and $K_2CO_3$ (2.77 g, 20.1 mmol) in MeOH (100 mL) and the resulting suspension was stirred at rt for 18 h. The rxn mixture was concentrated in vacuo, dissolved in DCM and washed with sat. aq. NaHCO$_3$ and brine. The org. layer was dried (MgSO$_4$), filtered and evaporated to give the title compound (E-1) a yellow oil that was used further without purification. LC-MS B: $t_R$=0.75 min; [M+H]$^+$=196.28.

Synthesis of Intermediate E-2

2,3-Dimethyl-benzaldehyde oxime (E-2-1)

Hydroxylamine HCl (1.056 g, 15.2 mmol) was added to a rt solution of 2,3-dimethylbenzaldehyde (2.00 g, 14.9 mmol) and NaOAc (1.26 g, 15.3 mmol) in MeOH (8.5 mL) and the resulting suspension was stirred at rt for 2 h. The rxn mixture was concentrated in vacuo, then DCM and water were added. The layers were separated and the aq. layer was extracted with DCM. The combined org. layers were dried (MgSO$_4$), filtered and concentrated in vacuo to give the title compound (E-2-1) as a white solid that was used further without purification. LC-MS B: $t_R$=0.66 min; [M+H]$^+$=150.15.

Listed in Table 12 below are compounds of structure E-2, prepared according to the above procedure (see E-2-1). All aldehydes were commercially available.

TABLE 12

| E-2 | SM Aldehyde | Name | $t_R$ [min] LC/MS-Method | MS-data m/z [M + H]$^+$ |
|---|---|---|---|---|
| E-2-2 | 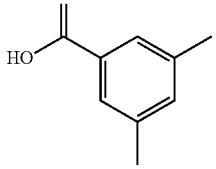 | 3,5-Dimethyl-benzaldehyde oxime | 0.69 B | 191.28 [M + H + MeCN]$^+$ |
| E-2-3 | 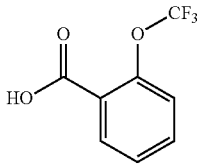 [SMILES: O=C(O)c1ccccc1OC(F)(F)F] | 2-Trifluoromethoxy-benzaldehyde oxime | 0.72 B | 247.12 [M + H + MeCN]$^+$ |
| E-2-4 | 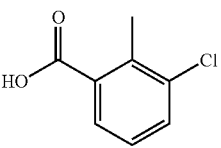 | 3-Chloro-2-methyl-benzaldehyde oxime | 0.71 B | 211.00 [M($^{35}$Cl) + H + MeCN]$^+$ |

TABLE 12-continued

| E-2 | SM Aldehyde | Name | $t_R$ [min] LC/MS-Method | MS-data m/z [M + H]$^+$ |
|---|---|---|---|---|
| E-2-5 | (structure: 2-trifluoromethoxy benzoic acid) | 2-Trifluoromethoxy-benzaldehyde oxime | 0.72 B | 247.12 [M + H + MeCN]$^+$ |
| E-2-6 | (structure: 2-isopropoxy pyridine-3-carboxylic acid) | 2-Isopropoxy-pyridine-3-carbaldehyde oxime | 0.65 B | 181.20 |
| E-2-7 | (structure: 2-methoxy pyridine-3-carboxylic acid) | 2-Methoxy-pyridine-3-carbaldehyde oxime | 0.46 B | 153.03 |
| E-2-8 | (structure: 2-ethoxy pyridine-3-carboxylic acid) | 2-Ethoxy-pyridine-3-carbaldehyde oxime | 0.55 B | 166.98 |
| E-2-9 | (structure: 3-fluoro-2-methoxy benzoic acid) | 3-Fluoro-2-methoxy-benzaldehyde oxime | 0.61 B | 211.12 [M + H + MeCN]$^+$ |

Synthesis of Intermediate E-3

(S)-2-(3-Phenyl-isoxazol-5-yl)-pyrrolidine-1-carboxylic acid tert-butyl ester (E-3-1)

Chloramine T trihydrate (741 mg, 3.26 mmol) was added to a rt solution of commercially available benzaldehyde oxime (394 mg, 3.26 mmol) in MeOH (15 mL) and the rxn mixture was stirred for 5 min, before a solution of E-1 (636 mg, 3.26 mmol) in MeOH (15.0 mL) was added. The rxn mixture was stirred at rt for 1 h, then heated to 60° C. for 1 h and at 50° C. for 18 h. The rxn mixture was concentrated, dissolved in DCM, washed with sat. aq. NaHCO$_3$ and the org. layer concentrated in vacuo. Purification by FC (Biotage SP1: EtOAc/hex 1:9 to 3:7) gave the title compound E-3-1 as a yellow oil. LC-MS B: $t_R$=0.89 min; [M+H]$^+$=315.22.

Listed in Table 13 below are compounds of structure E-3, prepared according to the above procedure (see E-3-1).

TABLE 13

| E-3 | SM Oxime (E-2) | Name | $t_R$ [min] LC/MS-Method | MS-data m/z [M + H]$^+$ |
|---|---|---|---|---|
| E-3-2 | E-2-2 | (S)-2-[3-(2,3-dimethylphenyl)isoxazol-5-yl]-pyrrolidine-1-carboxylic acid tert-butyl ester | 0.97 B | 343.09 |
| E-3-3 | E-2-3 | (S)-2-[3-(3,5-dimethylphenyl)isoxazol-5-yl]-pyrrolidine-1-carboxylic acid tert-butyl ester | 1.00 B | 343.12 |
| E-3-4 | E-2-4 | (S)-2-[3-(2-Methyl-3-chlorophenyl)isoxazol-5-yl]-pyrrolidine-1-carboxylic acid tert-butyl ester | 1.00 B | ($^{35}$Cl) 363.00 |
| E-3-5 | E-2-5 | (S)-2-[3-(2-(Trifluoromethoxy)phenyl)isoxazol-5-yl]-pyrrolidine-1-carboxylic acid tert-butyl ester | 0.98 B | 398.97 |
| E-3-6 | E-2-6 | (S)-2-[3-(2-Isopropoxypyridin-3-yl)isoxazol-5-yl]-pyrrolidine-1-carboxylic acid tert-butyl ester | 0.98 B | 374.03 |

TABLE 13-continued

| E-3 | SM Oxime (E-2) | Name | $t_R$ [min] LC/MS-Method | MS-data m/z [M + H]$^+$ |
|---|---|---|---|---|
| E-3-7 | E-2-7 | (S)-2-[3-(2-Methoxypyridin-3-yl)isoxazol-5-yl]-pyrrolidine-1-carboxylic acid tert-butyl ester | 0.86 B | 346.03 |
| E-3-8 | E-2-8 | (S)-2-[3-(2-Ethoxy-pyridin-3-yl)-isoxazol-5-yl]-pyrrolidine-1-carboxylic acid tert-butyl ester | 0.92 B | 360.04 |
| E-3-9 | E-2-9 | (S)-2-[3-(2-Methoxy-3-fluorophenyl)isoxazol-5-yl]-pyrrolidine-1-carboxylic acid tert-butyl ester | 0.93 B | 363.00 |

Synthesis of Intermediate E-4

3-Phenyl-5-(S)-pyrrolidin-2-yl-isoxazole (E-4-1)

TFA (1.2 mL, 15.7 mmol) was added to a 0° C. solution of E-3-1 (393 mg, 1.25 mmol) in DCM (10 mL) and the resulting rxn mixture was stirred at rt for 3 h. The rxn mixture was concentrated in vacuo, the residue dissolved in DCM and basified with 1M aq. NaOH. The layers were separated and the aq. layer was extracted with DCM (2×). The combined org. layers were dried (MgSO$_4$), filtered and concentrated in vacuo to give the title compound E-4-1 as an orange solid that was used further without purification. LC-MS B: $t_R$=0.44 min; [M+H]$^+$=215.23.

Listed in Table 14 below are compounds of structure E-4, prepared according to the above procedure (see E-4-1).

TABLE 14

| E-4 | SM (E-3) | Name | $t_R$ [min] LC/MS-Method | MS-data m/z [M + H]$^+$ |
|---|---|---|---|---|
| E-4-2 | E-3-2 | 3-(2,3-Dimethyl-phenyl)-5-(S)-pyrrolidin-2-yl-isoxazole | 0.54 B | 242.98 |
| E-4-3 | E-3-3 | 3-(3,5-Dimethyl-phenyl)-5-(S)-pyrrolidin-2-yl-isoxazole | 0.57 B | 243.03 |
| E-4-4 | E-3-4 | 3-(3-Chloro-2-methyl-phenyl)-5-(S)-pyrrolidin-2-yl-isoxazole | 0.57 B | ($^{35}$Cl) 263.03 |
| E-4-5 | E-3-5 | 5-(S)-Pyrrolidin-2-yl-3-(2-trifluoromethoxy-phenyl)-isoxazole | 0.56 B | 299.02 |
| E-4-6 | E-3-6 | 2-Methoxy-3-((S)-5-pyrrolidin-2-yl-isoxazol-3-yl)-pyridine | 0.51 B | 273.89 |
| E-4-7 | E-3-7 | 2-Isopropoxy-3-((S)-5-pyrrolidin-2-yl-isoxazol-3-yl)-pyridine | 0.4 B | 246.06 |
| E-4-8 | E-3-8 | 2-Ethoxy-3-((S)-5-pyrrolidin-2-yl-isoxazol-3-yl)-pyridine | 0.46 B | 301.08 |
| E-4-9 | E-3-9 | 3-(3-Fluoro-2-methoxy-phenyl)-5-(S)-pyrrolidin-2-yl-isoxazole | 0.49 B | 263.07 |

Synthesis of Intermediate E-5

(S)-tert-butyl 2-((hydroxyimino)methyl)pyrrolidine-1-carboxylate (E-5)

Hydroxylamine HCl (355 mg, 5.11 mmol) was added to a rt solution of Boc-L-prolinal (1.00 g, 5.02 mmol) and sodium acetate (423 mg, 5.15 mmol) in MeOH (4.5 mL) and stirred at rt overnight. The rxn mixture was concentrated and taken up in DCM and water. The layers were separated and the inorg. layer was extracted with DCM (1×). The combined org. layers were washed with brine (1×), dried (MgSO$_4$) and concentrated to yield the title compound E-5 as a colorless oil which was used in the next step without further purification. LC-MS A: $t_R$=0.66 min; [M+H]$^+$=215.21.

Synthesis of Intermediate E-6

1-Chloro-3-ethynyl-2-methyl benzene (E-6-2)

Dimethyl(1-diazo-2-oxopropyl)phosphonate (482 mg, 2.51 mmol) was added to a rt solution of 3-chloro-2-methylbenzaldehyde (388 mg, 2.51 mmol) and K$_2$CO$_3$ (694 mg, 5.02 mmol) in MeOH (25 mL) and the resulting solution was stirred overnight at rt. The rxn mixture was concentrated, DCM and sat. NaHCO$_3$ (2×) was added, the layers separated and the inorg. layer extracted with DCM (2×). The combined org. extracts were washed with brine (1×), dried (MgSO$_4$), filtered and concentrated to give the title compound E-6-2 as a brown liquid which was used further without purification. LC-MS A: $t_R$=0.91 min; [M+H]$^+$=no ionization. $^1$H NMR (CDCl$_3$) $\delta_H$: 7.39 (dd, J$_1$=15.3 Hz, J$_2$=7.7 Hz, 2H), 7.10 (t, J=7.8 Hz, 1H), 3.33 (s, 1H), 2.55 (s, 3H).

1-Ethynyl-2-(trifluoromethoxy)benzene (E-6-3)

Dimethyl(1-diazo-2-oxopropyl)phosphonate (1.11 mL, 7.36 mmol) was added to a rt solution of 2-(trifluoromethoxy)benzaldehyde (1.40 g, 7.36 mmol) and K$_2$CO$_3$ (2.04 g, 14.7 mmol) in MeOH (70 mL) and the resulting mixture was stirred at rt for 3 h. The rxn mixture was concentrated, DCM and sat. NaHCO$_3$ were added, the layers separated and the inorg. layer extracted with DCM (2×). The combined org. extracts were dried (MgSO$_4$), filtered and concentrated to give the title compound E-6-3 as a yellow oil which was used as such without further purification. LC-MS A: $t_R$=0.90 min; [M+H]$^+$=no ionization. $^1$H NMR (DMSO) $\delta_H$: 7.56 (m, 5H), 4.56 (s, 1H).

Synthesis of Intermediate E-7

(S)-2-(5-Phenyl-isoxazol-3-yl)-pyrrolidine-1-carboxylic acid tert-butyl ester (E-7-1)

Chloroamine T trihydrate (319 mg, 1.4 mmol) was added to a rt solution of E-5 (300 mg, 1.4 mmol) in MeOH (6.5 mL) and the resulting mixture was stirred at rt for 5 min before a solution of phenylacetylene (154 uL, 1.4 mmol) in MeOH (6.5 mL) was added. The resulting mixture was stirred at rt for 1 h, then heated to 60° C. for 3 h. The rxn mixture was concentrated, dissolved in DCM and washed with sat. aq. NaHCO$_3$ and brine. The org. layer was dried (MgSO$_4$), filtered and concentrated in vacuo. The crude was purified by FC (EtOAc/hex 2:3) to give the title compound E-7-1 as a colorless oil. LC-MS A: $t_R$=0.93 min; [M+H]$^+$=315.04.

Listed in Table 15 below are compounds of structure E-7, prepared according to the above procedure (see E-7-1).

TABLE 15

| E-7 | SM E-6 | Name | $t_R$ [min] LC/MS-Method | MS-data m/z [M + H]$^+$ |
|---|---|---|---|---|
| E-7-2 | E-6-2 | (S)-2-[5-(3-Chloro-2-methyl-phenyl)-isoxazol-3-yl]-pyrrolidine-1-carboxylic acid tert-butyl ester | 1.01 A | ($^{35}$Cl) 362.94 |
| E-7-3 | E-6-3 | (S)-2-[5-(2-Trifluoromethoxy-phenyl)-isoxazol-3-yl]-pyrrolidine-1-carboxylic acid tert-butyl ester | 1.01 A | 399.06 |

Synthesis of Intermediate E-8

5-Phenyl-3-(S)-pyrrolidin-2-yl-isoxazole HCl (E-8-1)

4 N HCl in dioxane (1.0 mL) was added to an ice-cooled solution of E-7-1 (150 mg, 0.48 mmol) in DCM (1 mL). The rxn mixture was stirred at rt for 2.5 h, then the solvent was removed in vacuo to yield the title compound as yellow oil which was used as such in the next step. LC-MS A: $t_R$=0.57 min; [M+H]$^+$=215.17.

Listed in Table 16 below are compounds of structure E-8, prepared according to the above procedure (see E-8-1).

TABLE 16

| E-8 | SM E-7 | Name | $t_R$ [min] LC/MS-Method | MS-data m/z [M + H]$^+$ |
|---|---|---|---|---|
| E-8-2 | E-7-2 | 5-(3-Chloro-2-methyl-phenyl)-3-(S)-pyrrolidin-2-yl-isoxazole HCl | 0.66 A | ($^{35}$Cl) 263.1 |
| E-8-3 | E-7-3 | 5-(2-Trifluoromethoxy-phenyl)-3-(S)-pyrrolidin-2-yl-isoxazole HCl | 0.66 A | 299.1 |

Synthesis of Intermediate F-1

3-Methyl-benzoic acid hydrazide (F-1-2)

Hydrazine monohydrate (2.07 mL, 66.6 mmol) was added to a rt solution of methyl 3-methylbenzoate (0.94 mL, 6.66 mmol) in EtOH (10 mL). The resulting solution was refluxed (80° C.) overnight. After the rxn mixture was concentrated in vacuo, ice water (30 mL) was added and stirred at rt for 15 min. The formed precipitate was filtered off and rinsed with toluene to give the title compound as a white solid. The mother liquid was extracted with DCM (3×). The combined org. layers and the solids were combined and concentrated in vacuo to yield the title compound F-1-2 as a white solid. LC-MS B: $t_R$=0.36 min; [M+H]$^+$=151.21.

3-Chloro-2-methyl-benzoic acid hydrazide (F-1-3)

TBTU (678 mg, 2.11 mmol) was added to a rt solution of 3-chloro-2-methylbenzoic acid (300 mg, 1.76 mmol) and DIPEA (0.9 mL, 5.28 mmol) in DMF (5.0 mL) and the resulting solution was stirred at rt for 15 min. The mixture was cooled to 0° C. and 1M hydrazine in THF (10.6 mL, 10.6 mmol) was added and the yellow solution was stirred at rt overnight. The rxn mixture was diluted with DCM and washed with sat. aq. NaHCO$_3$. The aq. layer was re-extracted with DCM (1×) and the combined org. layers were concentrated in vacuo to give the title compound F-1-3 as a light orange solid that was used further without purification. LC-MS A: $t_R$=0.50 min; [M($^{35}$Cl)+H]$^+$=185.24.

Listed in Table 17 below are compounds of structure F-1, prepared according to the above procedure (see F-1-2 for ester or F-1-3 for carboxylic acid as SM).

TABLE 17

| F-1 | SM | Name | $t_R$ [min] LC/MS-Method | MS-data m/z [M + H]$^+$ |
|---|---|---|---|---|
| F-1-4 | (structure) | 2-Methylbenzohydrazide | 0.37 A | 151.17 |
| F-1-5 | (structure) | 2-(Trifluoromethoxy)benzohydrazide | 0.50 A | 221.16 |
| F-1-6 | (structure) | 3-Fluoro-2-methylbenzohydrazide | 0.43 A | 168.98 |

TABLE 17-continued

| F-1 | SM | Name | t_R [min] LC/MS-Method | MS-data m/z [M + H]+ |
|---|---|---|---|---|
| F-1-7 | | 2-Ethoxybenzohydrazide | 0.50 A | 181.21 |
| F-1-8 | | 3-Fluoro-2-methoxybenzohydrazide | 0.46 A | 185.21 |
| F-1-9 | | 2-Ethoxynicotinohydrazide | 0.45 A | 182.18 |
| F-1-10 | | 2-Methoxybenzohydrazide | 0.43 A | 167.05 |
| F-1-11 | | 3,5-Dimethylbenzohydrazide | 0.43 A | 165.09 |
| F-1-12 | | 2-Ethylbenzohydrazide | 0.47 A | 165.02 |
| F-1-13 | | 3-Methoxybenzohydrazide | 0.43 A | 167.04 |
| F-1-14 | | 4-Methoxybenzohydrazide | 0.41 A | 167.05 |

TABLE 17-continued

| F-1 | SM | Name | $t_R$ [min] LC/MS-Method | MS-data m/z [M + H]$^+$ |
|---|---|---|---|---|
| F-1-15 | (structure) | 2-Propoxybenzohydrazide | 0.57 A | 195.24 |
| F-1-16 | (structure) | 3-Chloro-2-methoxybenzohydrazide | 0.50 A | ($^{35}$Cl) 201.09 |

Synthesis of Intermediate F-3

(S)-2-[5-(Phenyl)-[1,3,4]oxadiazol-2-yl]-pyrrolidine-1-carboxylic acid tert-butyl ester (F-3-1)

Step A:
PyBOP (945 mg, 1.81 mmol) was added to a 0° C. solution of Boc-L-proline (300 mg, 1.39 mmol), commercially available benzohydrazide (190 mg, 1.39 mmol) and DIPEA (0.716 mL, 4.18 mmol) in DCM (5.0 mL) and the resulting mixture was stirred at rt for 3 h. The rxn mixture was washed with water and the aq. layer was re-extracted with DCM (2×). The combined org. layers were concentrated in vacuo and purified by FC (Biotage SP1: EtOAc/hex 3:7 to 1:1) to give (S)-tert-butyl 2-(2-benzoylhydrazinecarbonyl)pyrrolidine-1-carboxylate F-2-1 as a white solid.

Step B:
1-Methoxy-N-triethylammoniosulfonyl-methanimidate (456 mg, 1.91 mmol) was added to a solution of F-2-1 (319 mg, 0.96 mmol) in dioxane (10 mL) and the resulting solution was irradiated in the microwave at 110° C. for 20 min. The mixture was diluted with a sat. aq. NaHCO$_3$, extracted with EtOAc (2×) and the combined org. layers were concentrated in vacuo to give the title compound F-3-1 that was used without further purification. LC-MS B: $t_R$=0.79 min; [M+H]$^+$=316.30.

Listed in Table 18 below are compounds of structure F-3, prepared according to the above procedure (see F-3-1).

TABLE 18

| F-3 | SM (F-1) | Name | $t_R$ [min] LC/MS-Method | MS-data m/z [M + H]$^+$ |
|---|---|---|---|---|
| F-3-2 | F-1-2 | (S)-2-(5-m-Tolyl-[1,3,4]oxadiazol-2-yl)-pyrrolidine-1-carboxylic acid tert-butyl ester | 0.85 B | 330.26 |
| F-3-3 | F-1-3 | (S)-2-[5-(3-Chloro-2-methyl-phenyl)-[1,3,4]oxadiazol-2-yl]-pyrrolidine-1-carboxylic acid tert-butyl ester | 0.94 A | ($^{35}$Cl) 364.10 |
| F-3-4 | F-1-4 | (S)-2-(5-o-Tolyl-[1,3,4]oxadiazol-2-yl)-pyrrolidine-1-carboxylic acid tert-butyl ester | 0.89 A | 330.20 |
| F-3-5 | F-1-5 | (S)-2-[5-(2-Trifluoromethoxy-phenyl)-[1,3,4]oxadiazol-2-yl]-pyrrolidine-1-carboxylic acid tert-butyl ester | 0.93 A | 400.08 |

Synthesis of Intermediate F-4

2-Phenyl-5-(S)-pyrrolidin-2-yl-[1,3,4]oxadiazole (F-4-1)

TFA (1.5 mL, 19.5 mmol) was added to a 0° C. solution of F-3-1 (500 mg, 1.57 mmol) in DCM (15.0 mL) and the resulting rxn mixture was stirred at rt for 4 h. The rxn mixture was concentrated in vacuo to remove TFA, the residue was dissolved in DCM and basified with 1M aq. NaOH to pH 12. The layers were separated and the aq. layer was extracted with DCM (1×). The combined org. layers were concentrated in vacuo to give the title compound F-4-1 as a yellow oil that was used without further purification. LC-MS B: $t_R$=0.38 min; [M+H]$^+$=216.30. Listed in Table 19 below are compounds of structure F-4, prepared according to the above procedure (see F-4-1).

TABLE 19

| F-4 | SM (F-3) | Name | $t_R$ [min] LC/MS-Method | MS-data m/z [M + H]$^+$ |
|---|---|---|---|---|
| F-4-2 | F-3-2 | 2-(S)-Pyrrolidin-2-yl-5-m-tolyl-[1,3,4]oxadiazole | 0.45 B | 230.28 |
| F-4-3 | F-3-3 | 2-(3-Chloro-2-methyl-phenyl)-5-(S)-pyrrolidin-2-yl-[1,3,4]oxadiazole | 0.58 A | ($^{35}$Cl) 264.15 |
| F-4-4 | F-3-4 | 2-(S)-Pyrrolidin-2-yl-5-o-tolyl-[1,3,4]oxadiazole | 0.53 A | 230.21 |
| F-4-5 | F-3-5 | 2-(S)-Pyrrolidin-2-yl-5-(2-trifluoromethoxy-phenyl)-[1,3,4]oxadiazole | 0.58 A | 300.16 |

Synthesis of G-3

(S)-1-(5-methyl-2-(2H-1,2,3-triazol-2-yl)benzoyl) pyrrolidine-2-carbohydrazide (G-3-1)

Hydrazine monohydrate (813 mg, 15.9 mmol) was added to a rt solution of (S)-methyl 1-(5-methyl-2-(2H-1,2,3-triazol-2-yl)benzoyl)pyrrolidine-2-carboxylate A-2-1 (500 mg, 1.59 mmol) in EtOH (2.3 mL) and the resulting suspension was heated to 80° C. for 1 h. The rxn mixture was concentrated in vacuo and diluted with water and DCM. The org. layer was separated and the aq. layer was extracted with DCM (1×). The combined org. layers were dried (MgSO$_4$), filtered and concentrated to give the title compound as a white foam. LC-MS A: $t_R$=0.57 min; [M+H]$^+$=315.18.

Synthesis of H-2

2-(S)-Pyrrolidin-2-yl-5-(2-trifluoromethoxy-phenyl)-[1,3,4]thiadiazole (H-2-1)

Step A:
TBTU (3.42 g, 10.7 mmol) was added to a rt solution of Boc-S-proline (1.53 g, 7.11 mmol) and DIPEA (3.65 mL, 21.3 mmol) in DCM (15 mL) and the rxn mixture was stirred for 10 min at rt, before hydrazide F-1-5 (3.13 g, 7.81 mmol) in DCM (5 mL) was added and stirring continued for 30 min. The rxn mixture was diluted with DCM and water, the org. layer separated and the aq. layer extracted with DCM (1×). The combined org. extracts were washed with brine, dried (MgSO$_4$), filtered and concentrated in vacuo. The crude oil was purified by FC (EtOAc/hept 7:3) to obtain (S)-2-[N'-(2-Trifluoromethoxy-benzoyl)-hydrazinocarbonyl]-pyrrolidine-1-carboxylic acid tert-butyl ester (F-2-5) as a white solid. LC-MS A: $t_R$=0.78 min; [M+H]$^+$=417.87
Step B:
Lawesson's reagent (194 mg, 0.479 mmol) was added to a rt solution of F-2-5 (200 mg, 0.48 mmol) in dioxane (2 mL) and the rxn mixture was heated in a sealed tube to 115° C. for 1.5 h. The mixture was allowed to reach rt, then the rxn mixture was quenched with water and extracted with EtOAc (2×). The combined org. extracts were dried (MgSO$_4$), filtered and concentrated. The crude oil was purified by FC (EtOAc/hept 2:3) to give (S)-2-[5-(2-trifluoromethoxy-phenyl)-[1,3,4]thiadiazol-2-yl]-pyrrolidine-1-carboxylic acid tert-butyl ester (H-1-1). LC-MS A: $t_R$=0.98 min; [M+H]$^+$=416.05
Step C:
4 M HCl in dioxane (0.44 mL, 1.76 mmol) was added dropwise to a 0° C. solution of H-1-1 (91 mg, 0.22 mmol) in DCM (1.2 mL) and stirred at rt for 7 h. The mixture was quenched with ice-cooled 2N aq. NaOH (2 mL) until pH 14, then extracted with DCM (2×) The combined org. extracts were dried (MgSO$_4$), filtered and concentrated in vacuo to obtain the title compound H-2-1 as a yellow oil: LC-MS A: $t_R$=0.61 min; [M+H]$^+$=316.11

Synthesis of Intermediate I-1

2-Bromo-1-(2-(trifluoromethoxy)phenyl)ethanone (I-1-2)

Phenyltrimethylammonium tribromide (1.20 g, 3.18 mmol) was added to a rt solution of 2'-(trifluoromethoxy)acetophenone (650 mg, 3.18 mmol) in THF (8.5 mL) and the resulting suspension was stirred at rt for 1 h. The rxn mixture was diluted with EtOAc and water. The org. layer was separated and the aq. layer was extracted with EtOAc (1×). The combined org. layers were dried (MgSO$_4$), filtered and the solvent was removed in vacuo to yield the title compound (I-1-2) as a colorless oil which was used further without purification. LC-MS A: $t_R$=0.89 min; [M+H]$^+$=no ionization. $^1$H NMR (DMSO) $\delta_H$: 7.97 (dd, J$_1$=7.7 Hz, J$_2$=1.7 Hz, 1H), 7.76 (m, 1H), 7.59 (m, 2H), 4.86 (s, 2H).

2-Bromo-1-(3-chloro-2-methylphenyl)ethanone (I-1-3)

The title compound was prepared from 1-(3-chloro-2-methylphenyl)ethanone in analogy to the procedure described for I-1-2. LC-MS A: $t_R$=0.89 min; [M+H]$^+$=no ionization. $^1$H NMR (DMSO) $\delta_H$: δ: 7.71 (m, 2H), 7.39 (m, 1H), 4.90 (s, 2H), 2.29 (m, 3H).

Synthesis of Intermediate I-2

(S)-2-Oxo-2-phenylethyl 1-(5-methyl-2-(2H-1,2,3-triazol-2-yl)benzoyl)pyrrolidine-2-carboxylate (I-2-1)

K$_2$CO$_3$ (107 mg, 0.78 mmol) was added to a rt solution of A-3-1 (200 mg, 0.67 mmol), 2-bromoacetophenone (135 mg, 0.67 mmol) in DMF (6.0 mL) and the suspension was stirred for 18 h. The rxn mixture was diluted with EtOAc and washed with water (1×). The aq. layer was re-extracted with EtOAc (2×) and the combined org. layers were concentrated in vacuo to yield the title compound as a yellow oil which was used further without purification. LC-MS A: $t_R$=0.88 min; [M+H]$^+$=419.04.

(S)-2-Oxo-2-(2-(trifluoromethoxy)phenyl)ethyl 1-(5-methyl-2-(2H-1,2,3-triazol-2-yl)benzoyl)pyrrolidine-2-carboxylate (I-2-2)

The title compound was prepared from I-1-2 in analogy to the procedure described for I-2-1. LC-MS A: $t_R$=0.95 min; [M+H]$^+$=503.07.

Synthesis of Intermediate J-1

2-Amino-1-(2-methoxyphenyl)ethanone HBr (J-1-2)

Step A:
2-Bromo-1-(2-methoxyphenyl)ethanone (5.0 g, 21.4 mmol) in CHCl$_3$ (10 mL) was added to a rt solution of hexamethylenetetramine (3.03 g, 21.4 mmol) in CHCl$_3$ (50 mL) and the rxn mixture was stirred at rt for 16 h. The suspension was filtered, the solid washed with CHCl$_3$ and concentrated in vacuo to yield (3r,5r,7r)-1-(2-(2-methoxyphenyl)-2-oxoethyl)-1,3,5,7-tetraazaadamantan-1-ium bromide which was used us such in the next step. LC-MS B: $t_R$=0.39 min; [M+H]$^+$=289.2.
Step B:
HBr (48% in H$_2$O, 28 mL) in MeOH (50 mL) was added dropwise to a solution of (3r,5r,7r)-1-(2-(2-methoxyphenyl)-2-oxoethyl)-1,3,5,7-tetraazaadamantan-1-ium bromide (9.0 g) in MeOH (100 mL) and the rxn mixture was stirred at rt overnight. The rxn mixture was concentrated in vacuo and the residue was triturated with CHCl$_3$, followed by crystallization in MeOH to yield the title compound as a beige solid. LC-MS B: $t_R$=0.33 min; [M+H]$^+$=166.26.

2-Amino-1-(3-chloro-phenyl)ethanone HBr (J-1-3)

The title compound was prepared from commercially available 2-bromo-1-(3-chlorophenyl)ethanone in analogy to the procedure described for J-1-2. LC-MS A: $t_R$=0.38 min; [M+H]$^+$=211.21.

2-Amino-1-(3-methoxyphenyl)ethanone HBr (J-1-4)

The title compound was prepared from commercially available 2 2-bromo-1-(3-methoxyphenyl)ethanone in analogy to the procedure described for J-1-2. LC-MS A: $t_R$=0.33 min; [M+H]$^+$=166.26.

Synthesis of Intermediate J-2

(S)-1-(5-Methyl-2-(2H-1,2,3-triazol-2-yl)benzoyl)-N-(2-oxo-2-phenylethyl)pyrrolidine-2-carboxamide (J-2-1)

TBTU (192 mg, 0.60 mmol) was added to a rt solution of A-3-1 (150 mg, 0.50 mmol), DIPEA (0.43 mL, 2.5 mmol) in DCM (2 mL) and the resulting rxn mixture was stirred at rt for 10 min before commercially available 2-amino-1-phenylethanone HCl (89 mg, 0.49 mmol) was added and stirring continued at rt overnight. The rxn mixture was washed with sat. NaHCO$_3$ solution and the organic layer was dried (MgSO$_4$), filtered and concentrated in vacuo to yield the title compound as a brownish oil which was used as such without further purification. LC-MS A: $t_R$=0.81 min; [M+H]$^+$=417.90.

(S)-1-(5-Methyl-2-(2H-1,2,3-triazol-2-yl)benzoyl)-N-(2-oxo-2-(o-tolyl)ethyl)pyrrolidine-2-carboxamide (J-2-2)

The title compound was prepared from A-3-1 and 2-amino-1-(o-tolyl)ethanone in analogy to the procedure described for J-2-1. LC-MS A: $t_R$=0.85 min; [M+H]$^+$=432.11.

Synthesis of Intermediate K-1

(S)-2-[5-(2-Trifluoromethoxy-phenyl)-4H-[1,2,4]triazol-3-yl]-pyrrolidine-1-carboxylic acid tert-butyl ester (K-1-1)

K$_2$CO$_3$ (51 mg, 0.39 mmol) was added to a rt solution of (S)-1-Boc-pyrrolidine-2-carbonitrile (433 mg, 2.21 mmol) and F-1-5 (200 mg, 0.74 mmol) in n-BuOH (2.9 mL) and the mixture was refluxed (oil bath at 125° C.) overnight. The mixture was concentrated in vacuo, then DCM and 1N HCl until pH 6 was added. The org. layer was separated and the aq. layer was extracted with DCM (2×). The combined org. layers were dried (MgSO$_4$), filtered and concentrated in vacuo. The crude was purified by FC (EtOAc/hept 1:1) to give title compound K-1-1. LC-MS A: $t_R$=0.84 min; [M+H]$^+$=399.04.

Listed in Table 20 below are compounds of structure K-1 prepared according to the above procedure (see K-1-1).

TABLE 20

| K-1 | SM (F-1) | Name | $t_R$ [min] LC/MS-Method | MS-data m/z [M + H]$^+$ |
|---|---|---|---|---|
| K-1-2 | Benzo hydrazide | (S)-2-(5-Phenyl-4H-[1,2,4]triazol-3-yl)-pyrrolidine-1-carboxylic acid tert-butyl ester | 0.75 A | 315.17 |
| K-1-3 | F-1-3 | (S)-2-[5-(3-Chloro-2-methyl-phenyl)-4H-[1,2,4]triazol-3-yl]-pyrrolidine-1-carboxylic acid tert-butyl ester | 0.84 A | ($^{35}$Cl) 363.10 |
| K-1-4 | F-1-6 | (S)-2-[5-(3-Fluoro-2-methyl-phenyl)-4H-[1,2,4]triazol-3-yl]-pyrrolidine-1-carboxylic acid tert-butyl ester | 0.81 A | 347.13 |
| K-1-5 | F-1-7 | (S)-2-[5-(2-Ethoxy-phenyl)-4H-[1,2,4]triazol-3-yl]-pyrrolidine-1-carboxylic acid tert-butyl ester | 0.80 A | 359.13 |
| K-1-6 | F-1-9 | (S)-2-[5-(2-Ethoxy-pyridin-3-yl)-4H-[1,2,4]triazol-3-yl]-pyrrolidine-1-carboxylic acid tert-butyl ester | 0.78 A | 360.12 |
| K-1-7 | F-1-8 | (S)-2-[5-(3-Fluoro-2-methoxy-phenyl)-4H-[1,2,4]triazol-3-yl]-pyrrolidine-1-carboxylic acid tert-butyl ester | 0.80 A | 363.10 |
| K-1-8 | F-1-10 | (S)-2-[5-(2-Methoxy-phenyl)-4H-[1,2,4]triazol-3-yl]-pyrrolidine-1-carboxylic acid tert-butyl ester | 0.76 A | 345.13 |
| K-1-9 | F-1-16 | (S)-2-[5-(3-Chloro-2-methoxy-phenyl)-4H-[1,2,4]triazol-3-yl]-pyrrolidine-1-carboxylic acid tert-butyl ester | 0.82 A | 379.10 |

Synthesis of Intermediate K-2

(S)-3-(2-Trifluoromethoxy-phenyl)-5-pyrrolidin-2-yl-4H-[1,2,4]triazole (K-2-1)

4 N HCl in dioxane (0.8 mL, 3.2 mmol) was added dropwise to a 0° C. solution of K-1-1 (156 mg, 0.39 mmol) in DCM (2.5 mL). The resulting mixture was allowed to warm to rt and stirred at rt for 45 min. The rxn mixture was quenched with 2 N NaOH at 0° C. until pH 6, then extracted with DCM (2×). The combined org. extracts were dried (MgSO$_4$), filtered and concentrated in vacuo to obtain the title compound K-2-1 as an oil that was used as such without further purification. LC-MS A: $t_R$=0.55 min; [M+H]$^+$=299.13.

Listed in Table 21 below are compounds of structure K-2, prepared according to the above procedure (see K-2-1).

TABLE 21

| K-2 | SM (K-1) | Name | $t_R$ [min] LC/MS-Method | MS-data m/z [M + H]$^+$ |
|---|---|---|---|---|
| K-2-2 | K-1-2 | (S)-3-Phenyl-5-pyrrolidin-2-yl-4H-[1,2,4]triazole | 0.46 A | 215.18 |
| K-2-3 | K-1-3 | (S)-3-(3-Chloro-2-methyl-phenyl)-5-pyrrolidin-2-yl-4H-[1,2,4]triazole | 0.55 A | ($^{35}$Cl) 263.08 |
| K-2-4 | K-1-4 | (S)-3-(3-Fluoro-2-methyl-phenyl)-5-pyrrolidin-2-yl-4H-[1,2,4]triazole | 0.50 A | 247.11 |
| K-2-5 | K-1-5 | (S)-3-(2-Ethoxyphenyl)-5-(pyrrolidin-2-yl)-4H-1,2,4-triazole | 0.55 A | 259.06 |
| K-2-6 | K-1-6 | (S)-2-Ethoxy-3-(5-(pyrrolidin-2-yl)-4H-1,2,4-triazol-3-yl)pyridine | 0.52 A | 260.12 |

TABLE 21-continued

| SM<br>K-2 | (K-1) | Name | $t_R$ [min]<br>LC/MS-<br>Method | MS-data<br>m/z<br>$[M + H]^+$ |
|---|---|---|---|---|
| K-2-7 | K-1-7 | (S)-3-(3-Fluoro-2-methoxy-phenyl)-5-pyrrolidin-2-yl-4H-[1,2,4]triazole | 0.52<br>A | 263.10 |
| K-2-8 | K-1-8 | (S)-3-(2-Methoxy-phenyl)-5-pyrrolidin-2-yl-4H-[1,2,4]triazole | 0.51<br>A | 245.14 |
| K-2-9 | K-1-9 | (S)-3-(3-Chloro-2-methoxy-phenyl)-5-pyrrolidin-2-yl-4H-[1,2,4]triazole | 0.55<br>A | ($^{35}$Cl)<br>279.09 |

Synthesis of Intermediate L-2

0.5 M NaOMe solution in MeOH (1.29 mL, 0.645 mmol) was added to a rt solution of Boc-S-pyrrolidine-2-carbonitrile (1.50 g, 6.45 mmol) in MeOH (4.3 mL) and the resulting mixture was stirred at rt overnight. Next morning, ammonium bromide (631 mg, 6.45 mmol) was added and stirring at rt was continued for 2 h, then the rxn mixture was concentrated in vacuo. The residue was triturated with Et$_2$O to yield the title compound L-2 as a white solid which was used further without purification. LC-MS A: $t_R$=0.45 min; [M+H]$^+$=214.17.

Synthesis of Intermediate L-3

(S)-2-(5-Phenyl-1H-imidazol-2-yl)-pyrrolidine-1-carboxylic acid tert-butyl ester (L-3-1)

K$_2$CO$_3$ (953 mg, 6.89 mmol) was added to a rt solution of L-2 (1.01 g, 3.45 mmol) in DMF (6 mL) and stirred at rt for 5 min, before 2-bromoacetophenone (350 mg, 1.72 mmol) was added and the mixture stirred at rt for 3 days. The rxn mixture was extracted with EtOAc (2×) and the combined org. layers were washed with water (1×), concentrated in vacuo and purified by prep.
HPLC (method G) to give the title compound L-3-1 as a yellow solid. LC-MS A: $t_R$=0.63 min; [M+H]$^+$=314.14.

(S)-2-[4-(2-Methoxy-phenyl)-1H-imidazol-2-yl]-pyrrolidine-1-carboxylic acid tert-butyl ester (L-3-6)

Step A:
HATU (4.94 g, 13.0 mmol) was added to a rt solution of Boc-S-proline (2.66 g, 12.4 mmol), J-1-2 (4.35 g, 12.4 mmol) and DIPEA (10.6 mL, 61.8 mmol) in DCM (100 mL) and the rxn mixture was stirred at rt for 1 h. The rxn mixture was concentrated in vacuo, to the residue was added EtOAc (200 mL) and the org. layer was washed with H$_2$O (100 mL) and brine (100 mL). The org. layer was dried (MgSO$_4$), filtered and concentrated in vacuo. The crude was purified by FC (Biotage SP1: EtOAc/hept 1:1 to 3:2) to give (S)-tert-butyl 2-((2-(2-methoxyphenyl)-2-oxoethyl)carbamoyl)pyrrolidine-1-carboxylate L-1-1. LC-MS B: $t_R$=0.58 min; [M+H]$^+$=344.22.
Step B:
Acetic acid (13 mL) was added to a rt solution of L-1-1 (3.09 g, 8.52 mmol) and ammonium acetate (19.70 g, 256 mmol) in xylene (25 mL) and the rxn mixture was heated to 130° C. for 1.5 h. The rxn mixture was allowed to reach rt and was poured on ice, then 25% ammonium hydroxide solution was added until basic, and extracted with EtOAc (2×). The combined org. layers were dried (MgSO$_4$), filtered and concentrated in vacuo to yield the title compound L-3-6 which was used further without purification. LC-MS B: $t_R$=0.58 min; [M+H]$^+$=344.22.

Listed in Table 22 below are compounds of structure L-3, prepared according to the above procedures (L-3-1 or L-3-6).

TABLE 22

| SM<br>L-3 | I-1<br>or J-1 | Name | $t_R$ [min]<br>LC/MS-<br>Method | MS-data<br>m/z<br>$[M + H]^+$ |
|---|---|---|---|---|
| L-3-2 | I-1-3 | (S)-2-[5-(3-Chloro-2-methyl-phenyl)-1H-imidazol-2-yl]-pyrrolidine-1-carboxylic acid tert-butyl ester | 0.71<br>A | 362.10 |
| L-3-3 | I-1-4* | (S)-2-[5-(2-Ethoxy-phenyl)-1H-imidazol-2-yl]-pyrrolidine-1-carboxylic acid tert-butyl ester | 0.71<br>A | 358.12 |
| L-3-4 | I-1-5* | (S)-2-[5-(2-Trifluoromethyl-phenyl)-1H-imidazol-2-yl]-pyrrolidine-1-carboxylic acid tert-butyl ester | 0.69<br>A | 382.05 |
| L-3-5 | I-1-2 | (S)-2-[5-(2-Trifluoromethoxy-phenyl)-1H-imidazol-2-yl]-pyrrolidine-1-carboxylic acid tert-butyl ester | 0.71<br>A | 398.08 |
| L-3-7 | J-1-3 | (S)-2-[4-(3-Chloro-phenyl)-1H-imidazol-2-yl]-pyrrolidine-1-carboxylic acid tert-butyl ester | 0.60<br>B | 348.17 |
| L-3-8 | J-1-4 | (S)-2-[4-(3-Methoxy-phenyl)-1H-imidazol-2-yl]-pyrrolidine-1-carboxylic acid tert-butyl ester | 0.57<br>B | 344.01 |

*Commercially available: I-1-4 = 2-bromo-1-(2-ethoxyphenyl)ethanone; I-1-5 = 2-bromo-1-(2-(trifluoromethyl)phenyl)ethanone Synthesis of Intermediate L-4

5-Phenyl-2-(S)-pyrrolidin-2-yl-1H-imidazole (L-4-1)

4N HCl in dioxane (1.5 mL, 6.04 mmol) was added to a 0° C. solution of L-3-1 (235 mg, 0.75 mmol) in DCM (12 mL) and the resulting mixture was stirred at rt for 4 h. The rxn mixture was concentrated in vacuo to yield the title compound as a yellow oil which was used further without purification. LC-MS A: $t_R$=0.44 min; [M+H]$^+$=214.21.

Listed in Table 23 below are compounds of structure L-4, prepared according to the above procedure (L-4-1).

TABLE 23

| SM<br>L-4 | L-3 | Name | $t_R$ [min]<br>LC/MS-<br>Method | MS-data<br>m/z<br>$[M + H]^+$ |
|---|---|---|---|---|
| L-4-2 | L-3-2 | 5-(3-Chloro-2-methyl-phenyl)-2-(S)-pyrrolidin-2-yl-1H-imidazole | 0.55<br>A | 262.13 |
| L-4-3 | L-3-3 | 5-(2-Ethoxy-phenyl)-2-(S)-pyrrolidin-2-yl-1H-imidazole | 0.51<br>A | 258.16 |
| L-4-4 | L-3-4 | 2-(S)-Pyrrolidin-2-yl-5-(2-trifluoromethyl-phenyl)-1H-imidazole | 0.55<br>A | 282.11 |
| L-4-5 | L-3-5 | 2-(S)-Pyrrolidin-2-yl-5-(2-trifluoromethoxy-phenyl)-1H-imidazole | 0.61<br>A | 298.09 |
| L-4-6 | L-3-6 | 4-(2-Methoxy-phenyl)-2-(S)-pyrrolidin-2-yl-1H-imidazole | 0.38<br>B | 244.17 |
| L-4-7 | L-3-7 | 4-(3-Chloro-phenyl)-2-(S)-pyrrolidin-2-yl-1H-imidazole | 0.49<br>B | 248.12 |
| L-4-8 | L-3-8 | 4-(3-Methoxy-phenyl)-2-(S)-pyrrolidin-2-yl-1H-imidazole | 0.40<br>B | 244.16 |

Synthesis of Intermediate M-1

(S)-tert-Butyl 2-(2-bromoacetyl)pyrrolidine-1-carboxylate (M-1)

Step A:

Isobutyl chloroformate (1.82 mL, 13.9 mmol) was added to a 0° C. solution of Boc-L-proline (2.00 g, 9.29 mmol) and DIPEA (2.75 ml, 16.1 mmol) in THF (20 mL) and the solution was stirred at 0° C. for 4 h before MeCN (10 mL) was added. A solution of trimethylsilyldiazomethane solution (2.0 M in hexane; 9.3 mL, 18.6 mmol) in a THF/MeOH-mixture (6.4 mL/6.4 mL) was added dropwise over 10 min to the rxn mixture. After stirring at 0° C. for 3.5 h, the rxn mixture was allowed to reach rt overnight. The mixture was concentrated in vacuo and the crude was purified by FC (EtOAc/hept 3:7) to obtain (S)-tert-butyl 2-(2-diazoacetyl)pyrrolidine-1-carboxylate as a yellow oil. LC-MS A: $t_R$=0.70 min; $[M+H]^+$=no ionization.

Step B:

HBr (48% in water (100 uL) was added to a 0° C. solution of (S)-tert-butyl 2-(2-diazoacetyl)pyrrolidine-1-carboxylate (462 mg, 0.869 mmol) in Et$_2$O (2.2 mL) and the rxn mixture was stirred at 0° C. for 5 min. The mixture was diluted with EtOAc, washed with sat. aq. NaHCO$_3$ and brine. The org. layer was dried (MgSO$_4$), filtered and concentrated, then purified by FC (EtOAc/hept 3:7) to yield title compound M-1 as a colorless oil. LC-MS A: $t_R$=0.81 min; $[M+H]^+$=235.96.

Synthesis of Intermediate M-2

3-Chloro-2-methylbenzimidamide (M-2-1)

Trimethylaluminium in hepatane (2M, 9.9 mL, 19.8 mmol) was added dropwise to a 0° C. suspension of ammonium chloride (1.07 g, 19.8 mmol) in toluene (6.4 mL) and stirred for 15 min at rt before 3-chloro-2-methylbenzonitrile (1.02 g, 6.6 mmol) in toluene (6.4 mL) was added. The resulting mixture was heated at 80° C. for 40 h, then added to a freshly prepared mixture of trimethylaluminium in heptanes (2 Mm, 4.95 mL), ammonium chloride (535 mg) in toluene (3 mL). The resulting mixture was heated at 80° C. for 15 h. The rxn mixture was allowed to reach rt, DCM (90 mL) and silica gel (27 g) were added and stirred vigorously for 10 min. The silica gel was filtered off, washed with DCM/MeOH and the filtrate was concentrated in vacuo to give a white solid. The solid was dissolved with 10% aq. HCl (100 mL) and Et$_2$O (100 mL). The org. layer was separated, dried (MgSO$_4$), filtered and concentrated in vacuo to recover remaining starting material. The inorg. layer was basified with 12.5 N aq. NaOH, extracted with DCM (2×) and the combined DCM-extracts were dried (MgSO$_4$), filtered and concentrated in vacuo to yield the title compound M-2-1 as a beige solid. LC-MS A: $t_R$=0.40 min; $[M(^{35}Cl)+H]^+$=169.01.

Synthesis of Intermediate M-3

(S)-2-(2-Phenyl-3H-imidazol-4-yl)-pyrrolidine-1-carboxylic acid tert-butyl ester (M-3-1)

Compound M-1 (231 mg, 0.672 mmol) dissolved in DMF (1.3 mL) was added to a rt suspension of commercially available benzamidine (170 mg, 1.34 mmol) and K$_2$CO$_3$ (372 mg, 2.69 mmol) in DMF (1 mL) and the resulting mixture was stirred at rt for 1 h, then heated at 65° C. for 8 h. To the rxn mixture were added EtOAc and water and the phases were separated. The inorg. layer was extracted with EtOAc (2×). The combined org. extracts were dried (MgSO$_4$), filtered and concentrated in vacuo. The crude was purified by FC (EtOAc/hept 3:2) to give the title compound M-3-1 as a colorless oil. LC-MS A: $t_R$=0.63 min; $[M+H]^+$=314.21.

(S)-2-[2-(3-Chloro-2-methyl-phenyl)-3H-imidazol-4-yl]-pyrrolidine-1-carboxylic acid tert-butyl ester (M-3-2)

The title compound was prepared from M-1 and M-2-1 in analogy to the procedure described for M-3-1. LC-MS A: $t_R$=0.69 min; $[M(^{35}Cl)+H]^+$=362.14.

Synthesis of Intermediate M-4

2-Phenyl-5-(S)-pyrrolidin-2-yl-1H-imidazole HCl (M-4-1)

4N HCl in dioxane (1.3 mL, 5.2 mmol) was added to a 0° C. solution of M-3-1 (188 mg, 0.52 mmol) in DCM (2 mL) and the rxn mixture was stirred at rt for 3 h. The rxn mixture was concentrated in vacuo to give the title compound M-4-1 as a white solid. LC-MS A: $t_R$=0.35 min; $[M+H]^+$=214.13.

2-(3-Chloro-2-methyl-phenyl)-5-(S)-pyrrolidin-2-yl-1H-imidazole HCl (M-4-2)

The title compound was prepared from M-3-2 in analogy to the procedure described for M-4-1. LC-MS A: $t_R$=0.45 min; $[M(^{35}Cl)+H]^+$=262.10.

Synthesis of Intermediate N-1

(S)-2-(3-Phenyl-propynoyl)-pyrrolidine-1-carboxylic acid tert-butyl ester (N-1-1)

Ethylmagnesium bromide (1.0 M in THF (3.9 mL, 3.89 mmol) was added dropwise to a 0° C. solution of commercially available phenylacetylene (374 mg, 3.66 mmol) in THF (10 mL) and the resulting rxn mixture was stirred at 0° C. for 10 min and at rt for 1 h. N-Boc-L-proline N'-methoxy-N'-methylamide (700 mg, 2.71 mmol) dissolved in THF (9.0 mL) was added at 0° C. and the resulting mixture was allowed to reach rt overnight. The rxn mixture was quenched with sat. aq. NH$_4$Cl and extracted with EtOAc (2×). The combined org. layers were washed with water and brine, dried (MgSO$_4$), filtered and concentrated in vacuo to give the title compound N-1-1 as a yellow oil which was used further without purification. LC-MS A: $t_R$=0.94 min; $[M+H]^+$=no ionization.

(S)-2-(3-(3-Chloro-2-methylphenyl)propioloyl)pyrrolidine-1-carboxyic acid tert-butyl ester (N-1-2)

The title compound was prepared from E-6-2 in analogy to the procedure described for N-1-1. LC-MS A: $t_R$=1.01 min; $[M(^{35}Cl)+H]^+$=348.12.

(S)-2-(3-(2-Trifluoromethoxyphenyl)propioloyl) pyrrolidine-1-carboxyic acid tert-butyl ester (N-1-3)

The title compound was prepared from E-6-3 in analogy to the procedure described for N-1-1. LC-MS A: $t_R$=1.01 min; $[M+H]^+$=384.08.

Synthesis of Intermediate N-2

(S)-2-(5-Phenyl-2H-pyrazol-3-yl)-pyrrolidine-1-carboxylic acid tert-butyl ester (N-2-1)

Hydrazine hydrate (80%, 0.145 mL) was added to rt solution of N-1-1 (659 mg, 1.98 mmol) in EtOH (18 mL) and the resulting mixture was heated to 85° C. for 80 min. The rxn mixture was concentrated and the residue was taken up in DCM and $H_2O$. The org. layer was collected and the inorg. layer was extracted with DCM. The combined org. extracts were dried ($MgSO_4$), filtered and concentrated. The crude was purified by FC (Biotage SP1: EtOAc/hex 3:7 to 1:1) to give the title compound N-2-1 as an off-white foam. LC-MS A: $t_R$=0.84 min; $[M+H]^+$=314.19.

(S)-2-[5-(3-Chloro-2-methyl-phenyl)-2H-pyrazol-3-yl]-pyrrolidine-1-carboxylic acid tert-butyl ester (N-2-2)

The title compound was prepared from N-1-2 in analogy to the procedure described for N-2-1. LC-MS A: $t_R$=0.92 min; $[M(^{35}Cl)+H]^+$=362.13.

(S)-2-[5-(2-Trifluoromethoxy-phenyl)-2H-pyrazol-3-yl]-pyrrolidine-1-carboxylic acid tert-butyl ester (N-2-3)

The title compound was prepared from N-1-3 in analogy to the procedure described for N-2-1. LC-MS A: $t_R$=0.93 min; $[M+H]^+$=398.06.

Synthesis of Intermediate N-3

3-Phenyl-5-(S)-pyrrolidin-2-yl-1H-pyrazole HCl (N-3-1)

4N HCl in dioxane (5.0 mL, 20.1 mmol) was added to a 0° C. solution of N-2-1 (758 mg, 2.42 mmol) in DCM (10 mL) and the resulting mixture was stirred at rt overnight. The rxn mixture was concentrated in vacuo and triturated with $Et_2O$ to give the title compound N-3-1 as an off-white solid which was used further without purification. LC-MS A: $t_R$=0.53 min; $[M+H]^+$=214.13.

3-(3-Chloro-2-methyl-phenyl)-5-(S)-pyrrolidin-2-yl-1H-pyrazole HCl (N-3-2)

The title compound was prepared from N-2-3 in analogy to the procedure described for N-3-1. LC-MS A: $t_R$=0.61 min; $[M(^{35}Cl)+H]^+$=262.08.

5-(S)-Pyrrolidin-2-yl-3-(2-trifluoromethoxy-phenyl)-1H-pyrazole HCl (N-3-3)

The title compound was prepared from N-2-3 in analogy to the procedure described for N-3-1. LC-MS A: $t_R$=0.62 min; $[M+H]^+$=298.10.

Synthesis of Intermediate O-1

(S)-2-Methoxycarbonimidoyl-pyrrolidine-1-carboxylic acid tert-butyl ester (O-1)

A solution of Boc-(S)-pyrrolidine-2-carbonitrile (100 mg, 0.51 mmol, 1 eq) in MeOH (1.8 mL) was added to a rt solution of NaOMe in MeOH (5.4 M, 100 uL) in MeOH (2 mL) and the resulting mixture was stirred at rt overnight. The reaction was quenched with sat. aq. $KH_2PO_4$ until pH 6. The rxn mixture was concentrated in vacuo and the residue was taken up in DCM and $H_2O$. The org. layer was separated and the inorg. layer was extracted with DCM (1×). The combined org. extracts were dried ($MgSO_4$), filtered and concentrated in vacuo to give the title compound O-1 as an oil which was used further without purification. LC-MS A: $t_R$=0.51 min; $[M+H]^+$=229.11.

Synthesis of Intermediate O-3

(S)-2-(1-Phenyl-1H-[1,2,4]triazol-3-yl)-pyrrolidine-1-carboxylic acid tert-butyl ester (O-3-1)

Phenylhydrazine (42 uL, 0.412 mmol) was added to a rt solution of O-1 (94 mg, 0.41 mmol) and TEA (172 uL, 1.24 mmol) in MeOH (1.5 mL) and the resulting mixture was stirred at rt for 4 d. The mixture was concentrated in vacuo, then the residue was dissolved in pyridine (1.53 mL, 18.9 mmol) and triethyl orthoformate (1.54 mL, 9.06 mmol) was added. The mixture was heated to 120° C. for 1 h 30, then the rxn mixture was concentrated in vacuo, dissolved in DCM, washed with sat. aq. citric acid, sat. aq. $NaHCO_3$ and brine. The org. layer was dried ($MgSO_4$), filtered and concentrated in vacuo. The crude was purified by FC (EtOAc/hept 2:3) to give the title compound O-3-1 as an oil. LC-MS A: $t_R$=0.82 min; $[M+H]^+$=315.17.

Synthesis of Intermediate O-4

1-Phenyl-3-(S)-pyrrolidin-2-yl-1H-[1,2,4]triazole (O-4-1)

TFA (180 uL, 2.39 mmol) was added to a rt solution of O-3-1 (75 mg, 0.24 mmol) in DCM (1 mL) and the resulting mixture was stirred at rt overnight. The rxn mixture was cooled to 0° C., then diluted with DCM and basified with 4N aq. NaOH. The layers were separated and the inorg. layer was extracted with DCM (1×). The combined org. extracts were dried ($MgSO_4$), filtered and concentrated in vacuo to give the title compound O-4-1 which was used further without purification. LC-MS A: $t_R$=0.48 min; $[M+H]^+$=215.13.

Synthesis of Intermediate P-1

Phenylazide (P-1-1)

tert-Butyl nitrite (0.4 mL, 3 mmol), followed by trimethylsilylazide (0.33 mL, 2.4 mmol) was added to a 0° C. solution of phenylamine (0.18 mL, 2 mmol) in MeCN (4.0 mL) and the resulting mixture was stirred at rt for 2 h. The rxn mixture was carefully concentrated in vacuo to give the title compound P-1-1 which was used immediately in the next step. LC-MS A: $t_R$=0.8 min; $[M+H]^+$=no ionization.

Synthesis of Intermediate P-2

(S)-2-(1-Phenyl-1H-1,2,3-triazol-4-yl)pyrrolidine-1-carboxylic acid tert-butyl ester (P-2-1)

P-1-1 (73 mg, 0.62 mmol) was added to a rt solution of E-1 (100 mg, 0.51 mmol) in DMF (1.0 mL) and the resulting mixture was heated at 150° C. (pre-heated oilbath) for 15 min, then P-1-1 (73 mg, 0.62 mmol) was added to the 150° C. hot rxn mixture and stirred for another 10 min. This addition was repeated for a third time. The rxn mixture was allowed to reach rt, then directly purified by prep. HPLC (method G) (elimination of wrong isomer) to give the title compound P-2-1 as a brown oil. LC-MS A: $t_R$=0.85 min; [M+H]$^+$=315.18.

Synthesis of Intermediate P-3

(S)-1-Phenyl-4-(pyrrolidin-2-yl)-1H-1,2,3-triazole (P-3-1)

4N HCl in dioxane (0.62 mL, 2.47 mmol) was added to a 0° C. solution of P-2-1 (72 mg, 0.23 mmol) in DCM (3 mL) and the resulting mixture was stirred at rt for 3 h. The rxn mixture was concentrated in vacuo to give the title compound P-3-1 as a brown oil which was used further without purification. LC-MS A: $t_R$=0.49 min; [M+H]$^+$=215.12.

Synthesis of Intermediate Q-1

(S)-2-Methyl-pyrrolidine-1,2-dicarboxylic acid 1-tert-butyl ester HCl

A solution of Boc$_2$O (145 g, 0.66 mol) in MeCN (200 mL) was added dropwise to a 10-15° C. solution of commercially available 2-methyl-L-proline HCl and TEA (254 mL, 1.81 mol) in a 1/1 mixture of MeCN/H$_2$O (800 mL). The reaction mixture was allowed to reach rt and stirred at rt for 2 h to 2 days, then the MeCN was evaporated in vacuo, the residue quenched with 2N aq. NaOH (250 mL) and washed with diethylether (2×). The inorg. layer was cooled to 0° C., then the product was precipitated by adding 25% aq. HCl until pH 2. The product was filtered off, washed with cold water and dried in vacuo to yield the title compound Q-1 as a beige solid. LC-MS A: $t_R$=0.68 min; [M+H]$^+$=230.13

Synthesis of Intermediate Q-3

(S)-2-Methyl-2-(3-phenyl-[1,2,4]oxadiazol-5-yl)-pyrrolidine-1-carboxylic acid tert-butyl ester (Q-3-1)

Step A:
PyBOP (1.36 g, 2.62 mmol) was added to a 0° C. solution of Q-1 (500 mg, 2.18 mmol), benzamidoxime (324 mg, 2.38 mmol) and DIPEA (1.12 mL) in DCM (22 mL). The resulting mixture was stirred at rt for 16 h, then concentrated in vacuo to yield Q-2-1 that was used further without purification. LC-MS B: $t_R$=0.74 min; [M+H]$^+$=348.15.
Step B:
The crude Q-2-1 was taken up in dioxane (35 mL) and refluxed (90 to 105° C.) for 2 days. The rxn mixture was concentrated in vacuo and purified by FC (Biotage SP1: EtOAc/hex 3:7) to give the title compound Q-3-1 as a yellow oil. LC-MS B: $t_R$=0.94 min; [M+H]$^+$=330.18.

Synthesis of Intermediate Q-4

5-((S)-2-Methyl-pyrrolidin-2-yl)-3-phenyl-[1,2,4]oxadiazole (Q-4-1)

TFA (1.37 mL, 17.9 mmol) was added to a 0° C. solution of Q-3-1 (470 mg, 1.43 mmol) in DCM (5.0 mL) and the resulting mixture was stirred at rt for 1 h. The rxn mixture was cooled to 0° C., then diluted with DCM and basified with 1N aq. NaOH. The org. layer was separated and the inorg. layer was extracted with DCM (1×). The combined org. extracts were dried (MgSO$_4$), filtered and concentrated in vacuo to give the title compound Q-4-1 as a brown oil which was used further without purification. LC-MS B: $t_R$=0.47 min; [M+H]$^+$=230.19.

Synthesis of Intermediate Q-5

(S)-2-Methyl-1-(5-methyl-2-[1,2,3]triazol-2-yl-benzoyl)-pyrrolidine-2-carboxylic acid Step A:
Thionylchloride (33 mL, 450 mmol) was added to A-1-2 (6.10 g, 30.0 mmol) and the solution was stirred at 60° C., then the reaction mixture was concentrated in vacuo by coevaporation with toluene to yield 5-methyl-2-(2H-1,2,3-triazol-2-yl)benzoyl chloride which was used as such in the next step.
Step B:
A solution of 5-methyl-2-(2H-1,2,3-triazol-2-yl)benzoyl chloride in DCM (180 mL) was added dropwise to a −20° C. solution of 2-methyl-L-proline HCl (4.97 g, 30 mmol) and TEA (16.6 mL, 120 mmol) in pyridine (121 mL) and DCM (120 mL). The reaction mixture was allowed to reach rt and stirring was continued at rt for 16 h. After the reaction mixture was quenched with methylamine in THF (18.8 mL), the mixture was concentrated in vacuo, dissolved in DCM and washed with sat. KH$_2$PO$_4$ solution (2×). The org. layer was dried (MgSO$_4$), filtered, concentrated and purified by FC (Biotage SP1: EtOAc/hept.) to yield the title compound Q-5 as a white solid. LC-MS A: $t_R$=0.71 min; [M+H]$^+$=315.23.

Synthesis of Intermediate R-1

(S)-2-Carbamoyl-2-methyl-pyrrolidine-1-carboxylic acid tert-butyl ester

Ethyl chloroformate (0.5 mL, 5.12 mmol) was added to a 0° C. solution of Q-1 (988 mg, 4.33 mmol) and TEA (1.22 mL, 8.76 mmol) in THF (10 mL) and the rxn mixture was stirred at 0° C. for 30 min. A solution of 25% aq. NH$_4$OH (7.5 mL) was added at 0° C. and the resulting mixture was allowed to reach rt and stirring was continued at rt for 45 min. The mixture was concentrated in vacuo, then DCM and water was added. The org. layer was separated and the inorg. layer was extracted with DCM (2×). The combined org. extracts were dried (MgSO$_4$), filtered and concentrated in vacuo to give the title compound R-1 as a yellow solid that was used as such in the next step without further purification. LC-MS A: $t_R$=0.58 min; [M+H]$^+$=229.07.

Synthesis of Intermediate R-2

(S)-2-Cyano-2-methyl-pyrrolidine-1-carboxylic acid tert-butyl ester

Trifluoroacetic anhydride (0.85 mL, 5.95 mmol) was added to a 0° C. solution of R-1 (752 mg, 3.29 mmol) and TEA (1.38 mL, 9.88 mmol) in DCM (9 mL) and the resulting mixture was stirred for 15 min at 0° C. and at rt overnight. The mixture was diluted with DCM, washed with water (1×), dried (MgSO$_4$), filtered and concentrated in vacuo. The crude was purified by FC (Biotage SP1: EtOAc/hex 1:1) to give the title compound R-2 as a yellow oil. LC-MS A: $t_R$=0.8 min; [M+H]$^+$=211.21.

Synthesis of Intermediate R-3

(S)-2-Methyl-2-[5-(2-trifluoromethoxy-phenyl)-4H-[1,2,4]triazol-3-yl]-pyrrolidine-1-carboxylic acid tert-butyl ester (R-3-1)

$K_2CO_3$ (1.22 g, 8.86 mmol) was added to a rt solution of R-2 (3.73 g, 17.7 mmol), F-1-5 (3.90 g, 17.7 mmol) in n-butanol (35 mL) and the rxn mixture was stirred at 120° C. for 3 days. The rxn mixture was cooled to rt, then concentrated in vacuo. To the residue was added DCM and water and the mixture was acidified with 1N aq. HCl. The org. layer was separated and the inorg. layer was extracted with DCM (1×). The combined org. extracts were dried ($MgSO_4$), filtered, concentrated in vacuo and the crude purified by FC (Biotage SP1: EtOAc/hept. 1:9 to 3:7) followed by prep. HPLC (method E) to give the title compound R-3-1 as a white foam. LC-MS A: $t_R$=0.87 min; $[M+H]^+$=413.17.

(S)-2-[5-(3-Chloro-2-methyl-phenyl)-4H-[1,2,4]triazol-3-yl]-2-methyl-pyrrolidine-1-carboxylic acid tert-butyl ester (R-3-2)

The title compound R-3-2 was prepared from R-2 and F-1-3 in analogy to the above described method (see R-3-1). LC-MS A: $t_R$=0.85 min; $[M(^{35}Cl)+H]^+$=377.21.

Synthesis of Intermediate R-4

3-((S)-2-Methyl-pyrrolidin-2-yl)-5-(2-trifluoromethoxy-phenyl)-4H-[1,2,4]triazole (R-4-1)

4N HCl in dioxane (1.3 mL, 5.2 mmol) was added to a 0° C. solution of R-3-1 (128 mg, 0.31 mmol) in DCM (3 mL) and the resulting mixture was stirred at rt for 2 h. The rxn mixture was concentrated in vacuo to give the title compound R-4-1 as a white foam which was used further without purification. LC-MS A: $t_R$=0.58 min; $[M+H]^+$=313.18.

3-(3-Chloro-2-methyl-phenyl)-5-((S)-2-methyl-pyrrolidin-2-yl)-4H-[1,2,4]triazole (R-4-2)

The title compound R-4-2 was prepared from R-3-2 in analogy to the above described method (see R-4-1). LC-MS A: $t_R$=0.58 min; $[M(^{35}Cl)+H]^+$=277.13.

EXAMPLE COMPOUNDS

Example 1

(5-Methyl-2-[1,2,3]triazol-2-yl-phenyl)-[(S)-2-(3-phenyl-[1,2,4]oxadiazol-5-yl)-pyrrolidin-1-yl]-methanone Step A:
PyBOP (260 mg, 0.50 mmol) was added to a rt solution of A-3-3 (100 mg, 0.33 mmol) and DIPEA (0.171 mL, 1.0 mmol) in DCM (3 mL) and after stirring for 10 min, commercially available hydroxyl-benzamidine (59 mg, 0.40 mmol) was added and the resulting mixture was stirred at rt for 1-18 h. The mixture was quenched with water and extracted with DCM (2×). The combined org. extracts were washed with brine, dried ($MgSO_4$), filtered and the solvent was evaporated in vacuo to give the crude product A-5-1 that was used further without purification.

Step B:
The crude A-5-1 was dissolved in dioxane (4.0 mL) and heated to reflux (90° C.) for 18 h to 4 days. The solvent was removed in vacuo and the residue was purified by prep. HPLC (method F) to give the title compound as a beige solid. LC-MS A: $t_R$=0.93 min; $[M+H]^+$=401.14.

Listed in Table 24 below are example compounds, prepared according to the above mentioned method, from the corresponding hydroxyamidine A-4 and carboxylic acid A-3-3, prepared as described above (see Example 1).

TABLE 24

| Ex No. | A-4 | Compound of Formula (I) |
|---|---|---|
| 2 | A-4-01 | (5-Methyl-2-[1,2,3]triazol-2-yl-phenyl)-[(S)-2-(3-m-tolyl-[1,2,4]oxadiazol-5-yl)-pyrrolidin-1-yl]-methanone; LC-MS B: $t_R$ = 0.96 min; $[M + H]^+$ = 415.33 |
| 3 | A-4-02 | {(S)-2-[3-(3-Methoxy-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.94 min; $[M + H]^+$ = 431.38 |
| 4 | A-4-03 | (5-Methyl-2-[1,2,3]triazol-2-yl-phenyl)-[(S)-2-(3-pyridin-3-yl-[1,2,4]oxadiazol-5-yl)-pyrrolidin-1-yl]-methanone; LC-MS A: $t_R$ = 0.79 min; $[M + H]^+$ = 402.29 |
| 5 | A-4-04 | (5-Methyl-2-[1,2,3]triazol-2-yl-phenyl)-[(S)-2-(3-p-tolyl-[1,2,4]oxadiazol-5-yl)-pyrrolidin-1-yl]-methanone; LC-MS A: $t_R$ = 0.96 min; $[M + H]^+$ = 415.24 |
| 6 | A-4-05 | {(S)-2-[3-(2-Cyclopropyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.94 min; $[M + H]^+$ = 441.94 |
| 7 | A-4-06 | {(S)-2-[3-(2-Methoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.81 min; $[M + H]^+$ = 430.99 |
| 8 | A-4-07 | {(S)-2-[3-(2-Methoxy-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.76 min; $[M + H]^+$ = 431.99 |
| 9 | A-4-09 | {(S)-2-[3-(3,5-Difluoro-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.92 min; $[M + H]^+$ = 437.01 |
| 10 | A-4-10 | {(S)-2-[3-(2,3-Difluoro-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.88 min; $[M + H]^+$ = 436.92 |
| 11 | A-4-12 | {(S)-2-[3-(3,5-Dimethyl-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.99 min; $[M + H]^+$ = 429.38 |
| 12 | A-4-13 | {(S)-2-[3-(4,6-Dimethyl-pyridin-2-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.83 min; $[M + H]^+$ = 430.28 |
| 13 | A-4-14 | {(S)-2-[3-(2,3-Dimethyl-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.98 min; $[M + H]^+$ = 429.25 |
| 14 | A-4-16 | {(S)-2-[3-(3-Fluoro-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.95 min; $[M + H]^+$ = 419.23 |
| 15 | A-4-17 | {(S)-2-[3-(1H-Indol-3-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.89 min; $[M + H]^+$ = 440.00 |

TABLE 24-continued

| Ex No. | A-4 | Compound of Formula (I) |
|---|---|---|
| 16 | A-4-19 | (5-Methyl-2-[1,2,3]triazol-2-yl-phenyl)-[(S)-2-(3-o-tolyl-[1,2,4]oxadiazol-5-yl)-pyrrolidin-1-yl]-methanone; LC-MS A: $t_R$ = 0.96 min; [M + H]$^+$ = 415.25 |
| 17 | A-4-21 | (5-Methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.98 min; [M + H]$^+$ = 485.05 |
| 18 | A-4-22 | {(S)-2-[3-(3-Chloro-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.94 min; [M($^{35}$Cl) + H]$^+$ = 434.97 |
| 19 | A-4-23 | {(S)-2-[3-(2,2-Difluoro-benzo[1,3]dioxol-5-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.96 min; [M + H]$^+$ = 481.00 |
| 20 | A-4-24 | {(S)-2-[3-(3,4-Difluoro-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.97 min; [M + H]$^+$ = 436.98 |
| 21 | A-4-25 | {(S)-2-[3-(2-Chloro-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.89 min; [M($^{35}$Cl) + H]$^+$ = 435.08 |
| 22 | A-4-26 | [(S)-2-(3-Benzo[1,3]dioxol-5-yl-[1,2,4]oxadiazol-5-yl)-pyrrolidin-1-yl]-(5-methyl-2-[1,2,3]triazol-2-yl-phenyl)-methanone; LC-MS B: $t_R$ = 0.86 min; [M + H]$^+$ = 445.11 |
| 23 | A-4-27 | {(S)-2-[3-(3-Chloro-2-methyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.99 min; [M($^{35}$Cl) + H]$^+$= 449.05 |
| 24 | A-4-28 | {(S)-2-[3-(2-Chloro-6-methyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.91 min; [M($^{35}$Cl) + H]$^+$ = 449.09 |
| 25 | A-4-29 | {(S)-2-[3-(2-Ethyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.97 min; [M + H]$^+$ = 429.16 |
| 26 | A-4-30 | {(S)-2-[3-(3-Fluoro-2-methyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.94 min; [M + H]$^+$ = 433.10 |
| 27 | A-4-31 | {(S)-2-[3-(2-Chloro-3-methyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.94 min; [M($^{35}$Cl) + H]$^+$= 449.02 |
| 28 | A-4-32 | {(S)-2-[3-(2-Chloro-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.78 min; [M($^{35}$Cl) + H]$^+$= 436.14 |
| 29 | A-4-33 | (5-Methyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone; LC-MS B: $t_R$ = 0.96 min; [M + H]$^+$ = 468.91 |
| 30 | A-4-34 | {(S)-2-[3-(3-Chloro-pyrazin-2-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.84 min; [M($^{35}$Cl) + H]$^+$= 436.93 |
| 31 | A-4-35 | {(S)-2-[3-(2-Hydroxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.77 min; [M + H]$^+$ = 416.94 |
| 32 | A-4-36 | {(S)-2-[3-(2-Methoxy-pyridin-4-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.83 min; [M + H]$^+$ = 431.97 |
| 33 | A-4-37 | {(S)-2-[3-(2-Difluoromethoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.87 min; [M + H]$^+$ = 467.01 |
| 34 | A-4-38 | {(S)-2-[3-(3-Fluoro-2-methoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.86 min; [M + H]$^+$ = 449.77 |
| 35 | A-4-39 | {(S)-2-[3-(2-Fluoro-3-methoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.84 min; [M + H]$^+$ = 449.77 |
| 36 | A-4-40 | {(S)-2-[3-(2-Chloro-4-methyl-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.78 min; [M($^{35}$Cl) + H]$^+$= 449.69 |
| 37 | A-4-41 | {(S)-2-[3-(3,5-Dimethyl-pyridin-4-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.62 min; [M + H]$^+$ = 430.01 |
| 38 | A-4-42 | {(S)-2-[3-(2,3-Dihydro-benzo[1,4]dioxin-5-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.88 min; [M + H]$^+$ = 458.94 |
| 39 | A-4-43 | {(S)-2-[3-(1H-Indol-4-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.82 min; [M + H]$^+$ = 439.96 |
| 40 | A-4-44 | {(S)-2-[3-(2-Ethoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.87 min; [M + H]$^+$ = 445.02 |
| 41 | A-4-45 | {(S)-2-[3-(2-Ethoxy-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.84 min; [M + H]$^+$ = 446.00 |
| 42 | A-4-46 | {(S)-2-[3-(5-Methoxy-1H-indol-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.89 min; [M + H]$^+$ = 469.99 |
| 43 | A-4-47 | {(S)-2-[3-(3-Difluoromethoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.90 min; [M + H]$^+$ = 466.95 |
| 44 | A-4-48 | {(S)-2-[3-(2-Methoxymethyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.87 min; [M + H]$^+$ = 445.0 |
| 45 | A-4-49 | (5-Methyl-2-[1,2,3]triazol-2-yl-phenyl)-{(S)-2-[3-(2-propoxy-phenyl)-[1,2,4]oxadiazol-5-yl]-pyrrolidin-1-yl}-methanone LC-MS A: $t_R$ = 0.97 min; [M + H]$^+$ = 458.97 |
| 46 | A-4-50 | {(S)-2-[3-(1H-Indol-7-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.90 min; [M + H]$^+$ = 439.97 |
| 47 | A-4-51 | {(S)-2-[3-(3,5-Dimethoxy-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.96 min; [M + H]$^+$ = 461.11 |
| 48 | A-4-52 | {(S)-2-[3-(2-Cyclobutoxy-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.92 min; [M + H]$^+$ = 471.98 |
| 49 | A-4-53 | {(S)-2-[3-(2-Cyclopentyloxy-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.97 min; [M + H]$^+$ = 485.99 |
| 50 | A-4-54 | (5-Methyl-2-[1,2,3]triazol-2-yl-phenyl)-{(S)-2-[3-(1H-pyrrolo[2,3-b]pyridin-3-yl)-[1,2,4]oxadiazol-5-yl]-pyrrolidin-1-yl}-methanone; LC-MS B: $t_R$ = 0.70 min; [M + H]$^+$ = 440.94 |
| 51 | A-4-55 | {(S)-2-[3-(1-Methyl-1H-pyrrolo[2,3-b]pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.78 min; [M + H]$^+$ = 454.95 |
| 52 | A-4-56 | [(S)-2-(3-Benzo[1,3]dioxol-4-yl-[1,2,4]oxadiazol-5-yl)-pyrrolidin-1-yl]-(5-methyl-2-[1,2,3]triazol-2-yl-phenyl)-methanone; LC-MS A: $t_R$ = 0.90 min; [M + H]$^+$ = 444.92 |

TABLE 24-continued

| Ex No. | A-4 | Compound of Formula (I) |
|---|---|---|
| 53 | A-4-57 | {(S)-2-[3-(2-Ethyl-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.65 min; [M + H]$^+$ = 429.94 |
| 54 | A-4-58 | (5-Methyl-2-[1,2,3]triazol-2-yl-phenyl)-{(S)-2-[3-(2-methyl-3-trifluoromethyl-phenyl)-[1,2,4]oxadiazol-5-yl]-pyrrolidin-1-yl}-methanone; LC-MS B: $t_R$ = 0.98 min; [M + H]$^+$ = 482.98 |
| 55 | A-4-59 | {(S)-2-[3-(3-Ethoxy-pyridin-4-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.80 min; [M + H]$^+$ = 445.97 |
| 56 | A-4-60 | {(S)-2-[3-(2-Ethoxy-3-fluoro-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.92 min; [M + H]$^+$ = 462.99 |
| 57 | A-4-61 | {(S)-2-[3-(1-Methyl-1H-indol-3-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.94 min; [M + H]$^+$ = 454.02 |
| 58 | A-4-62 | {(S)-2-[3-(4-Methyl-pyridin-3-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.74 min; [M + H]$^+$ = 416.36 |
| 59 | A-4-63 | {(S)-2-[3-(2,3-Dimethoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.83 min; [M + H]$^+$ = 461.03 |
| 60 | A-4-64 | {(S)-2-[3-(1-Methyl-1H-pyrazol-4-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.79 min; [M + H]$^+$ = 405.08 |
| 61 | A-4-65 | {(S)-2-[3-(5-Ethyl-4-methyl-pyridin-2-yl)-[1,2,4]oxadiazol-5-yl]-pyrrolidin-1-yl}-(5-methyl-2-[1,2,3]triazol-2-yl-phenyl)-methanone; L LC-MS B: $t_R$ = 0.81 min; [M + H]$^+$ = 443.99 |
| 62 | A-4-66 | {(S)-2-[3-(4,5-Dimethyl-pyridin-2-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.76 min; [M + H]$^+$ = 430.04 |
| 63 | A-4-67 | {(S)-2-[3-(5,6-Dimethyl-pyridin-2-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.77 min; [M + H]$^+$ = 430.01 |
| 64 | A-4-68 | {(S)-2-[3-(4-Hydroxy-2-methoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.63 min; [M + H]$^+$ = 446.95 |
| 65 | A-4-69 | {(S)-2-[3-(2,6-Dimethyl-pyridin-4-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.60 min; [M + H]$^+$ = 430.00 |
| 66 | A-4-70 | {(S)-2-[3-(2-Methoxy-6-methyl-pyridin-4-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.89 min; [M + H]$^+$ = 446.00 |
| 67 | A-4-71 | {(S)-2-[3-(6-Isobutyl-4-methyl-pyridin-2-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.92 min; [M + H]$^+$ = 472.06 |
| 68 | A-4-72 | {(S)-2-[3-(2-Methyl-pyridin-4-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.59 min; [M + H]$^+$ = 416.0 |
| 69 | A-4-73 | {(S)-2-[3-(2,6-Difluoro-3-methoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.84 min; [M + H]$^+$ = 466.97 |
| 70 | A-4-74 | {(S)-2-[3-(2-Chloro-3-methoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.86 min; [M($^{35}$Cl) + H]$^+$ = 465.03 |
| 71 | A-4-75 | {(S)-2-[3-(2-Isopropoxy-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.89 min; [M + H]$^+$ = 460.03 |
| 72 | A-4-76 | {(S)-2-[3-(2-Fluoro-6-methoxy-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.82 min; [M + H]$^+$ = 448.92 |
| 73 | A-4-77 | {(S)-2-[3-(2-Chloro-pyridin-4-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.83 min; [M($^{35}$Cl) + H]$^+$ = 435.92 |
| 74 | A-4-78 | {(S)-2-[3-(1-Methyl-1H-indol-4-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.89 min; [M + H]$^+$ = 454.04 |
| 75 | A-4-79 | (5-Methyl-2-[1,2,3]triazol-2-yl-phenyl)-{(S)-2-[3-(1H-pyrrolo[2,3-b]pyridin-4-yl)-[1,2,4]oxadiazol-5-yl]-pyrrolidin-1-yl}-methanone; LC-MS B: $t_R$ = 0.72 min; [M + H]$^+$ = 441.01 |
| 76 | A-4-80 | {(S)-2-[3-(2-Fluoro-6-methyl-phenyl)-[1,2,4]oxadiazol-5-yl]-pyrrolidin-1-yl}-(5-methyl-2-[1,2,3]triazol-2-yl-phenyl)-methanone; LC-MS B: $t_R$ = 0.87 min; [M + H]$^+$ = 432.92 |
| 77 | A-4-81 | {(S)-2-[3-(1-Methyl-1H-indol-7-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.89 min; [M + H]$^+$ = 454.00 |
| 78 | A-4-82 | {(S)-2-[3-(2-Methyl-pyridin-3-yl)-[1,2,4]oxadiazol-5-yl]-pyrrolidin-1-yl}-(5-methyl-2-[1,2,3]triazol-2-yl-phenyl)-methanone; LC-MS B: $t_R$ = 0.61 min; [M + H]$^+$ = 415.99 |
| 79 | A-4-83 | {(S)-2-[3-(4-Methyl-1H-indol-3-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.90 min; [M + H]$^+$ = 453.96 |
| 80 | A-4-8 | {(S)-2-[3-(3,4-Dimethyl-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.99 min; [M + H]$^+$ = 429.12 |
| 81 | A-4-11 | {(S)-2-[3-(2,4-Dimethyl-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 1.00 min; [M + H]$^+$ = 429.11 |
| 82 | A-4-85 | {(S)-2-[3-(3,4-Dimethoxy-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.91 min; [M + H]$^+$ = 461.12 |
| 83 | A-4-18 | {(S)-2-[3-(3-Methyl-pyridin-2-yl)-[1,2,4]oxadiazol-5-yl]-pyrrolidin-1-yl}-(5-methyl-2-[1,2,3]triazol-2-yl-phenyl)-methanone; LC-MS A: $t_R$ = 0.82 min; [M + H]$^+$ = 416.11 |
| 84 | A-4-20 | {(S)-2-[3-(2,5-Dimethyl-phenyl)-[1,2,4]oxadiazol-5-yl]-pyrrolidin-1-yl}-(5-methyl-2-[1,2,3]triazol-2-yl-phenyl)-methanone; LC-MS A: $t_R$ = 0.99 min; [M + H]$^+$ = 429.09 |

Example 85

1-(3-{5-[(S)-1-(5-Methyl-2-[1,2,3]triazol-2-yl-benzoyl)-pyrrolidin-2-yl]-[1,2,4]oxadiazol-3-yl}-indol-1-yl)-ethanone NaH 60% (3.3 mg, 0.07 mmol) was added to a rt solution of Example 15 (20 mg, 0.05 mmol) and TEA (19 uL, 0.14 mmol) in THF (1 mL) and the resulting suspension was stirred at rt for 1 h, then acetyl chloride (1 drop) was added and stirred at rt for another 1 h. The rxn mixture was concentrated and purified by prep. HPLC (method G) to give the title compound as a beige solid. LC-MS B: $t_R$=0.90 min; $[M+H]^+$=481.69.

Example 86

{(S)-2-[3-(2-Difluoromethoxy-pyridin-3-yl)-[1,2,4]oxadiazol-5-yl]-pyrrolidin-1-yl}-(5-methyl-2-[1,2,3]triazol-2-yl-phenyl)-methanone Step A:
PyBOP (208 mg, 0.4 mmol) was added to a rt solution of carboxylic acid A-3-1 (100 mg, 0.33 mmol), hydroxyamidine-derivative A-4-83 (102 mg, 0.67 mmol) and DIPEA (0.17 mL, 1.0 mmol) in DCM (2 mL). After stirring at rt for 1 h, the rxn mixture was concentrated and dioxane (2 mL) was added. The resulting solution was heated to 80° C. for 2 days. The crude was purified by prep. HPLC (method G) followed by a prep. TLC (DCM/MeOH 9:19 yielding {(S)-2-[3-(2-hydroxy-pyridin-3-yl)-[1,2,4]oxadiazol-5-yl]-pyrrolidin-1-yl}-(5-methyl-2-[1,2,3]triazol-2-yl-phenyl)-methanone as a yellow oil. LC-MS B: $t_R$=0.59 min; $[M+H]^+$=417.68.

Step B:
NaH 60% (4 mg, 0.1 mmol) was added to a rt solution of {(S)-2-[3-(2-hydroxy-pyridin-3-yl)-[1,2,4]oxadiazol-5-yl]-pyrrolidin-1-yl}-(5-methyl-2-[1,2,3]triazol-2-yl-phenyl)-methanone (15 mg, 0.04 mmol) in MeCN (0.6 mL). The resulting suspension was stirred at rt for 10 min, then a solution of 2,2-difluoro-2-(fluorosulfonyl)acetic acid (6 uL, 0.06 mmol) in MeCN (63 uL) was added. The resulting rxn mixture was stirred at rt for 18 h, then diluted with water and extracted with DCM (3×). The combined org. layers were concentrated, dried (MgSO$_4$), filtered and concentrated in vacuo. Purification by prep. TLC (DCM/MeOH 95:5) afforded the title compound as a colorless oil. LC-MS B: $t_R$=0.84 min; $[M+H]^+$=467.91.

Example 87

((S)-2-{3-[2-(2-Hydroxy-ethyl)-phenyl]-[1,2,4]oxadiazol-5-yl}-pyrrolidin-1-yl)-(5-methyl-2-[1,2,3]triazol-2-yl-phenyl)-methanone Step A:
To a solution of 2-(2-hydroxyethyl)benzonitrile (200 mg, 1.36 mmol) in THF (8 mL), 1H-imidazole (102 mg, 1.49 mmol), followed by tert-butylchlorodimethylsilane (209 mg, 1.39 mmol) was added. The resulting yellow suspension was stirred at rt for 18 h, then quenched with sat aq. NH$_4$Cl and extracted with EtOAc (2×). The combined org. layers were concentrated in vacuo to yield 2-(2-((tert-butyldimethylsilyl)oxy)ethyl)benzonitrile as a yellow oil that was used without further purification. LC-MS B: $t_R$=1.06 min; $[M+H]^+$=262.09.

Step B:
Hydroxylamine HCl (214 mg, 3.06 mmol) was added to a rt solution of 2-(2-((tert-butyldimethylsilyl)oxy)ethyl)benzonitrile (399 mg, 1.53 mmol) and NaHCO$_3$ (257 mg, 3.06 mmol) in MeOH (5 mL) and the resulting suspension was stirred at 65° C. for 2 days. The rxn mixture was concentrated to yield 2-(2-((tert-butyldimethylsilyl)oxy)ethyl)-N-hydroxybenzamidine that was used further without purification. LC-MS B: $t_R$=0.69 min; $[M+H]^+$=295.11.

Step C:
PyBOP (129 mg, 0.25 mmol) was added to a rt solution of carboxylic acid A-3-1 (60 mg, 0.20 mmol) and DIPEA (103 uL, 0.60 mmol) in DCM (1 mL) and the rxn mixture was stirred for 5 min, before a solution of 2-(2-((tert-butyldimethylsilyl)oxy)ethyl)-N-hydroxybenzamidine (126 mg, 0.21 mmol) in DCM (1 mL) was added and stirring was continued at rt for 18 h. The rxn mixture was concentrated in vacuo, then dioxane (2 mL) was added and the resulting solution was heated to 80° C. for 18 h. The crude was concentrated and purified by prep. HPLC (method G) to yield (S)-(2-(3-(2-(2-((tert-butyldimethylsilyl)oxy)ethyl)phenyl)-1,2,4-oxadiazol-5-yl)pyrrolidin-1-yl)(5-methyl-2-(2H-1,2,3-triazol-2-yl)phenyl)methanone as a colorless oil. LC-MS B: $t_R$=1.16 min; $[M+H]^+$=559.03.

Step D:
Tetrabutylammonium fluoride (1M in THF, 27 uL, 0.027 mmol) was added to a rt solution of (S)-(2-(3-(2-(2-((tert-butyldimethylsilyl)oxy)ethyl)phenyl)-1,2,4-oxadiazol-5-yl)pyrrolidin-1-yl)(5-methyl-2-(2H-1,2,3-triazol-2-yl)phenyl)methanone (10 mg, 0.02 mmol) in THF (1 mL) and stirred at rt for 3 h. The rxn mixture was concentrated and the residue was quenched with sat. aq. NaHCO$_3$. The org. layer was separated and the aq. layer was extracted with DCM (1×). The combined org. layers were evaporated and purified by prep. HPLC (method G) to give the title compound as a beige solid. LC-MS B: $t_R$=0.77 min; $[M+H]^+$=444.96.

General Method F for Amide Formation: TBTU/DIPEA DMF

TBTU (1.1 mmol) was added to a solution of the required carboxylic acid A-1 (1.0 mmol) and DIPEA (2.0 mmol) in DMF (2.0 mL). After stirring at rt for 10 min a solution of the required amine B-3 (1.0 mmol) in DMF (1.0 mL) was added. The resulting rxn mixture was stirred at rt for up to 3 d before being purified directly by prep. HPLC (method G) to furnish the desired product.

General Method G for Amide Formation: HATU/DIPEA DMF/DCM

A solution of DIPEA (0.4 mmol, 4 eq.) in DCM/DMF 1:1 (200 uL) was added to a solution of carboxylic acid A-1 (0.1 mmol) in DCM/DMF 1:1 (200 uL) followed by a solution of the required amine B-3 (0.1 mmol) in DCM/DMF 1:1 (200 uL) and a solution of HATU (0.105 mmol) in DMF.

After the rxn mixture was stirred overnight, the mixtures were diluted with DCM/DMF 1:1 (1 mL) and PL-HCO$_3$ (1.87 mmol/g) (213 mg, 0.4 mmol) was added and stirred for 1 h. The resin was filtered off, washed with DCM/MeOH 1:1 and concentrated in vacuo. Purification by prep. HPLC (method G) furnished the desired product.

General Method H for Amide Formation: EDC/DMAP DMF
EDC HCl (0.15 mmol) was added to a rt solution of the required carboxylic acid A-1 (0.1 mmol) and DMAP (0.02 mmol) in DMF (0.5 mL). After stirring at rt for 10 min, a solution of the required amine B-3 (0.1 mmol) in DMF (0.5 mL) was added. The resulting rxn mixture was stirred at rt for hours up to days before being purified directly by prep. HPLC (method G) to furnish the desired product.

Listed in Table 25 below are example compounds, prepared according to the above mentioned method, from corresponding amine B-3 and carboxylic acid A-1.

TABLE 25

| Ex. No. | SM A-1 | SM B-3 | GM | Compound of Formula (I) |
|---|---|---|---|---|
| 88 | A-1-35 | B-3-1 | G | {(S)-2-[3-(3-Chloro-2-methyl-phenyl)-[1,2,4]oxadiazol-5-yl]-pyrrolidin-1-yl}-(4-methyl-biphenyl-2-yl)-methanone; LC-MS A: $t_R$ = 1.08 min; [M($^{35}$Cl) + H]$^+$ = 458.08 |
| 89 | A-1-28 | B-3-1 | G | {(S)-2-[3-(3-Chloro-2-methyl-phenyl)-[1,2,4]oxadiazol-5-yl]-pyrrolidin-1-yl}-(5-methyl-2-pyrazol-1-yl-phenyl)-methanone; LC-MS A: $t_R$ = 0.99 min; [M($^{35}$Cl) + H]$^+$ = 448.06 |
| 90 | A-1-38 | B-3-1 | G | {(S)-2-[3-(3-Chloro-2-methyl-phenyl)-[1,2,4]oxadiazol-5-yl]-pyrrolidin-1-yl}-(5-methyl-2-pyridin-2-yl-phenyl)-methanone; LC-MS A: $t_R$ = 0.91 min; [M($^{35}$Cl) + H]$^+$ = 459.09 |
| 91 | A-1-53 | B-3-1 | G | {(S)-2-[3-(3-Chloro-2-methyl-phenyl)-[1,2,4]oxadiazol-5-yl]-pyrrolidin-1-yl}-(2-methyl-5-m-tolyl-oxazol-4-yl)-methanone; LC-MS A: $t_R$ = 1.03 min; [M($^{35}$Cl) + H]$^+$ = 463.08 |
| 92 | A-1-42 | B-3-1 | G | {(S)-2-[3-(3-Chloro-2-methyl-phenyl)-[1,2,4]oxadiazol-5-yl]-pyrrolidin-1-yl}-(5-m-tolyl-oxazol-4-yl)-methanone; LC-MS A: $t_R$ = 1.02 min; [M($^{35}$Cl) + H]$^+$ = 448.97 |
| 93 | A-1-4 | B-3-1 | F | {(S)-2-[3-(3-Chloro-2-methyl-phenyl)-[1,2,4]oxadiazol-5-yl]-pyrrolidin-1-yl}-(2-[1,2,3]triazol-2-yl-phenyl)-methanone; LC-MS B: $t_R$ = 0.93 min; [M($^{35}$Cl) + H]$^+$ = 434.82 |
| 94 | A-1-43 | B-3-1 | G | {(S)-2-[3-(3-Chloro-2-methyl-phenyl)-[1,2,4]oxadiazol-5-yl]-pyrrolidin-1-yl}-[5-(3-chloro-phenyl)-thiazol-4-yl]-methanone; LC-MS A: $t_R$ = 1.02 min; [M($^{35}$Cl) + H]$^+$ = 484.99 |
| 95 | A-1-6 | B-3-1 | F | {(S)-2-[3-(3-Chloro-2-methyl-phenyl)-[1,2,4]oxadiazol-5-yl]-pyrrolidin-1-yl}-(4,5-dimethyl-2-[1,2,3]triazol-2-yl-phenyl)-methanone; LC-MS B: $t_R$ = 1.01 min; [M($^{35}$Cl) + H]$^+$ = 462.97 |
| 96 | A-1-3 | B-3-1 | F | {(S)-2-[3-(3-Chloro-2-methyl-phenyl)-[1,2,4]oxadiazol-5-yl]-pyrrolidin-1-yl}-(4-methyl-2-[1,2,3]triazol-2-yl-phenyl)-methanone; LC-MS B: $t_R$ = 0.97 min; [M($^{35}$Cl) + H]$^+$ = 448.85 |
| 97 | A-1-21 | B-3-1 | G | {(S)-2-[3-(3-Chloro-2-methyl-phenyl)-[1,2,4]oxadiazol-5-yl]-pyrrolidin-1-yl}-(2-[1,2,3]triazol-2-yl-5-trifluoromethyl-phenyl)-methanone; LC-MS A: $t_R$ = 1.04 min; [M($^{35}$Cl) + H]$^+$ = 503.07 |
| 98 | A-1-18 | B-3-1 | G | {(S)-2-[3-(3-Chloro-2-methyl-phenyl)-[1,2,4]oxadiazol-5-yl]-pyrrolidin-1-yl}-(2-methyl-6-[1,2,3]triazol-2-yl-phenyl)-methanone; LC-MS A: $t_R$ = 1.01 min; [M($^{35}$Cl) + H]$^+$ = 448.97 |
| 99 | A-1-23 | B-3-1 | G | {(S)-2-[3-(3-Chloro-2-methyl-phenyl)-[1,2,4]oxadiazol-5-yl]-pyrrolidin-1-yl}-(2-[1,2,3]triazol-2-yl-5-trifluoromethoxy-phenyl)-methanone; LC-MS A: $t_R$ = 1.04 min; [M($^{35}$Cl) + H]$^+$ = 519.05 |
| 100 | A-1-10 | B-3-1 | F | {(S)-2-[3-(3-Chloro-2-methyl-phenyl)-[1,2,4]oxadiazol-5-yl]-pyrrolidin-1-yl}-(5-methoxy-2-[1,2,3]triazol-2-yl-phenyl)-methanone; LC-MS B: $t_R$ = 1.00 min; [M($^{35}$Cl) + H]$^+$ = 464.97 |
| 101 | A-1-39 | B-3-1 | F | {(S)-2-[3-(3-Chloro-2-methyl-phenyl)-[1,2,4]oxadiazol-5-yl]-pyrrolidin-1-yl}-(4-methoxy-biphenyl-2-yl)-methanone; LC-MS B: $t_R$ = 1.08 min; [M + H]$^+$ = 473.94 |
| 102 | A-1-47 | B-3-1 | F | {(S)-2-[3-(3-Chloro-2-methyl-phenyl)-[1,2,4]oxadiazol-5-yl]-pyrrolidin-1-yl}-(5-phenyl-3H-imidazol-4-yl)-methanone; LC-MS B: $t_R$ = 0.74 min; [M($^{35}$Cl) + H]$^+$ = 433.65 |
| 103 | A-1-11 | B-3-1 | F | {(S)-2-[3-(3-Chloro-2-methyl-phenyl)-[1,2,4]oxadiazol-5-yl]-pyrrolidin-1-yl}-(5-methoxy-4-methyl-2-[1,2,3]triazol-2-yl-phenyl)-methanone; LC-MS B: $t_R$ = 0.99 min; [M($^{35}$Cl) + H]$^+$ = 478.93 |
| 104 | A-1-7 | B-3-1 | F | {(S)-2-[3-(3-Chloro-2-methyl-phenyl)-[1,2,4]oxadiazol-5-yl]-pyrrolidin-1-yl}-(5-fluoro-2-[1,2,3]triazol-2-yl-phenyl)-methanone; LC-MS B: $t_R$ = 0.95 min; [M($^{35}$Cl) + H]$^+$ = 452.95 |
| 105 | A-1-13 | B-3-1 | F | {(S)-2-[3-(3-Chloro-2-methyl-phenyl)-[1,2,4]oxadiazol-5-yl]-pyrrolidin-1-yl}-(5-methoxy-4-methyl-2-pyrazol-1-yl-phenyl)-methanone; LC-MS B: $t_R$ = 0.98 min; [M($^{35}$Cl) + H]$^+$ = 477.98 |
| 106 | A-1-29 | B-3-1 | F | {(S)-2-[3-(3-Chloro-2-methyl-phenyl)-[1,2,4]oxadiazol-5-yl]-pyrrolidin-1-yl}-(5-methoxy-2-pyrazol-1-yl-phenyl)-methanone; LC-MS B: $t_R$ = 0.92 min; [M($^{35}$Cl) + H]$^+$ = 463.98 |
| 107 | A-1-51 | B-3-1 | F | [2,2']Bipyridinyl-3-yl-{(S)-2-[3-(3-chloro-2-methyl-phenyl)-[1,2,4]oxadiazol-5-yl]-pyrrolidin-1-yl}-methanone; LC-MS B: $t_R$ = 0.96 min; [M($^{35}$Cl) + H]$^+$ = 445.98 |
| 108 | A-1-14 | B-3-1 | F | {(S)-2-[3-(3-Chloro-2-methyl-phenyl)-[1,2,4]oxadiazol-5-yl]-pyrrolidin-1-yl}-(6-methyl-3-[1,2,3]triazol-2-yl-pyridin-2-yl)-methanone; LC-MS B: $t_R$ = 0.89 min; [M($^{35}$Cl) + H]$^+$ = 449.68 |
| 109 | A-1-31 | B-3-1 | F | {(S)-2-[3-(3-Chloro-2-methyl-phenyl)-[1,2,4]oxadiazol-5-yl]-pyrrolidin-1-yl}-(6-methyl-3-pyrazol-1-yl-pyridin-2-yl)-methanone; LC-MS B: $t_R$ = 0.95 min; [M($^{35}$Cl) + H]$^+$ = 448.99 |
| 110 | A-1-24 | B-3-1 | F | {(S)-2-[3-(3-Chloro-2-methyl-phenyl)-[1,2,4]oxadiazol-5-yl]-pyrrolidin-1-yl}-(4,5-difluoro-2-[1,2,3]triazol-2-yl-phenyl)-methanone; LC-MS B: $t_R$ = 0.98 min; [M($^{35}$Cl) + H]$^+$ = 470.91 |

TABLE 25-continued

| Ex. No. | SM A-1 | SM B-3 | GM | Compound of Formula (I) |
|---|---|---|---|---|
| 111 | A-1-32 | B-3-1 | F | {(S)-2-[3-(3-Chloro-2-methyl-phenyl)-[1,2,4]oxadiazol-5-yl]-pyrrolidin-1-yl}-(4-fluoro-2-pyrazol-1-yl-phenyl)-methanone; <br> LC-MS B: $t_R$ = 0.95 min; [M($^{35}$Cl) + H]$^+$ = 451.92 |
| 112 | A-1-8 | B-3-1 | F | {(S)-2-[3-(3-Chloro-2-methyl-phenyl)-[1,2,4]oxadiazol-5-yl]-pyrrolidin-1-yl}-(4-fluoro-2-[1,2,3]triazol-2-yl-phenyl)-methanone; <br> LC-MS B: $t_R$ = 0.96 min; [M($^{35}$Cl) + H]$^+$ = 452.92 |
| 113 | A-1-30 | B-3-1 | F | {(S)-2-[3-(3-Chloro-2-methyl-phenyl)-[1,2,4]oxadiazol-5-yl]-pyrrolidin-1-yl}-(3-fluoro-2-pyrazol-1-yl-phenyl)-methanone; <br> LC-MS A: $t_R$ = 0.96 min; [M($^{35}$Cl) + H]$^+$ = 451.93 |
| 114 | A-1-15 | B-3-1 | F | {(S)-2-[3-(3-Chloro-2-methyl-phenyl)-[1,2,4]oxadiazol-5-yl]-pyrrolidin-1-yl}-(3-fluoro-2-[1,2,3]triazol-2-yl-phenyl)-methanone; LC-MS A: $t_R$ = 0.95 min; [M($^{35}$Cl) + H]$^+$ = 452.91 |
| 115 | A-1-25 | B-3-1 | F | {(S)-2-[3-(3-Chloro-2-methyl-phenyl)-[1,2,4]oxadiazol-5-yl]-pyrrolidin-1-yl}-(4,5-dimethyl-2-pyrazol-1-yl-phenyl)-methanone; <br> LC-MS B: $t_R$ = 1.00 min; [M($^{35}$Cl) + H]$^+$ = 461.92 |
| 116 | A-1-40 | B-3-1 | F | {(S)-2-[3-(3-Chloro-2-methyl-phenyl)-[1,2,4]oxadiazol-5-yl]-pyrrolidin-1-yl}-[5-fluoro-2-(2H-pyrazol-3-yl)-phenyl]-methanone; <br> LC-MS B: $t_R$ = 0.88 min; [M($^{35}$Cl) + H]$^+$ = 451.89 |
| 117 | A-1-41 | B-3-1 | F | {(S)-2-[3-(3-Chloro-2-methyl-phenyl)-[1,2,4]oxadiazol-5-yl]-pyrrolidin-1-yl}-[3-fluoro-2-(2H-pyrazol-3-yl)-phenyl]-methanone; <br> LC-MS B: $t_R$ = 0.87 min; [M($^{35}$Cl) + H]$^+$ = 451.89 |
| 118 | A-1-20 | B-3-1 | F | {(S)-2-[3-(3-Chloro-2-methyl-phenyl)-[1,2,4]oxadiazol-5-yl]-pyrrolidin-1-yl}-(4-methoxy-2-[1,2,3]triazol-2-yl-phenyl)-methanone; <br> LC-MS A: $t_R$ = 0.97 min; [M($^{35}$Cl) + H]$^+$ = 464.88 |
| 119 | A-1-17 | B-3-1 | F | {(S)-2-[3-(3-Chloro-2-methyl-phenyl)-[1,2,4]oxadiazol-5-yl]-pyrrolidin-1-yl}-(3,5-dimethyl-2-[1,2,3]triazol-2-yl-phenyl)-methanone; <br> LC-MS B: $t_R$ = 0.99 min; [M($^{35}$Cl) + H]$^+$ = 462.95 |
| 120 | A-1-36 | B-3-1 | F | {(S)-2-[3-(3-Chloro-2-methyl-phenyl)-[1,2,4]oxadiazol-5-yl]-pyrrolidin-1-yl}-(2-oxazol-2-yl-phenyl)-methanone; <br> LC-MS A: $t_R$ = 0.95 min; [M($^{35}$Cl) + H]$^+$ = 434.86 |
| 121 | A-1-16 | B-3-1 | F | {(S)-2-[3-(3-Chloro-2-methyl-phenyl)-[1,2,4]oxadiazol-5-yl]-pyrrolidin-1-yl}-(4-chloro-2-[1,2,3]triazol-2-yl-phenyl)-methanone; <br> LC-MS B: $t_R$ = 1.01 min; [M($^{35}$Cl) + H]$^+$ = 468.90 |
| 122 | A-1-22 | B-3-1 | F | {(S)-2-[3-(3-Chloro-2-methyl-phenyl)-[1,2,4]oxadiazol-5-yl]-pyrrolidin-1-yl}-(2-[1,2,3]triazol-2-yl-4-trifluoromethyl-phenyl)-methanone; <br> LC-MS A: $t_R$ = 1.03 min; [M($^{35}$Cl) + H]$^+$ = 502.97 |
| 123 | A-1-44 | B-3-1 | F | {(S)-2-[3-(3-Chloro-2-methyl-phenyl)-[1,2,4]oxadiazol-5-yl]-pyrrolidin-1-yl}-[5-(3-fluoro-phenyl)-2-methyl-thiazol-4-yl]-methanone; <br> LC-MS B: $t_R$ = 1.01 min; [M($^{35}$Cl) + H]$^+$ = 483.01 |
| 124 | A-1-46 | B-3-1 | F | {(S)-2-[3-(3-Chloro-2-methyl-phenyl)-[1,2,4]oxadiazol-5-yl]-pyrrolidin-1-yl}-[5-(2-fluoro-phenyl)-2-methyl-thiazol-4-yl]-methanone; <br> LC-MS B: $t_R$ = 1.01 min; [M($^{35}$Cl) + H]$^+$ = 483.01 |
| 125 | A-1-45 | B-3-1 | F | {(S)-2-[3-(3-Chloro-2-methyl-phenyl)-[1,2,4]oxadiazol-5-yl]-pyrrolidin-1-yl}-[5-(4-fluoro-phenyl)-2-methyl-thiazol-4-yl]-methanone; <br> LC-MS B: $t_R$ = 1.01 min; [M($^{35}$Cl) + H]$^+$ = 482.99 |
| 126 | A-1-54 | B-3-1 | F | {(S)-2-[3-(3-Chloro-2-methyl-phenyl)-[1,2,4]oxadiazol-5-yl]-pyrrolidin-1-yl}-(2-methyl-5-m-tolyl-thiazol-4-yl)-methanone; <br> LC-MS B: $t_R$ = 1.03 min; [M($^{35}$Cl) + H]$^+$ = 480.17 |
| 127 | A-1-49 | B-3-1 | F | {(S)-2-[3-(3-Chloro-2-methyl-phenyl)-[1,2,4]oxadiazol-5-yl]-pyrrolidin-1-yl}-[4-(3-chloro-phenyl)-2-methyl-pyrimidin-5-yl]-methanone; <br> LC-MS B: $t_R$ = 1.01 min; [M($^{35}$Cl) + H]$^+$ = 494.03 |
| 128 | A-1-48 | B-3-1 | F | {(S)-2-[3-(3-Chloro-2-methyl-phenyl)-[1,2,4]oxadiazol-5-yl]-pyrrolidin-1-yl}-[3-(3-methoxy-phenyl)-pyrazin-2-yl]-methanone; <br> LC-MS B: $t_R$ = 0.96 min; [M($^{35}$Cl) + H]$^+$ = 476.06 |
| 129 | A-1-27 | B-3-1 | F | {(S)-2-[3-(3-Chloro-2-methyl-phenyl)-[1,2,4]oxadiazol-5-yl]-pyrrolidin-1-yl}-(3,4-dimethyl-2-[1,2,3]triazol-2-yl-phenyl)-methanone; <br> LC-MS A: $t_R$ = 1.0 min; [M($^{35}$Cl) + H]$^+$ = 463.09 |
| 130 | A-1-26 | B-3-1 | F | {(S)-2-[3-(3-Chloro-2-methyl-phenyl)-[1,2,4]oxadiazol-5-yl]-pyrrolidin-1-yl}-(4-fluoro-5-methoxy-2-[1,2,3]triazol-2-yl-phenyl)-methanone; <br> LC-MS B: $t_R$ = 0.99 min; [M($^{35}$Cl) + H]$^+$ = 483.05 |
| 131 | A-1-37 | B-3-1 | F | {(S)-2-[3-(3-Chloro-2-methyl-phenyl)-[1,2,4]oxadiazol-5-yl]-pyrrolidin-1-yl}-(5-methyl-2-oxazol-2-yl-phenyl)-methanone; <br> LC-MS B: $t_R$ = 0.98 min; [M($^{35}$Cl) + H]$^+$ = 448.96 |
| 132 | A-1-33 | B-3-1 | F | {(S)-2-[3-(3-Chloro-2-methyl-phenyl)-[1,2,4]oxadiazol-5-yl]-pyrrolidin-1-yl}-(5-fluoro-3-methyl-2-[1,2,3]triazol-2-yl-phenyl)-methanone; <br> LC-MS A: $t_R$ = 1.00 min; [M($^{35}$Cl) + H]$^+$ = 467.04 |
| 133 | A-1-12 | B-3-1 | F | {(S)-2-[3-(3-Chloro-2-methyl-phenyl)-[1,2,4]oxadiazol-5-yl]-pyrrolidin-1-yl}-(4,5-dimethoxy-2-[1,2,3]triazol-2-yl-phenyl)-methanone; <br> LC-MS A: $t_R$ = 0.95 min; [M($^{35}$Cl) + H]$^+$ = 495.07 |
| 134 | A-1-50 | B-3-2 | G | [2-(3-Methyl-[1,2,4]oxadiazol-5-yl)-phenyl]-{(S)-2-[3-(2-trifluoromethoxy-phenyl)-[1,2,4]oxadiazol-5-yl]-pyrrolidin-1-yl}-methanone, <br> LC-MS A: $t_R$ = 0.96 min; [M + H]$^+$ = 486.09 |
| 135 | A-1-52 | B-3-2 | F | Biphenyl-2-yl-{(S)-2-[3-(2-trifluoromethoxy-phenyl)-[1,2,4]oxadiazol-5-yl]-pyrrolidin-1-yl}-methanone; <br> LC-MS A: $t_R$ = 1.02 min; [M + H]$^+$ = 479.96 |

TABLE 25-continued

| Ex. No. | SM A-1 | SM B-3 | GM | Compound of Formula (I) |
|---|---|---|---|---|
| 136 | A-1-35 | B-3-2 | G | (4-Methyl-biphenyl-2-yl)-{(S)-2-[3-(2-trifluoromethoxy-phenyl)-[1,2,4]oxadiazol-5-yl]-pyrrolidin-1-yl}-methanone; LC-MS A: $t_R$ = 1.06 min; [M + H]$^+$ = 494.12 |
| 137 | A-1-28 | B-3-2 | G | (5-Methyl-2-pyrazol-1-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.98 min; [M + H]$^+$ = 484.12 |
| 138 | A-1-38 | B-3-2 | F | (5-Methyl-2-pyridin-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.92 min; [M + H]$^+$ = 494.92 |
| 139 | A-1-53 | B-3-2 | G | (2-Methyl-5-m-tolyl-oxazol-4-yl)-{(S)-2-[3-(2-trifluoromethoxy-phenyl)-[1,2,4]oxadiazol-5-yl]-pyrrolidin-1-yl}-methanone; LC-MS A: $t_R$ = 1:02 min; [M + H]$^+$ = 499.10 |
| 140 | A-1-42 | B-3-2 | G | (5-m-Tolyl-oxazol-4-yl)-{(S)-2-[3-(2-trifluoromethoxy-phenyl)-[1,2,4]oxadiazol-5-yl]-pyrrolidin-1-yl}-methanone; LC-MS A: $t_R$ = 1.00 min; [M + H]$^+$ = 485.09 |
| 141 | A-1-4 | B-3-2 | F | (2-[1,2,3]Triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.95 min; [M + H]$^+$ = 470.91 |
| 142 | A-1-43 | B-3-2 | G | [5-(3-Chloro-phenyl)-thiazol-4-yl]-{(S)-2-[3-(2-trifluoromethoxy-phenyl)-[1,2,4]oxadiazol-5-yl]-pyrrolidin-1-yl}-methanone; LC-MS A: $t_R$ = 1.01 min; [M($^{35}$Cl) + H]$^+$ = 521.02 |
| 143 | A-1-5 | B-3-2 | G | (5-Chloro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.01 min; [M($^{35}$Cl) + H]$^+$ = 505.05 |
| 144 | A-1-9 | B-3-2 | G | (2-Fluoro-3-methoxy-6-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.98 min; [M + H]$^+$ = 519.11 |
| 145 | A-1-1 | B-3-2 | F | (2-Fluoro-3-methyl-6-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.99 min; [M + H]$^+$ = 502.89 |
| 146 | A-1-6 | B-3-2 | F | (4,5-Dimethyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.01 min; [M + H]$^+$ = 498.97 |
| 147 | A-1-3 | B-3-2 | F | (4-Methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.98 min; [M + H]$^+$ = 484.91 |
| 148 | A-1-21 | B-3-2 | G | (2-[1,2,3]Triazol-2-yl-5-trifluoromethyl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.02 min; [M + H]$^+$ = 539.07 |
| 149 | A-1-18 | B-3-2 | G | (2-Methyl-6-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.00 min; [M + H]$^+$ = 485.10 |
| 150 | A-1-23 | B-3-2 | G | (2-[1,2,3]Triazol-2-yl-5-trifluoromethoxy-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.03 min; [M + H]$^+$ = 555.06 |
| 151 | A-1-10 | B-3-2 | G | (5-Methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.97 min; [M + H]$^+$ = 501.11 |
| 152 | A-1-39 | B-3-2 | F | (4-Methoxy-biphenyl-2-yl)-{(S)-2-[3-(2-trifluoromethoxy-phenyl)-[1,2,4]oxadiazol-5-yl]-pyrrolidin-1-yl}-methanone; LC-MS B: $t_R$ = 1.00 min; [M + H]$^+$ = 509.95 |
| 153 | A-1-47 | B-3-2 | F | (5-Phenyl-3H-imidazol-4-yl)-{(S)-2-[3-(2-trifluoromethoxy-phenyl)-[1,2,4]oxadiazol-5-yl]-pyrrolidin-1-yl}-methanone; LC-MS B: $t_R$ = 0.87 min; [M + H]$^+$ = 469.95 |
| 154 | A-1-11 | B-3-2 | F | (5-Methoxy-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.01 min; [M + H]$^+$ = 515.10 |
| 155 | A-1-7 | B-3-2 | F | (5-Fluoro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.91 min; [M + H]$^+$ = 488.96 |
| 156 | A-1-13 | B-3-2 | F | (5-Methoxy-4-methyl-2-pyrazol-1-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.93 min; [M + H]$^+$ = 513.76 |
| 157 | A-1-29 | B-3-2 | F | (5-Methoxy-2-pyrazol-1-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.88 min; [M + H]$^+$ = 499.97 |
| 158 | A-1-51 | B-3-2 | F | [2,2']Bipyridinyl-3-yl-{(S)-2-[3-(2-trifluoromethoxy-phenyl)-[1,2,4]oxadiazol-5-yl]-pyrrolidin-1-yl}-methanone; LC-MS B: $t_R$ = 0.83 min; [M + H]$^+$ = 481.73 |
| 159 | A-1-14 | B-3-2 | F | (6-Methyl-3-[1,2,3]triazol-2-yl-pyridin-2-yl)-{(S)-2-[3-(2-trifluoromethoxy-phenyl)-[1,2,4]oxadiazol-5-yl]-pyrrolidin-1-yl}-methanone; LC-MS B: $t_R$ = 0.93 min; [M + H]$^+$ = 485.95 |
| 160 | A-1-31 | B-3-2 | F | (6-Methyl-3-pyrazol-1-yl-pyridin-2-yl)-{(S)-2-[3-(2-trifluoromethoxy-phenyl)-[1,2,4]oxadiazol-5-yl]-pyrrolidin-1-yl}-methanone; LC-MS B: $t_R$ = 0.84 min; [M + H]$^+$ = 484.96 |

TABLE 25-continued

| Ex. No. | SM A-1 | SM B-3 | GM | Compound of Formula (I) |
|---|---|---|---|---|
| 161 | A-1-24 | B-3-2 | F | (4,5-Difluoro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.94 min; [M + H]$^+$ = 506.94 |
| 162 | A-1-32 | B-3-2 | F | (4-Fluoro-2-pyrazol-1-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.91 min; [M + H]$^+$ = 487.96 |
| 163 | A-1-8 | B-3-2 | F | (4-Fluoro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.92 min; [M + H]$^+$ = 488.93 |
| 164 | A-1-30 | B-3-2 | F | (3-Fluoro-2-pyrazol-1-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.95 min; [M + H]$^+$ = 487.93 |
| 165 | A-1-15 | B-3-2 | F | (3-Fluoro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.94 min; [M + H]$^+$ = 488.92 |
| 166 | A-1-29 | B-3-2 | F | (4,5-Dimethyl-2-pyrazol-1-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.96 min; [M + H]$^+$ = 497.66 |
| 167 | A-1-40 | B-3-2 | F | [5-Fluoro-2-(2H-pyrazol-3-yl)-phenyl]-{(S)-2-[3-(2-trifluoromethoxy-phenyl)-[1,2,4]oxadiazol-5-yl]-pyrrolidin-1-yl}-methanone; LC-MS B: $t_R$ = 0.84 min; [M + H]$^+$ = 487.89 |
| 168 | A-1-41 | B-3-2 | F | [3-Fluoro-2-(2H-pyrazol-3-yl)-phenyl]-{(S)-2-[3-(2-trifluoromethoxy-phenyl)-[1,2,4]oxadiazol-5-yl]-pyrrolidin-1-yl}-methanone; LC-MS B: $t_R$ = 0.84 min; [M + H]$^+$ = 487.90 |
| 169 | A-1-20 | B-3-2 | F | (4-Methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.95 min; [M + H]$^+$ = 500.90 |
| 170 | A-1-17 | B-3-2 | F | (3,5-Dimethyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.95 min; [M + H]$^+$ = 498.95 |
| 171 | A-1-36 | B-3-2 | F | (2-Oxazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.94 min; [M + H]$^+$ = 470.93 |
| 172 | A-1-16 | B-3-2 | F | (4-Chloro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS B: $t_R$ = 0.97 min; [M($^{35}$Cl) + H]$^+$ = 504.91 |
| 173 | A-1-22 | B-3-2 | F | (2-[1,2,3]Triazol-2-yl-4-trifluoromethyl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.01 min; [M + H]$^+$ = 538.96 |
| 174 | A-1-26 | B-3-2 | F | (4-Fluoro-5-methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.98 min; [M + H]$^+$ = 519.04 |
| 175 | A-1-37 | B-3-2 | F | (5-Methyl-2-oxazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.97 min; [M + H]$^+$ = 485.06 |
| 176 | A-1-33 | B-3-2 | F | (5-Fluoro-3-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.98 min; [M + H]$^+$ = 503.08 |
| 177 | A-1-12 | B-3-2 | F | (4,5-Dimethoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.94 min; [M + H]$^+$ = 531.09 |
| 178 | A-1-4 | B-3-3 | F | (2-[1,2,3]Triazol-2-yl-phenyl)-{(S)-2-[3-(2-trifluoromethyl-phenyl)-[1,2,4]oxadiazol-5-yl]-pyrrolidin-1-yl}-methanone; LC-MS B: $t_R$ = 0.85 min; [M + H]$^+$ = 454.92 |
| 179 | A-1-5 | B-3-3 | F | (5-Chloro-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone; LC-MS B: $t_R$ = 0.92 min; [M($^{35}$Cl) + H]$^+$ = 488.90 |
| 180 | A-1-3 | B-3-3 | F | (4-Methyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone; LC-MS B: $t_R$ = 0.90 min; [M + H]$^+$ = 468.94 |
| 181 | A-1-6 | B-3-3 | F | (4,5-Dimethyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone; LC-MS B: $t_R$ = 0.93 min; [M + H]$^+$ = 482.95 |
| 182 | A-1-11 | B-3-3 | F | (5-Methoxy-4-methyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone; LC-MS B: $t_R$ = 0.92 min; [M + H]$^+$ = 498.92 |
| 183 | A-1-41 | B-3-3 | F | [3-Fluoro-2-(2H-pyrazol-3-yl)-phenyl]-{(S)-2-[3-(2-trifluoromethyl-phenyl)-[1,2,4]oxadiazol-5-yl]-pyrrolidin-1-yl}-methanone; LC-MS B: $t_R$ = 0.80 min; [M + H]$^+$ = 471.92 |
| 184 | A-1-38 | B-3-3 | F | (5-Methyl-2-pyridin-2-yl-phenyl)-{(S)-2-[3-(2-trifluoromethyl-phenyl)-[1,2,4]oxadiazol-5-yl]-pyrrolidin-1-yl}-methanone; LC-MS B: $t_R$ = 0.80 min; [M + H]$^+$ = 478.97 |
| 185 | A-1-4 | B-3-4 | F | {(S)-2-[3-(2-Difluoromethoxy-phenyl)-[1,2,4]oxadiazol-5-yl]-pyrrolidin-1-yl}-(2-[1,2,3]triazol-2-yl-phenyl)-methanone; LC-MS B: $t_R$ = 0.83 min; [M + H]$^+$ = 452.92 |

TABLE 25-continued

| Ex. No. | SM A-1 | SM B-3 | GM | Compound of Formula (I) |
|---|---|---|---|---|
| 186 | A-1-5 | B-3-4 | F | (5-Chloro-2-[1,2,3]triazol-2-yl-phenyl)-{(S)-2-[3-(2-difluoromethoxy-phenyl)-[1,2,4]oxadiazol-5-yl]-pyrrolidin-1-yl}-methanone; LC-MS B: $t_R$ = 0.89 min; [M$^{35}$Cl) + H]$^+$ = 486.89 |
| 187 | A-1-3 | B-3-4 | F | {(S)-2-[3-(2-Difluoromethoxy-phenyl)-[1,2,4]oxadiazol-5-yl]-pyrrolidin-1-yl}-(4-methyl-2-[1,2,3]triazol-2-yl-phenyl)-methanone; LC-MS B: $t_R$ = 0.87 min; [M + H]$^+$ = 466.92 |
| 188 | A-1-6 | B-3-4 | F | {(S)-2-[3-(2-Difluoromethoxy-phenyl)-[1,2,4]oxadiazol-5-yl]-pyrrolidin-1-yl}-(4,5-dimethyl-2-[1,2,3]triazol-2-yl-phenyl)-methanone; LC-MS B: $t_R$ = 0.91 min; [M + H]$^+$ = 480.95 |
| 189 | A-1-11 | B-3-4 | F | {(S)-2-[3-(2-Difluoromethoxy-phenyl)-[1,2,4]oxadiazol-5-yl]-pyrrolidin-1-yl}-(5-methoxy-4-methyl-2-[1,2,3]triazol-2-yl-phenyl)-methanone; LC-MS B: $t_R$ = 0.90 min; [M + H]$^+$ = 496.88 |
| 190 | A-1-41 | B-3-4 | F | {(S)-2-[3-(2-Difluoromethoxy-phenyl)-[1,2,4]oxadiazol-5-yl]-pyrrolidin-1-yl}-[3-fluoro-2-(2H-pyrazol-3-yl)-phenyl]-methanone; LC-MS B: $t_R$ = 0.77 min; [M + H]$^+$ = 469.93 |
| 191 | A-1-38 | B-3-4 | F | {(S)-2-[3-(2-Difluoromethoxy-phenyl)-[1,2,4]oxadiazol-5-yl]-pyrrolidin-1-yl}-(5-methyl-2-pyridin-2-yl-phenyl)-methanone; LC-MS B: $t_R$ = 0.77 min; [M + H]$^+$ = 476.97 |
| 192 | A-1-17 | B-3-5 | F | (3,5-Dimethyl-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS B: $t_R$ = 0.88 min; [M + H]$^+$ = 462.99 |
| 193 | A-1-4 | B-3-5 | F | {(S)-2-[3-(3-Fluoro-2-methoxy-phenyl)-[1,2,4]oxadiazol-5-yl]-pyrrolidin-1-yl}-(2-[1,2,3]triazol-2-yl-phenyl)-methanone; LC-MS B: $t_R$ = 0.82 min; [M + H]$^+$ = 434.90 |
| 194 | A-1-5 | B-3-5 | F | (5-Chloro-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS B: $t_R$ = 0.90 min; [M($^{35}$Cl) + H]$^+$ = 486.92 |
| 195 | A-1-3 | B-3-5 | F | {(S)-2-[3-(3-Fluoro-2-methoxy-phenyl)-[1,2,4]oxadiazol-5-yl]-pyrrolidin-1-yl}-(4-methyl-2-[1,2,3]triazol-2-yl-phenyl)-methanone; LC-MS B: $t_R$ = 0.87 min; [M + H]$^+$ = 448.91 |
| 196 | A-1-6 | B-3-5 | F | (4,5-Dimethyl-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS B: $t_R$ = 0.91 min; [M + H]$^+$ = 462.99 |
| 197 | A-1-34 | B-3-5 | F | {(S)-2-[3-(3-Fluoro-2-methoxy-phenyl)-[1,2,4]oxadiazol-5-yl]-pyrrolidin-1-yl}-(3-methyl-2-[1,2,3]triazol-2-yl-phenyl)-methanone; LC-MS B: $t_R$ = 0.84 min; [M + H]$^+$ = 448.93 |
| 198 | A-1-14 | B-3-5 | F | {(S)-2-[3-(3-Fluoro-2-methoxy-phenyl)-[1,2,4]oxadiazol-5-yl]-pyrrolidin-1-yl}-(6-methyl-3-[1,2,3]triazol-2-yl-pyridin-2-yl)-methanone; LC-MS B: $t_R$ = 0.77 min; [M + H]$^+$ = 449.69 |
| 199 | A-1-10 | B-3-5 | F | {(S)-2-[3-(3-Fluoro-2-methoxy-phenyl)-[1,2,4]oxadiazol-5-yl]-pyrrolidin-1-yl}-(5-methoxy-2-[1,2,3]triazol-2-yl-phenyl)-methanone; LC-MS B: $t_R$ = 0.84 min; [M + H]$^+$ = 464.91 |
| 200 | A-1-7 | B-3-5 | F | {(S)-2-[3-(3-Fluoro-2-methoxy-phenyl)-[1,2,4]oxadiazol-5-yl]-pyrrolidin-1-yl}-(5-fluoro-2-[1,2,3]triazol-2-yl-phenyl)-methanone; LC-MS B: $t_R$ = 0.84 min; [M + H]$^+$ = 452.93 |
| 201 | A-1-11 | B-3-5 | F | {(S)-2-[3-(3-Fluoro-2-methoxy-phenyl)-[1,2,4]oxadiazol-5-yl]-pyrrolidin-1-yl}-(5-methoxy-4-methyl-2-[1,2,3]triazol-2-yl-phenyl)-methanone; LC-MS B: $t_R$ = 0.90 min; [M + H]$^+$ = 478.97 |
| 202 | A-1-41 | B-3-5 | F | {(S)-2-[3-(3-Fluoro-2-methoxy-phenyl)-[1,2,4]oxadiazol-5-yl]-pyrrolidin-1-yl}-[3-fluoro-2-(2H-pyrazol-3-yl)-phenyl]-methanone; LC-MS B: $t_R$ = 0.77 min; [M + H]$^+$ = 451.95 |
| 203 | A-1-38 | B-3-5 | F | {(S)-2-[3-(3-Fluoro-2-methoxy-phenyl)-[1,2,4]oxadiazol-5-yl]-pyrrolidin-1-yl}-(5-methyl-2-pyridin-2-yl-phenyl)-methanone; LC-MS B: $t_R$ = 0.76 min; [M + H]$^+$ = 458.97 |
| 204 | A-1-16 | B-3-5 | F | (4-Chloro-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS B: $t_R$ = 0.90 min; [M($^{35}$Cl) + H]$^+$ = 468.92 |
| 205 | A-1-22 | B-3-5 | F | {(S)-2-[3-(3-Fluoro-2-methoxy-phenyl)-[1,2,4]oxadiazol-5-yl]-pyrrolidin-1-yl}-(2-[1,2,3]triazol-2-yl-4-trifluoromethyl-phenyl)-methanone; LC-MS A: $t_R$ = 0.97 min; [M + H]$^+$ = 502.99 |
| 206 | A-1-26 | B-3-5 | F | {(S)-2-[3-(3-Fluoro-2-methoxy-phenyl)-[1,2,4]oxadiazol-5-yl]-pyrrolidin-1-yl}-(4-fluoro-5-methoxy-2-[1,2,3]triazol-2-yl-phenyl)-methanone; LC-MS A: $t_R$ = 0.93 min; [M + H]$^+$ = 483.05 |
| 207 | A-1-33 | B-3-5 | F | {(S)-2-[3-(3-Fluoro-2-methoxy-phenyl)-[1,2,4]oxadiazol-5-yl]-pyrrolidin-1-yl}-(5-fluoro-3-methyl-2-[1,2,3]triazol-2-yl-phenyl)-methanone; LC-MS A: $t_R$ = 0.93 min; [M + H]$^+$ = 467.09 |
| 208 | A-1-12 | B-3-5 | F | (4,5-Dimethoxy-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS A: $t_R$ = 0.88 min; [M + H]$^+$ = 495.11 |
| 209 | A-1-17 | B-3-6 | F | (3,5-Dimethyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS B: $t_R$ = 0.85 min; [M + H]$^+$ = 460.02 |
| 210 | A-1-5 | B-3-6 | F | (5-Chloro-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS B: $t_R$ = 0.87 min; [M$^{35}$Cl] + H]$^+$ = 465.67 |

TABLE 25-continued

| Ex. No. | SM A-1 | SM B-3 | GM | Compound of Formula (I) |
|---|---|---|---|---|
| 211 | A-1-3 | B-3-6 | F | {(S)-2-[3-(2-Ethoxy-pyridin-3-yl)-[1,2,4]oxadiazol-5-yl]-pyrrolidin-1-yl}-(4-methyl-2-[1,2,3]triazol-2-yl-phenyl)-methanone; LC-MS B: $t_R$ = 0.84 min; [M + H]$^+$ = 445.98 |
| 212 | A-1-6 | B-3-6 | F | (4,5-Dimethyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS B: $t_R$ = 0.88 min; [M + H]$^+$ = 460.01 |
| 213 | A-1-14 | B-3-6 | F | {(S)-2-[3-(2-Ethoxy-pyridin-3-yl)-[1,2,4]oxadiazol-5-yl]-pyrrolidin-1-yl}-(6-methyl-3-[1,2,3]triazol-2-yl-pyridin-2-yl)-methanone; LC-MS B: $t_R$ = 0.73 min; [M + H]$^+$ = 447.00 |
| 214 | A-1-7 | B-3-6 | F | {(S)-2-[3-(2-Ethoxy-pyridin-3-yl)-[1,2,4]oxadiazol-5-yl]-pyrrolidin-1-yl}-(5-fluoro-2-[1,2,3]triazol-2-yl-phenyl)-methanone; LC-MS B: $t_R$ = 0.81 min; [M + H]$^+$ = 449.70 |
| 215 | A-1-13 | B-3-6 | F | {(S)-2-[3-(2-Ethoxy-pyridin-3-yl)-[1,2,4]oxadiazol-5-yl]-pyrrolidin-1-yl}-(5-methoxy-4-methyl-2-[1,2,3]triazol-2-yl-phenyl)-methanone; LC-MS B: $t_R$ = 0.87 min; [M + H]$^+$ = 476.01 |
| 216 | A-1-41 | B-3-6 | F | {(S)-2-[3-(2-Ethoxy-pyridin-3-yl)-[1,2,4]oxadiazol-5-yl]-pyrrolidin-1-yl}-[3-fluoro-2-(2H-pyrazol-3-yl)-phenyl]-methanone; LC-MS B: $t_R$ = 0.73 min; [M + H]$^+$ = 448.92 |
| 217 | A-1-38 | B-3-6 | F | {(S)-2-[3-(2-Ethoxy-pyridin-3-yl)-[1,2,4]oxadiazol-5-yl]-pyrrolidin-1-yl}-(5-methyl-2-pyridin-2-yl-phenyl)-methanone; LC-MS B: $t_R$ = 0.72 min; [M + H]$^+$ = 455.99 |
| 218 | A-1-4 | B-3-6 | F | {(S)-2-[3-(2-Ethoxy-pyridin-3-yl)-[1,2,4]oxadiazol-5-yl]-pyrrolidin-1-yl}-(2-[1,2,3]triazol-2-yl-phenyl)-methanone; LC-MS B: $t_R$ = 0.79 min; [M + H]$^+$ = 431.97 |
| 219 | A-1-34 | B-3-6 | F | {(S)-2-[3-(2-Ethoxy-pyridin-3-yl)-[1,2,4]oxadiazol-5-yl]-pyrrolidin-1-yl}-(3-methyl-2-[1,2,3]triazol-2-yl-phenyl)-methanone; LC-MS B: $t_R$ = 0.80 min; [M + H]$^+$ = 455.98 |
| 220 | A-1-10 | B-3-6 | F | {(S)-2-[3-(2-Ethoxy-pyridin-3-yl)-[1,2,4]oxadiazol-5-yl]-pyrrolidin-1-yl}-(5-methoxy-2-[1,2,3]triazol-2-yl-phenyl)-methanone; LC-MS B: $t_R$ = 0.8 min; [M + H]$^+$ = 461.98 |
| 221 | A-1-16 | B-3-6 | F | (4-Chloro-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS B: $t_R$ = 0.88 min; [M($^{35}$Cl) + H]$^+$ = 465.66 |
| 222 | A-1-22 | B-3-6 | F | {(S)-2-[3-(2-Ethoxy-pyridin-3-yl)-[1,2,4]oxadiazol-5-yl]-pyrrolidin-1-yl}-(2-[1,2,3]triazol-2-yl-4-trifluoromethyl-phenyl)-methanone; LC-MS A: $t_R$ = 0.95 min; [M + H]$^+$ = 500.02 |
| 223 | A-1-26 | B-3-6 | F | {(S)-2-[3-(2-Ethoxy-pyridin-3-yl)-[1,2,4]oxadiazol-5-yl]-pyrrolidin-1-yl}-(4-fluoro-5-methoxy-2-[1,2,3]triazol-2-yl-phenyl)-methanone; LC-MS A: $t_R$ = 0.90 min; [M + H]$^+$ = 480.09 |
| 224 | A-1-37 | B-3-6 | F | {(S)-2-[3-(2-Ethoxy-pyridin-3-yl)-[1,2,4]oxadiazol-5-yl]-pyrrolidin-1-yl}-(5-methyl-2-oxazol-2-yl-phenyl)-methanone; LC-MS A: $t_R$ = 0.89 min; [M + H]$^+$ = 446.08 |
| 225 | A-1-33 | B-3-6 | F | {(S)-2-[3-(2-Ethoxy-pyridin-3-yl)-[1,2,4]oxadiazol-5-yl]-pyrrolidin-1-yl}-(5-fluoro-3-methyl-2-[1,2,3]triazol-2-yl-phenyl)-methanone; LC-MS A: $t_R$ = 0.90 min; [M + H]$^+$ = 464.10 |
| 226 | A-1-12 | B-3-6 | F | (4,5-Dimethoxy-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS A: $t_R$ = 0.85 min; [M + H]$^+$ = 492.14 |
| 227 | A-1-4 | B-3-7 | F | {(S)-2-[3-(2-Methoxy-phenyl)-[1,2,4]oxadiazol-5-yl]-pyrrolidin-1-yl}-(2-[1,2,3]triazol-2-yl-phenyl)-methanone; LC-MS A: $t_R$ = 0.85 min; [M + H]$^+$ = 416.90 |
| 228 | A-1-5 | B-3-7 | F | (5-Chloro-2-[1,2,3]triazol-2-yl-phenyl)-{(S)-2-[3-(2-methoxy-phenyl)-[1,2,4]oxadiazol-5-yl]-pyrrolidin-1-yl}-methanone; LC-MS A: $t_R$ = 0.91 min; [M($^{35}$Cl) + H]$^+$ = 450.87 |
| 229 | A-1-3 | B-3-7 | F | {(S)-2-[3-(2-Methoxy-phenyl)-[1,2,4]oxadiazol-5-yl]-pyrrolidin-1-yl}-(4-methyl-2-[1,2,3]triazol-2-yl-phenyl)-methanone; LC-MS A: $t_R$ = 0.89 min; [M + H]$^+$ = 430.95 |
| 230 | A-1-6 | B-3-7 | F | (4,5-Dimethyl-2-[1,2,3]triazol-2-yl-phenyl)-{(S)-2-[3-(2-methoxy-phenyl)-[1,2,4]oxadiazol-5-yl]-pyrrolidin-1-yl}-methanone; LC-MS A: $t_R$ = 0.91 min; [M + H]$^+$ = 444.95 |
| 231 | A-1-11 | B-3-7 | F | (5-Methoxy-4-methyl-2-[1,2,3]triazol-2-yl-phenyl)-{(S)-2-[3-(2-methoxy-phenyl)-[1,2,4]oxadiazol-5-yl]-pyrrolidin-1-yl}-methanone; LC-MS A: $t_R$ = 0.91 min; [M + H]$^+$ = 460.98 |
| 232 | A-1-10 | B-3-7 | F | {(S)-2-[3-(2-Methoxy-phenyl)-[1,2,4]oxadiazol-5-yl]-pyrrolidin-1-yl}-(5-methoxy-2-[1,2,3]triazol-2-yl-phenyl)-methanone; LC-MS A: $t_R$ = 0.86 min; [M + H]$^+$ = 446.95 |
| 233 | A-1-7 | B-3-7 | F | (5-Fluoro-2-[1,2,3]triazol-2-yl-phenyl)-{(S)-2-[3-(2-methoxy-phenyl)-[1,2,4]oxadiazol-5-yl]-pyrrolidin-1-yl}-methanone; LC-MS A: $t_R$ = 0.87 min; [M + H]$^+$ = 434.89 |
| 234 | A-1-40 | B-3-7 | F | [5-Fluoro-2-(2H-pyrazol-3-yl)-phenyl]-{(S)-2-[3-(2-methoxy-phenyl)-[1,2,4]oxadiazol-5-yl]-pyrrolidin-1-yl}-methanone; LC-MS A: $t_R$ = 0.81 min; [M + H]$^+$ = 433.68 |
| 235 | A-1-14 | B-3-7 | F | {(S)-2-[3-(2-Methoxy-phenyl)-[1,2,4]oxadiazol-5-yl]-pyrrolidin-1-yl}-(6-methyl-3-[1,2,3]triazol-2-yl-pyridin-2-yl)-methanone; LC-MS A: $t_R$ = 0.81 min; [M + H]$^+$ = 431.93 |

TABLE 25-continued

| Ex. No. | SM A-1 | SM B-3 | GM | Compound of Formula (I) |
|---|---|---|---|---|
| 236 | A-1-5 | B-3-8 | F | {(S)-2-[3-(2-Chloro-phenyl)-[1,2,4]oxadiazol-5-yl]-pyrrolidin-1-yl}-(5-chloro-2-[1,2,3]triazol-2-yl-phenyl)-methanone; LC-MS A: $t_R$ = 0.95 min; [M($^{35}$Cl) + H]$^+$ = 454.85 |
| 237 | A-1-3 | B-3-8 | F | {(S)-2-[3-(2-Chloro-phenyl)-[1,2,4]oxadiazol-5-yl]-pyrrolidin-1-yl}-(4-methyl-2-[1,2,3]triazol-2-yl-phenyl)-methanone; LC-MS A: $t_R$ = 0.94 min; [M($^{35}$Cl) + H]$^+$ = 434.86 |
| 238 | A-1-6 | B-3-8 | F | {(S)-2-[3-(2-Chloro-phenyl)-[1,2,4]oxadiazol-5-yl]-pyrrolidin-1-yl}-(4,5-dimethyl-2-[1,2,3]triazol-2-yl-phenyl)-methanone; LC-MS A: $t_R$ = 0.96 min; [M($^{35}$Cl) + H]$^+$ = 448.89 |
| 239 | A-1-11 | B-3-8 | F | {(S)-2-[3-(2-Chloro-phenyl)-[1,2,4]oxadiazol-5-yl]-pyrrolidin-1-yl}-(5-methoxy-4-methyl-2-[1,2,3]triazol-2-yl-phenyl)-methanone; LC-MS A: $t_R$ = 0.96 min; [M($^{35}$Cl) + H]$^+$ = 464.90 |
| 240 | A-1-10 | B-3-8 | F | {(S)-2-[3-(2-Chloro-phenyl)-[1,2,4]oxadiazol-5-yl]-pyrrolidin-1-yl}-(5-methoxy-2-[1,2,3]triazol-2-yl-phenyl)-methanone; LC-MS A: $t_R$ = 0.92 min; [M($^{35}$Cl) + H]$^+$ = 450.86 |
| 241 | A-1-7 | B-3-8 | F | {(S)-2-[3-(2-Chloro-phenyl)-[1,2,4]oxadiazol-5-yl]-pyrrolidin-1-yl}-(5-fluoro-2-[1,2,3]triazol-2-yl-phenyl)-methanone; LC-MS A: $t_R$ = 0.96 min; [M($^{35}$Cl) + H]$^+$ = 469.88 |
| 242 | A-1-14 | B-3-8 | F | {(S)-2-[3-(2-Chloro-phenyl)-[1,2,4]oxadiazol-5-yl]-pyrrolidin-1-yl}-(6-methyl-3-[1,2,3]triazol-2-yl-pyridin-2-yl)-methanone; LC-MS A: $t_R$ = 0.87 min; [M($^{35}$Cl) + H]$^+$ = 435.86 |
| 243 | A-1-4 | B-3-8 | F | {(S)-2-[3-(2-Chloro-phenyl)-[1,2,4]oxadiazol-5-yl]-pyrrolidin-1-yl}-(2-[1,2,3]triazol-2-yl-phenyl)-methanone; LC-MS A: $t_R$ = 0.90 min; [M($^{35}$Cl) + H]$^+$ = 420.88 |
| 244 | A-1-4 | B-3-9 | F | {(S)-2-[3-(3-Fluoro-2-methyl-phenyl)-[1,2,4]oxadiazol-5-yl]-pyrrolidin-1-yl}-(2-[1,2,3]triazol-2-yl-phenyl)-methanone; LC-MS A: $t_R$ = 0.94 min; [M + H]$^+$ = 418.90 |
| 245 | A-1-5 | B-3-9 | F | (5-Chloro-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone; LC-MS A: $t_R$ = 0.98 min; [M($^{35}$Cl) + H]$^+$ = 452.92 |
| 246 | A-1-3 | B-3-9 | F | {(S)-2-[3-(3-Fluoro-2-methyl-phenyl)-[1,2,4]oxadiazol-5-yl]-pyrrolidin-1-yl}-(4-methyl-2-[1,2,3]triazol-2-yl-phenyl)-methanone; LC-MS A: $t_R$ = 0.97 min; [M + H]$^+$ = 432.90 |
| 247 | A-1-6 | B-3-9 | F | (4,5-Dimethyl-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone; LC-MS A: $t_R$ = 0.99 min; [M + H]$^+$ = 446.98 |
| 248 | A-1-11 | B-3-9 | F | {(S)-2-[3-(3-Fluoro-2-methyl-phenyl)-[1,2,4]oxadiazol-5-yl]-pyrrolidin-1-yl}-(5-methoxy-4-methyl-2-[1,2,3]triazol-2-yl-phenyl)-methanone; LC-MS A: $t_R$ = 0.99 min; [M + H]$^+$ = 462.98 |
| 249 | A-1-10 | B-3-9 | F | {(S)-2-[3-(3-Fluoro-2-methyl-phenyl)-[1,2,4]oxadiazol-5-yl]-pyrrolidin-1-yl}-(5-methoxy-2-[1,2,3]triazol-2-yl-phenyl)-methanone; LC-MS A: $t_R$ = 0.95 min; [M + H]$^+$ = 448.91 |
| 250 | A-1-7 | B-3-9 | F | {(S)-2-[3-(3-Fluoro-2-methyl-phenyl)-[1,2,4]oxadiazol-5-yl]-pyrrolidin-1-yl}-(5-fluoro-2-[1,2,3]triazol-2-yl-phenyl)-methanone; LC-MS A: $t_R$ = 0.95 min; [M + H]$^+$ = 436.93 |
| 251 | A-1-34 | B-3-9 | F | {(S)-2-[3-(3-Fluoro-2-methyl-phenyl)-[1,2,4]oxadiazol-5-yl]-pyrrolidin-1-yl}-(3-methyl-2-[1,2,3]triazol-2-yl-phenyl)-methanone; LC-MS A: $t_R$ = 0.94 min; [M + H]$^+$ = 432.91 |
| 252 | A-1-14 | B-3-9 | F | {(S)-2-[3-(3-Fluoro-2-methyl-phenyl)-[1,2,4]oxadiazol-5-yl]-pyrrolidin-1-yl}-(6-methyl-3-[1,2,3]triazol-2-yl-pyridin-2-yl)-methanone; LC-MS A: $t_R$ = 0.90 min; [M + H]$^+$ = 433.72 |
| 253 | A-1-41 | B-3-9 | F | {(S)-2-[3-(3-Fluoro-2-methyl-phenyl)-[1,2,4]oxadiazol-5-yl]-pyrrolidin-1-yl}-[3-fluoro-2-(2H-pyrazol-3-yl)-phenyl]-methanone; LC-MS A: $t_R$ = 0.89 min; [M + H]$^+$ = 435.95 |
| 254 | A-1-41 | B-3-10 | F | {(S)-2-[3-(2-Ethoxy-phenyl)-[1,2,4]oxadiazol-5-yl]-pyrrolidin-1-yl}-[3-fluoro-2-(2H-pyrazol-3-yl)-phenyl]-methanone; LC-MS A: $t_R$ = 0.85 min; [M + H]$^+$ = 447.95 |
| 255 | A-1-5 | B-3-10 | F | (5-Chloro-2-[1,2,3]triazol-2-yl-phenyl)-{(S)-2-[3-(2-ethoxy-phenyl)-[1,2,4]oxadiazol-5-yl]-pyrrolidin-1-yl}-methanone; LC-MS A: $t_R$ = 0.95 min; [M($^{35}$Cl) + H]$^+$ = 464.92 |
| 256 | A-1-3 | B-3-10 | F | {(S)-2-[3-(2-Ethoxy-phenyl)-[1,2,4]oxadiazol-5-yl]-pyrrolidin-1-yl}-(4-methyl-2-[1,2,3]triazol-2-yl-phenyl)-methanone; LC-MS A: $t_R$ = 0.93 min; [M + H]$^+$ = 444.98 |
| 257 | A-1-6 | B-3-10 | F | (4,5-Dimethyl-2-[1,2,3]triazol-2-yl-phenyl)-{(S)-2-[3-(2-ethoxy-phenyl)-[1,2,4]oxadiazol-5-yl]-pyrrolidin-1-yl}-methanone; LC-MS A: $t_R$ = 0.96 min; [M + H]$^+$ = 459.01 |
| 258 | A-1-11 | B-3-10 | F | {(S)-2-[3-(2-Ethoxy-phenyl)-[1,2,4]oxadiazol-5-yl]-pyrrolidin-1-yl}-(5-methoxy-4-methyl-2-[1,2,3]triazol-2-yl-phenyl)-methanone; LC-MS A: $t_R$ = 0.95 min; [M + H]$^+$ = 475.01 |
| 259 | A-1-14 | B-3-10 | F | {(S)-2-[3-(2-Ethoxy-phenyl)-[1,2,4]oxadiazol-5-yl]-pyrrolidin-1-yl}-(6-methyl-3-[1,2,3]triazol-2-yl-pyridin-2-yl)-methanone; LC-MS A: $t_R$ = 0.86 min; [M + H]$^+$ = 445.98 |
| 260 | A-1-4 | B-3-10 | F | {(S)-2-[3-(2-Ethoxy-phenyl)-[1,2,4]oxadiazol-5-yl]-pyrrolidin-1-yl}-(2-[1,2,3]triazol-2-yl-phenyl)-methanone; LC-MS A: $t_R$ = 0.89 min; [M + H]$^+$ = 430.96 |

TABLE 25-continued

| Ex. No. | SM A-1 | SM B-3 | GM | Compound of Formula (I) |
|---|---|---|---|---|
| 261 | A-1-10 | B-3-10 | F | {(S)-2-[3-(2-Ethoxy-phenyl)-[1,2,4]oxadiazol-5-yl]-pyrrolidin-1-yl}-(5-methoxy-2-[1,2,3]triazol-2-yl-phenyl)-methanone; LC-MS A: $t_R$ = 0.91 min; [M + H]$^+$ = 460.99 |
| 262 | A-1-34 | B-3-10 | F | {(S)-2-[3-(2-Ethoxy-phenyl)-[1,2,4]oxadiazol-5-yl]-pyrrolidin-1-yl}-(3-methyl-2-[1,2,3]triazol-2-yl-phenyl)-methanone; LC-MS A: $t_R$ = 0.90 min; [M + H]$^+$ = 444.97 |
| 263 | A-1-7 | B-3-10 | F | {(S)-2-[3-(2-Ethoxy-phenyl)-[1,2,4]oxadiazol-5-yl]-pyrrolidin-1-yl}-(5-fluoro-2-[1,2,3]triazol-2-yl-phenyl)-methanone; LC-MS A: $t_R$ = 0.91 min; [M + H]$^+$ = 448.91 |
| 264 | A-1-5 | B-3-1 | F | {(S)-2-[3-(3-Chloro-2-methyl-phenyl)-[1,2,4]oxadiazol-5-yl]-pyrrolidin-1-yl}-(5-chloro-2-[1,2,3]triazol-2-yl-phenyl)-methanone; LC-MS B: $t_R$ = 1.06 min; [M($^{35}$Cl) + H]$^+$ = 468.98 |
| 265 | A-1-9 | B-3-1 | G | {(S)-2-[3-(3-Chloro-2-methyl-phenyl)-[1,2,4]oxadiazol-5-yl]-pyrrolidin-1-yl}-(2-fluoro-3-methoxy-6-[1,2,3]triazol-2-yl-phenyl)-methanone; LC-MS A: $t_R$ = 0.99 min; [M($^{35}$Cl) + H]$^+$ = 483.08 |
| 266 | A-1-1 | B-3-1 | F | {(S)-2-[3-(3-Chloro-2-methyl-phenyl)-[1,2,4]oxadiazol-5-yl]-pyrrolidin-1-yl}-(2-fluoro-3-methyl-6-[1,2,3]triazol-2-yl-phenyl)-methanone; LC-MS B: $t_R$ = 0.99 min; [M($^{35}$Cl) + H]$^+$ = 466.88 |
| 267 | A-1-50 | B-3-1 | G | {(S)-2-[3-(3-Chloro-2-methyl-phenyl)-[1,2,4]oxadiazol-5-yl]-pyrrolidin-1-yl}-[2-(3-methyl-[1,2,4]oxadiazol-5-yl)-phenyl]-methanone; LC-MS A: $t_R$ = 0.97 min; [M($^{35}$Cl) + H]$^+$ = 449.84 |
| 268 | A-1-52 | B-3-1 | G | Biphenyl-2-yl-{(S)-2-[3-(3-chloro-2-methyl-phenyl)-[1,2,4]oxadiazol-5-yl]-pyrrolidin-1-yl}-methanone; LC-MS A: $t_R$ = 1.05 min; [M($^{35}$Cl) + H]$^+$ = 444.08 |
| 269 | A-1-56 | B-3-1 | F | {(S)-2-[3-(3-Chloro-2-methyl-phenyl)-[1,2,4]oxadiazol-5-yl]-pyrrolidin-1-yl}-(5-methoxy-4-methyl-2-pyrimidin-2-yl-phenyl)-methanone; LC-MS A: $t_R$ = 1.02 min; [M($^{35}$Cl) + H]$^+$ = 490.07 |
| 270 | A-1-2 | B-3-12 | F | (5-Methyl-2-[1,2,3]triazol-2-yl-phenyl)-{(S)-2-[3-(3-trifluoromethoxy-phenyl)-[1,2,4]oxadiazol-5-yl]-pyrrolidin-1-yl}-methanone; LC-MS A: $t_R$ = 1.01 min; [M + H]$^+$ = 485.10 |
| 271 | A-1-27 | B-3-2 | F | (3,4-Dimethyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.99 min; [M + H]$^+$ = 499.11 |
| 272 | A-1-27 | B-3-5 | F | (3,4-Dimethyl-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS A: $t_R$ = 0.93 min; [M + H]$^+$ = 463.09 |
| 273 | A-1-27 | B-3-6 | F | (3,4-Dimethyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS A: $t_R$ = 0.91 min; [M + H]$^+$ = 460.14 |
| 274 | A-1-55 | B-3-1 | F | {(S)-2-[3-(3-Chloro-2-methyl-phenyl)-[1,2,4]oxadiazol-5-yl]-pyrrolidin-1-yl}-(5-methyl-2-pyrimidin-2-yl-phenyl)-methanone; LC-MS A: $t_R$ = 0.99 min; [M($^{35}$Cl) + H]$^+$ = 460.08 |
| 275 | A-1-19 | B-3-2 | F | 4-[1,2,3]Triazol-2-yl-3-{(S)-2-[3-(2-trifluoromethoxy-phenyl)-[1,2,4]oxadiazol-5-yl]-pyrrolidine-1-carbonyl}-benzonitrile; LC-MS A: $t_R$ = 0.96 min; [M + H]$^+$ = 496.08 |
| 276 | A-1-19 | B-3-1 | F | 3-{(S)-2-[3-(3-Chloro-2-methyl-phenyl)-[1,2,4]oxadiazol-5-yl]-pyrrolidine-1-carbonyl}-4-[1,2,3]triazol-2-yl-benzonitrile; LC-MS A: $t_R$ = 0.97 min; [M($^{35}$Cl) + H]$^+$ = 460.07 |
| 277 | A-1-19 | B-3-9 | F | 3-{(S)-2-[3-(3-Fluoro-2-methyl-phenyl)-[1,2,4]oxadiazol-5-yl]-pyrrolidine-1-carbonyl}-4-[1,2,3]triazol-2-yl-benzonitrile; LC-MS A: $t_R$ = 0.95 min; [M + H]$^+$ = 444.09 |
| 278 | A-1-19 | B-3-5 | F | 3-{(S)-2-[3-(3-Fluoro-2-methoxy-phenyl)-[1,2,4]oxadiazol-5-yl]-pyrrolidine-1-carbonyl}-4-[1,2,3]triazol-2-yl-benzonitrile; LC-MS A: $t_R$ = 0.91 min; [M + H]$^+$ = 460.99 |
| 279 | A-1-19 | B-3-6 | F | 3-{(S)-2-[3-(2-Ethoxy-pyridin-3-yl)-[1,2,4]oxadiazol-5-yl]-pyrrolidine-1-carbonyl}-4-[1,2,3]triazol-2-yl-benzonitrile; LC-MS A: $t_R$ = 0.88 min; [M + H]$^+$ = 457.11 |
| 280 | A-1-59 | B-3-1 | F | (4-Chloro-5-methoxy-2-[1,2,3]triazol-2-yl-phenyl)-{(S)-2-[3-(3-chloro-2-methyl-phenyl)-[1,2,4]oxadiazol-5-yl]-pyrrolidin-1-yl}-methanone; LC-MS A: $t_R$ = 1.02 min; [M($^{35}$Cl) + H]$^+$ = 499.02 |
| 281 | A-1-59 | B-3-2 | F | (4-Chloro-5-methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.01 min; [M($^{35}$Cl) + H]$^+$ = 535.03 |
| 282 | A-1-59 | B-3-5 | F | (4-Chloro-5-methoxy-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS A: $t_R$ = 0.97 min; [M($^{35}$Cl) + H]$^+$ = 499.03 |
| 283 | A-1-59 | B-3-11 | F | (4-Chloro-5-methoxy-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone; LC-MS A: $t_R$ = 1.0 min; [M($^{35}$Cl) + H]$^+$ = 512.98 |
| 284 | A-1-59 | B-3-6 | F | (4-Chloro-5-methoxy-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS A: $t_R$ = 0.94 min; [M($^{35}$Cl) + H]$^+$ = 496.07 |
| 285 | A-1-56 | B-3-2 | H | (5-Methoxy-4-methyl-2-pyrimidin-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.01 min; [M + H]$^+$ = 526.09 |

TABLE 25-continued

| Ex. No. | SM A-1 | SM B-3 | GM | Compound of Formula (I) |
|---|---|---|---|---|
| 286 | A-1-56 | B-3-5 | H | {(S)-2-[3-(3-Fluoro-2-methoxy-phenyl)-[1,2,4]oxadiazol-5-yl]-pyrrolidin-1-yl}-(5-methoxy-4-methyl-2-pyrimidin-2-yl-phenyl)-methanone; LC-MS A: $t_R$ = 0.95 min; [M + H]$^+$ = 490.10 |
| 287 | A-1-56 | B-3-6 | H | {(S)-2-[3-(2-Ethoxy-pyridin-3-yl)-[1,2,4]oxadiazol-5-yl]-pyrrolidin-1-yl}-(5-methoxy-4-methyl-2-pyrimidin-2-yl-phenyl)-methanone; LC-MS A: $t_R$ = 0.92 min; [M + H]$^+$ = 487.11 |
| 288 | A-1-4 | B-3-11 | F | {(S)-2-[3-(2-Ethoxy-3-fluoro-phenyl)-[1,2,4]oxadiazol-5-yl]-pyrrolidin-1-yl}-(2-[1,2,3]triazol-2-yl-phenyl)-methanone; LC-MS A: $t_R$ = 0.94 min; [M + H]$^+$ = 448.99 |
| 289 | A-1-3 | B-3-11 | F | {(S)-2-[3-(2-Ethoxy-3-fluoro-phenyl)-[1,2,4]oxadiazol-5-yl]-pyrrolidin-1-yl}-(4-methyl-2-[1,2,3]triazol-2-yl-phenyl)-methanone; LC-MS A: $t_R$ = 0.97 min; [M + H]$^+$ = 463.09 |
| 290 | A-1-6 | B-3-11 | F | (4,5-Dimethyl-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone; LC-MS A: $t_R$ = 1.00 min; [M + H]$^+$ = 477.10 |
| 291 | A-1-11 | B-3-11 | F | {(S)-2-[3-(2-Ethoxy-3-fluoro-phenyl)-[1,2,4]oxadiazol-5-yl]-pyrrolidin-1-yl}-(5-methoxy-4-methyl-2-[1,2,3]triazol-2-yl-phenyl)-methanone; LC-MS A: $t_R$ = 0.99 min; [M + H]$^+$ = 493.10 |
| 292 | A-1-26 | B-3-11 | F | {(S)-2-[3-(2-Ethoxy-3-fluoro-phenyl)-[1,2,4]oxadiazol-5-yl]-pyrrolidin-1-yl}-(4-fluoro-5-methoxy-2-[1,2,3]triazol-2-yl-phenyl)-methanone; LC-MS A: $t_R$ = 0.97 min; [M + H]$^+$ = 496.98 |
| 293 | A-1-58 | B-3-1 | F | {(S)-2-[3-(3-Chloro-2-methyl-phenyl)-[1,2,4]oxadiazol-5-yl]-pyrrolidin-1-yl}-(5-chloro-4-methyl-2-[1,2,3]triazol-2-yl-phenyl)-methanone; LC-MS A: $t_R$ = 1.05 min; [M($^{35}$Cl) + H]$^+$ = 483.00 |
| 294 | A-1-16 | B-3-9 | F | (4-Chloro-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone; LC-MS A: $t_R$ = 1.00 min; [M($^{35}$Cl) + H]$^+$ = 453.03 |
| 295 | A-1-59 | B-3-9 | F | (4-Chloro-5-methoxy-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone; LC-MS A: $t_R$ = 1.00 min; [M($^{35}$Cl) + H]$^+$ = 483.05 |
| 296 | A-1-61 | B-3-1 | F | {(S)-2-[3-(3-Chloro-2-methyl-phenyl)-[1,2,4]oxadiazol-5-yl]-pyrrolidin-1-yl}-(3-chloro-2-[1,2,3]triazol-2-yl-phenyl)-methanone; LC-MS A: $t_R$ = 0.98 min; [M($^{35}$Cl) + H]$^+$ = 468.99 |
| 297 | A-1-61 | B-3-5 | F | (3-Chloro-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone; LC-MS A: $t_R$ = 0.91 min; [M($^{35}$Cl) + H]$^+$ = 469.02 |
| 298 | A-1-61 | B-3-2 | F | (3-Chloro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 0.97 min; [M($^{35}$Cl) + H]$^+$ = 505.01 |
| 299 | A-1-58 | B-3-2 | F | (5-Chloro-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone; LC-MS A: $t_R$ = 1.04 min; [M($^{35}$Cl) + H]$^+$ = 519.03 |
| 300 | A-1-58 | B-3-11 | F | (5-Chloro-4-methyl-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone; LC-MS A: $t_R$ = 1.02 min; [M($^{35}$Cl) + H]$^+$ = 497.09 |
| 301 | A-1-58 | B-3-6 | F | (5-Chloro-4-methyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone; LC-MS A: $t_R$ = 0.97 min; [M($^{35}$Cl) + H]$^+$ = 480.09 |

General Method I for Amide Formation: PvBOP/DIPEA

Example 302

(5-Methyl-2-[1,2,3]triazol-2-yl-phenyl)-[(S)-2-(5-phenyl-[1,2,4]oxadiazol-3-yl)-pyrrolidin-1-yl]-methanone Step A:
PyBOP (124 mg, 0.24 mmol) was added to a 0° C. solution of C-2-1 (50 mg, 0.16 mmol), benzoic acid (30 mg, 0.25 mmol) and DIPEA (82 uL, 0.48 mmol) in DCM (2.0 mL). The resulting mixture was stirred at rt for 3 h, then water was added. The org. layer was separated and the aq. layer was extracted with DCM (2×). The combined org. extracts were dried (MgSO$_4$), filtered and concentrated in vacuo to give (S)—N-(benzoyloxy)-1-(5-methyl-2-(2H-1,2,3-triazol-2-yl)benzoyl)pyrrolidine-2-carboximidamide C-4-1 that was used further without purification.

Step B:
The crude C-4-1 was dissolved in dioxane (2.0 mL) and heated to reflux (90° C.) for 18 h to 4 days. The solvent was removed in vacuo and the residue was purified by prep. HPLC (method G) to give the title compound as an off-white solid. LC-MS B: $t_R$=0.86 min; [M+H]$^+$=401.12.

General Method J for Amide Formation: TBTU/DIPEA

Example 303

(5-Methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone Step A:
TBTU (567 mg, 1.76 mmol) was added to a rt solution of 2-(trifluoromethoxy)benzoic acid (250 mg, 1.18 mmol) and DIPEA (0.60 mL, 3.53 mmol) in DCM (6.0 mL). After stirring for 15 min, a solution of C-2-1 (509 mg, 1.29 mmol) in DCM (1.0 mL) and DMF (0.3 mL) was added. The resulting mixture was stirred at rt for 1 h, then diluted with DCM and water. The layers were separated and the aq. layer extracted with DCM (1×). The combined org. extracts were washed with brine, dried (MgSO$_4$), filtered and concentrated in vacuo to give (S)-1-(5-methyl-2-(2H-1,2,3-triazol-2-yl)

benzoyl)-N-((2-(trifluoromethoxy)benzoyl)oxy)pyrrolidine-2-carboximidamide C-4-2 that was used further without purification.

Step B:

The crude C-4-2 was dissolved in dioxane (7.0 mL) and heated to reflux (90° C.) for 18 h to 4 days. The solvent was removed in vacuo and the residue was purified by FC (EtOAc/hept 3:2) to give the title compound as a colorless paste. LC-MS A: $t_R$=0.98 min; $[M+H]^+$=484.96.

General Method K for Amide Formation: EDC/HOBt

Example 304

(4,5-Dimethyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone Step A:

EDC (59 mg, 0.31 mmol) was added to a rt solution of indazole-3-carboxylic acid (40 mg, 0.25 mmol), HOBT (40 mg, 0.30 mmol) and DIPEA (63 uL, 0.37 mmol) in DCM (1.8 mL). After stirring for 10 min, C-2-1 (86 mg, 0.259 mmol) was added. The resulting mixture was stirred at rt for 18 h, then diluted with DCM and water. The layers were separated and the aq. layer extracted with DCM (1×). The combined org. extracts were washed with brine, dried (MgSO$_4$), filtered and concentrated in vacuo to give (S)-1-(4,5-dimethyl-2-(2H-1,2,3-triazol-2-yl)benzoyl)-N-((2-(trifluoromethoxy)benzoyl)oxy)pyrrolidine-2-carboximidamide C-4-3 that was used further without purification.

Step B:

The crude C-4-3 was dissolved in dioxane (3.5 mL) and heated to reflux (90° C.) for 2 days. The solvent was removed in vacuo and the residue was purified by prep. HPLC (method F) to give the title compound as a foam. LC-MS A: $t_R$=0.86 min; $[M+H]^+$=441.08.

Listed in Table 26 below are compounds of structure of formula (I), prepared according to the above procedure.

TABLE 26

| Ex. No. | SM C-2 | SM C-3 | GM | Compound of Formula (I) |
|---|---|---|---|---|
| 305 | C-2-1 | 3-methylbenzoic acid | I | (5-Methyl-2-[1,2,3]triazol-2-yl-phenyl)-[(S)-2-(5-m-tolyl-[1,2,4]oxadiazol-3-yl)-pyrrolidin-1-yl]-methanone; LC-MS B: $t_R$ = 0.92 min; $[M + H]^+$ = 415.26 |
| 306 | C-2-1 | 2-ethoxybenzoic acid | J | {(S)-2-[5-(2-Ethoxy-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.94 min; $[M + H]^+$ = 444.96 |
| 307 | C-2-1 | 2,3-dihydrobenzofuran-7-carboxylic acid | J | {(S)-2-[5-(2,3-Dihydro-benzofuran-7-yl)-[1,2,4]oxadiazol-3-yl]-pyrrolidin-1-yl}-(5-methyl-2-[1,2,3]triazol-2-yl-phenyl)-methanone; LC-MS A: $t_R$ = 0.90 min; $[M + H]^+$ = 442.93 |
| 308 | C-2-2 | 2-(trifluoromethoxy)benzoic acid | J | (5-Methoxy-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone; LC-MS A: $t_R$ = 1.00 min; $[M + H]^+$ = 514.89 |
| 309 | C-2-2 | 2-ethoxybenzoic acid | J | {(S)-2-[5-(2-Ethoxy-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.92 min; $[M + H]^+$ = 474.96 |
| 310 | C-2-2 | 3-fluoro-2-methylbenzoic acid | J | {(S)-2-[5-(3-Fluoro-2-methyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 1.00 min; $[M + H]^+$ = 462.93 |

TABLE 26-continued

| Ex. No. | SM C-2 | SM C-3 | GM | Compound of Formula (I) |
|---|---|---|---|---|
| 311 | C-2-2 | (2-ethoxy-pyridine-3-carboxylic acid) | J | {(S)-2-[5-(2-Ethoxy-pyridin-3-yl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.94 min; [M + H]$^+$ = 475.95 |
| 312 | C-2-3 | (1H-indazole-3-carboxylic acid) | K | {(S)-2-[5-(1H-Indazol-3-yl)-[1,2,4]oxadiazol-3-yl]-pyrrolidin-1-yl}-(5-methyl-2-[1,2,3]triazol-2-yl-phenyl)-methanone; LC-MS A: $t_R$ = 0.86 min; [M + H]$^+$ = 441.08 |
| 313 | C-2-1 | (imidazo[2,1-b]thiazole-5-carboxylic acid) | K | [(S)-2-(5-Imidazo[2,1-b]thiazol-5-yl-[1,2,4]oxadiazol-3-yl)-pyrrolidin-1-yl]-(5-methyl-2-[1,2,3]triazol-2-yl-phenyl)-methanone; LC-MS A: $t_R$ = 0.84 min; [M + H]$^+$ = 447.03 |
| 314 | C-2-1 | (6-trifluoromethyl-pyridine-2-carboxylic acid) | J | (5-Methyl-2-[1,2,3]triazol-2-yl-phenyl)-{(S)-2-[5-(6-trifluoromethyl-pyridin-2-yl)-[1,2,4]oxadiazol-3-yl]-pyrrolidin-1-yl}-methanone; LC-MS A: $t_R$ = 0.93 min; [M + H]$^+$ = 470.09 |
| 315 | C-2-1 | (4-trifluoromethyl-pyridine-2-carboxylic acid) | J | (5-Methyl-2-[1,2,3]triazol-2-yl-phenyl)-{(S)-2-[5-(4-trifluoromethyl-pyridin-2-yl)-[1,2,4]oxadiazol-3-yl]-pyrrolidin-1-yl}-methanone; LC-MS A: $t_R$ = 0.92 min; [M + H]$^+$ = 470.06 |
| 316 | C-2-1 | (4-chloro-6-methoxy-pyridine-2-carboxylic acid) | J | {(S)-2-[5-(4-Chloro-6-methoxy-pyridin-2-yl)-[1,2,4]oxadiazol-3-yl]-pyrrolidin-1-yl}-(5-methyl-2-[1,2,3]triazol-2-yl-phenyl)-methanone; LC-MS A: $t_R$ = 0.97 min; [M + H]$^+$ = 465.95 |
| 317 | C-2-1 | (4-chloro-6-methyl-pyridine-2-carboxylic acid) | J | {(S)-2-[5-(4-Chloro-6-methyl-pyridin-2-yl)-[1,2,4]oxadiazol-3-yl]-pyrrolidin-1-yl}-(5-methyl-2-[1,2,3]triazol-2-yl-phenyl)-methanone; LC-MS A: $t_R$ = 0.94 min; [M + H]$^+$ = 549.10 |

General Method L for Amide Formation:
TBTU/DIPEA DMF

Example 318

{(S)-2-[5-(3-Chloro-2-methyl-phenyl)-[1,2,4]oxadiazol-3-yl]-pyrrolidin-1-yl}-(5-methyl-2-[1,2,3]triazol-2-yl-phenyl)-methanone TBTU (664 mg, 2.07 mmol) was added to a rt solution of carboxylic acid A-1 (350 mg, 1.72 mmol) and DIPEA (1.47 mL, 8.61 mmol) in DMF (5 mL) and after stirring for 10 min, D-4-1 (743 mg, 1.72 mmol) was added. The resulting mixture was stirred at rt for 2 h, then the rxn mixture was concentrated, dissolved in DMF and purified by prep. HPLC (method G) to give the title compound as an off-white solid. LC-MS B: $t_R$=0.99 min; [M($^{35}$Cl)+H]$^+$=449.91.

Listed in Table 27 below are compounds of structure of formula (I), prepared according to the above procedure (General Method L).

TABLE 27

| Ex. No. | SM D-4 | SM A-1 | Compound of Formula (I) |
|---|---|---|---|
| 319 | D-4-3 | A-1-2 | {(S)-2-[5-(2-Ethoxy-3-fluoro-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.97 min; [M + H]$^+$ = 463.12 |
| 320 | D-4-1 | A-1-11 | {(S)-2-[5-(3-Chloro-2-methyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 1.02 min; [M($^{35}$Cl) + H]$^+$ = 479.10 |
| 321 | D-4-1 | A-1-6 | {(S)-2-[5-(3-Chloro-2-methyl-phenyl)-[1,2,4]oxadiazol-3-yl]-pyrrolidin-1-yl}-(4,5-dimethyl-2-[1,2,3]triazol-2-yl-phenyl)-methanone; LC-MS A: $t_R$ = 1.03 min; [M($^{35}$Cl) + H]$^+$ = 463.10 |
| 322 | D-4-1 | A-1-26 | {(S)-2-[5-(3-Chloro-2-methyl-phenyl)-[1,2,4]oxadiazol-3-yl]-pyrrolidin-1-yl}-(4-fluoro-5-methoxy-2-[1,2,3]triazol-2-yl-phenyl)-methanone; LC-MS A: $t_R$ = 1.00 min; [M($^{35}$Cl) + H]$^+$ = 483.09 |
| 323 | D-4-3 | A-1-11 | {(S)-2-[5-(2-Ethoxy-3-fluoro-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.99 min; [M + H]$^+$ = 493.14 |
| 324 | D-4-3 | A-1-6 | (4,5-Dimethyl-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone; LC-MS A: $t_R$ = 1.00 min; [M + H]$^+$ = 477.16 |
| 325 | D-4-3 | A-1-26 | {(S)-2-[5-(2-Ethoxy-3-fluoro-phenyl)-[1,2,4]oxadiazol-3-yl]-pyrrolidin-1-yl}-(4-fluoro-5-methoxy-2-[1,2,3]triazol-2-yl-phenyl)-methanone; LC-MS A: $t_R$ = 0.97 min; [M + H]$^+$ = 496.98 |
| 326 | D-4-3 | A-1-10 | {(S)-2-[5-(2-Ethoxy-3-fluoro-phenyl)-[1,2,4]oxadiazol-3-yl]-pyrrolidin-1-yl}-(5-methoxy-2-[1,2,3]triazol-2-yl-phenyl)-methanone; LC-MS A: $t_R$ = 0.95 min; [M + H]$^+$ = 479.12 |
| 327 | D-4-3 | A-1-5 | (5-Chloro-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone; LC-MS A: $t_R$ = 0.99 min; [M($^{35}$Cl) + H]$^+$ = 483.08 |
| 328 | D-4-3 | A-1-3 | {(S)-2-[5-(2-Ethoxy-3-fluoro-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.97 min; [M + H]$^+$ = 463.10 |
| 329 | D-4-3 | A-1-16 | (4-Chloro-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone; LC-MS A: $t_R$ = 0.99 min; [M($^{35}$Cl) + H]$^+$ = 483.08 |
| 330 | D-4-4 | A-1-2 | {(S)-2-[5-(2-Ethoxy-pyridin-3-yl)-[1,2,4]oxadiazol-3-yl]-pyrrolidin-1-yl}-(5-methyl-2-[1,2,3]triazol-2-yl-phenyl)-methanone; LC-MS A: $t_R$ = 0.92 min; [M + H]$^+$ = 446.12 |
| 331 | D-4-4 | A-1-6 | (4,5-Dimethyl-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone; LC-MS A: $t_R$ = 0.96 min; [M + H]$^+$ = 460.16 |
| 332 | D-4-4 | A-1-26 | {(S)-2-[5-(2-Ethoxy-pyridin-3-yl)-[1,2,4]oxadiazol-3-yl]-pyrrolidin-1-yl}-(4-fluoro-5-methoxy-2-[1,2,3]triazol-2-yl-phenyl)-methanone; LC-MS A: $t_R$ = 0.92 min; [M + H]$^+$ = 480.14 |
| 333 | D-4-5 | A-1-55 | {(S)-2-[5-(3-Fluoro-2-methyl-phenyl)-[1,2,4]oxadiazol-3-yl]-pyrrolidin-1-yl}-(2-[1,2,3]triazol-2-yl-phenyl)-methanone; LC-MS A: $t_R$ = 0.94 min; [M + H]$^+$ = 419.02 |
| 334 | D-4-6 | A-1-4 | {(S)-2-[5-(3-Fluoro-2-methoxy-phenyl)-[1,2,4]oxadiazol-3-yl]-pyrrolidin-1-yl}-(2-[1,2,3]triazol-2-yl-phenyl)-methanone; LC-MS A: $t_R$ = 0.90 min; [M + H]$^+$ = 435.04 |
| 335 | D-4-5 | A-1-4 | {(S)-2-[5-(3-Fluoro-2-methyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.98 min; [M + H]$^+$ = 432.99 |
| 336 | D-4-6 | A-1-2 | {(S)-2-[5-(3-Fluoro-2-methoxy-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.94 min; [M + H]$^+$ = 449.01 |
| 337 | D-4-5 | A-1-2 | {(S)-2-[5-(3-Fluoro-2-methyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.98 min; [M + H]$^+$ = 433.04 |
| 338 | D-4-6 | A-1-3 | {(S)-2-[5-(3-Fluoro-2-methoxy-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.94 min; [M + H]$^+$ = 449.00 |
| 339 | D-4-5 | A-1-6 | (4,5-Dimethyl-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone; LC-MS A: $t_R$ = 1.00 min; [M + H]$^+$ = 447.10 |
| 340 | D-4-6 | A-1-6 | (4,5-Dimethyl-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone; LC-MS A: $t_R$ = 0.97 min; [M + H]$^+$ = 463.10 |
| 341 | D-4-6 | A-1-11 | {(S)-2-[5-(3-Fluoro-2-methoxy-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.95 min; [M + H]$^+$ = 479.10 |
| 342 | D-4-5 | A-1-5 | (5-Chloro-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone; LC-MS A: $t_R$ = 0.99 min; [M($^{35}$Cl) + H]$^+$ = 453.03 |
| 343 | D-4-6 | A-1-5 | (5-Chloro-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone; LC-MS A: $t_R$ = 0.96 min; [M($^{35}$Cl) + H]$^+$ = 469.03 |
| 344 | D-4-4 | A-1-16 | (4-Chloro-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone; LC-MS A: $t_R$ = 0.95 min; [M($^{35}$Cl) + H]$^+$ = 465.74 |

TABLE 27-continued

| Ex. No. | SM D-4 | SM A-1 | Compound of Formula (I) |
|---|---|---|---|
| 345 | D-4-4 | A-1-3 | {(S)-2-[5-(2-Ethoxy-pyridin-3-yl)-[1,2,4]oxadiazol-3-yl]-pyrrolidin-1-yl}-(4-methyl-2-[1,2,3]triazol-2-yl-phenyl)-methanone; LC-MS A: $t_R$ = 0.92 min; [M($^{35}$Cl) + H]$^+$ = 446.09 |
| 346 | D-4-4 | A-1-5 | (5-Chloro-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone; LC-MS A: $t_R$ = 0.95 min; [M($^{35}$Cl) + H]$^+$ = 465.78 |
| 347 | D-4-13 | A-1-59 | {(S)-2-[5-(3-Chloro-2-methoxy-phenyl)-[1,2,4]oxadiazol-3-yl]-pyrrolidin-1-yl}-(4-chloro-5-methoxy-2-[1,2,3]triazol-2-yl-phenyl)-methanone; LC-MS A: $t_R$ = 0.99 min; [M($^{35}$Cl) + H]$^+$ = 515.00 |
| 348 | D-4-13 | A-1-11 | {(S)-2-[5-(3-Chloro-2-methoxy-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 1.0 min; [M($^{35}$Cl) + H]$^+$ = 495.05 |
| 349 | D-4-13 | A-1-16 | {(S)-2-[5-(3-Chloro-2-methoxy-phenyl)-[1,2,4]oxadiazol-3-yl]-pyrrolidin-1-yl}-(4-chloro-2-[1,2,3]triazol-2-yl-phenyl)-methanone; LC-MS A: $t_R$ = 0.99 min; [M($^{35}$Cl) + H]$^+$ = 484.98 |
| 350 | D-4-12 | A-1-59 | (4-Chloro-5-methoxy-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone; LC-MS A: $t_R$ = 0.97 min; [M($^{35}$Cl) + H]$^+$ = 495.05 |
| 351 | D-4-13 | A-1-2 | {(S)-2-[5-(3-Chloro-2-methoxy-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.96 min; [M($^{35}$Cl) + H]$^+$ = 464.97 |
| 352 | D-4-10 | A-1-59 | (4-Chloro-5-methoxy-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone; LC-MS A: $t_R$ = 0.99 min; [M($^{35}$Cl) + H]$^+$ = 495.04 |
| 353 | D-4-11 | A-1-59 | (4-Chloro-5-methoxy-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone; LC-MS A: $t_R$ = 1.00 min; [M($^{35}$Cl) + H]$^+$ = 495.06 |
| 354 | D-4-13 | A-1-3 | {(S)-2-[5-(3-Chloro-2-methoxy-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.96 min; [M($^{35}$Cl) + H]$^+$ = 465.00 |
| 355 | D-4-14 | A-1-59 | (4-Chloro-5-methoxy-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone; LC-MS A: $t_R$ = 1.00 min; [M($^{35}$Cl) + H]$^+$ = 495.05 |
| 356 | D-4-14 | A-1-6 | (4,5-Dimethyl-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone; LC-MS A: $t_R$ = 1.00 min; [M + H]$^+$ = 459.10 |
| 357 | D-4-13 | A-1-5 | {(S)-2-[5-(3-Chloro-2-methoxy-phenyl)-[1,2,4]oxadiazol-3-yl]-pyrrolidin-1-yl}-(5-chloro-2-[1,2,3]triazol-2-yl-phenyl)-methanone; LC-MS A: $t_R$ = 0.98 min; [M($^{35}$Cl) + H]$^+$ = 484.98 |
| 358 | D-4-14 | A-1-11 | {(S)-2-[5-(3-Methoxy-2-methyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.99 min; [M + H]$^+$ = 475.12 |
| 359 | D-4-14 | A-1-2 | {(S)-2-[5-(3-Methoxy-2-methyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.97 min; [M + H]$^+$ = 445.08 |
| 360 | D-4-13 | A-1-6 | {(S)-2-[5-(3-Chloro-2-methoxy-phenyl)-[1,2,4]oxadiazol-3-yl]-pyrrolidin-1-yl}-(4,5-dimethyl-2-[1,2,3]triazol-2-yl-phenyl)-methanone; LC-MS A: $t_R$ = 0.99 min; [M($^{35}$Cl) + H]$^+$ = 479.04 |
| 361 | D-4-14 | A-1-5 | (5-Chloro-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone; LC-MS A: $t_R$ = 0.99 min; [M($^{35}$Cl) + H]$^+$ = 465.01 |
| 362 | D-4-14 | A-1-16 | (4-Chloro-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone; LC-MS A: $t_R$ = 1.00 min; [M($^{35}$Cl) + H]$^+$ = 464.99 |
| 363 | D-4-6 | A-1-61 | (3-Chloro-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone; LC-MS A: $t_R$ = 0.91 min; [M($^{35}$Cl) + H]$^+$ = 469.01 |
| 364 | D-4-14 | A-1-3 | {(S)-2-[5-(3-Methoxy-2-methyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.97 min; [M + H]$^+$ = 445.08 |
| 365 | D-4-2 | A-1-58 | (5-Chloro-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone; LC-MS A: $t_R$ = 1.03 min; [M($^{35}$Cl) + H]$^+$ = 519.03 |
| 366 | D-4-3 | A-1-58 | (5-Chloro-4-methyl-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone; LC-MS A: $t_R$ = 1.02 min; [M($^{35}$Cl) + H]$^+$ = 497.08 |
| 367 | D-4-1 | A-1-59 | (4-Chloro-5-methoxy-2-[1,2,3]triazol-2-yl-phenyl)-{(S)-2-[5-(3-chloro-2-methyl-phenyl)-[1,2,4]oxadiazol-3-yl]-pyrrolidin-1-yl}-methanone; LC-MS A: $t_R$ = 1.02 min; [M($^{35}$Cl) + H]$^+$ = 499.03 |
| 368 | D-4-6 | A-1-59 | (4-Chloro-5-methoxy-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone; LC-MS A: $t_R$ = 0.97 min; [M($^{35}$Cl) + H]$^+$ = 499.04 |
| 369 | D-4-3 | A-1-59 | (4-Chloro-5-methoxy-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone; LC-MS A: $t_R$ = 0.99 min; [M($^{35}$Cl) + H]$^+$ = 512.96 |

TABLE 27-continued

| Ex. No. | SM D-4 | SM A-1 | Compound of Formula (I) |
|---|---|---|---|
| 370 | D-4-4 | A-1-59 | (4-Chloro-5-methoxy-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone; LC-MS A: $t_R$ = 0.95 min; [M($^{35}$Cl) + H]$^+$ = 496.06 |
| 371 | D-4-1 | A-1-58 | {(S)-2-[5-(3-Chloro-2-methyl-phenyl)-[1,2,4]oxadiazol-3-yl]-pyrrolidin-1-yl}-(5-chloro-4-methyl-2-[1,2,3]triazol-2-yl-phenyl)-methanone; LC-MS A: $t_R$ = 1.05 min; [[M($^{35}$Cl) + H]$^+$ = 483.01 |
| 372 | D-4-5 | A-1-26 | (4-Fluoro-5-methoxy-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone; LC-MS A: $t_R$ = 0.97 min; [M + H]$^+$ = 467.05 |
| 373 | D-4-6 | A-1-26 | {(S)-2-[5-(3-Fluoro-2-methoxy-phenyl)-[1,2,4]oxadiazol-3-yl]-pyrrolidin-1-yl}-(4-fluoro-5-methoxy-2-[1,2,3]triazol-2-yl-phenyl)-methanone; LC-MS A: $t_R$ = 0.93 min; [M + H]$^+$ = 483.06 |
| 374 | D-4-2 | A-1-3 | (4-Methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone; LC-MS A: $t_R$ = 0.99 min; [M + H]$^+$ = 485.06 |
| 375 | D-4-2 | A-1-59 | (4-Chloro-5-methoxy-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone; LC-MS A: $t_R$ = 1.01 min; [M($^{35}$Cl) + H]$^+$ = 535.02 |
| 376 | D-4-2 | A-1-16 | (4-Chloro-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone; LC-MS A: $t_R$ = 1.01 min; [M($^{35}$Cl) + H]$^+$ = 505.01 |
| 377 | D-4-2 | A-1-5 | (5-Chloro-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone; LC-MS A: $t_R$ = 1.00 min; [M($^{35}$Cl) + H]$^+$ = 505.01 |
| 378 | D-4-6 | A-1-16 | (4-Chloro-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone; LC-MS A: $t_R$ = 0.96 min; [M($^{35}$Cl) + H]$^+$ = 469.02 |
| 379 | D-4-5 | A-1-16 | (4-Chloro-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone; LC-MS A: $t_R$ = 1.0 min; [M($^{35}$Cl) + H]$^+$ = 453.02 |
| 380 | D-4-4 | A-1-58 | (5-Chloro-4-methyl-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone; LC-MS A: $t_R$ = 0.98 min; [M($^{35}$Cl) + H]$^+$ = 480.09 |
| 381 | D-4-12 | A-1-16 | (4-Chloro-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone; LC-MS A: $t_R$ = 0.97 min; [M($^{35}$Cl) + H]$^+$ = 465.00 |
| 382 | D-4-10 | A-1-6 | (4,5-Dimethyl-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone; LC-MS A: $t_R$ = 1.00 min; [M + H]$^+$ = 459.11 |
| 383 | D-4-11 | A-1-6 | (4,5-Dimethyl-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone; LC-MS A: $t_R$ = 1.00 min; [M + H]$^+$ = 459.11 |
| 384 | D-4-12 | A-1-6 | (4,5-Dimethyl-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone; LC-MS A: $t_R$ = 0.97 min; [M + H]$^+$ = 459.10 |
| 385 | D-4-10 | A-1-11 | {(S)-2-[5-(3-Methoxy-5-methyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.99 min; [M + H]$^+$ = 475.12 |
| 386 | D-4-11 | A-1-11 | {(S)-2-[5-(5-Methoxy-2-methyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.99 min; [M + H]$^+$ = 475.11 |
| 387 | D-4-12 | A-1-11 | {(S)-2-[5-(2-Methoxy-5-methyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 0.95 min; [M + H]$^+$ = 475.11 |
| 388 | D-4-7 | A-1-2 | {(S)-2-[5-(2,3-Dimethyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ 1.00 = min; [M + H]$^+$ = 428.495 |
| 389 | D-4-8 | A-1-2 | {(S)-2-[5-(2-Ethyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.99 min; [M + H]$^+$ = 429.07 |
| 390 | D-4-9 | A-1-2 | {(S)-2-[5-(2,5-Dimethyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.98 min; [M + H]$^+$ = 429.07 |
| 391 | D-4-7 | A-1-3 | {(S)-2-[5-(2,3-Dimethyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 1.00 min; [M + H]$^+$ = 429.07 |
| 392 | D-4-8 | A-1-3 | {(S)-2-[5-(2-Ethyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.99 min; [M + H]$^+$ = 429.07 |
| 393 | D-4-9 | A-1-3 | {(S)-2-[5-(2,5-Dimethyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.98 min; [M + H]$^+$ = 429.07 |
| 394 | D-4-7 | A-1-3 | (5-Chloro-2-[1,2,3]triazol-2-yl-phenyl)-{(S)-2-[5-(2,3-dimethyl-phenyl)-[1,2,4]oxadiazol-3-yl]-pyrrolidin-1-yl}-methanone; LC-MS A: $t_R$ = 1.02 min; [M($^{35}$Cl) + H]$^+$ = 449.06 |
| 395 | D-4-8 | A-1-5 | (5-Chloro-2-[1,2,3]triazol-2-yl-phenyl)-{(S)-2-[5-(2-ethyl-phenyl)-[1,2,4]oxadiazol-3-yl]-pyrrolidin-1-yl}-methanone; LC-MS A: $t_R$ = 1.01 min; [M($^{35}$Cl) + H]$^+$ = 448.97 |
| 396 | D-4-9 | A-1-3 | (5-Chloro-2-[1,2,3]triazol-2-yl-phenyl)-{(S)-2-[5-(2,5-dimethyl-phenyl)-[1,2,4]oxadiazol-3-yl]-pyrrolidin-1-yl}-methanone; LC-MS A: $t_R$ = 1.00 min; [M($^{35}$Cl) + H]$^+$ = 448.97 |
| 397 | D-4-7 | A-1-16 | (4-Chloro-2-[1,2,3]triazol-2-yl-phenyl)-{(S)-2-[5-(2,3-dimethyl-phenyl)-[1,2,4]oxadiazol-3-yl]-pyrrolidin-1-yl}-methanone; LC-MS A: $t_R$ = 1.02 min; [M($^{35}$Cl) + H]$^+$ = 449.03 |

TABLE 27-continued

| Ex. No. | SM D-4 | SM A-1 | Compound of Formula (I) |
|---|---|---|---|
| 398 | D-4-8 | A-1-16 | (4-Chloro-2-[1,2,3]triazol-2-yl-phenyl)-{(S)-2-[5-(2-ethyl-phenyl)-[1,2,4]oxadiazol-3-yl]-pyrrolidin-1-yl}-methanone; LC-MS A: $t_R$ = 1.01 min; [M($^{35}$Cl) + H]$^+$ = 449.02 |
| 399 | D-4-9 | A-1-16 | (4-Chloro-2-[1,2,3]triazol-2-yl-phenyl)-{(S)-2-[5-(2,5-dimethyl-phenyl)-[1,2,4]oxadiazol-3-yl]-pyrrolidin-1-yl}-methanone; LC-MS A: $t_R$ = 1.01 min; [M($^{35}$Cl) + H]$^+$ = 449.04 |
| 400 | D-4-7 | A-1-6 | {(S)-2-[5-(2,3-Dimethyl-phenyl)-[1,2,4]oxadiazol-3-yl]-pyrrolidin-1-yl}-(4,5-dimethyl-2-[1,2,3]triazol-2-yl-phenyl)-methanone; LC-MS A: $t_R$ = 1.02 min; [M + H]$^+$ = 443.09 |
| 401 | D-4-8 | A-1-6 | (4,5-Dimethyl-2-[1,2,3]triazol-2-yl-phenyl)-{(S)-2-[5-(2-ethyl-phenyl)-[1,2,4]oxadiazol-3-yl]-pyrrolidin-1-yl}-methanone; LC-MS A: $t_R$ = 1.02 min; [M + H]$^+$ = 443.11 |
| 402 | D-4-9 | A-1-6 | {(S)-2-[5-(2,5-Dimethyl-phenyl)-[1,2,4]oxadiazol-3-yl]-pyrrolidin-1-yl}-(4,5-dimethyl-2-[1,2,3]triazol-2-yl-phenyl)-methanone; LC-MS A: $t_R$ = 1.01 min; [M + H]$^+$ = 443.09 |
| 403 | D-4-7 | A-1-11 | {(S)-2-[5-(2,3-Dimethyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 1.01 min; [M + H]$^+$ = 459.11 |
| 404 | D-4-8 | A-1-11 | {(S)-2-[5-(2-Ethyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 1.01 min; [M + H]$^+$ = 459.11 |
| 405 | D-4-9 | A-1-11 | {(S)-2-[5-(2,5-Dimethyl-phenyl)-[1,2,4]oxadiazol-3-yl]-pyrrolidin-1-yl}-(5-methoxy-4-methyl-2-[1,2,3]triazol-2-yl-phenyl)-methanone; LC-MS A: $t_R$ = 1.00 min; [M + H]$^+$ = 459.10 |
| 406 | D-4-7 | A-1-59 | (4-Chloro-5-methoxy-2-[1,2,3]triazol-2-yl-phenyl)-{(S)-2-[5-(2,3-dimethyl-phenyl)-[1,2,4]oxadiazol-3-yl]-pyrrolidin-1-yl}-methanone; LC-MS A: $t_R$ = 1.02 min; [M($^{35}$Cl) + H]$^+$ = 479.06 |
| 407 | D-4-8 | A-1-59 | (4-Chloro-5-methoxy-2-[1,2,3]triazol-2-yl-phenyl)-{(S)-2-[5-(2-ethyl-phenyl)-[1,2,4]oxadiazol-3-yl]-pyrrolidin-1-yl}-methanone; LC-MS A: $t_R$ = 1.01 min; [M($^{35}$Cl) + H]$^+$ = 479.07 |
| 408 | D-4-9 | A-1-59 | (4-Chloro-5-methoxy-2-[1,2,3]triazol-2-yl-phenyl)-{(S)-2-[5-(2,5-dimethyl-phenyl)-[1,2,4]oxadiazol-3-yl]-pyrrolidin-1-yl}-methanone; LC-MS A: $t_R$ = 1.01 min; [M($^{35}$Cl) + H]$^+$ = 479.05 |
| 409 | D-4-10 | A-1-2 | {(S)-2-[5-(3-Methoxy-5-methyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.97 min; [M + H]$^+$ = 445.10 |
| 410 | D-4-11 | A-1-2 | {(S)-2-[5-(5-Methoxy-2-methyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.97 min; [M + H]$^+$ = 445.09 |
| 411 | D-4-12 | A-1-2 | {(S)-2-[5-(2-Methoxy-5-methyl-phenyl)-[1,2,4]oxadiazol-3-yl]-pyrrolidin-1-yl}-(5-methyl-2-[1,2,3]triazol-2-yl-phenyl)-methanone; LC-MS A: $t_R$ = 0.94 min; [M + H]$^+$ = 445.09 |
| 412 | D-4-10 | A-1-3 | {(S)-2-[5-(3-Methoxy-5-methyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.97 min; [M + H]$^+$ = 445.08 |
| 413 | D-4-11 | A-1-3 | {(S)-2-[5-(5-Methoxy-2-methyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.97 min; [M + H]$^+$ = 445.09 |
| 414 | D-4-12 | A-1-3 | {(S)-2-[5-(2-Methoxy-5-methyl-phenyl)-[1,2,4]oxadiazol-3-yl]-pyrrolidin-1-yl}-(4-methyl-2-[1,2,3]triazol-2-yl-phenyl)-methanone; LC-MS A: $t_R$ = 0.94 min; [M + H]$^+$ = 445.08 |
| 415 | D-4-10 | A-1-5 | (5-Chloro-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone; LC-MS A: $t_R$ = 0.99 min; [M($^{35}$Cl) + H]$^+$ = 464.99 |
| 416 | D-4-11 | A-1-5 | (5-Chloro-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone; LC-MS A: $t_R$ = 0.99 min; [M($^{35}$Cl) + H]$^+$ = 465.00 |
| 417 | D-4-12 | A-1-5 | (5-Chloro-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone; LC-MS A: $t_R$ = 0.96 min; [M($^{35}$Cl) + H]$^+$ = 465.03 |
| 418 | D-4-10 | A-1-16 | (4-Chloro-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone; LC-MS A: $t_R$ = 0.99 min; [M($^{35}$Cl) + H]$^+$ = 465.00 |
| 419 | D-4-11 | A-1-16 | (4-Chloro-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone; LC-MS A: $t_R$ = 1.00 min; [M($^{35}$Cl) + H]$^+$ = 465.00 |

General Method M for Amide Formation: TBTU/DIPEA DMF

Example 420

(5-Methyl-2-[1,2,3]triazol-2-yl-phenyl)-[(S)-2-(3-phenyl-isoxazol-5-yl)-pyrrolidin-1-yl]-methanone TBTU (58 mg, 0.18 mmol) was added to a rt solution of carboxylic acid A-1-2 (31 mg, 0.15 mmol) and DIPEA (77 ul, 0.45 mmol) in DMF (0.5 mL), the rxn mixture was stirred at rt for 10 min, before E-4-1 (32 mg, 0.15 mmol) was added and stirring was continued for 18 h. The rxn mixture was directly purified by prep. HPLC (method G) to give the title compound as an off-white foam. LC-MS B: $t_R$=0.85 min; [M+H]$^+$=400.10.

Listed in Table 28 below are compounds of structure of formula (I), prepared according to the above procedure (General Method M).

TABLE 28

| Ex. No. | SM E-4 or E7 | SM A-1 | Compound of Formula (I) |
|---|---|---|---|
| 421 | E-4-1 | A-1-57 | [5-(3-Chloro-phenyl)-2-methyl-thiazol-4-yl]-[(S)-2-(3-phenyl-isoxazol-5-yl)-pyrrolidin-1-yl]-methanone; LC-MS B: $t_R$ = 0.91 min; [M($^{35}$Cl) + H]$^+$ = 449.67 |
| 422 | E-4-2 | A-1-2 | {(S)-2-[3-(2,3-Dimethyl-phenyl)-isoxazol-5-yl]-pyrrolidin-1-yl}-(5-methyl-2-[1,2,3]triazol-2-yl-phenyl)-methanone; LC-MS B: $t_R$ = 0.92 min; [M + H]$^+$ = 427.98 |
| 423 | E-4-3 | A-1-2 | {(S)-2-[3-(3,5-Dimethyl-phenyl)-isoxazol-5-yl]-pyrrolidin-1-yl}-(5-methyl-2-[1,2,3]triazol-2-yl-phenyl)-methanone; LC-MS B: $t_R$ = 0.95 min; [M + H]$^+$ = 427.99 |
| 424 | E-4-4 | A-1-2 | {(S)-2-[3-(3-Chloro-2-methyl-phenyl)-isoxazol-5-yl]-pyrrolidin-1-yl}-(5-methyl-2-[1,2,3]triazol-2-yl-phenyl)-methanone; LC-MS B: $t_R$ = 0.95 min; [M($^{35}$Cl) + H]$^+$ = 447.93 |
| 425 | E-4-5 | A-1-2 | (5-Methyl-2-[1,2,3]triazol-2-yl-phenyl)-{(S)-2-[3-(2-trifluoromethoxy-phenyl)-isoxazol-5-yl]-pyrrolidin-1-yl}-methanone; LC-MS B: $t_R$ = 0.94 min; [M + H]$^+$ = 483.98 |
| 426 | E-4-7 | A-1-2 | {(S)-2-[3-(2-Methoxy-pyridin-3-yl)-isoxazol-5-yl]-pyrrolidin-1-yl}-(5-methyl-2-[1,2,3]triazol-2-yl-phenyl)-methanone; LC-MS B: $t_R$ = 0.81 min; [M + H]$^+$ = 430.91 |
| 427 | E-4-6 | A-1-2 | {(S)-2-[3-(2-Isopropoxy-pyridin-3-yl)-isoxazol-5-yl]-pyrrolidin-1-yl}-(5-methyl-2-[1,2,3]triazol-2-yl-phenyl)-methanone; LC-MS B: $t_R$ = 0.92 min; [M + H]$^+$ = 458.97 |
| 428 | E-4-8 | A-1-2 | {(S)-2-[3-(2-Ethoxy-pyridin-3-yl)-isoxazol-5-yl]-pyrrolidin-1-yl}-(5-methyl-2-[1,2,3]triazol-2-yl-phenyl)-methanone; LC-MS B: $t_R$ = 0.87 min; [M + H]$^+$ = 444.99 |
| 429 | E-4-9 | A-1-2 | {(S)-2-[3-(3-Fluoro-2-methoxy-phenyl)-isoxazol-5-yl]-pyrrolidin-1-yl}-(5-methyl-2-[1,2,3]triazol-2-yl-phenyl)-methanone; LC-MS B: $t_R$ = 0.89 min; [M + H]$^+$ = 447.97 |
| 430 | E-8-1 | A-1-2 | (5-Methyl-2-[1,2,3]triazol-2-yl-phenyl)-[(S)-2-(5-phenyl-isoxazol-3-yl)-pyrrolidin-1-yl]-methanone; LC-MS A: $t_R$ = 0.93 min; [M + H]$^+$ = 400.09 |
| 431 | E-8-2 | A-1-2 | {(S)-2-[5-(3-Chloro-2-methyl-phenyl)-isoxazol-3-yl]-pyrrolidin-1-yl}-(5-methyl-2-[1,2,3]triazol-2-yl-phenyl)-methanone; LC-MS A: $t_R$ = 0.99 min; [M($^{35}$Cl) + H]$^+$ = 448.10 |
| 432 | E-8-1 | A-1-11 | (5-Methoxy-4-methyl-2-[1,2,3]triazol-2-yl-phenyl)-[(S)-2-(5-phenyl-isoxazol-3-yl)-pyrrolidin-1-yl]-methanone; LC-MS A: $t_R$ = 0.95 min; [M + H]$^+$ = 430.11 |
| 433 | E-8-2 | A-1-11 | {(S)-2-[5-(3-Chloro-2-methyl-phenyl)-isoxazol-3-yl]-pyrrolidin-1-yl}-(5-methoxy-4-methyl-2-[1,2,3]triazol-2-yl-phenyl)-methanone; LC-MS A: $t_R$ = 1.01 min; [M($^{35}$Cl) + H]$^+$ = 478.12 |
| 434 | E-8-3 | A-1-2 | (5-Methyl-2-[1,2,3]triazol-2-yl-phenyl)-{(S)-2-[5-(2-trifluoromethoxy-phenyl)-isoxazol-3-yl]-pyrrolidin-1-yl}-methanone; LC-MS A: $t_R$ = 1.00. min; [M + H]$^+$ = 484.14 |
| 435 | E-8-3 | A-1-3 | (4-Methyl-2-[1,2,3]triazol-2-yl-phenyl)-{(S)-2-[5-(2-trifluoromethoxy-phenyl)-isoxazol-3-yl]-pyrrolidin-1-yl}-methanone; LC-MS A: $t_R$ = 1.00 min; [M + H]$^+$ = 484.13 |
| 436 | E-8-3 | A-1-11 | (5-Methoxy-4-methyl-2-[1,2,3]triazol-2-yl-phenyl)-{(S)-2-[5-(2-trifluoromethoxy-phenyl)-isoxazol-3-yl]-pyrrolidin-1-yl}-methanone; LC-MS A: $t_R$ = 1.02 min; [M + H]$^+$ = 513.99 |
| 437 | E-8-3 | A-1-59 | (4-Chloro-5-methoxy-2-[1,2,3]triazol-2-yl-phenyl)-{(S)-2-[5-(2-trifluoromethoxy-phenyl)-isoxazol-3-yl]-pyrrolidin-1-yl}-methanone; LC-MS A: $t_R$ = 1.02 min; [M($^{35}$Cl) + H]$^+$ = 534.03 |

General Method N for Amide Formation: TBTU/DIPEA DMF or DCM

Example 438

(5-Methyl-2-[1,2,3]triazol-2-yl-phenyl)-[(S)-2-(5-m-tolyl-[1,3,4]oxadiazol-2-yl)-pyrrolidin-1-yl]-methanone TBTU (56 mg, 0.174 mmol) was added to a rt solution of carboxylic acid A-1-2 (29 mg, 0.15 mmol) and DIPEA (70 uL, 0.43 mmol) in DMF (1 mL) and the rxn mixture was stirred for 10 min, before F-4-2 (33 mg, 0.15 mmol) was added and stirring continued for 1 h. The rxn mixture was directly purified by prep. HPLC (method G) to give the title compound as a colorless oil. LC-MS B: $t_R$=0.82 min; [M+H]$^+$=415.23.

Listed in Table 29 below are compounds of structure of formula (I), prepared according to the above procedure (General Method M).

TABLE 29

| Ex. No. | SM F-4 | SM A-1 | Compound of Formula (I) |
|---|---|---|---|
| 439 | F-4-1 | A-1-2 | (5-Methyl-2-[1,2,3]triazol-2-yl-phenyl)-[(S)-2-(5-phenyl-[1,3,4]oxadiazol-2-yl)-pyrrolidin-1-yl]-methanone; LC-MS B: $t_R$ = 0.77 min; [M + H]$^+$ = 401.16 |
| 440 | F-4-3 | A-1-2 | {(S)-2-[5-(3-Chloro-2-methyl-phenyl)-[1,3,4]oxadiazol-2-yl]-pyrrolidin-1-yl}-(5-methyl-2-[1,2,3]triazol-2-yl-phenyl)-methanone; LC-MS B: $t_R$ = 0.93 min; [M($^{35}$Cl) + H]$^+$ = 448.98 |

TABLE 29-continued

| Ex. No. | SM F-4 | SM A-1 | Compound of Formula (I) |
|---|---|---|---|
| 441 | F-4-4 | A-1-2- | (5-Methyl-2-[1,2,3]triazol-2-yl-phenyl)-[(S)-2-(5-o-tolyl-[1,3,4]oxadiazol-2-yl)-pyrrolidin-1-yl]-methanone; LC-MS A: $t_R$ = 0.88 min; $[M + H]^+$ = 415.08 |
| 442 | F-4-5 | A-1-2 | (5-Methyl-2-[1,2,3]triazol-2-yl-phenyl)-{(S)-2-[5-(2-trifluoromethoxy-phenyl)-[1,3,4]oxadiazol-2-yl]-pyrrolidin-1-yl}-methanone; LC-MS A: $t_R$ = 0.93 min; $[M + H]^+$ = 485.06 |
| 443 | F-4-5 | A-1-44 | [5-(3-Fluoro-phenyl)-2-methyl-thiazol-4-yl]-{(S)-2-[5-(2-trifluoromethoxy-phenyl)-[1,3,4]oxadiazol-2-yl]-pyrrolidin-1-yl}-methanone; LC-MS A: $t_R$ = 0.94 min; $[M + H]^+$ = 519.01 |
| 444 | F-4-5 | A-1-46 | [5-(2-Fluoro-phenyl)-2-methyl-thiazol-4-yl]-{(S)-2-[5-(2-trifluoromethoxy-phenyl)-[1,3,4]oxadiazol-2-yl]-pyrrolidin-1-yl}-methanone; LC-MS A: $t_R$ = 0.94 min; $[M + H]^+$ = 519.01 |
| 445 | F-4-3 | A-1-11 | {(S)-2-[5-(3-Chloro-2-methyl-phenyl)-[1,3,4]oxadiazol-2-yl]-pyrrolidin-1-yl}-(5-methoxy-4-methyl-2-[1,2,3]triazol-2-yl-phenyl)-methanone; LC-MS A: $t_R$ = 0.96 min; $[M(^{35}Cl) + H]^+$ = 479.06 |
| 446 | F-4-3 | A-1-59 | (4-Chloro-5-methoxy-2-[1,2,3]triazol-2-yl-phenyl)-{(S)-2-[5-(3-chloro-2-methyl-phenyl)-[1,3,4]oxadiazol-2-yl]-pyrrolidin-1-yl}-methanone; LC-MS A: $t_R$ = 0.97 min; $[M(^{35}Cl) + H]^+$ = 498.97 |
| 447 | F-4-3 | A-1-6 | {(S)-2-[5-(3-Chloro-2-methyl-phenyl)-[1,3,4]oxadiazol-2-yl]-pyrrolidin-1-yl}-(4,5-dimethyl-2-[1,2,3]triazol-2-yl-phenyl)-methanone; LC-MS A: $t_R$ = 0.96 min; $[M(^{35}Cl) + H]^+$ = 463.07 |

Example 448

{(S)-2-[5-(3-Fluoro-2-methoxy-phenyl)-[1,3,4]oxadiazol-2-yl]-pyrrolidin-1-yl}-(5-methyl-2-[1,2,3]triazol-2-yl-phenyl)-methanone Step A:

PyBOP (78 mg, 0.15 mmol) was added to a rt solution of 3-fluoro-2-methoxybenzoic acid (20 mg, 0.12 mmol) and DIPEA (60 uL, 0.35 mmol) in DCM. The rxn mixture was stirred for 10 min, then G-3-1 (36 mg, 0.12 mmol) was added and stirring continued overnight. The mixture was concentrated to yield crude (S)—N'-(3-fluoro-2-methoxy-benzoyl)-1-(5-methyl-2-(2H-1,2,3-triazol-2-yl)benzoyl)pyrrolidine-2-carbohydrazide G-4-1 which was used further without purification. LC-MS A: $t_R$=0.80 min; $[M+H]^+$= 467.09.

Step B:

Burgess' reagent (55 mg, 0.23 mmol) was added to a rt solution of crude G-4-1 in dioxane (2.0 mL) and the rxn mixture was irradiated in the microwave at 110° C. for 30 min to 1 h, then the rxn mixture was concentrated, dissolved in DMF and directly purified by prep. HPLC (method G) to yield the title compound as a yellow solid. LC-MS A: $t_R$=0.87 min; $[M+H]^+$=449.00.

Listed in Table 30 below are compounds of structure of formula (I), prepared according to the above procedure (Example 448), using hydrazide G-3-1.

TABLE 30

| Ex. No. | SM C-3 | Compound of Formula (I) |
|---|---|---|
| 449 | | {(S)-2-[5-(2-Ethoxy-3-fluoro-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.91 min; $[M + H]^+$ = 463.07 |
| 450 | | {(S)-2-[5-(2-Ethoxy-pyridin-3-yl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.85 min; $[M + H]^+$ = 446.08 |
| 451 | | {(S)-2-[5-(3,5-Dimethyl-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.92 min; $[M + H]^+$ = 429.07 |

TABLE 30-continued

| Ex. No. | SM C-3 | Compound of Formula (I) |
|---|---|---|
| 452 | 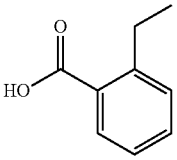 | {(S)-2-[5-(2-Ethyl-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.92 min; [M + H]$^+$ = 429.07 |
| 453 | 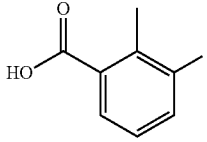 | {(S)-2-[5-(3-Fluoro-2-methyl-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.91 min; [M + H]$^+$ = 433.01 |
| 454 | 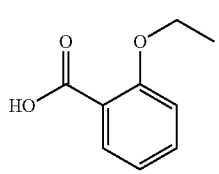 | {(S)-2-[5-(2-Ethoxy-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.88 min; [M + H]$^+$ = 445.09 |
| 455 | 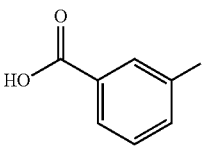 | {(S)-2-[5-(3-Chloro-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.90 min; [M($^{35}$Cl) + H]$^+$ = 435.00 |
| 456 | 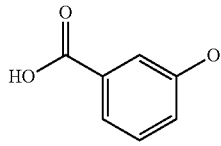 | {(S)-2-[5-(3-Methoxy-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.87 min; [M + H]$^+$ = 431.05 |
| 457 | 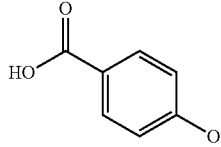 | {(S)-2-[5-(4-Methoxy-phenyl)-[1,3,4]oxadiazol-2-yl]-pyrrolidin-1-yl}-(5-methyl-2-[1,2,3]triazol-2-yl-phenyl)-methanone<br>LC-MS A: $t_R$ = 0.86 min; [M + H]$^+$ = 431.05 |

Example 458

(5-Methyl-2-[1,2,3]triazol-2-yl-phenyl)-{(S)-2-[5-(2-trifluoromethoxy-phenyl)-[1,3,4]thiadiazol-2-yl]-pyrrolidin-1-yl}-methanone TBTU (80 mg, 0.25 mmol) was added to a rt solution of carboxylic acid A-1-2 (39 mg, 0.19 mmol) and DIPEA (80 uL, 0.48 mmol) in DMF (0.7 mL). After 15 min, H-2-1 (65 mg, 0.21 mmol) was added and the resulting mixture was stirred at rt for 2 h. The rxn mixture was directly purified by prep. HPLC (method F) to give the title compound as white solid. LC-MS A: $t_R$=0.98 min; [M+H]$^+$=501.08.

Example 459

(5-Methyl-2-[1,2,3]triazol-2-yl-phenyl)-[(S)-2-(4-phenyl-oxazol-2-yl)-pyrrolidin-1-yl]-methanone Boron trifluoride diethyl etherate (5 drops) was added to a rt solution of I-2-1 (413 mg, 0.67 mmol) and acetamide (204 mg, 3.45 mmol) in diethylether (2.5 mL) and o-xylene (1.5 mL). The yellow solution was stirred at 120° C. overnight and at 140° C. for another 24 h. The rxn mixture was diluted with EtOAc and washed with water (1x). The org. layer was concentrated in vacuo and the residue was purified by prep. HPLC (method E) to give the title compound as an off-white solid. LC-MS A: $t_R$=0.90 min; [M+H]$^+$=400.13.

Example 460

(5-Methyl-2-[1,2,3]triazol-2-yl-phenyl)-{(S)-2-[4-(2-trifluoromethoxy-phenyl)-oxazol-2-yl]-pyrrolidin-1-yl}-methanone The title compound was prepared from I-2-2 in analogy to the procedure described for Example 459. LC-MS A: $t_R$=1.00 min; [M+H]$^+$=484.10.

Example 461

(5-Methyl-2-[1,2,3]triazol-2-yl-phenyl)-[(S)-2-(5-phenyl-oxazol-2-yl)-pyrrolidin-1-yl]-methanone Polyphosphoric acid (4.08 g, 17 mmol) was added to J-2-1 (337 mg, 0.50 mmol) at rt and the solution was heated to 150° C. for 1 h. The rxn mixture was poured into ice-water and basified with sat. aq. Na$_2$CO$_3$. The aq. layer was extracted with EtOAc (2×) and the combined org. extracts were dried (MgSO$_4$), filtered and concentrated in vacuo. The residue was purified by prep. HPLC (method G) to yield the title compound as a yellow solid. LC-MS A: t$_R$=0.86 min; [M+H]$^+$=400.14.

Example 462

(5-Methyl-2-[1,2,3]triazol-2-yl-phenyl)-[(S)-2-(5-o-tolyl-oxazol-2-yl)-pyrrolidin-1-yl]-methanone The title compound was prepared from J-2-2 in analogy to the procedure described for Example 461. LC-MS A: t$_R$=0.92 min; [M+H]$^+$=413.48.

General Method O for Amide Formation: TBTU/DIPEA DMF or DCM

Example 463

(5-Methyl-2-[1,2,3]triazol-2-yl-phenyl)-[(S)-2-(5-phenyl-4H-[1,2,4]triazol-3-yl)-pyrrolidin-1-yl]-methanone TBTU (56 mg, 0.17 mmol) was added to a rt solution of carboxylic acid A-1-2 (29 mg, 0.15 mmol) and DIPEA (70 uL, 0.43 mmol) in DMF (1 mL). After stirring for 10 min, K-2-2 (33 mg, 0.15 mmol) was added and the resulting mixture was stirred at rt for 1 h, then the rxn mixture was directly purified by prep. HPLC (method G) to give the title compound as a colorless oil. LC-MS: t$_R$=0.80 min; [M+H]$^+$=400.07.

General Method P for Amide Formation: EDC/HOBt DMF or DCM

Example 464

{(S)-2-[5-(2-Methoxy-phenyl)-4H-[1,2,4]triazol-3-yl]-pyrrolidin-1-yl}-(5-methyl-2-[1,2,3]triazol-2-yl-phenyl)-methanone EDC-HCl (71 mg, 0.37 mmol) was added to a rt solution of A-1-2 (30 mg, 0.148 mmol), HOBT (24 mg, 0.18 mmol) and DIPEA (50 uL, 0.30 mmol) in DMF (1 mL) and the rxn mixture was stirred for 5 min before K-2-8 (40 mg, 0.16 mmol) was added and stirring continued for 1 h. The mixture was directly purified by prep. HPLC (method F) to give the title compound as an off-white solid. LC-MS A: t$_R$=0.80 min; [M+H]$^+$=430.11.

Listed in Table 31 below are compounds of structure of formula (I), prepared according to the above procedures (General Method O or P).

TABLE 31

| Ex. No. | SM A-1 | SM K-2 | GM | Compound of Formula (I) |
|---|---|---|---|---|
| 465 | A-1-2 | K-2-1 | O | (5-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: t$_R$ = 0.82 min; [M + H]$^+$ = 484.09 |
| 466 | A-1-6 | K-2-8 | P | (4,5-Dimethyl-2-[1,2,3]triazol-2-yl-phenyl)-{(S)-2-[5-(2-methoxy-phenyl)-4H-[1,2,4]triazol-3-yl]-pyrrolidin-1-yl}-methanone; LC-MS A: t$_R$ = 0.83 min; [M + H]$^+$ = 444.15 |
| 467 | A-1-59 | K-2-8 | P | (4-Chloro-5-methoxy-2-[1,2,3]triazol-2-yl-phenyl)-{(S)-2-[5-(2-methoxy-phenyl)-4H-[1,2,4]triazol-3-yl]-pyrrolidin-1-yl}-methanone; LC-MS A: t$_R$ = 0.84 min; [M($^{35}$Cl) + H]$^+$ = 480.12 |
| 468 | A-1-11 | K-2-8 | P | (5-Methoxy-4-methyl-2-[1,2,3]triazol-2-yl-phenyl)-{(S)-2-[5-(2-methoxy-phenyl)-4H-[1,2,4]triazol-3-yl]-pyrrolidin-1-yl}-methanone; LC-MS A: t$_R$ = 0.83 min; [M + H]$^+$ = 460.17 |
| 469 | A-1-58 | K-2-8 | P | (5-Chloro-4-methyl-2-[1,2,3]triazol-2-yl-phenyl)-{(S)-2-[5-(2-methoxy-phenyl)-4H-[1,2,4]triazol-3-yl]-pyrrolidin-1-yl}-methanone; LC-MS A: t$_R$ = 0.87 min; [M($^{35}$Cl) + H]$^+$ = 464.12 |
| 470 | A-1-16 | K-2-8 | P | (4-Chloro-2-[1,2,3]triazol-2-yl-phenyl)-{(S)-2-[5-(2-methoxy-phenyl)-4H-[1,2,4]triazol-3-yl]-pyrrolidin-1-yl}-methanone; LC-MS A: t$_R$ = 0.78 min; [M($^{35}$Cl) + H]$^+$ = 449.95 |
| 471 | A-1-3 | K-2-8 | P | {(S)-2-[5-(2-Methoxy-phenyl)-4H-[1,2,4]triazol-3-yl]-pyrrolidin-1-yl}-(4-methyl-2-[1,2,3]triazol-2-yl-phenyl)-methanone; LC-MS A: t$_R$ = 0.80 min; [M + H]$^+$ = 430.13 |
| 472 | A-1-59 | K-2-7 | P | (4-Chloro-5-methoxy-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone; LC-MS A: t$_R$ = 0.87 min; [M($^{35}$Cl) + H]$^+$ = 498.00 |
| 473 | A-1-11 | K-2-7 | P | {(S)-2-[5-(3-Fluoro-2-methoxy-phenyl)-4H-[1,2,4]triazol-3-yl]-pyrrolidin-1-yl}-(5-methoxy-4-methyl-2-[1,2,3]triazol-2-yl-phenyl)-methanone; LC-MS A: t$_R$ = 0.87 min; [M + H]$^+$ = 478.17 |
| 474 | A-1-6 | K-2-7 | P | (4,5-Dimethyl-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone; LC-MS A: t$_R$ = 0.87 min; [M + H]$^+$ = 462.17 |
| 475 | A-1-58 | K-2-7 | P | (5-Chloro-4-methyl-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone; LC-MS A: t$_R$ = 0.90 min; [M($^{35}$Cl) + H]$^+$ = 482.01 |
| 476 | A-1-16 | K-2-7 | P | (4-Chloro-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone; LC-MS A: t$_R$ = 0.86 min; [M($^{35}$Cl) + H]$^+$ = 468.10 |

TABLE 31-continued

| Ex. No. | SM A-1 | SM K-2 | GM | Compound of Formula (I) |
|---|---|---|---|---|
| 477 | A-1-3 | K-2-7 | P | {(S)-2-[5-(3-Fluoro-2-methoxy-phenyl)-4H-[1,2,4]triazol-3-yl]-pyrrolidin-1-yl}-(4-methyl-2-[1,2,3]triazol-2-yl-phenyl)-methanone; LC-MS A: $t_R$ = 0.84 min; [M + H]$^+$ = 448.14 |
| 478 | A-1-59 | K-2-6 | P | (4-Chloro-5-methoxy-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone; LC-MS A: $t_R$ = 0.86 min; [M($^{35}$Cl) + H]$^+$ = 495.13 |
| 479 | A-1-11 | K-2-6 | P | {(S)-2-[5-(2-Ethoxy-pyridin-3-yl)-4H-[1,2,4]triazol-3-yl]-pyrrolidin-1-yl}-(5-methoxy-4-methyl-2-[1,2,3]triazol-2-yl-phenyl)-methanone; LC-MS A: $t_R$ = 0.85 min; [M + H]$^+$ = 475.17 |
| 480 | A-1-6 | K-2-6 | P | (4,5-Dimethyl-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone; LC-MS A: $t_R$ = 0.86 min; [M + H]$^+$ = 459.18 |
| 481 | A-1-16 | K-2-6 | P | (4-Chloro-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone; LC-MS A: $t_R$ = 0.85 min; [M($^{35}$Cl) + H]$^+$ = 465.03 |
| 482 | A-1-3 | K-2-6 | P | {(S)-2-[5-(2-Ethoxy-pyridin-3-yl)-4H-[1,2,4]triazol-3-yl]-pyrrolidin-1-yl}-(4-methyl-2-[1,2,3]triazol-2-yl-phenyl)-methanone; LC-MS A: $t_R$ = 0.82 min; [M + H]$^+$ = 445.15 |
| 483 | A-1-63 | K-2-1 | O | (5-Phenyl-thiazol-4-yl)-{(S)-2-[5-(2-trifluoromethoxy-phenyl)-4H-[1,2,4]triazol-3-yl]-pyrrolidin-1-yl}-methanone; LC-MS A: $t_R$ = 0.86 min; [M + H]$^+$ = 485.92 |
| 484 | A-1-64 | K-2-1 | O | (5-Phenyl-oxazol-4-yl)-{(S)-2-[5-(2-trifluoromethoxy-phenyl)-4H-[1,2,4]triazol-3-yl]-pyrrolidin-1-yl}-methanone; LC-MS A: $t_R$ = 0.84 min; [M + H]$^+$ = 470.03 |
| 485 | A-1-65 | K-2-1 | O | (5-m-Tolyl-thiazol-4-yl)-{(S)-2-[5-(2-trifluoromethoxy-phenyl)-4H-[1,2,4]triazol-3-yl]-pyrrolidin-1-yl}-methanone; LC-MS A: $t_R$ = 0.89 min; [M + H]$^+$ = 500.00 |
| 486 | A-1-42 | K-2-1 | O | (5-m-Tolyl-oxazol-4-yl)-{(S)-2-[5-(2-trifluoromethoxy-phenyl)-4H-[1,2,4]triazol-3-yl]-pyrrolidin-1-yl}-methanone; LC-MS A: $t_R$ = 0.87 min; [M + H]$^+$ = 484.00 |
| 487 | A-1-58 | K-2-6 | P | (5-Chloro-4-methyl-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone; LC-MS A: $t_R$ = 0.82 min; [M + H]$^+$ = 479.14 |
| 488 | A-1-2 | K-2-9 | P | {(S)-2-[5-(3-Chloro-2-methoxy-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.86 min; [M + H]$^+$ = 464.11 |
| 489 | A-1-3 | K-2-9 | P | {(S)-2-[5-(3-Chloro-2-methoxy-phenyl)-4H-[1,2,4]triazol-3-yl]-pyrrolidin-1-yl}-(4-methyl-2-[1,2,3]triazol-2-yl-phenyl)-methanone; LC-MS A: $t_R$ = 0.86 min; [M + H]$^+$ = 464.12 |
| 490 | A-1-11 | K-2-9 | P | {(S)-2-[5-(3-Chloro-2-methoxy-phenyl)-4H-[1,2,4]triazol-3-yl]-pyrrolidin-1-yl}-(5-methoxy-4-methyl-2-[1,2,3]triazol-2-yl-phenyl)-methanone; LC-MS A: $t_R$ = 0.83 min; [M + H]$^+$ = 494.11 |
| 491 | A-1-59 | K-2-9 | P | {(S)-2-[5-(3-Chloro-2-methoxy-phenyl)-4H-[1,2,4]triazol-3-yl]-pyrrolidin-1-yl}-(4-chloro-5-methoxy-2-[1,2,3]triazol-2-yl-phenyl)-methanone; LC-MS A: $t_R$ = 0.85 min; [M + H]$^+$ = 513.95 |
| 492 | A-1-6 | K-2-9 | P | {(S)-2-[5-(3-Chloro-2-methoxy-phenyl)-4H-[1,2,4]triazol-3-yl]-pyrrolidin-1-yl}-(4,5-dimethyl-2-[1,2,3]triazol-2-yl-phenyl)-methanone; LC-MS A: $t_R$ = 0.90 min; [M + H]$^+$ = 478.15 |
| 493 | A-1-2 | K-2-3 | O | {(S)-2-[5-(3-Chloro-2-methyl-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.89 min; [M($^{35}$Cl) + H]$^+$ = 448.08 |
| 494 | A-1-2 | K-2-4 | O | {(S)-2-[5-(3-Fluoro-2-methyl-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.86 min; [M + H]$^+$ = 432.06 |
| 495 | A-1-2 | K-2-5 | O | {(S)-2-[5-(2-Ethoxy-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.85 min; [M + H]$^+$ = 444.19 |
| 496 | A-1-2 | K-2-6 | O | {(S)-2-[5-(2-Ethoxy-pyridin-3-yl)-4H-[1,2,4]triazol-3-yl]-pyrrolidin-1-yl}-(5-methyl-2-[1,2,3]triazol-2-yl-phenyl)-methanone; LC-MS A: $t_R$ = 0.82 min; [M + H]$^+$ = 445.06 |
| 497 | A-1-2 | K-2-7 | O | {(S)-2-[5-(3-Fluoro-2-methoxy-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.84 min; [M + H]$^+$ = 448.08 |
| 498 | A-1-6 | K-2-1 | O | (4,5-Dimethyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.93 min; [M + H]$^+$ = 497.68 |
| 499 | A-1-11 | K-2-1 | O | (5-Methoxy-4-methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.93 min; [M + H]$^+$ = 513.61 |
| 500 | A-1-58 | K-2-1 | O | (5-Chloro-4-methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.95 min; [M($^{35}$Cl) + H]$^+$ = 517.91 |
| 501 | A-1-3 | K-2-1 | O | (4-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.9 min; [M + H]$^+$ = 484.01 |

TABLE 31-continued

| Ex. No. | SM A-1 | SM K-2 | GM | Compound of Formula (I) |
|---|---|---|---|---|
| 502 | A-1-16 | K-2-1 | O | (4-Chloro-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.92 min; [M($^{35}$Cl) + H]$^+$ = 503.89 |
| 503 | A-1-4 | K-2-1 | O | (2-[1,2,3]Triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.86 min; [M + H]$^+$ = 470.08 |
| 504 | A-1-5 | K-2-1 | O | (5-Chloro-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.92 min; [M($^{35}$Cl) + H]$^+$ = 503.93 |
| 505 | A-1-53 | K-2-1 | O | (2-Methyl-5-m-tolyl-oxazol-4-yl)-{(S)-2-[5-(2-trifluoromethoxy-phenyl)-4H-[1,2,4]triazol-3-yl]-pyrrolidin-1-yl}-methanone; LC-MS A: $t_R$ = 0.89 min; [M + H]$^+$ = 497.78 |
| 506 | A-1-62 | K-2-1 | O | (2-Methyl-5-phenyl-thiazol-4-yl)-{(S)-2-[5-(2-trifluoromethoxy-phenyl)-4H-[1,2,4]triazol-3-yl]-pyrrolidin-1-yl}-methanone; LC-MS A: $t_R$ = 0.89 min; [M + H]$^+$ = 500.05 |
| 507 | A-1-54 | K-2-1 | O | (2-Methyl-5-m-tolyl-thiazol-4-yl)-{(S)-2-[5-(2-trifluoromethoxy-phenyl)-4H-[1,2,4]triazol-3-yl]-pyrrolidin-1-yl}-methanone; LC-MS A: $t_R$ = 0.91 min; [M + H]$^+$ = 513.64 |
| 508 | A-1-52 | K-2-1 | O | Biphenyl-2-yl-{(S)-2-[5-(2-trifluoromethoxy-phenyl)-4H-[1,2,4]triazol-3-yl]-pyrrolidin-1-yl}-methanone; LC-MS A: $t_R$ = 0.95 min; [M + H]$^+$ = 479.03 |
| 509 | A-1-59 | K-2-1 | O | (4-Chloro-5-methoxy-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.93 min; [M($^{35}$Cl) + H]$^+$ = 533.95 |
| 510 | A-1-18 | K-2-1 | O | (2-Methyl-6-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; LC-MS A: $t_R$ = 0.89 min; [M + H]$^+$ = 485.10 |

General Method Q for Triazole Formation

Example 511

{(S)-2-[5-(3,5-Dimethyl-phenyl)-4H-[1,2,4]triazol-3-yl]-pyrrolidin-1-yl}-(5-methyl-2-[1,2,3]triazol-2-yl-phenyl)-methanone K$_2$CO$_3$ (9 mg, 0.07 mmol) was added to a rt solution of F-1-11 (20 mg, 0.12 mmol), C-1 (65 mg, 0.24 mmol) in n-BuOH (0.8 mL) and the resulting mixture was irradiated at 145° C. for 30 min in the mW (with cooling function), followed by irradiation at 160° C. for 1 h without cooling function). The mixture was concentrated in vacuo, DCM was added and acidified with 2N aq. HCl. The org. layer was separated and the inorg. layer was extracted with DCM (2×). The combined org. extracts were dried (MgSO$_4$), filtered and concentrated. The crude was purified by prep. HPLC (method F), followed by FC (EtOAc/hept 9:1) to give the title compound as a white solid. LC-MS A: $t_R$=0.88 min; [M+H]$^+$=428.12.

Listed in Table 32 below are compounds of structure of formula (I), prepared according to the above procedures (General Method Q).

TABLE 32

| Ex. No. | SM C-1 | SM F-1 | Compound of Formula (I) |
|---|---|---|---|
| 512 | C-1 | F-1-12 | {(S)-2-[5-(2-Ethyl-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.87 min; [M + H]$^+$ = 428.15 |
| 513 | C-1 | F-1-13 | {(S)-2-[5-(3-Methoxy-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.82 min; [M + H]$^+$ = 430.51 |
| 514 | C-1 | F-1-14 | {(S)-2-[5-(4-Methoxy-phenyl)-4H-[1,2,4]triazol-3-yl]-pyrrolidin-1-yl}-(5-methyl-2-[1,2,3]triazol-2-yl-phenyl)-methanone; LC-MS A: $t_R$ = 0.80 min; [M + H]$^+$ = 430.11 |
| 515 | C-1 | F-1-15 | (5-Methyl-2-[1,2,3]triazol-2-yl-phenyl)-{(S)-2-[5-(2-propoxy-phenyl)-4H-[1,2,4]triazol-3-yl]-pyrrolidin-1-yl}-methanone; LC-MS A: $t_R$ = 0.89 min; [M + H]$^+$ = 458.18 |

General Method R for Amid Formation HATU/DIPEA

Example 516

{(S)-2-[5-(2-Methoxy-phenyl)-1H-imidazol-2-yl]-pyrrolidin-1-yl}-(5-methyl-2-[1,2,3]triazol-2-yl-phenyl)-methanone HATU (40 mg, 0.11 mmol) was added to a rt solution of A-1-2 (20 mg, 0.1 mmol) and DIPEA (40 uL, 0.23 mmol) in DMF (0.5 mL) and the resulting mixture was stirred for 5 min before a solution of L-4-6 (30 mg, 0.10 mmol) and DIPEA (40 uL, 0.234 mmol) in DMF (0.5 mL) was added. The rxn mixture was stirred at rt for 48 h, then directly purified by prep. HPLC (method E) to yield the title compound as a yellow oil. LC-MS A: $t_R$=0.72 min; [M+H]$^+$=429.06.

Listed in Table 33 below are compounds of structure of formula (I), prepared according to the above procedures (General Method R).

TABLE 33

| Ex. No. | SM A-1 | SM L-4 or M-5 | Compound of Formula (I) |
|---|---|---|---|
| 517 | A-1-3 | L-4-5 | (4-Methyl-2-[1,2,3]triazol-2-yl-phenyl)-{(S)-2-[5-(2-trifluoromethoxy-phenyl)-1H-imidazol-2-yl]-pyrrolidin-1-yl}-methanone; LC-MS A: $t_R$ = 0.75 min; [M + H]$^+$ = 483.14 |
| 518 | A-1-3 | L-4-3 | {(S)-2-[5-(2-Ethoxy-phenyl)-1H-imidazol-2-yl]-pyrrolidin-1-yl}-(4-methyl-2-[1,2,3]triazol-2-yl-phenyl)-methanone; LC-MS A: $t_R$ = 0.75 min; [M + H]$^+$ = 443.17 |
| 519 | A-1-2 | M-4-1 | (5-Methyl-2-[1,2,3]triazol-2-yl-phenyl)-[(S)-2-(2-phenyl-3H-imidazol-4-yl)-pyrrolidin-1-yl]-methanone; LC-MS A: $t_R$ = 0.67 min; [M + H]$^+$ = 399.11 |
| 520 | A-1-3 | M-4-1 | (4-Methyl-2-[1,2,3]triazol-2-yl-phenyl)-[(S)-2-(2-phenyl-3H-imidazol-4-yl)-pyrrolidin-1-yl]-methanone; LC-MS A: $t_R$ = 0.67 min; [M + H]$^+$ = 399.11 |
| 521 | A-1-2 | M-4-2 | {(S)-2-[2-(3-Chloro-2-methyl-phenyl)-3H-imidazol-4-yl]-pyrrolidin-1-yl}-(5-methyl-2-[1,2,3]triazol-2-yl-phenyl)-methanone; LC-MS A: $t_R$ = 0.71 min; [M($^{35}$Cl) + H]$^+$ = 447.08 |
| 522 | A-1-3 | M-4-2 | {(S)-2-[2-(3-Chloro-2-methyl-phenyl)-3H-imidazol-4-yl]-pyrrolidin-1-yl}-(4-methyl-2-[1,2,3]triazol-2-yl-phenyl)-methanone; LC-MS A: $t_R$ = 0.71 min; [M($^{35}$Cl) + H]$^+$ = 447.11 |
| 523 | A-1-2 | L-4-7 | {(S)-2-[5-(3-Chloro-phenyl)-1H-imidazol-2-yl]-pyrrolidin-1-yl}-(5-methyl-2-[1,2,3]triazol-2-yl-phenyl)-methanone; LC-MS A: $t_R$ = 0.73 min; [M($^{35}$Cl) + H]$^+$ = 432.95 |
| 524 | A-1-2 | L-4-8 | {(S)-2-[5-(3-Methoxy-phenyl)-1H-imidazol-2-yl]-pyrrolidin-1-yl}-(5-methyl-2-[1,2,3]triazol-2-yl-phenyl)-methanone; LC-MS A: $t_R$ = 0.71 min; [M + H]$^+$ = 429.22 |
| 525 | A-1-2 | L-4-2 | {(S)-2-[5-(3-Chloro-2-methyl-phenyl)-1H-imidazol-2-yl]-pyrrolidin-1-yl}-(5-methyl-2-[1,2,3]triazol-2-yl-phenyl)-methanone; LC-MS A: $t_R$ = 0.73 min; [M + H]$^+$ = 447.08 |
| 526 | A-1-2 | L-4-3 | {(S)-2-[5-(2-Ethoxy-phenyl)-1H-imidazol-2-yl]-pyrrolidin-1-yl}-(5-methyl-2-[1,2,3]triazol-2-yl-phenyl)-methanone; LC-MS A: $t_R$ = 0.75 min; [M + H]$^+$ = 443.03 |
| 527 | A-1-2 | L-4-1 | (5-Methyl-2-[1,2,3]triazol-2-yl-phenyl)-[(S)-2-(5-phenyl-1H-imidazol-2-yl)-pyrrolidin-1-yl]-methanone; LC-MS A: $t_R$ = 0.68 min; [M + H]$^+$ = 399.09 |
| 528 | A-1-2 | L-4-4 | (5-Methyl-2-[1,2,3]triazol-2-yl-phenyl)-{(S)-2-[5-(2-trifluoromethyl-phenyl)-1H-imidazol-2-yl]-pyrrolidin-1-yl}-methanone; LC-MS A: $t_R$ = 0.73 min; [M + H]$^+$ = 467.10 |
| 529 | A-1-2 | L-4-5 | (5-Methyl-2-[1,2,3]triazol-2-yl-phenyl)-{(S)-2-[5-(2-trifluoromethoxy-phenyl)-1H-imidazol-2-yl]-pyrrolidin-1-yl}-methanone; LC-MS A: $t_R$ = 0.75 min; [M + H]$^+$ = 483.10 |

General Method S for Amid Formation
HATU/DIPEA

Example 530

(5-Methyl-2-[1,2,3]triazol-2-yl-phenyl)-[(S)-2-(5-phenyl-2H-pyrazol-3-yl)-pyrrolidin-1-yl]-methanone HATU (90 mg, 0.24 mmol) was added to a rt solution of A-1-2 (40 mg, 0.20 mmol), N-3-1 (56 mg, 0.20 mmol) and DIPEA (168 uL, 0.98 mmol) in DMF (0.7 mL) and the resulting rxn mixture was stirred at rt overnight. The rxn mixture was directly purified by prep. HPLC (method G) to give the title compound as a yellow oil. LC-MS A: $t_R$=0.86 min; [M+H]$^+$=399.1

Listed in Table 34 below are compounds of structure of formula (I), prepared according to the above procedures (General Method S).

TABLE 34

| Ex. No. | SM A-1 | SM N-3 | Compound of Formula (I) |
|---|---|---|---|
| 531 | A-1-3 | N-3-2 | {(S)-2-[5-(3-Chloro-2-methyl-phenyl)-2H-pyrazol-3-yl]-pyrrolidin-1-yl}-(4-methyl-2-[1,2,3]triazol-2-yl-phenyl)-methanone; LC-MS A: $t_R$ = 0.94 min; [M($^{35}$Cl) + H]$^+$ = 447.08 |
| 532 | A-1-2 | N-3-3 | (5-Methyl-2-[1,2,3]triazol-2-yl-phenyl)-{(S)-2-[5-(2-trifluoromethoxy-phenyl)-2H-pyrazol-3-yl]-pyrrolidin-1-yl}-methanone; LC-MS A: $t_R$ = 0.95 min; [M + H]$^+$ = 483.13 |
| 533 | A-1-3 | N-3-3 | (4-Methyl-2-[1,2,3]triazol-2-yl-phenyl)-{(S)-2-[5-(2-trifluoromethoxy-phenyl)-2H-pyrazol-3-yl]-pyrrolidin-1-yl}-methanone; LC-MS A: $t_R$ = 0.95 min; [M + H]$^+$ = 483.10 |
| 534 | A-1-2 | N-3-2 | {(S)-2-[5-(3-Chloro-2-methyl-phenyl)-2H-pyrazol-3-yl]-pyrrolidin-1-yl}-(5-methyl-2-[1,2,3]triazol-2-yl-phenyl)-methanone; LC-MS A: $t_R$ = 0.93 min; [M($^{35}$Cl) + H]$^+$ = 447.07 |

Example 535

(5-Methyl-2-[1,2,3]triazol-2-yl-phenyl)-[(S)-2-(1-phenyl-1H-[1,2,4]triazol-3-yl)-pyrrolidin-1-yl]-methanone TBTU (62 mg, 0.19 mmol) was added to a rt solution of A-1-2 (32 mg, 0.15 mmol) and DIPEA (64 uL, 0.37 mmol) in DMF (0.6 mL) and the resulting mixture was stirred for 20 min at rt before a solution of O-4-1 (51 mg, 0.18 mmol) and DIPEA (41 uL, 0.18 mmol) in DMF (0.5 mL) was added and stirring was continued for 1.5 h. The rxn mixture was purified by prep. HPLC (method F), followed by FC (EtOAc/hept 24/1) to give the title compound as a white solid. LC-MS A: $t_R$=0.78 min; [M+H]$^+$=400.06.

Example 536

(5-Methyl-2-[1,2,3]triazol-2-yl-phenyl)-[(S)-2-(1-phenyl-1H-[1,2,3]triazol-4-yl)-pyrrolidin-1-yl]-methanone HATU (46 mg, 0.12 mmol) was added to a rt solution of A-1-2 (20 mg, 0.1 mmol), P-3-1 (30 mg, 0.12 mmol) and DIPEA (86 uL, 0.5 mmol) in DMF (1.0 mL) and the rxn mixture was stirred at rt overnight. The rxn mixture was directly purified by prep. HPLC (method E), to give the title compound as an orange oil. LC-MS A: $t_R$=0.85 min; [M+H]$^+$=400.05.

General Method T for Amid Formation
TBTU/DIPEA in DMF

Example 537

[(S)-2-Methyl-2-(3-phenyl-[1,2,4]oxadiazol-5-yl)-pyrrolidin-1-yl]-(2-[1,2,3]triazol-2-yl-phenyl)-methanone TBTU (58 mg, 0.18 mmol) was added to a rt solution of A-1-4 (28 mg, 0.15 mmol) and DIPEA (77 uL, 0.45 mmol) in DMF (0.5 mL) and the resulting mixture was stirred for 5 min at rt before Q-4 (34 mg, 0.15 mmol) was added and stirring was continued at rt overnight. The rxn mixture was purified by prep. HPLC (method G) to give the title compound as an off-white foam. LC-MS B: $t_R$=0.86 min; $[M+H]^+$=401.02.

Listed in Table 35 below are compounds of structure of formula (I), prepared according to the above procedure (General Method T).

TABLE 35

| Ex. No. | SM A-1 | SM Q-4 | Compound of Formula (I) |
|---|---|---|---|
| 538 | A-1-43 | Q-4 | [5-(3-Chloro-phenyl)-thiazol-4-yl]-[(S)-2-methyl-2-(3-phenyl-[1,2,4]oxadiazol-5-yl)-pyrrolidin-1-yl]-methanone; LC-MS B: $t_R$ = 0.95 min; $[M(^{35}Cl) + H]^+$ = 450.89 |
| 539 | A-1-42 | Q-4 | [(S)-2-Methyl-2-(3-phenyl-[1,2,4]oxadiazol-5-yl)-pyrrolidin-1-yl]-(5-m-tolyl-oxazol-4-yl)-methanone; LC-MS B : $t_R$ = 0.94 min; $[M + H]^+$ = 415.05 |

Example 540

[(S)-2-Methyl-2-(3-phenyl-[1,2,4]oxadiazol-5-yl)-pyrrolidin-1-yl]-(5-methyl-2-[1,2,3]triazol-2-yl-phenyl)-methanone Step A:
PyBOP (104 mg, 0.2 mmol) was added to a rt solution of Q-5 (52 mg, 0.17 mmol) and DIPEA (86 uL, 0.5 mmol) in DCM (3 mL) and after stirring for 10 min, commercially available benzamidoxime (23 mg, 0.17 mmol) was added and the resulting mixture was stirred at rt for 2 h. The mixture was concentrated in vacuo to give the crude product Q-6 that was used further without purification.
Step B:
The crude Q-6 was dissolved in dioxane (1.3 mL) and pyridine (0.3 mL) and heated to reflux (90° C.) for 2 days. The solvent was removed in vacuo and the residue was purified by FC (EtOAc/hex 5:3) to give the title compound as a yellowish foam. LC-MS A: $t_R$=0.96 min; $[M+H]^+$= 415.08.

Example 541

{(S)-2-[3-(3-Chloro-2-methyl-phenyl)-[1,2,4]oxadiazol-5-yl]-2-methyl-pyrrolidin-1-yl}-(5-methyl-2-[1,2,3]triazol-2-yl-phenyl)-methanone The title compound 541 was prepared from Q-5 and A-4-27 in analogy to the above described method (see example 540). LC-MS A: $t_R$=1.02. min; $[M(^{35}Cl)+H]^+$= 463.02.

General Method U for Amid Formation HATU/DIPEA in DMF

Example 542

(5-Methyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone HATU (23 mg, 0.06 mmol) was added to a rt solution of A-1-2 (10 mg, 0.05 mmol), R-4-1 (16 mg, 0.05 mmol) and DIPEA (26 uL, 0.15 mmol) in DMF (0.5 mL) and the resulting rxn mixture was stirred at rt overnight. To the rxn mixture was added NH$_4$OH (250 uL) to eliminate a sideproduct, followed by the addition of formic acid (500 uL). The crude was purified by prep. HPLC (method E) to give the title compound as a yellow oil. LC-MS A: $t_R$=0.93 min; $[M+H]^+$=498.14.

Listed in Table 36 below are compounds of structure of formula (I), prepared according to the above procedure (General Method U).

TABLE 36

| Ex. No. | SM A-1 | SM R-4 | Compound of Formula (I) |
|---|---|---|---|
| 543 | A-1-3 | R-4-1 | (4-Methyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone; LC-MS A: $t_R$ = 0.93 min; $[M + H]^+$ = 498.14 |
| 544 | A-1-16 | R-4-1 | (4-Chloro-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone; LC-MS A: $t_R$ = 0.94 min; $[M(^{35}Cl) + H]^+$ = 518.18 |
| 545 | A-1-58 | R-4-1 | (5-Chloro-4-methyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone; LC-MS A: $t_R$ = 0.98 min; $[M(^{35}Cl) + H]^+$ = 532.27 |
| 546 | A-1-6 | R-4-1 | (4,5-Dimethyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone; LC-MS A: $t_R$ = 0.96 min; $[M + H]^+$ = 512.32 |
| 547 | A-1-5 | R-4-1 | (5-Chloro-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone; LC-MS A: $t_R$ = 0.94 min; $[M(^{35}Cl) + H]^+$ = 518.26 |
| 548 | A-1-66 | R-4-1 | (5-Methyl-biphenyl-2-yl)-{(S)-2-methyl-2-[5-(2-trifluoromethoxy-phenyl)-4H-[1,2,4]triazol-3-yl]-pyrrolidin-1-yl}-methanone; LC-MS A: $t_R$ = 1.0 min; $[M + H]^+$ = 507.32 |
| 549 | A-1-35 | R-4-1 | (4-Methyl-biphenyl-2-yl)-{(S)-2-methyl-2-[5-(2-trifluoromethoxy-phenyl)-4H-[1,2,4]triazol-3-yl]-pyrrolidin-1-yl}-methanone; LC-MS A: $t_R$ = 1.0 min; $[M + H]^+$ = 507.34 |
| 550 | A-1-2 | R-4-2 | {(S)-2-[5-(3-Chloro-2-methyl-phenyl)-4H-[1,2,4]triazol-3-yl]-2-methyl-pyrrolidin-1-yl}-(5-methyl-2-[1,2,3]triazol-2-yl-phenyl)-methanone; LC-MS A: $t_R$ = 0.91 min; $[M(^{35}Cl) + H]^+$ = 462.27 |
| 551 | A-1-3 | R-4-2 | {(S)-2-[5-(3-Chloro-2-methyl-phenyl)-4H-[1,2,4]triazol-3-yl]-2-methyl-pyrrolidin-1-yl}-(4-methyl-2-[1,2,3]triazol-2-yl-phenyl)-methanone; LC-MS A: $t_R$ = 0.91 min; $[M(^{35}Cl) + H]^+$ = 462.26 |

TABLE 36-continued

| Ex. No. | SM A-1 | SM R-4 | Compound of Formula (I) |
|---|---|---|---|
| 552 | A-1-58 | R-4-2 | {(S)-2-[5-(3-Chloro-2-methyl-phenyl)-4H-[1,2,4]triazol-3-yl]-2-methyl-pyrrolidin-1-yl}-(5-chloro-4-methyl-2-[1,2,3]triazol-2-yl-phenyl)-methanone; LC-MS A: $t_R$ = 0.96 min; [M($^{35}$Cl) + H]$^+$ = 496.26 |
| 553 | A-1-6 | R-4-2 | {(S)-2-[5-(3-Chloro-2-methyl-phenyl)-4H-[1,2,4]triazol-3-yl]-2-methyl-pyrrolidin-1-yl}-(4,5-dimethyl-2-[1,2,3]triazol-2-yl-phenyl)-methanone; LC-MS A: $t_R$ = 0.94 min; [M($^{35}$Cl) + H]$^+$ = 476.32 |
| 554 | A-1-5 | R-4-2 | {(S)-2-[5-(3-Chloro-2-methyl-phenyl)-4H-[1,2,4]triazol-3-yl]-2-methyl-pyrrolidin-1-yl}-(5-chloro-2-[1,2,3]triazol-2-yl-phenyl)-methanone; LC-MS A: $t_R$ = 0.92 min; [M($^{35}$Cl) + H]$^+$ = 482.12 |
| 555 | A-1-16 | R-4-2 | {(S)-2-[5-(3-Chloro-2-methyl-phenyl)-4H-[1,2,4]triazol-3-yl]-2-methyl-pyrrolidin-1-yl}-(4-chloro-2-[1,2,3]triazol-2-yl-phenyl)-methanone; LC-MS A: $t_R$ = 0.92 min; [M($^{35}$Cl) + H]$^+$ = 482.12 |
| 556 | A-1-35 | R-4-2 | {(S)-2-[5-(3-Chloro-2-methyl-phenyl)-4H-[1,2,4]triazol-3-yl]-2-methyl-pyrrolidin-1-yl}-(4-methyl-biphenyl-2-yl)-methanone; LC-MS A: $t_R$ = 0.99 min; [M($^{35}$Cl) + H]$^+$ = 471.30 |
| 557 | A-1-66 | R-4-2 | {(S)-2-[5-(3-Chloro-2-methyl-phenyl)-4H-[1,2,4]triazol-3-yl]-2-methyl-pyrrolidin-1-yl}-(5-methyl-biphenyl-2-yl)-methanone; LC-MS A: $t_R$ = 0.98 min; [M($^{35}$Cl) + H]$^+$ = 471.29 |

REFERENCE COMPOUNDS

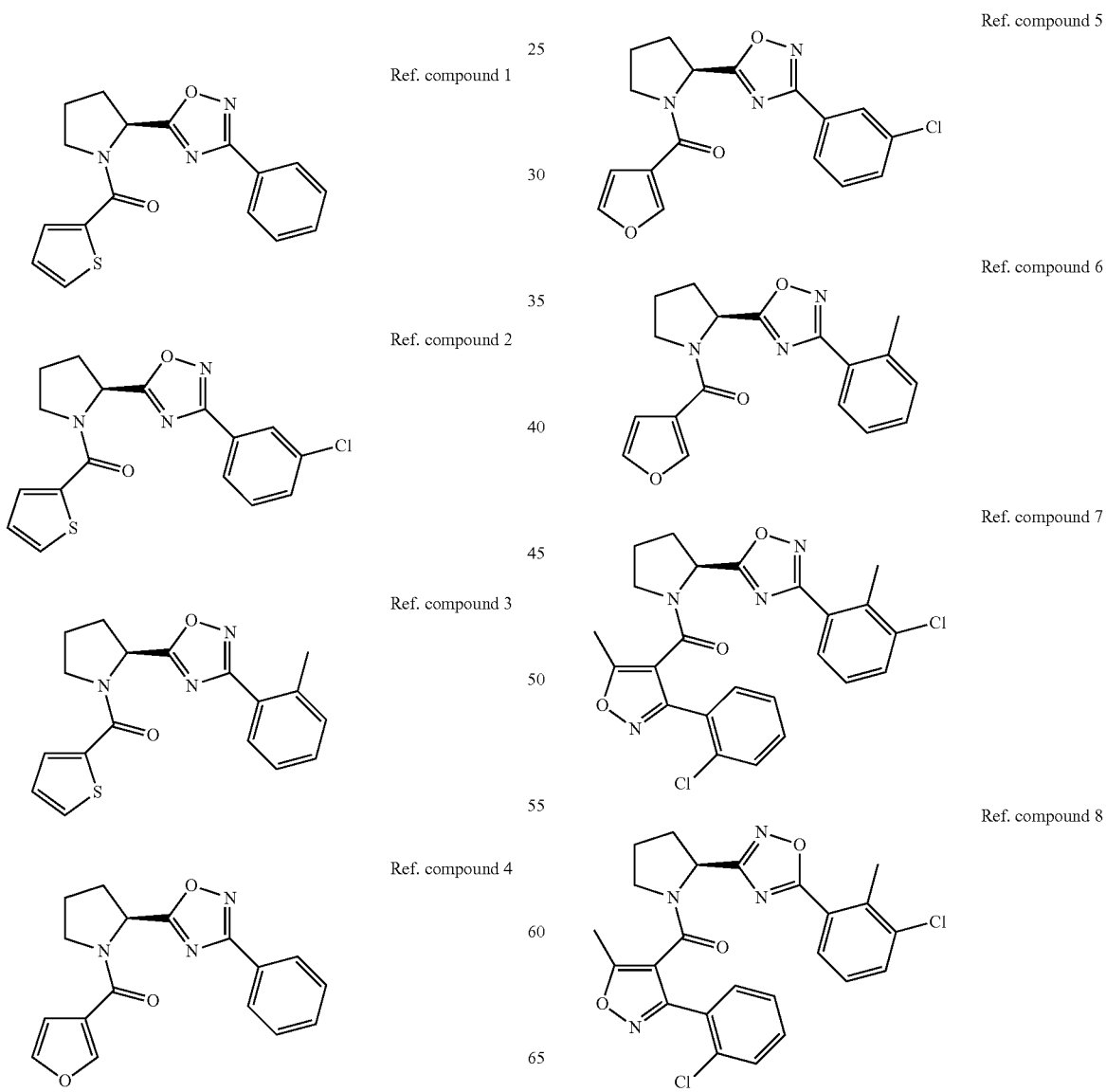

-continued

Ref. compound 9

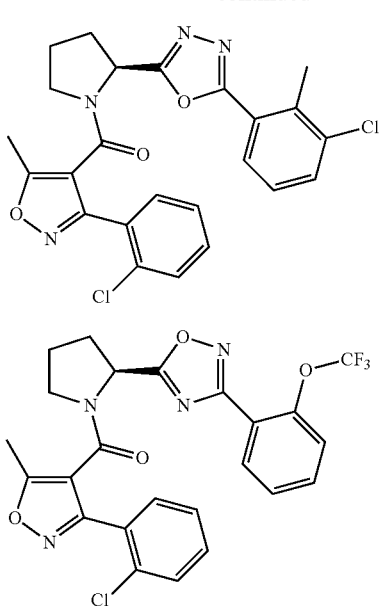

Ref. compound 10

Reference compound 1: [(S)-2-(3-Phenyl-[1,2,4]
oxadiazol-5-yl)-pyrrolidin-1-yl]-thiophen-2-yl-
methanone Step A: (S)-Methyl
1-(thiophene-2-carbonyl)pyrrolidine-2-carboxylate TBTU (3.96 g, 12.3 mmol) was added to a rt solution of 2-thiophenecarboxylic acid (1.32 g, 10.3 mmol) and DIPEA (5.3 mL, 30.8 mmol) in DCM (70 mL) and the resulting mixture was stirred at rt for 15 min, before S-proline methyl ester HCl (1.70 g, 10.3 mmol) was added. After stirring at rt overnight, the rxn mixture was diluted with water, the org. layer separated and the aq. layer extracted with DCM (2×). The combined extracts were dried (MgSO$_4$), filtered and concentrated in vacuo and purified by FC (Biotage SP1: EtOAc/hex 1:4 to 1:2) to yield (S)-methyl 1-(thiophene-2-carbonyl)pyrrolidine-2-carboxylate as a brownish oil. LC-MS B: $t_R$=0.54 min; [M+H]$^+$=240.23.

Step B: (S)-1-(Thiophene-2-carbonyl)pyrrolidine-2-carboxylic acid 1M aq. NaOH (20 mL) was added to (S)-methyl 1-(thiophene-2-carbonyl)pyrrolidine-2-carboxylate (2.48 g, 10.3 mmol) in THF (50 mL) and the resulting mixture was stirred at rt overnight. The rxn mixture was cooled to 0° C., acidified with 1M aq. HCl (20 mL) to reach pH 1 and extracted with DCM (3×). The combined org. extracts were dried (MgSO$_4$), filtered and concentrated in vacuo to give (S)-1-(thiophene-2-carbonyl)pyrrolidine-2-carboxylic acid as a white solid that was used without further purification. LC-MS B: $t_R$=0.45 min; [M+H]$^+$=226.21.

Step C: (S)—N-((1-(Thiophene-2-carbonyl)pyrrolidine-2-carbonyl)oxy)benzimidamide PyBOP (156 mg, 0.3 mmol) was added to a rt solution of (S)-1-(thiophene-2-carbonyl)pyrrolidine-2-carboxylic acid (45 mg, 0.2 mmol) and DIPEA (103 uL, 0.6 mmol) in DCM (1.0 mL) and the rxn mixture was stirred at rt for 20 min, before N-hydroxy-benzamidine (27 mg, 0.2 mmol) was added and the resulting mixture was stirred at rt overnight. The rxn mixture was concentrated in vacuo and the residue was used as such for the next step.

Step D (S)—N-((1-(thiophene-2-carbonyl)pyrrolidine-2-carbonyl)oxy)benzimidamide was dissolved in dioxane (2.0 mL) and stirred at 90° C. overnight. The rxn mixture was concentrated in vacuo and purified by prep. HPLC (method G) to give the title compound (Ref. 1) as an off-white solid. LC-MS B: $t_R$=0.79 min; [M+H]$^+$=326.27.

Reference compound 2: {(S)-2-[3-(3-Chloro-phenyl)-[1,2,4]oxadiazol-5-yl]-pyrrolidin-1-yl}-thiophen-2-yl-methanone The title compound was prepared from (S)-1-(thiophene-2-carbonyl)pyrrolidine-2-carboxylic acid and A-4-22 following the procedure described for Reference compound 1 (Step C and D). LC-MS B: $t_R$=0.88 min; [M($^{35}$Cl)+H]$^+$=360.23.

Reference compound 3: Thiophen-2-yl-[(S)-2-(3-o-tolyl-[1,2,4]oxadiazol-5-yl)-pyrrolidin-1-yl]-methanone The title compound was prepared from (S)-1-(thiophene-2-carbonyl)pyrrolidine-2-carboxylic acid and A-4-19 following the procedure described for Reference compound 1 (Step C and D). LC-MS B: $t_R$=0.93 min; [M+H]$^+$=339.98.

Reference compound 4: Furan-3-yl-[(S)-2-(3-phenyl-[1,2,4]oxadiazol-5-yl)-pyrrolidin-1-yl]-methanone Step A: (S)-Methyl
1-(furan-3-carbonyl)pyrrolidine-2-carboxylate TBTU (3.96 g, 12.3 mmol) was added to a rt solution of furan-3-carboxylic acid (1.17 g, 10.3 mmol) and DIPEA (5.3 mL, 30.8 mmol) in DCM (70 mL) and the resulting mixture was stirred at rt for 15 min, before S-proline methyl ester HCl (1.70 g, 10.3 mmol) was added. After stirring at rt overnight, the rxn mixture was diluted with water, the org. layer separated and the aq. layer extracted with DCM (2×). The combined extracts were dried (MgSO$_4$), filtered and concentrated in vacuo and purified by FC (Biotage SP1: EtOAc/hex 1:2) to yield (S)-methyl 1-(furan-3-carbonyl)pyrrolidine-2-carboxylate as a white solid. LC-MS B: $t_R$=0.47 min; [M+H]$^+$=224.22.

Step B:
(S)-1-(Furan-3-carbonyl)pyrrolidine-2-carboxylic acid 1M aq. NaOH (15 mL) was added to (S)-methyl 1-(furan-3-carbonyl)pyrrolidine-2-carboxylate (1.37 g, 6.14 mmol) in THF (50 mL) and the resulting mixture was stirred at rt for 3 h. The rxn mixture was cooled to 0° C., acidified with 1M aq. HCl (20 mL) to reach pH 1 and extracted with DCM (3×). The combined org. extracts were dried (MgSO$_4$), filtered and concentrated in vacuo to give (S)-1-(furan-3- carbonyl)pyrrolidine-2-carboxylic acid as a yellow oil that was used without further purification. LC-MS B: $t_R$=0.39 min; [M+H]$^+$=210.24.

Step C: (S)—N-((1-(Furan-3-carbonyl)pyrrolidine-2-carbonyl)oxy)benzimidamide

PyBOP (156 mg, 0.3 mmol) was added to a rt solution of (S)-1-(thiophene-2-carbonyl)pyrrolidine-2-carboxylic acid (45 mg, 0.2 mmol) and DIPEA (103 uL, 0.6 mmol) in DCM (1.0 mL) and the rxn mixture was stirred at rt for 20 min, before N-hydroxy-benzamidine (27 mg, 0.2 mmol) was added and the resulting mixture was stirred at rt overnight. The rxn mixture was concentrated in vacuo and the residue was used as such for the next step.

Step D (S)—N-((1-(furan-3-carbonyl)pyrrolidine-2-carbonyl) oxy)benzimidamide was dissolved in dioxane (2.0 mL) and stirred at 90° C. overnight. The rxn mixture was concentrated in vacuo and purified by prep. HPLC (method G) to give the title compound (Ref. 4) as a brownish solid. LC-MS B: $t_R$=0.74 min; [M+H]$^+$=310.31.

Reference compound 5: {(S)-2-[3-(3-Chloro-phenyl)-[1,2,4]oxadiazol-5-yl]-pyrrolidin-1-yl}-furan-3-yl-methanone The title compound was prepared from (S)-1-(furan-3-carbonyl)pyrrolidine-2-carboxylic acid and A-4-22 following the procedure described for Reference compound 1 (Step C and D). LC-MS B: $t_R$=0.82 min; [M($^{35}$Cl)+H]$^+$=344.27.

Reference compound 6: Furan-3-yl-[(S)-2-(3-o-tolyl-[1,2,4]oxadiazol-5-yl)-pyrrolidin-1-yl]-methanone The title compound was prepared from (S)-1-(furan-3-carbonyl)pyrrolidine-2-carboxylic acid and A-4-19 following the procedure described for Reference compound 4 (Step C and D). LC-MS B: $t_R$=0.79 min; [M+H]$^+$=324.32.

Reference compound 7: {(S)-2-[3-(3-Chloro-2-methyl-phenyl)-[1,2,4]oxadiazol-5-yl]-pyrrolidin-1-yl}-[3-(2-chloro-phenyl)-5-methyl-isoxazol-4-yl]-methanone The title compound was prepared from A-1-60 and B-3-1 following the procedure described in General Method F. LC-MS A: $t_R$=1.02 min; [M($^{35}$Cl)+H]$^+$=483.0.

Reference compound 8: {(S)-2-[5-(3-Chloro-2-methyl-phenyl)-[1,2,4]oxadiazol-3-yl]-pyrrolidin-1-yl}-[3-(2-chloro-phenyl)-5-methyl-isoxazol-4-yl]-methanone The title compound was prepared from A-1-60 and D-4-1 following the procedure described in General Method F. LC-MS A: $t_R$=1.02 min; [M($^{35}$Cl)+H]$^+$=483.0.

Reference compound 9: {(S)-2-[5-(3-Chloro-2-methyl-phenyl)-[1,3,4]oxadiazol-2-yl]-pyrrolidin-1-yl}-[3-(2-chloro-phenyl)-5-methyl-isoxazol-4-yl]-methanone The title compound was prepared from A-1-60 and F-4-3 following the procedure described in General Method F. LC-MS A: $t_R$=0.95 min; [M($^{35}$Cl)+H]$^+$=483.0.

Reference compound 10: [3-(2-Chloro-phenyl)-5-methyl-isoxazol-4-yl]-{(S)-2-[3-(2-trifluoromethoxy-phenyl)-[1,2,4]oxadiazol-5-yl]-pyrrolidin-1-yl}-methanone The title compound was prepared from A-1-60 and B-3-2 following the procedure described in General Method F. LC-MS A: $t_R$=1.00 min; [M($^{35}$Cl)+H]$^+$=519.01.

II. Biological Assays

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 μg/mL G418, 100 U/mL penicillin, 100 μg/mL streptomycin and 10% heat inactivated fetal calf serum (FCS). The cells are seeded at 20,000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH: water (1:1), diluted in HBSS containing 0.1% bovine serum albumin (BSA), $NaHCO_3$: 0.375 g/L and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/L and 20 mM HEPES. On the day of the assay, 50 μL of staining buffer (HBSS containing 1% FCS, 20 mM HEPES, $NaHCO_3$: 0.375 g/L, 5 mM probenecid (Sigma) and 3 μM of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at rt for 30 min before measurement.

Within the Fluorescent Imaging Plate Reader (FLIPR Tetra, Molecular Devices), antagonists are added to the plate in a volume of 10 μL/well, incubated for 120 min and finally 10 μL/well of agonist is added. Fluorescence is measured for each well at 1 second intervals, and the height of each fluorescence peak is compared to the height of the fluorescence peak induced by 3 nM orexin-A with vehicle in place of antagonist. The $IC_{50}$ value (the concentration of compound needed to inhibit 50% of the agonistic response) is determined and may be normalized using the obtained $IC_{50}$ value of an on-plate reference compound. Optimized conditions were achieved by adjustment of pipetting speed and cell splitting regime. The calculated $IC_{50}$ values may fluctuate depending on the daily cellular assay performance. Fluctuations of this kind are known to those skilled in the art. In the case where $IC_{50}$ values have been determined several times for the same compound, the geometric mean has been given. Antagonistic activities of example compounds are shown in Table 37.

TABLE 37

| Ex No. | $IC_{50}$ OX1 [nM] | $IC_{50}$ OX2 [nM] |
|---|---|---|
| 1 | 373 | 40 |
| 2 | 253 | 41 |
| 3 | 182 | 34 |

TABLE 37-continued

| Ex No. | IC$_{50}$ OX1 [nM] | IC$_{50}$ OX2 [nM] |
|---|---|---|
| 4 | >5040 | 897 |
| 5 | 403 | 554 |
| 6 | 21 | 27 |
| 7 | 64 | 37 |
| 8 | 156 | 74 |
| 9 | 853 | 242 |
| 10 | 1041 | 150 |
| 11 | 58 | 6 |
| 12 | 796 | 816 |
| 13 | 70 | 13 |
| 14 | 392 | 295 |
| 15 | 21 | 8 |
| 16 | 128 | 16 |
| 17 | 8 | 5 |
| 18 | 91 | 32 |
| 19 | 1860 | 652 |
| 20 | 600 | 177 |
| 21 | 339 | 19 |
| 22 | 942 | 322 |
| 23 | 40 | 7 |
| 24 | 472 | 104 |
| 25 | 19 | 11 |
| 26 | 77 | 5 |
| 27 | 125 | 8 |
| 28 | 2611 | 33 |
| 29 | 249 | 39 |
| 30 | 3600 | 365 |
| 31 | 2910 | 259 |
| 32 | 2290 | 955 |
| 33 | 62 | 9 |
| 34 | 51 | 8 |
| 35 | 952 | 142 |
| 36 | >5640 | 379 |
| 37 | >5640 | 1060 |
| 38 | 23 | 12 |
| 39 | 658 | 92 |
| 40 | 22 | 4 |
| 41 | 22 | 7 |
| 42 | 112 | 108 |
| 43 | 284 | 23 |
| 44 | 110 | 14 |
| 45 | 112 | 125 |
| 46 | 4 | 9 |
| 47 | 316 | 90 |
| 48 | 45 | 58 |
| 49 | 89 | 233 |
| 50 | 131 | 75 |
| 51 | 15 | 11 |
| 52 | 182 | 25 |
| 53 | 315 | 97 |
| 54 | 216 | 46 |
| 55 | 241 | 41 |
| 56 | 16 | 7 |
| 57 | 7 | 4 |
| 58 | >5040 | 536 |
| 59 | 1216 | 47 |
| 60 | >1420 | 419 |
| 61 | 1480 | 271 |
| 62 | >1630 | 242 |
| 63 | 1420 | 361 |
| 64 | 198 | 52 |
| 65 | 758 | 375 |
| 66 | 302 | 155 |
| 67 | 1252 | 333 |
| 68 | 6670 | 915 |
| 69 | 1840 | 163 |
| 70 | 623 | 53 |
| 71 | 8 | 22 |
| 72 | 901 | 57 |
| 73 | 3480 | 1160 |
| 74 | 254 | 6 |
| 75 | 1570 | 261 |
| 76 | 901 | 40 |
| 77 | 52 | 8 |
| 78 | 2290 | 29 |
| 79 | 2751 | 1068 |
| 80 | 252 | 16 |
| 81 | 309 | 19 |
| 82 | 874 | 131 |
| 83 | 3470 | 302 |
| 84 | 63 | 8 |
| 85 | 28 | 23 |
| 86 | 103 | 40 |
| 87 | 439 | 70 |
| 88 | 49 | 11 |
| 89 | 97 | 14 |
| 90 | 137 | 25 |
| 91 | 104 | 91 |
| 92 | 120 | 53 |
| 93 | 399 | 28 |
| 94 | 237 | 201 |
| 95 | 13 | 3 |
| 96 | 109 | 12 |
| 97 | 568 | 194 |
| 98 | 462 | 127 |
| 99 | 895 | 614 |
| 100 | 92 | 8 |
| 101 | 9 | 6 |
| 102 | 171 | 287 |
| 103 | 30 | 2 |
| 104 | 1030 | 38 |
| 105 | 133 | 8 |
| 106 | 327 | 28 |
| 107 | 1040 | 79 |
| 108 | 554 | 68 |
| 109 | 976 | 199 |
| 110 | 1690 | 159 |
| 111 | 1150 | 261 |
| 112 | 833 | 121 |
| 113 | 1200 | 146 |
| 114 | 1080 | 83 |
| 115 | 78 | 6 |
| 116 | 457 | 34 |
| 117 | 211 | 5 |
| 118 | 260 | 48 |
| 119 | 188 | 24 |
| 120 | 483 | 37 |
| 121 | 145 | 15 |
| 122 | 933 | 221 |
| 123 | 133 | 111 |
| 124 | 145 | 77 |
| 125 | 353 | 80 |
| 126 | 221 | 118 |
| 127 | 581 | 125 |
| 128 | 200 | 181 |
| 129 | 419 | 287 |
| 130 | 188 | 16 |
| 131 | 45 | 8 |
| 132 | 831 | 250 |
| 133 | 522 | 36 |
| 134 | 274 | 219 |
| 135 | 60 | 17 |
| 136 | 12 | 9 |
| 137 | 33 | 23 |
| 138 | 49 | 30 |
| 139 | 124 | 62 |
| 140 | 100 | 45 |
| 141 | 59 | 29 |
| 142 | 123 | 80 |
| 143 | 47 | 34 |
| 144 | 26 | 83 |
| 145 | 19 | 15 |
| 146 | 5 | 5 |
| 147 | 31 | 15 |
| 148 | 241 | 285 |
| 149 | 184 | 85 |
| 150 | 457 | 341 |
| 151 | 27 | 27 |
| 152 | 9 | 35 |
| 153 | 781 | 460 |
| 154 | 30 | 2 |
| 155 | 174 | 43 |
| 156 | 80 | 14 |
| 157 | 99 | 73 |
| 158 | 323 | 140 |
| 159 | 88 | 71 |

TABLE 37-continued

| Ex No. | IC$_{50}$ OX1 [nM] | IC$_{50}$ OX2 [nM] |
|---|---|---|
| 160 | 238 | 212 |
| 161 | 751 | 204 |
| 162 | 818 | 347 |
| 163 | 495 | 87 |
| 164 | 333 | 171 |
| 165 | 286 | 79 |
| 166 | 26 | 7 |
| 167 | 114 | 43 |
| 168 | 27 | 10 |
| 169 | 137 | 90 |
| 170 | 55 | 35 |
| 171 | 104 | 30 |
| 172 | 56 | 18 |
| 173 | 132 | 116 |
| 174 | 174 | 70 |
| 175 | 14 | 12 |
| 176 | 258 | 151 |
| 177 | 126 | 140 |
| 178 | 549 | 132 |
| 179 | 371 | 189 |
| 180 | 183 | 126 |
| 181 | 86 | 37 |
| 182 | 276 | 29 |
| 183 | 190 | 91 |
| 184 | 311 | 133 |
| 185 | 523 | 75 |
| 186 | 138 | 17 |
| 187 | 79 | 31 |
| 188 | 20 | 3 |
| 189 | 47 | 5 |
| 190 | 53 | 14 |
| 191 | 119 | 27 |
| 192 | 135 | 15 |
| 193 | 263 | 25 |
| 194 | 77 | 9 |
| 195 | 71 | 11 |
| 196 | 10 | 2 |
| 197 | 354 | 93 |
| 198 | 485 | 85 |
| 199 | 83 | 12 |
| 200 | 307 | 32 |
| 201 | 27 | 2 |
| 202 | 53 | 10 |
| 203 | 56 | 16 |
| 204 | 65 | 10 |
| 205 | 340 | 43 |
| 206 | 409 | 10 |
| 207 | 1810 | 565 |
| 208 | 225 | 20 |
| 209 | 56 | 21 |
| 210 | 49 | 10 |
| 211 | 81 | 37 |
| 212 | 6 | 3 |
| 213 | 169 | 46 |
| 214 | 360 | 75 |
| 215 | 18 | 3 |
| 216 | 76 | 27 |
| 217 | 40 | 14 |
| 218 | 331 | 99 |
| 219 | 228 | 170 |
| 220 | 53 | 16 |
| 221 | 152 | 44 |
| 222 | 351 | 121 |
| 223 | 253 | 17 |
| 224 | 19 | 6 |
| 225 | 964 | 600 |
| 226 | 160 | 148 |
| 227 | 852 | 425 |
| 228 | 272 | 134 |
| 229 | 163 | 240 |
| 230 | 23 | 15 |
| 231 | 66 | 15 |
| 232 | 134 | 78 |
| 233 | 1410 | 341 |
| 234 | 962 | 430 |
| 235 | 361 | 992 |
| 236 | 1850 | 150 |
| 237 | 844 | 186 |

TABLE 37-continued

| Ex No. | IC$_{50}$ OX1 [nM] | IC$_{50}$ OX2 [nM] |
|---|---|---|
| 238 | 104 | 16 |
| 239 | 378 | 24 |
| 240 | 1330 | 147 |
| 241 | 3110 | 804 |
| 242 | 4360 | 1440 |
| 243 | 2680 | 312 |
| 244 | 306 | 18 |
| 245 | 262 | 21 |
| 246 | 135 | 14 |
| 247 | 17 | 3 |
| 248 | 64 | 2 |
| 249 | 151 | 8 |
| 250 | 489 | 38 |
| 251 | 626 | 90 |
| 252 | 1210 | 143 |
| 253 | 174 | 5 |
| 254 | 69 | 20 |
| 255 | 36 | 8 |
| 256 | 43 | 20 |
| 257 | 4 | 1 |
| 258 | 27 | 4 |
| 259 | 352 | 99 |
| 260 | 392 | 63 |
| 261 | 26 | 9 |
| 262 | 1110 | 145 |
| 263 | 505 | 105 |
| 264 | 165 | 14 |
| 265 | 112 | 76 |
| 266 | 115 | 14 |
| 267 | 501 | 177 |
| 268 | 233 | 31 |
| 269 | 177 | 12 |
| 270 | 282 | 32 |
| 271 | 69 | 189 |
| 272 | 149 | 252 |
| 273 | 148 | 134 |
| 274 | 171 | 29 |
| 275 | 210 | 161 |
| 276 | 762 | 243 |
| 277 | 1480 | 297 |
| 278 | 1110 | 199 |
| 279 | 296 | 135 |
| 280 | 54 | 4 |
| 281 | 42 | 17 |
| 282 | 44 | 1 |
| 283 | 34 | 7 |
| 284 | 32 | 5 |
| 285 | 90 | 56 |
| 286 | 90 | 6 |
| 287 | 73 | 42 |
| 288 | 666 | 52 |
| 289 | 44 | 37 |
| 290 | 9 | 5 |
| 291 | 21 | 5 |
| 292 | 348 | 52 |
| 293 | 32 | 10 |
| 294 | 155 | 17 |
| 295 | 78 | 3 |
| 296 | 582 | 272 |
| 297 | 690 | 478 |
| 298 | 531 | 517 |
| 299 | 25 | 19 |
| 300 | 14 | 10 |
| 301 | 19 | 6 |
| 302 | 258 | 207 |
| 303 | 13 | 4 |
| 304 | 4 | 3 |
| 305 | 164 | 74 |
| 306 | 36 | 2 |
| 307 | 130 | 3 |
| 308 | 22 | 4 |
| 309 | 13 | 1 |
| 310 | 59 | 2 |
| 311 | 16 | 4 |
| 312 | 204 | 89 |
| 313 | 661 | 76 |
| 314 | 249 | 314 |
| 315 | 1050 | 2130 |

TABLE 37-continued

| Ex No. | IC$_{50}$ OX1 [nM] | IC$_{50}$ OX2 [nM] |
|---|---|---|
| 316 | 54 | 19 |
| 317 | 2480 | 1620 |
| 318 | 42 | 7 |
| 319 | 11 | 2 |
| 320 | 25 | 1 |
| 321 | 7 | 1 |
| 322 | 158 | 6 |
| 323 | 9 | 1 |
| 324 | 3 | 1 |
| 325 | 151 | 6 |
| 326 | 27 | 3 |
| 327 | 38 | 4 |
| 328 | 16 | 4 |
| 329 | 16 | 4 |
| 330 | 5 | 2 |
| 331 | 1 | 0.5 |
| 332 | 99 | 4 |
| 333 | 644 | 17 |
| 334 | 320 | 12 |
| 335 | 65 | 4 |
| 336 | 45 | 3 |
| 337 | 112 | 14 |
| 338 | 27 | 4 |
| 339 | 15 | 2 |
| 340 | 3 | 0.4 |
| 341 | 13 | 1 |
| 342 | 152 | 13 |
| 343 | 46 | 3 |
| 344 | 26 | 10 |
| 345 | 33 | 11 |
| 346 | 23 | 2 |
| 347 | 15 | 1 |
| 348 | 10 | 1 |
| 349 | 27 | 3 |
| 350 | 36 | 2 |
| 351 | 22 | 4 |
| 352 | 19 | 4 |
| 353 | 54 | 5 |
| 354 | 12 | 5 |
| 355 | 188 | 8 |
| 356 | 57 | 7 |
| 357 | 81 | 17 |
| 358 | 128 | 10 |
| 359 | 325 | 30 |
| 360 | 7 | 1 |
| 361 | 127 | 61 |
| 362 | 171 | 100 |
| 363 | 155 | 111 |
| 364 | 265 | 157 |
| 365 | 13 | 6 |
| 366 | 5 | 3 |
| 367 | 20 | 2 |
| 368 | 11 | 1 |
| 369 | 15 | 2 |
| 370 | 9 | 1 |
| 371 | 18 | 7 |
| 372 | 377 | 29 |
| 373 | 212 | 5 |
| 374 | 18 | 11 |
| 375 | 67 | 6 |
| 376 | 23 | 11 |
| 377 | 68 | 15 |
| 378 | 30 | 2 |
| 379 | 52 | 5 |
| 380 | 3 | 1 |
| 381 | 136 | 28 |
| 382 | 10 | 4 |
| 383 | 30 | 4 |
| 384 | 22 | 2 |
| 385 | 26 | 8 |
| 386 | 118 | 7 |
| 387 | 57 | 3 |
| 388 | 381 | 15 |
| 389 | 35 | 15 |
| 390 | 73 | 6 |
| 391 | 68 | 14 |
| 392 | 17 | 17 |
| 393 | 57 | 10 |
| 394 | 134 | 12 |
| 395 | 31 | 10 |
| 396 | 134 | 15 |
| 397 | 85 | 5 |
| 398 | 33 | 18 |
| 399 | 77 | 10 |
| 400 | 36 | 4 |
| 401 | 7 | 3 |
| 402 | 164 | 2 |
| 403 | 25 | 2 |
| 404 | 23 | 3 |
| 405 | 33 | 1 |
| 406 | 22 | 2 |
| 407 | 15 | 3 |
| 408 | 31 | 2 |
| 409 | 45 | 12 |
| 410 | 140 | 14 |
| 411 | 99 | 9 |
| 412 | 109 | 80 |
| 413 | 163 | 30 |
| 414 | 331 | 35 |
| 415 | 193 | 49 |
| 416 | 152 | 20 |
| 417 | 271 | 21 |
| 418 | 85 | 25 |
| 419 | 207 | 16 |
| 420 | 1060 | 133 |
| 421 | 571 | 717 |
| 422 | 152 | 4 |
| 423 | 81 | 39 |
| 424 | 8 | 4 |
| 425 | 4 | 10 |
| 426 | 414 | 30 |
| 427 | 80 | 292 |
| 428 | 67 | 28 |
| 429 | 98 | 26 |
| 430 | 359 | 51 |
| 431 | 19 | 2 |
| 432 | 322 | 16 |
| 433 | 19 | 1 |
| 434 | 21 | 5 |
| 435 | 35 | 31 |
| 436 | 49 | 13 |
| 437 | 62 | 15 |
| 438 | 1490 | 359 |
| 439 | 1800 | 1410 |
| 440 | 141 | 21 |
| 441 | 946 | 105 |
| 442 | 184 | 118 |
| 443 | 68 | 45 |
| 444 | 83 | 60 |
| 445 | 157 | 9 |
| 446 | 82 | 6 |
| 447 | 30 | 5 |
| 448 | 762 | 236 |
| 449 | 280 | 236 |
| 450 | 182 | 95 |
| 451 | 535 | 326 |
| 452 | 249 | 211 |
| 453 | 398 | 80 |
| 454 | 1140 | 375 |
| 455 | 835 | 1690 |
| 456 | 1740 | 536 |
| 457 | 17000 | 3436 |
| 458 | 176 | 112 |
| 459 | 129 | 295 |
| 460 | 10 | 16 |
| 461 | 115 | 465 |
| 462 | 117 | 184 |
| 463 | 704 | 209 |
| 464 | 49 | 124 |
| 465 | 76 | 10 |
| 466 | 26 | 69 |
| 467 | 63 | 10 |
| 468 | 84 | 35 |
| 469 | 25 | 45 |
| 470 | 57 | 31 |
| 471 | 49 | 127 |

TABLE 37-continued

| Ex No. | IC$_{50}$ OX1 [nM] | IC$_{50}$ OX2 [nM] |
|---|---|---|
| 472 | 19 | 2 |
| 473 | 57 | 6 |
| 474 | 16 | 8 |
| 475 | 11 | 2 |
| 476 | 27 | 3 |
| 477 | 55 | 15 |
| 478 | 27 | 11 |
| 479 | 21 | 17 |
| 480 | 8 | 9 |
| 481 | 26 | 21 |
| 482 | 68 | 94 |
| 483 | 1620 | 1790 |
| 484 | 5020 | 3000 |
| 485 | 1300 | 1230 |
| 486 | 2360 | 3130 |
| 487 | 23 | 8 |
| 488 | 136 | 14 |
| 489 | 62 | 10 |
| 490 | 120 | 2 |
| 491 | 33 | 1 |
| 492 | 27 | 3 |
| 493 | 1143 | 29 |
| 494 | 847 | 27 |
| 495 | 39 | 38 |
| 496 | 57 | 50 |
| 497 | 49 | 46 |
| 498 | 9 | 2 |
| 499 | 29 | 3 |
| 500 | 8 | 2 |
| 501 | 27 | 4 |
| 502 | 17 | 3 |
| 503 | 156 | 27 |
| 504 | 104 | 5 |
| 505 | 1670 | 592 |
| 506 | 171 | 116 |
| 507 | 107 | 135 |
| 508 | 239 | 84 |
| 509 | 22 | 3 |
| 510 | 477 | 53 |
| 511 | 642 | 113 |
| 512 | 652 | 80 |
| 513 | 812 | 181 |
| 514 | >6560 | 3490 |
| 515 | 400 | 646 |
| 516 | 18 | 18 |
| 517 | 6 | 2 |
| 518 | 2 | 1 |
| 519 | 1390 | 720 |
| 520 | 650 | 392 |
| 521 | 2510 | 681 |
| 522 | 2110 | 367 |
| 523 | 428 | 103 |
| 524 | 709 | 45 |
| 525 | 343 | 88 |
| 526 | 28 | 5 |
| 527 | 389 | 109 |
| 528 | 493 | 117 |
| 529 | 10 | 2 |
| 530 | 386 | 222 |
| 531 | 255 | 57 |
| 532 | 286 | 146 |
| 533 | 258 | 81 |
| 534 | 410 | 53 |
| 535 | 47 | 363 |
| 536 | 3430 | 2140 |
| 537 | 3980 | 2880 |
| 538 | 941 | 2810 |
| 539 | 560 | 1780 |
| 540 | 211 | 581 |
| 541 | 104 | 114 |
| 542 | 33 | 28 |
| 543 | 10 | 20 |
| 544 | 5 | 6 |
| 545 | 4 | 8 |
| 546 | 4 | 8 |
| 547 | 25 | 34 |
| 548 | 35 | 65 |
| 549 | 31 | 64 |
| 550 | 272 | 178 |
| 551 | 43 | 24 |
| 552 | 9 | 7 |
| 553 | 14 | 6 |
| 554 | 120 | 34 |
| 555 | 27 | 11 |
| 556 | 870 | 857 |
| 557 | 292 | 224 |
| Ref 1 | >8500 | >10000 |
| Ref 2 | 4260 | 7230 |
| Ref 3 | 6270 | >10000 |
| Ref 4 | >8500 | >10000 |
| Ref 5 | >8500 | >10000 |
| Ref 6 | >8500 | >10000 |
| Ref 7 | 529 | 593 |
| Ref 8 | >26200 | >21800 |
| Ref 9 | 11100 | >21800 |
| Ref 10 | 782 | 2190 |

Compounds of the present invention may be further characterized with regard to their general pharmacokinetic and pharmacological properties using conventional assays well known in the art; for example relating to their metabolism and their pharmacokinetic (PK) properties in different species (such as clearance by human liver microsomes; PK in rat or dog); or relating to their ability to cross the blood-brain barrier, using for example a human P-glycoprotein 1 (MDR 1) substrate assay, or an in vivo assay to determine drug concentrations in the brain, e.g. in rats after oral dosing; or relating to their functional behavior in different disease related animal models {for example: the sedative effect of the compound using Electroencephalography (EEG) and Electromyography (EMG) signal measurements [F. Jenck et al., Nature Medicine 2007, 13, 150-155]; the effect of the compound in the fear-potentiated startle paradigm [Fendt M et al., Neuroscience Biobehav Rev. 1999, 23, 743-760; WO2009/0047723]; the effect of the compound on stress-induced hyperthermia [Vinkers C H et al., European J Pharmacol. 2008, 585, 407-425]; the effect of the compound on morphine-induced locomotor sensitization [Vanderschuren L J M J et al., in Self D W, Staley J K (eds.) "Behavioral Neuroscience of Drug Addiction", Current Topics in Behavioral Neurosciences 3 (2009), 179-195]}; or for their properties with regard to drug safety and/or toxicological properties using conventional assays well known in the art, for example relating to cytochrome P450 enzyme inhibition and time dependent inhibition, pregnane X receptor (PXR) activation, glutathione binding, or phototoxic behavior.

Measurement of Brain and Systemic Concentration after Oral Administration:

In order to assess brain penetration, the concentration of the compound is measured in plasma ([P]), and brain ([B]), sampled 3 h (or at different time points) following oral administration (e.g. 100 mg/kg) to male wistar rats. The compounds are formulated e.g. in 100% PEG 400. Samples are collected in the same animal at the same time point (+/−5 min). Blood is sampled from the vena cava caudalis into containers with EDTA as anticoagulant and centrifuged to yield plasma. Brain is sampled after cardiac perfusion of 10 mL NaCl 0.9% and homogenized into one volume of cold phosphate buffer (pH 7.4). All samples are extracted with MeOH and analyzed by LC-MS/MS. Concentrations are determined with the help of calibration curves.

Results obtained for the compound of Example 95:
(3 h after oral administration (100 mg/kg), n=3): [P]=309 ng/ml; [B]=483 ng/g.
Results obtained for the compound of Example 154:
(3 h after oral administration (100 mg/kg), n=3): [P]=2237 ng/ml; [B]=3253 ng/g.
Results obtained for the compound of Example 308:
(3 h after oral administration (100 mg/kg), n=3): [P]=1763 ng/ml; [B]=1585 ng/g.
Results obtained for the compound of Example 502:
(3 h after oral administration (100 mg/kg), n=3): [P]=2773 ng/ml; [B]=1639 ng/g.
Results obtained for the compound of Example 544:
(3 h after oral administration (100 mg/kg), n=3): [P]=1073 ng/ml; [B]=1123 ng/g.

Sleep Effects: EEG, EMG and Behavioural Indices of Alertness Recorded by Radiotelemetry In Vivo in Wistar Rats.

Electroencephalography (EEG) and Electromyography (EMG) signals were measured by telemetry using TL11M2-F20-EET miniature radiotelemetric implants (Data Science Int.) with two pairs of differential leads.

Surgical implantation was performed under general anesthesia with Ketamin/Xylazin, for cranial placement of one differential pair of EEG electrodes and one pair of EMG leads inserted in either side of the muscles of the neck. After surgery, rats recovered in a thermoregulated chamber and received analgesic treatment with subcutaneous buprenorphine twice a day for 2 d. They were then housed individually and allowed to recover for a minimum of 2 weeks. Thereafter, rats—in their home cage—were placed in a ventilated sound-attenuating box, on a 12-h light/12-h dark cycle, for acclimatization before continuous EEG/EMG recordings started. The telemetric technology that we used in this study allows accurate and stress-free acquisition of biosignals in rats placed in their familiar home cage environment, with no recording leads restricting their movements. Variables analyzed included four different stages of vigilance and sleep, spontaneous activity in the home cage and body temperature. Sleep and wake stages were evaluated using a rodent scoring software (Somnologica Science) directly processing electrical biosignals on 10 s contiguous epochs. The scoring is based on frequency estimation for EEG and amplitude discrimination for EMG and locomotor activity. Using these measurements, the software determines the probability that all components within each epoch best represent active waking (AW), quiet waking (QW), non-REM-sleep (NREM) or REM-sleep (REM). The percentage of total time spent in AW, QW, NREM- and REM-sleep was calculated per 12 h light or dark period. The latency to the onset of the first significant NREM- and REM-sleep episodes and the number and duration of those episodes were also calculated. AW, QW, NREM- and REM-sleep, home cage activity and body temperature were measured at baseline for at least one total circadian cycle (12 h-night, 12 h-day) before a test compound was administered. If baseline measurements indicated that animals were stable, test compound or vehicle was given in the evening by oral gavage at the end of the baseline 12-h day period, immediately before the nocturnal rise in orexin and activity in rats. All variables were subsequently recorded for 12 h following administration of the orexin receptor antagonist.

The compound of Example 95 has been tested in this assay (oral dosage: 100 mg/kg po; effects analyzed over 12 hours): Results are: −7.3% on active wake, −20.3% on home cage activity, +11.2% on NREM sleep, +7.8% on REM sleep; when compared to vehicle controls. The compound of Example 154 has been tested in this assay (oral dosage: 100 mg/kg po; effects analyzed over 12 hours): Results are: −13.9% on active wake, −26.8% on home cage activity, +7.3% on NREM sleep, +0.9% on REM sleep; when compared to vehicle controls. The compound of Example 308 has been tested in this assay (oral dosage: 100 mg/kg po; effects analyzed over 12 hours): Results are: −24.0% on active wake, −41.4% on home cage activity, +14.3% on NREM sleep, +35.2% on REM sleep; when compared to vehicle controls. The compound of Example 502 has been tested in this assay (oral dosage: 100 mg/kg po; effects analyzed over 12 hours): Results are: −19.4% on active wake, −47.1% on home cage activity, +24.2% on NREM sleep, +47.0% on REM sleep; when compared to vehicle controls. The compound of Example 544 has been tested in this assay (oral dosage: 30 mg/kg po; effects analyzed over 12 hours): Results are: −9.6% on active wake, −18.5% on home cage activity, +19.4% on NREM sleep, +5.6% on REM sleep; when compared to vehicle controls.

The invention claimed is:
1. A compound of formula (I)

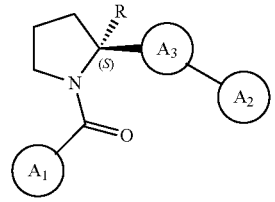

Formula (I)

wherein the carbon atom at position 2 of the pyrrolidine ring is in absolute (S)-configuration;

R represents hydrogen or methyl;

ring $A_3$ represents a mew di-substituted 5-membered heteroarylene ring containing one, two or three heteroatoms; wherein at least one of said heteroatoms is nitrogen, and the remaining is/are independently selected from oxygen, sulfur and nitrogen;

ring $A_2$ represents aryl or 5- to 10-membered heteroaryl; wherein said aryl or 5- to 10-membered heteroaryl is independently unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, hydroxy, $(C_{1-4})$alkoxy-$(C_{1-3})$alkyl, hydroxy-$(C_{1-3})$alkyl, —CO—$(C_{1-4})$alkyl, and $(C_{3-6})$cycloalkyl-oxy-; or ring $A_2$ represents a 2,3-dihydro-benzo[1,4]dioxinyl, a 2,3-dihydro-benzofuranyl, or a benzo[1,3]dioxolyl group optionally di-substituted with fluoro; and ring $A_1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of $A_1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;

and the other of said substituents, if present, is/are independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy;

provided that ring A$_1$ is not isoxazol-4-yl, substituted in position 5 with (C$_{1-4}$)alkyl, attached to the rest of the molecule at position 4, and carrying said further ortho-substitutent in position 3;

with the exception of the compound (1,1'-biphenyl)-2-yl-{(S)-2-[3-(3-pyridinyl)-1H-1,2,4-triazol-5-yl]-1-pyrrolidinyl}-methanone;

or a pharmaceutically acceptable salt thereof.

2. The compound according to claim 1; wherein the ring A$_3$ is a meta di-substituted 5-membered heteroarylene ring selected from the group consisting of oxadiazol-diyl, triazol-diyl, isoxazol-diyl, oxazol-diyl, thiazol-diyl, pyrazol-diyl, imidazol-diyl, isothiazol-diyl, and thiadiazol-diyl;

or a pharmaceutically acceptable salt thereof.

3. The compound according to claim 1; which is also a compound of the formula (IV):

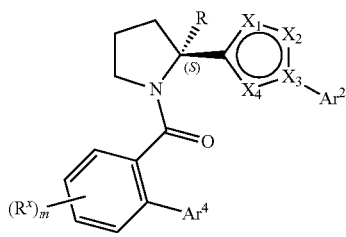

Formula (IV)

wherein the carbon atom at position 2 of the pyrrolidine ring is in absolute (S)-configuration;
wherein
R represents hydrogen or methyl;
the ring

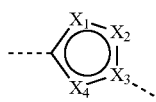

represents a meta di-substituted 5-membered heteroarylene ring containing one, two or three heteroatoms at any of the positions X$_1$, X$_2$, X$_3$, and/or X$_4$; wherein at least one of said heteroatoms is nitrogen, and the remaining, if present, is/are independently selected from oxygen, sulfur and nitrogen;

Ar$^2$ represents phenyl or 5- to 10-membered heteroaryl; wherein said phenyl or 5- to 10-membered heteroaryl is independently unsubstituted, or mono-, di-, or tri-substituted; wherein the substituents are independently selected from the group consisting of (C$_{1-4}$)alkyl, (C$_{1-4}$)alkoxy, (C$_{3-6}$)cycloalkyl, halogen, cyano, (C$_{1-3}$)fluoroalkyl, (C$_{1-3}$)fluoroalkoxy, hydroxy, (C$_{1-4}$)alkoxy-(C$_{1-3}$)alkyl, hydroxy-(C$_{1-3}$)alkyl, —CO—(C$_{1-4}$)alkyl, and (C$_{3-6}$)cycloalkyl-oxy-; or Ar$^2$ represents a 2,3-dihydro-benzo[1,4]dioxinyl, a 2,3-dihydro-benzofuranyl, or a benzo[1,3]dioxolyl group optionally di-substituted with fluoro;

(R$^x$)$_m$ represents one or two optional substituents independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy; and Ar$^4$ represents phenyl or 5- or 6-membered heteroaryl; wherein said phenyl or 5- or 6-membered heteroaryl substituent is independently unsubstituted, mono-, di-, or tri-substituted, wherein the substituents are independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxyl;

with the exception of the compound (1,1'-biphenyl)-2-yl-{(S)-2-[3-(3-pyridinyl)-1H-1,2,4-triazol-5-yl]-1-pyrrolidinyl}-methanone;

or a pharmaceutically acceptable salt thereof.

4. The compound according to claim 3; wherein the ring

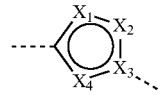

represents a group selected from the group consisting of [1,2,4]oxadiazol-3,5-diyl, [1,2,4]triazol-3,5-diyl, [1,2,4]triazol-1,3-diyl, 1H-pyrazol-3,5-diyl, imidazol-2,4-diyl, isoxazol-3,5-diyl, oxazol-2,4-diyl, oxazol-2,5-diyl, thiazol-2,4-diyl, [1,3,4]thiadiazol-2,5-diyl, and [1,3,4]oxadiazol-2,5-diyl;

or a pharmaceutically acceptable salt thereof.

5. The compound according to claim 4; wherein
Ar$^4$ is selected from the group consisting of unsubstituted triazolyl; unsubstituted pyrazolyl; unsubstituted oxazolyl; oxadiazolyl mono-substituted with methyl; unsubstituted pyridyl; unsubstituted pyrimidinyl; and unsubstituted or mono-substituted phenyl wherein the substituent is selected from the group consisting of (C$_{1-4}$)alkyl, (C$_{1-4}$)alkoxy, and halogen; and (R$^x$)$_m$ represents one or two optional substituents independently selected from (C$_{1-4}$)alkyl, (C$_{1-4}$)alkoxy, halogen, cyano, (C$_{1-3}$)fluoroalkyl, and (C$_{1-3}$)fluoroalkoxy;

or a pharmaceutically acceptable salt thereof.

6. The compound according to claim 4; wherein
Ar$^4$ is unsubstituted triazolyl; or unsubstituted pyrimidinyl; and (R$^x$)$_m$ represents one or two substituents independently selected from (C$_{1-4}$)alkyl, (C$_{1-4}$)alkoxy, halogen, cyano, (C$_{1-3}$)fluoroalkyl, and (C$_{1-3}$)fluoroalkoxy;

or a pharmaceutically acceptable salt thereof.

7. The compound according to claim 3; wherein the group

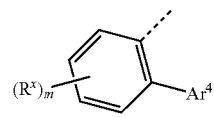

is a group independently selected from the following groups A) to D):

A)

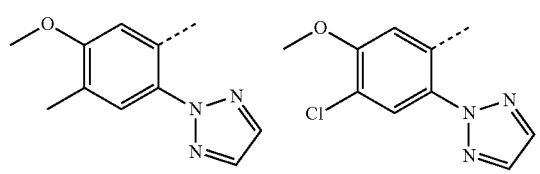

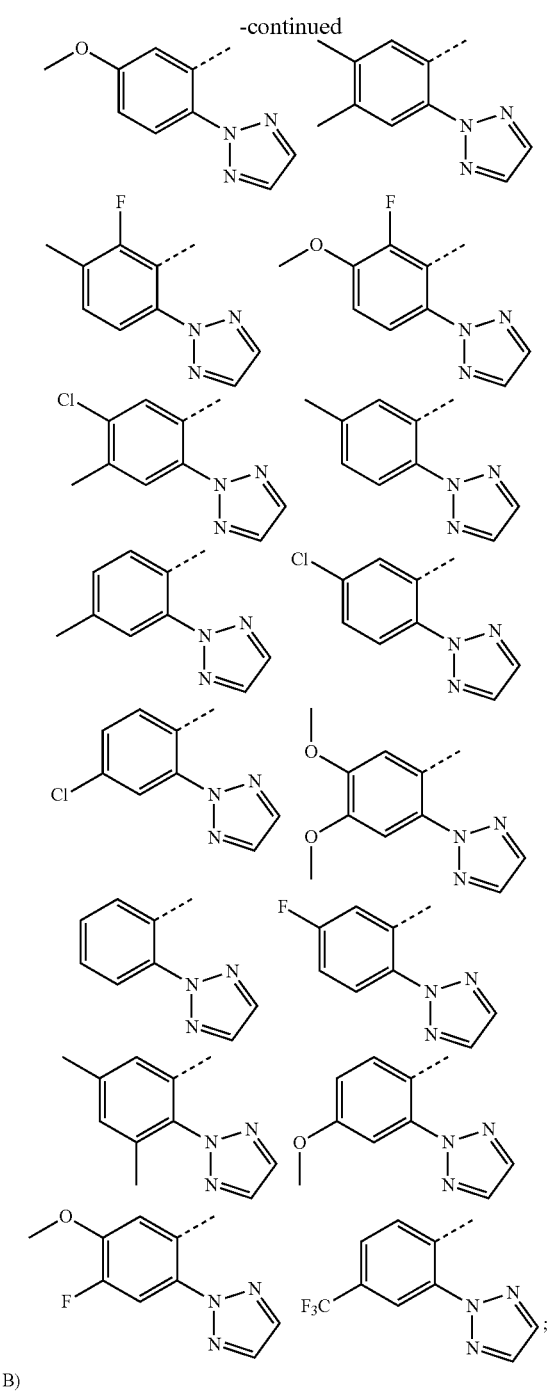
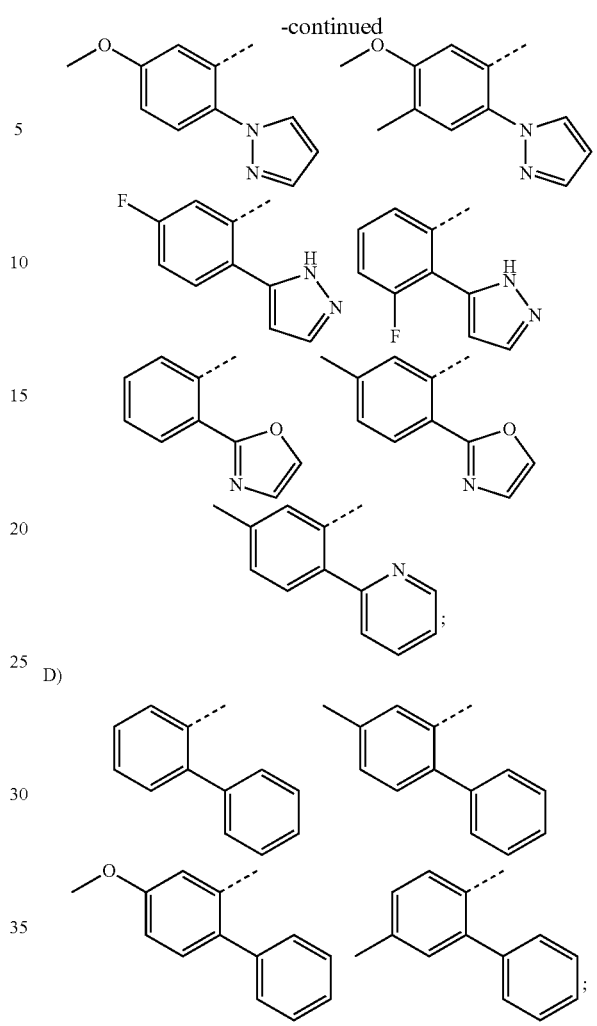

or a pharmaceutically acceptable salt thereof.

8. The compound according to claim 2; wherein the ring $A_2$ represents phenyl which is unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, $(C_{1-3})$fluoroalkoxy; hydroxy, $(C_{1-4})$alkoxy-$(C_{1-3})$alkyl, and hydroxy-$(C_{1-3})$alkyl; or a 2,3-dihydro-benzo[1,4]dioxinyl, a 2,3-dihydro-benzofuranyl, or a benzo[1,3]dioxolyl group which is optionally di-substituted with fluoro; or 6-membered heteroaryl; wherein said heteroaryl is independently unsubstituted, or mono-, or di-substituted; wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, $(C_{1-3})$fluoroalkoxy, and $(C_{3-6})$cycloalkyl-oxy-; or 8- to 10-membered heteroaryl; wherein said heteroaryl is independently unsubstituted, or mono-substituted; wherein the substituent is independently selected from the group consisting of $(C_{1-4})$alkyl, $(C_{1-4})$alkoxy, and —CO—$(C_{1-4})$alkyl;

or a pharmaceutically acceptable salt thereof.

9. The compound according to claim 2; wherein ring $A_2$ represents phenyl which is unsubstituted, or mono-, di-, or tri-substituted; wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, $(C_{1-3})$fluoroalkoxy; hydroxy, $(C_{1-4})$alkoxy-$(C_{1-3})$ alkyl, and hydroxy- $(C_{1-3})$alkyl; or 2,3-dihydro-benzo[1,4]dioxin-5-yl, 2,3-dihydro-benzofuran-7-yl, benzo[1,3]dioxol-4-yl, benzo[1,3]dioxol-5-yl, or 2,2-difluoro-benzo[1,3]dioxol-5-yl; or 5- or 6-membered heteroaryl selected from pyridyl, pyrazolyl, and pyrazinyl; wherein said heteroaryl is independently mono-, or di-substituted; wherein the substituents are independently selected from the group consisting of $(C_{1-4})$alkyl, $(C_{1-4})$alkoxy, halogen, $(C_{1-3})$ fluoroalkoxy, and $(C_{3-6})$cycloalkyl-oxy-; or 8- to 10-membered heteroaryl selected from indolyl, pyrrolopyridyl, imidazothiazolyl, and indazolyl; wherein said heteroaryl is independently unsubstituted, or mono-substituted; wherein the substituent is independently selected from the group consisting of $(C_{1-4})$ alkyl, $(C_{1-4})$alkoxy, and —CO—$(C_{1-4})$alkyl;

or a pharmaceutically acceptable salt thereof.

10. The compound according to claim 1; wherein the group $A_3$-$A_2$ represents a group
independently selected from the following groups A) to H):

A): [1,2,4]oxadiazol-3,5-diyl groups selected from the groups:

A1)

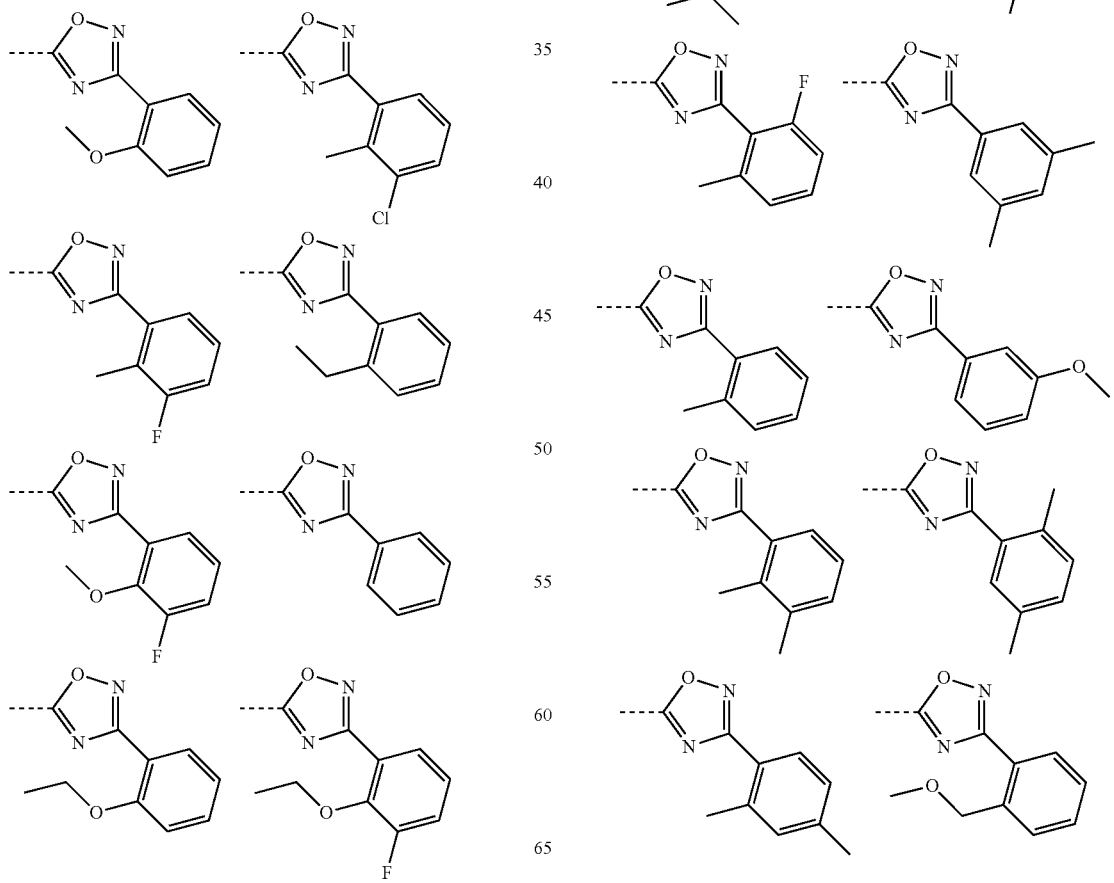

-continued
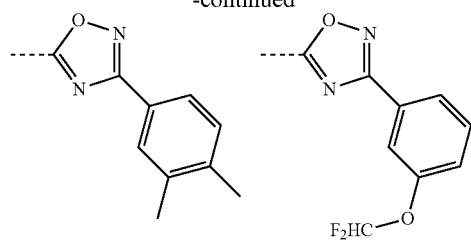
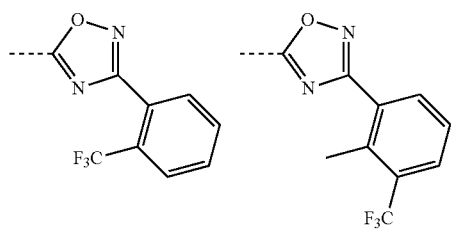
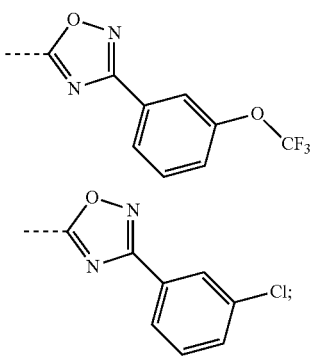
A2)
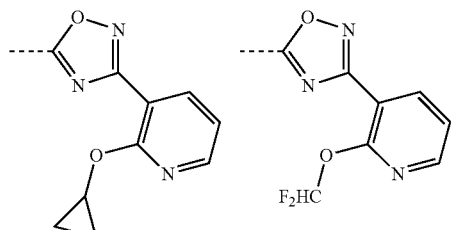
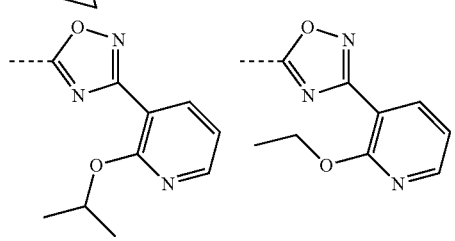
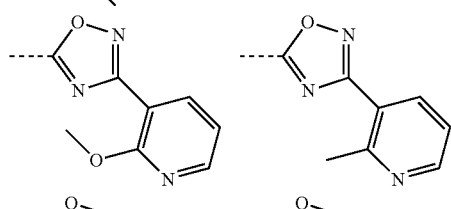
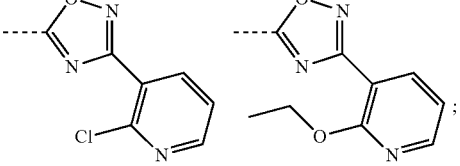
-continued
A3)
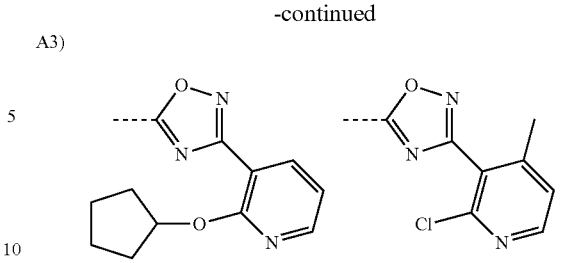
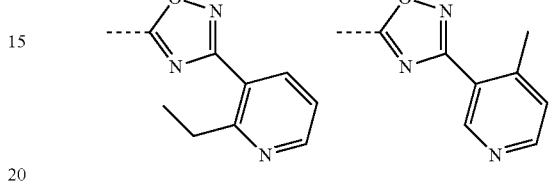
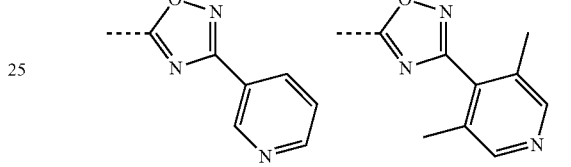
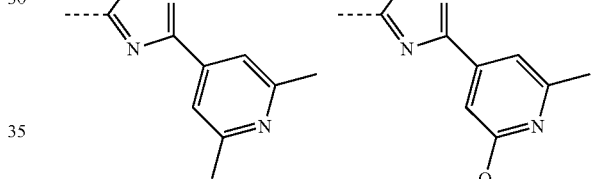
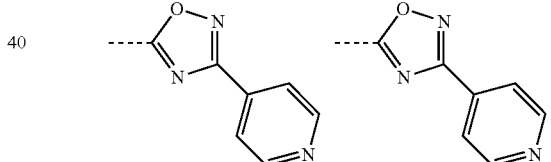
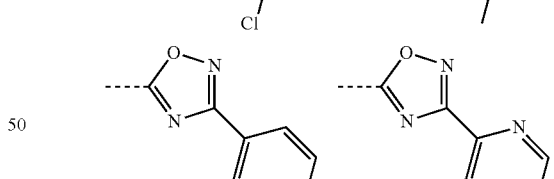
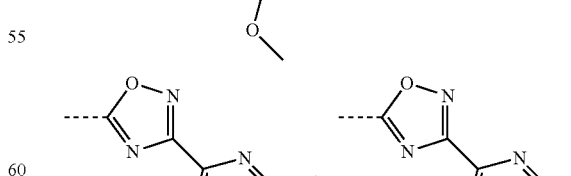

B): [1,2,4]oxadiazol-3,5-diyl groups selected from the groups:

B1)

-continued
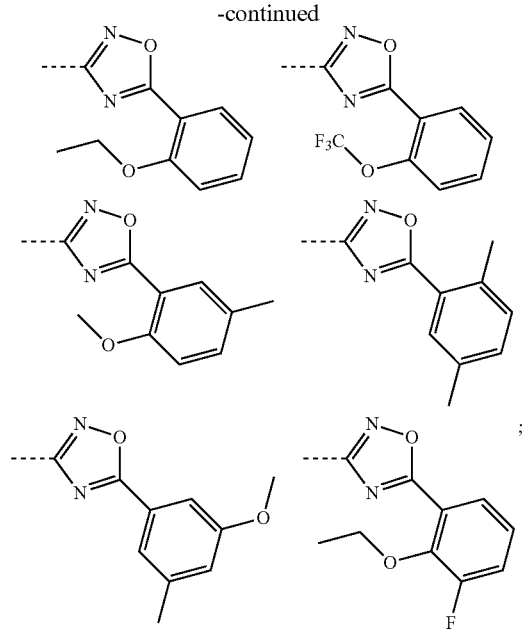
B2)
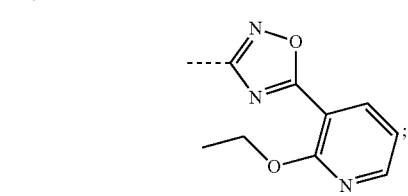
B3)
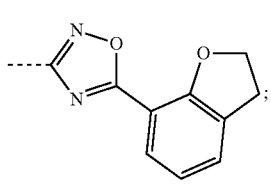
C): oxazol-2,4-diyl groups selected from:
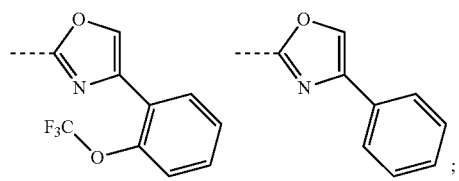
D): oxazol-2,5-diyl groups selected from:
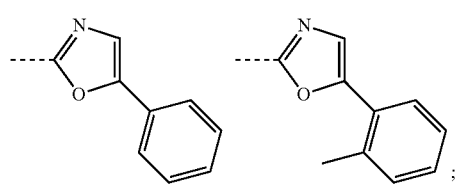
E): isoxazol-3,5-diyl groups selected from the groups:
E1)
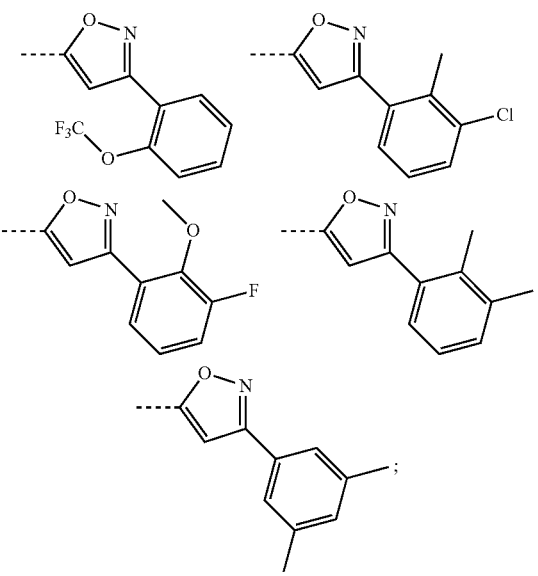
E2)
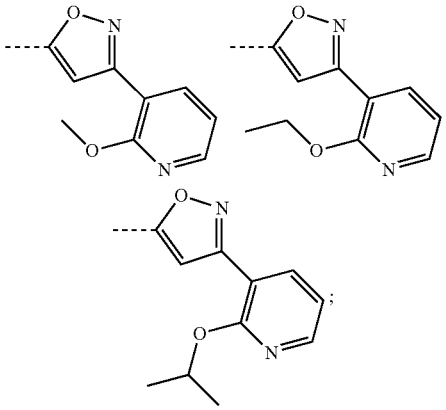
E3)
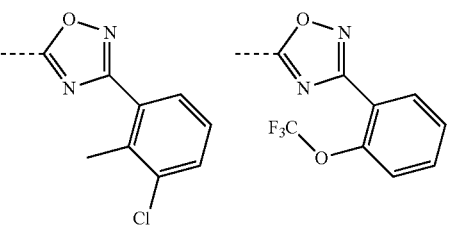
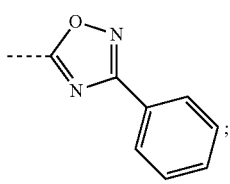
F): [1,2,4]triazol-3,5-diyl groups selected from the groups:

F1)
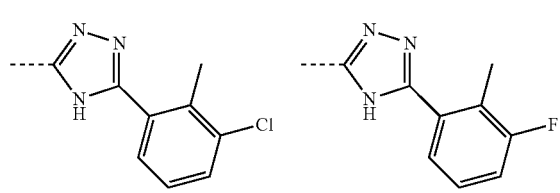
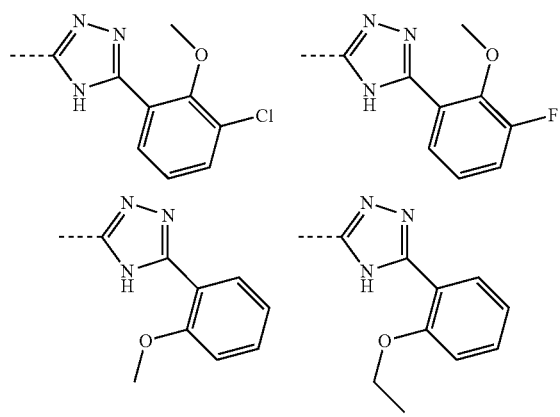
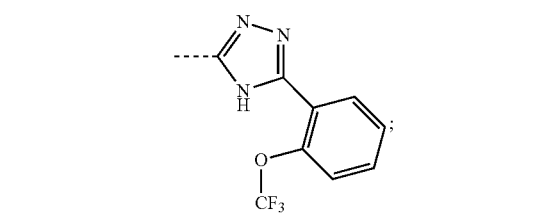
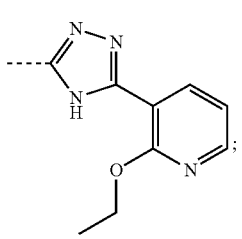
F2)
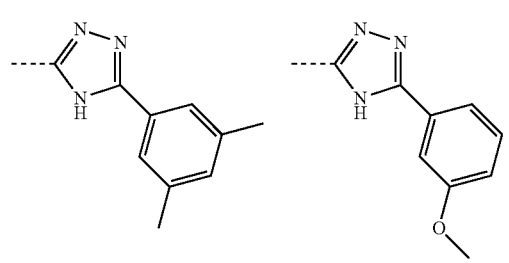
F3)
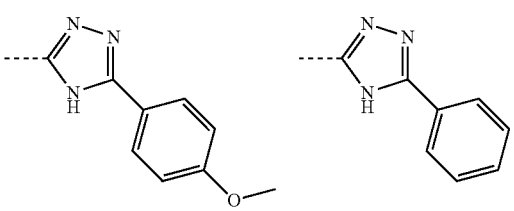
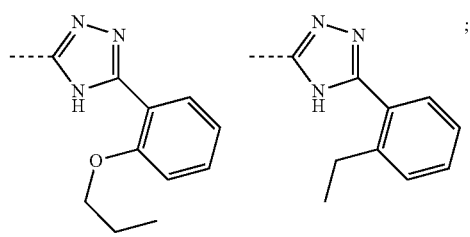
G): imidazol-2,4-diyl groups selected from the groups:
G1)
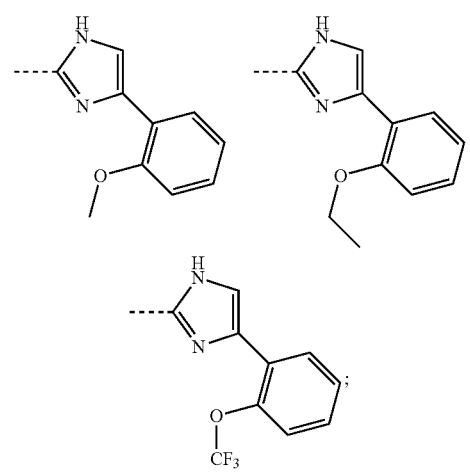
G2)
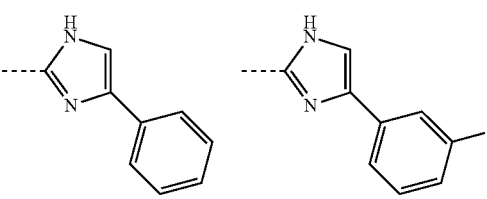
G3)
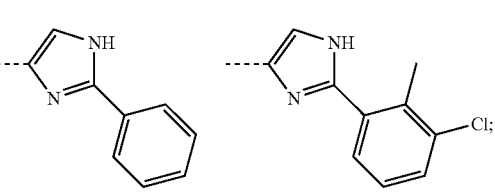

H): 1H-[1,2,4]triazol-1,3-diyl groups selected from:

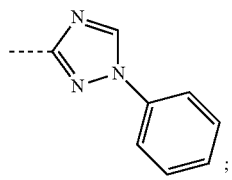

or a pharmaceutically acceptable salt thereof.

11. The compound according to claim 1 selected from the group consisting of:
{(S)-2-[3-(2-Cyclopropyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(1H-Indol-3-yl)-[1,2,4]oxadiazol-5-yl]-pyrrolidin-1-yl}-(5-methyl-2-[1,2,3]triazol-2-yl-phenyl)-methanone;
(5-Methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
{(S)-2-[3-(3-Chloro-2-methyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Ethyl-phenyl)-[1,2,4]oxadiazol-5-yl]-pyrrolidin-1-yl}-(5-methyl-2-[1,2,3]triazol-2-yl-phenyl)-methanone;
{(S)-2-[3-(3-Fluoro-2-methoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(2,3-Dihydro-benzo[,4]dioxin-5-yl)-[1,2,4]oxadiazol-5-yl]-pyrrolidin-1-yl}-(5-methyl-2-[1,2,3]triazol-2-yl-phenyl)-methanone;
{(S)-2-[3-(2-Ethoxy-phenyl)-[1,2,4]oxadiazol-5-yl]-pyrrolidin-1-yl}-(5-methyl-2-[1,2,3]triazol-2-yl-phenyl)-methanone;
{(S)-2-[3-(2-Ethoxy-pyridin-3-yl)-[1,2,4]oxadiazol-5-yl]-pyrrolidin-1-yl}-(5-methyl-2-[1,2,3]triazol-2-yl-phenyl)-methanone;
{(S)-2-[3-(1H-Indol-7-yl)-[1,2,4]oxadiazol-5-yl]-pyrrolidin-1-yl}-(5-methyl-2-[1,2,3]triazol-2-yl-phenyl)-methanone;
{(S)-2-[3-(1-Methyl-1H-pyrrolo [2,3-b]pyridin-3-yl)-[1,2,4]oxadiazol-5-yl]-pyrrolidin-1-yl}-(5-methyl-2-[1,2,3]triazol-2-yl-phenyl)-methanone;
{(S)-2-[3-(2-Ethoxy-3-fluoro-phenyl)-[1,2,4]oxadiazol-5-yl]-pyrrolidin-1-yl}-(5-methyl-2-[1,2,3]triazol-2-yl-phenyl)-methanone;
{(S)-2-[3-(1-Methyl-1H-indol-3-yl)-[1,2,4]oxadiazol-5-yl]-pyrrolidin-1-yl}-(5-methyl-2-[1,2,3]triazol-2-yl-phenyl)-methanone;
{(S)-2-[3-(2-Isopropoxy-pyridin-3-yl)-[1,2,4]oxadiazol-5-yl]-pyrrolidin-1-yl}-(5-methyl-2-[1,2,3]triazol-2-yl-phenyl)-methanone;
1-(3-{5-[(S)-1-(5-Methyl-2-[1,2,3]triazol-2-yl-benzoyl)-pyrrolidin-2-yl]-[1,2,4]oxadiazol-3-yl}-indol-1-yl)-ethanone;
{(S)-2-[3-(3-Chloro-2-methyl-phenyl)-[1,2,4]oxadiazol-5-yl]-pyrrolidin-1-yl}-(4-methyl-biphenyl-2-yl)-methanone;
{(S)-2-[3-(3-Chloro-2-methyl-phenyl)-[1,2,4]oxadiazol-5-yl]-pyrrolidin-1-yl}-(4,5-dimethyl-2-[1,2,3]triazol-2-yl-phenyl)-methanone;
{(S)-2-[3-(3-Chloro-2-methyl-phenyl)-[1,2,4]oxadiazol-5-yl]-pyrrolidin-1-yl}-(4-methoxy-biphenyl-2-yl)-methanone;
{(S)-2-[3-(3-Chloro-2-methyl-phenyl)-[1,2,4]oxadiazol-5-yl]-pyrrolidin-1-yl}-(5-methoxy-4-methyl-2-[1,2,3]triazol-2-yl-phenyl)-methanone;
{(S)-2-[3-(3-Chloro-2-methyl-phenyl)-[1,2,4]oxadiazol-5-yl]-pyrrolidin-1-yl}-(5-methyl-2-oxazol-2-yl-phenyl)-methanone;
(4-Methyl-biphenyl-2-yl)-{(S)-2-[3-(2-trifluoromethoxy-phenyl)-[1,2,4]oxadiazol-5-yl]-pyrrolidin-1-yl}-methanone;
(5-Methyl-2-pyrazol-1-yl-phenyl)-{(S)-2-[3-(2-trifluoromethoxy-phenyl)-[1,2,4]oxadiazol-5-yl]-pyrrolidin-1-yl}-methanone;
(5-Methyl-2-pyridin-2-yl-phenyl)-{(S)-2-[3-(2-trifluoromethoxy-phenyl)-[1,2,4]oxadiazol-5-yl]-pyrrolidin-1-yl}-methanone;
(5-Chloro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
(2-Fluoro-3-methyl-6-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
(4,5-Dimethyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
(4-Methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
(5-Methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
(4-Methoxy-biphenyl-2-yl)-{(S)-2-[3-(2-trifluoromethoxy-phenyl)-[1,2,4]oxadiazol-5-yl]-pyrrolidin-1-yl}-methanone;
(5-Methoxy-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
(4,5-Dimethyl-2-pyrazol-1-yl-phenyl)-{(S)-2-[3-(2-trifluoromethoxy-phenyl)-[1,2,4]oxadiazol-5-yl]-pyrrolidin-1-yl}-methanone;
[3-Fluoro-2-(2H-pyrazol-3-yl)-phenyl]-{(S)-2-[3-(2-trifluoromethoxy-phenyl)-[1,2,4]oxadiazol-5-yl]-pyrrolidin-1-yl}-methanone;
(5-Methyl-2-oxazol-2-yl-phenyl)-{(S)-2-[3-(2-trifluoromethoxy-phenyl)-[1,2,4]oxadiazol-5-yl]-pyrrolidin-1-yl}-methanone;
{(S)-2-[3-(2-Difluoromethoxy-phenyl)-[1,2,4]oxadiazol-5-yl]-pyrrolidin-1-yl}-(4,5-dimethyl-2-[1,2,3]triazol-2-yl-phenyl)-methanone;
{(S)-2-[3-(2-Difluoromethoxy-phenyl)-[1,2,4]oxadiazol-5-yl]-pyrrolidin-1-yl}-(5-methoxy-4-methyl-2-[1,2,3]triazol-2-yl-phenyl)-methanone;
(4,5-Dimethyl-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;
{(S)-2-[3-(3-Fluoro-2-methoxy-phenyl)-[1,2,4]oxadiazol-5-yl]-pyrrolidin-1-yl}-(5-methoxy-4-methyl-2-[1,2,3]triazol-2-yl-phenyl)-methanone;
(5-Chloro-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;
(4,5-Dimethyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-pyridin-3-yl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(2-Ethoxy-pyridin-3-yl)-[1,2,4]oxadiazol-5-yl]-pyrrolidin-1-yl}-(5-methyl-2-pyridin-2-yl-phenyl)-methanone;

{(S)-2-[3-(2-Ethoxy-pyridin-3-yl)-[1,2,4]oxadiazol-5-yl]-pyrrolidin-1-yl}-(5-methyl-2-oxazol-2-yl-phenyl)-methanone;

(4,5-Dimethyl-2-[1,2,3]triazol-2-yl-phenyl)-{(S)-2-[3-(2-methoxy-phenyl)-[1,2,4]oxadiazol-5-yl]-pyrrolidin-1-yl}-methanone;

(4,5-Dimethyl-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

(5-Chloro-2-[1,2,3]triazol-2-yl-phenyl)-{(S)-2-[3-(2-ethoxy-phenyl)-[1,2,4]oxadiazol-5-yl]-pyrrolidin-1-yl}-methanone;

{(S)-2-[3-(2-Ethoxy-phenyl)-[1,2,4]oxadiazol-5-yl]-pyrrolidin-1-yl}-(4-methyl-2-[1,2,3]triazol-2-yl-phenyl)-methanone;

(4,5-Dimethyl-2-[1,2,3]triazol-2-yl-phenyl)-{(S)-2-[3-(2-ethoxy-phenyl)-[1,2,4]oxadiazol-5-yl]-pyrrolidin-1-yl}-methanone;

{(S)-2-[3-(2-Ethoxy-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(2-Ethoxy-phenyl)-[1,2,4]oxadiazol-5-yl]-pyrrolidin-1-yl}-(5-methoxy-2-[1,2,3]triazol-2-yl-phenyl)-methanone;

(5-Methyl-2-[1,2,3]triazol-2-yl-phenyl)-{(S)-2-[5-(2-trifluoromethoxy-phenyl)-[1 1,2,4]oxadiazol-3-yl]-pyrrolidin-1-yl}-methanone;

(4,5-Dimethyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

{(S)-2-[5-(2-Ethoxy-phenyl)-[1,2,4]oxadiazol-3-yl]-pyrrolidin-1-yl}-(5-methyl-2-[1,2,3]triazol-2-yl-phenyl)-methanone;

(5-Methoxy-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

{(S)-2-[5-(2-Ethoxy-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(2-Ethoxy-pyridin-3-yl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(3-Chloro-2-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2-Ethoxy-3-fluoro-phenyl)-[1,2,4]oxadiazol-3-yl]-pyrrolidin-1-yl}-(5-methyl-2-[1,2,3]triazol-2-yl-phenyl)-methanone;

{(S)-2-[5-(3-Chloro-2-methyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(3-Chloro-2-methyl-phenyl)-[1,2,4]oxadiazol-3-yl]-pyrrolidin-1-yl}-(4,5-dimethyl-2-[1,2,3]triazol-2-yl-phenyl)-methanone;

{(S)-2-[5-(2-Ethoxy-3-fluoro-phenyl)-[1,2,4]oxadiazol-3-yl]-pyrrolidin-1-yl}-(5-methoxy-4-methyl-2-[1,2,3]triazol-2-yl-phenyl)-methanone;

(4,5-Dimethyl-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

{(S)-2-[5-(2-Ethoxy-3-fluoro-phenyl)-[1,2,4]oxadiazol-3-yl]-pyrrolidin-1-yl}-(5-methoxy-2-[1,2,3]triazol-2-yl-phenyl)-methanone;

(5-Chloro-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

{(S)-2-[5-(2-Ethoxy-3-fluoro-phenyl)-[1,2,4]oxadiazol-3-yl]-pyrrolidin-1-yl}-(4-methyl-2-[1,2,3]triazol-2-yl-phenyl)-methanone;

(4-Chloro-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

{(S)-2-[5-(2-Ethoxy-pyridin-3-yl)-[1,2,4]oxadiazol-3-yl]-pyrrolidin-1-yl}-(5-methyl-2-[1,2,3]triazol-2-yl-phenyl)-methanone;

(4,5-Dimethyl-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(3-Fluoro-2-methoxy-phenyl)-[1,2,4]oxadiazol-3-yl]-pyrrolidin-1-yl}-(5-methyl-2-[1,2,3]triazol-2-yl-phenyl)-methanone;

{(S)-2-[5-(3-Fluoro-2-methoxy-phenyl)-[1,2,4]oxadiazol-3-yl]-pyrrolidin-1-yl}-(4-methyl-2-[1,2,3]triazol-2-yl-phenyl)-methanone;

(4,5-Dimethyl-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

{(S)-2-[5-(3-Fluoro-2-methoxy-phenyl)-[1,2,4]oxadiazol-3-yl]-pyrrolidin-1-yl}-(5-methoxy-4-methyl-2-[1,2,3]triazol-2-yl-phenyl)-methanone;

(5-Chloro-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

{(S)-2-[3-(3-Chloro-2-methyl-phenyl)-isoxazol-5-yl]-pyrrolidin-1-yl}-(5-methyl-2-[1,2,3]triazol-2-yl-phenyl)-methanone;

(5-Methyl-2-[1,2,3]triazol-2-yl-phenyl)-{(S)-2-[3-(2-trifluoromethoxy-phenyl)-isoxazol-5-yl]-pyrrolidin-1-yl}-methanone;

(5-Methyl-2-[1,2,3]triazol-2-yl-phenyl)-{(S)-2-[4-(2-trifluoromethoxy-phenyl)-oxazol-2-yl]-pyrrolidin-1-yl}-methanone;

{(S)-2-[5-(3-Chloro-2-methyl-phenyl)-[1,3,4]oxadiazol-2-yl]-pyrrolidin-1-yl}-(4,5-dimethyl-2-[1,2,3]triazol-2-yl-phenyl)-methanone;

(4-Chloro-5-methoxy-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-3-fluoro-phenyl)-[1,2,4]oxadiazol-5-yl]-pyrrolidin-1-yl}-(4-methyl-2-[1,2,3]triazol-2-yl-phenyl)-methanone;

(4,5-Dimethyl-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone;

{(S)-2-[3-(2-Ethoxy-3-fluoro-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-chloro-4-methyl-2-[1,2,3]triazol-2-yl-phenyl)-methanone;

(4-Chloro-5-methoxy-2-[1,2,3]triazol-2-yl-phenyl)-{(S)-2-[5-(3-chloro-2-methyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(3-Chloro-2-methyl-phenyl)-[1,2,4]oxadiazol-3-yl]-pyrrolidin-1-yl}-(5-chloro-4-methyl-2-[1,2,3]triazol-2-yl-phenyl)-methanone;

(4-Methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(4-Chloro-2-[1,2,3]triazol-2-yl-phenyl)-{(S)-2-[5-(3-fluoro-2-methoxy-phenyl)-[1,2,4]oxadiazol-3-yl]-pyrrolidin-1-yl}-methanone;

{(S)-2-[5-(2-Ethoxy-phenyl)-4H-[1,2,4]triazol-3-yl]-pyrrolidin-1-yl}-(5-methyl-2-[1,2,3]triazol-2-yl-phenyl)-methanone;

{(S)-2-[5-(3-Fluoro-2-methoxy-phenyl)-4H-[1,2,4]triazol-3-yl]-pyrrolidin-1-yl}-(5-methyl-2-[1,2,3]triazol-2-yl-phenyl)-methanone;

{(S)-2-[5-(2-Ethyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2-Ethyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(2-ethyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2-ethyl-phenyl)-[1,2,4]oxadiazol-3-yl]-pyrrolidin-1-yl}-methanone;

{(S)-2-[5-(2,3-Dimethyl-phenyl)-[1,2,4]oxadiazol-3-yl]-pyrrolidin-1-yl}-(4,5-dimethyl-2-[1,2,3]triazol-2-yl-phenyl)-methanone;

(4,5-Dimethyl-2-[1,2,3]triazol-2-yl-phenyl)-{(S)-2-[5-(2-ethyl-phenyl)-[1,2,4]oxadiazol-3-yl]-pyrrolidin-1-yl}-methanone;

{(S)-2-[5-(2,3-Dimethyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(2-Ethyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(2,5-Dimethyl-phenyl)-[1,2,4]oxadiazol-3-yl]-pyrrolidin-1-yl}-(5-methoxy-4-methyl-2-[1,2,3]triazol-2-yl-phenyl)-methanone;

(4-Chloro-5-methoxy-2-[1,2,3]triazol-2-yl-phenyl)-{(S)-2-[5-(2,3-dimethyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2-ethyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(2,5-dimethyl-phenyl)-[1,2,4]oxadiazol-3-yl]-pyrrolidin-1-yl}-methanone;

{(S)-2-[5-(3-Methoxy-5-methyl-phenyl)-[1,2,4]oxadiazol-3-yl]-pyrrolidin-1-yl}-(5-methyl-2-[1,2,3]triazol-2-yl-phenyl)-methanone;

(4,5-Dimethyl-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

{(S)-2-[5-(3-Methoxy-5-methyl-phenyl)-[1,2,4]oxadiazol-3-yl]-pyrrolidin-1-yl}-(5-methoxy-4-methyl-2-[1,2,3]triazol-2-yl-phenyl)-methanone;

(4-Chloro-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(2-Ethoxy-pyridin-3-yl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(4-chloro-5-methoxy-2-[1,2,3]triazol-2-yl-phenyl)-methanone;

{(S)-2-[5-(3-Chloro-2-methoxy-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(3-Chloro-2-methoxy-phenyl)-[1,2,4]oxadiazol-3-yl]-pyrrolidin-1-yl}-(4-chloro-2-[1,2,3]triazol-2-yl-phenyl)-methanone;

(4-Chloro-5-methoxy-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(5-methyl-2-[1,2,3]triazol-2-yl-phenyl)-methanone;

(4-Chloro-5-methoxy-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(4-methyl-2-[1,2,3]triazol-2-yl-phenyl)-methanone;

{(S)-2-[5-(3-Chloro-2-methoxy-phenyl)-[1,2,4]oxadiazol-3-yl]-pyrrolidin-1-yl}-(4,5-dimethyl-2-[1,2,3]triazol-2-yl-phenyl)-methanone;

(4,5-Dimethyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(5-Methoxy-4-methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(4-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(4-Chloro-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(4-Chloro-5-methoxy-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(2-methoxy-phenyl)-4H-[1,2,4]triazol-3-yl]-pyrrolidin-1-yl}-methanone;

(4-Chloro-5-methoxy-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(4,5-Dimethyl-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(4-Chloro-2-[1,2,3]triazol-2-yl-phenyl)-{(S)-2-[5-(3-fluoro-2-methoxy-phenyl)-4H-[1,2,4]triazol-3-yl]-pyrrolidin-1-yl}-methanone;

(4-Chloro-5-methoxy-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone;

{(S)-2-[5-(2-Ethoxy-pyridin-3-yl)-4H-[1,2,4]triazol-3-yl]-pyrrolidin-1-yl}-(5-methoxy-4-methyl-2-[1,2,3]triazol-2-yl-phenyl)-methanone;

(4,5-Dimethyl-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone;

(4-Chloro-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone;

(5-Chloro-4-methyl-2-[1,2,3]triazol-2-yl-phenyl)-{(S)-2-[5-(2-ethoxy-pyridin-3-yl)-4H-[1,2,4]triazol-3-yl]-pyrrolidin-1-yl}-methanone;

{(S)-2-[5-(3-Chloro-2-methoxy-phenyl)-4H-[1,2,4]triazol-3-yl]-pyrrolidin-1-yl}-(4-chloro-5-methoxy-2-[1,2,3]triazol-2-yl-phenyl)-methanone;

{(S)-2-[5-(3-Chloro-2-methoxy-phenyl)-4H-[1,2,4]triazol-3-yl]-pyrrolidin-1-yl}-(4,5-dimethyl-2-[1,2,3]triazol-2-yl-phenyl)-methanone;

(5-Chloro-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(5-Chloro-4-methyl-2-[1,2,3]triazol-2-yl-phenyl)-{(S)-2-[3-(2-ethoxy-3-fluoro-phenyl)-[1,2,4]oxadiazol-5-yl]-pyrrolidin-1-yl}-methanone;

(5-Chloro-4-methyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

(5-Chloro-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(5-Chloro-4-methyl-2-[1,2,3]triazol-2-yl-phenyl)-{(S)-2-[5-(2-ethoxy-3-fluoro-phenyl)-[1,2,4]oxadiazol-3-yl]-pyrrolidin-1-yl}-methanone;

(5-Chloro-4-methyl-2-[1,2,3]triazol-2-yl-phenyl)-{(S)-2-[5-(2-ethoxy-pyridin-3-yl)-[1,2,4]oxadiazol-3-yl]-pyrrolidin-1-yl}-methanone;

{(S)-2-[5-(2-Methoxy-phenyl)-1H-imidazol-2-yl]-pyrrolidin-1-yl}-(5-methyl-2-[1,2,3]triazol-2-yl-phenyl)-methanone;

{(S)-2-[5-(2-Ethoxy-phenyl)-1H-imidazol-2-yl]-pyrrolidin-1-yl}-(5-methyl-2-[1,2,3]triazol-2-yl-phenyl)-methanone;

(5-Methyl-2-[1,2,3]triazol-2-yl-phenyl)-{(S)-2-[5-(2-trifluoromethoxy-phenyl)-1H-imidazol-2-yl]-pyrrolidin-1-yl}-methanone;

(4-Methyl-2-[1,2,3]triazol-2-yl-phenyl)-{(S)-2-[5-(2-trifluoromethoxy-phenyl)-1H-imidazol-2-yl]-pyrrolidin-1-yl}-methanone;

{(S)-2-[5-(2-Ethoxy-phenyl)-1H-imidazol-2-yl]-pyrrolidin-1-yl}-(4-methyl-2-[1,2,3]triazol-2-yl-phenyl)-methanone;

{(S)-2-[5-(3-Chloro-2-methyl-phenyl)-isoxazol-3-yl]-pyrrolidin-1-yl}-(5-methyl-2-[1,2,3]triazol-2-yl-phenyl)-methanone;

{(S)-2-[5-(3-Chloro-2-methyl-phenyl)-isoxazol-3-yl]-pyrrolidin-1-yl}-(5-methoxy-4-methyl-2-[1,2,3]triazol-2-yl-phenyl)-methanone;

(5-Methyl-2-[1,2,3]triazol-2-yl-phenyl)-{(S)-2-[5-(2-trifluoromethoxy-phenyl)-isoxazol-3-yl]-pyrrolidin-1-yl}-methanone;

(4-Methyl-2-[1,2,3]triazol-2-yl-phenyl)-{(S)-2-[5-(2-trifluoromethoxy-phenyl)-isoxazol-3-yl]-pyrrolidin-1-yl}-methanone;

(5-Methoxy-4-methyl-2-[1,2,3]triazol-2-yl-phenyl)-{(S)-2-[5-(2-trifluoromethoxy-phenyl)-isoxazol-3-yl]-pyrrolidin-1-yl}-methanone;

(5-Methyl-2-[1,2,3]triazol-2-yl-phenyl)-[(S)-2-(3-phenyl-[,2,4]oxadiazol-5-yl)-pyrrolidin-1-yl]-methanone;

(5-Methyl-2-[1,2,3]triazol-2-yl-phenyl)-[(S)-2-(3-m-tolyl-[1,2,4]oxadiazol-5-yl)-pyrrolidin-1-yl]-methanone;

{(S)-2-[3-(3-Methoxy-phenyl)-[1,2,4]oxadiazol-5-yl]-pyrrolidin-1-yl}-(5-methyl-2-[1,2,3]triazol-2-yl-phenyl)-methanone;

{(S)-2-[3-(2-Methoxy-phenyl)-[1,2,4]oxadiazol-5-yl]-pyrrolidin-1-yl}-(5-methyl-2-[1,2,3]triazol-2-yl-phenyl)-methanone;

{(S)-2-[3-(3,5-Dimethyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(2,3-Dimethyl-phenyl)-[1,2,4]oxadiazol-5-yl]-pyrrolidin-1-yl}-(5-methyl-2-[1,2,3]triazol-2-yl-phenyl)-methanone;

(5-Methyl-2-[1,2,3]triazol-2-yl-phenyl)-[(S)-2-(3-o-tolyl-[1,2,4]oxadiazol-5-yl)-pyrrolidin-1-yl]-methanone;

{(S)-2-[3-(3-Chloro-phenyl)-[1,2,4]oxadiazol-5-yl]-pyrrolidin-1-yl}-(5-methyl-2-[1,2,3]triazol-2-yl-phenyl)-methanone;

{(S)-2-[3-(2-Chloro-phenyl)-[1,2,4]oxadiazol-5-yl]-pyrrolidin-1-yl}-(5-methyl-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(2-Chloro-3-methyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(2-Chloro-pyridin-3-yl)-[1,2,4]oxadiazol-5-yl]-pyrrolidin-1-yl}-(5-methyl-2-[1,2,3]triazol-2-yl-phenyl)-methanone;

(5-Methyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone;

{(S)-2-[3-(2-Difluoromethoxy-phenyl)-[1,2,4]oxadiazol-5-yl]-pyrrolidin-1-yl}-(5-methyl-2-[1,2,3]triazol-2-yl-phenyl)-methanone;

{(S)-2-[3-(3-Difluoromethoxy-phenyl)-[1,2,4]oxadiazol-5-yl]-pyrrolidin-1-yl}-(5-methyl-2-[1,2,3]triazol-2-yl-phenyl)-methanone;

{(S)-2-[3-(2-Methoxymethyl-phenyl)-[1,2,4]oxadiazol-5-yl]-pyrrolidin-1-yl}-(5-methyl-2-[1,2,3]triazol-2-yl-phenyl)-methanone;

[(S)-2-(3-Benzo[1,3]dioxol-4-yl-[1,2,4]oxadiazol-5-yl)-pyrrolidin-1-yl]-(5-methyl-2-[1,2,3]triazol-2-yl-phenyl)-methanone;

(5-Methyl-2-[1,2,3]triazol-2-yl-phenyl)-{(S)-2-[3-(2-methyl-3-trifluoromethyl-phenyl)-[1,2,4]oxadiazol-5-yl]-pyrrolidin-1-yl}-methanone;

{(S)-2-[3-(3-Ethoxy-pyridin-4-yl)-[1,2,4]oxadiazol-5-yl]-pyrrolidin-1-yl}-(5-methyl-2-[1,2,3]triazol-2-yl-phenyl)-methanone;

{(S)-2-[3-(2,3-Dimethoxy-phenyl)-[1,2,4]oxadiazol-5-yl]-pyrrolidin-1-yl}-(5-methyl-2-[1,2,3]triazol-2-yl-phenyl)-methanone;

{(S)-2-[3-(1-Methyl-1H-indol-4-yl)-[1,2,4]oxadiazol-5-yl]-pyrrolidin-1-yl}-(5-methyl-2-[1,2,3]triazol-2-yl-phenyl)-methanone;

{(S)-2-[3-(2-Fluoro-6-methyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(1-Methyl-1H-indol-7-yl)-[1,2,4]oxadiazol-5-yl]-pyrrolidin-1-yl}-(5-methyl-2-[1,2,3]triazol-2-yl-phenyl)-methanone;

{(S)-2-[3-(2-Methyl-pyridin-3-yl)-[1,2,4]oxadiazol-5-yl]-pyrrolidin-1-yl}-(5-methyl-2-[1,2,3]triazol-2-yl-phenyl)-methanone;

{(S)-2-[3-(2-Difluoromethoxy-pyridin-3-yl)-[1,2,4]oxadiazol-5-yl]-pyrrolidin-1-yl}-(5-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-chloro-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(2-fluoro-3-methyl-6-[1,2,3]triazol-2-yl-phenyl)-methanone;

Biphenyl-2-yl-{(S)-2-[3-(3-chloro-2-methyl-phenyl)-[1,2,4]oxadiazol-5-yl]-pyrrolidin-1-yl}-methanone;

{(S)-2-[3-(3-Chloro-2-methyl-phenyl)-[1,2,4]oxadiazol-5-yl]-pyrrolidin-1-yl}-(5-methyl-2-pyrazol-1-yl-phenyl)-methanone;

{(S)-2-[3-(3-Chloro-2-methyl-phenyl)-[1,2,4]oxadiazol-5-yl]-pyrrolidin-1-yl}-(5-methyl-2-pyridin-2-yl-phenyl)-methanone;

{(S)-2-[3-(3-Chloro-2-methyl-phenyl)-[1,2,4]oxadiazol-5-yl]-pyrrolidin-1-yl}-(2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(4-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-methoxy-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-fluoro-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-methoxy-4-methyl-2-pyrazol-1-yl-phenyl)-methanone;

{(S)-2-[3-(3-Chloro-2-methyl-phenyl)-[1,2,4]oxadiazol-5-yl]-pyrrolidin-1-yl}-(5-methoxy-2-pyrazol-1-yl-phenyl)-methanone;

{(S)-2-[3-(3-Chloro-2-methyl-phenyl)-[1,2,4]oxadiazol-5-yl]-pyrrolidin-1-yl}-(4,5-dimethyl-2-pyrazol-1-yl-phenyl)-methanone;

{(S)-2-[3-(3-Chloro-2-methyl-phenyl)-[1,2,4]oxadiazol-5-yl]-pyrrolidin-1-yl}-[5-fluoro-2-(2H-pyrazol-3-yl)-phenyl]-methanone;

{(S)-2-[3-(3-Chloro-2-methyl-phenyl)-[1,2,4]oxadiazol-5-yl]-pyrrolidin-1-yl}-[3-fluoro-2-(2H-pyrazol-3-yl)-phenyl]-methanone;

{(S)-2-[3-(3-Chloro-2-methyl-phenyl)-[1,2,4]oxadiazol-5-yl]-pyrrolidin-1-yl}-(4-methoxy-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(3,5-dimethyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(2-oxazol-2-yl-phenyl)-methanone;

{(S)-2-[3-(3-Chloro-2-methyl-phenyl)-[1,2,4]oxadiazol-5-yl]-pyrrolidin-1-yl}-(4-chloro-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(4-fluoro-5-methoxy-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(4,5-dimethoxy-2-[1,2,3]triazol-2-yl-phenyl)-methanone;

Biphenyl-2-yl-{(S)-2-[3-(2-trifluoromethoxy-phenyl)-[1,2,4]oxadiazol-5-yl]-pyrrolidin-1-yl}-methanone;

(5-m-Tolyl-oxazol-4-yl)-{(S)-2-[3-(2-trifluoromethoxy-phenyl)-[1,2,4]oxadiazol-5-yl]-pyrrolidin-1-yl}-methanone;

(2-[1,2,3]Triazol-2-yl-phenyl)-{(S)-2-[3-(2-trifluoromethoxy-phenyl)-[1,2,4]oxadiazol-5-yl]-pyrrolidin-1-yl}-methanone;

(5-Fluoro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(5-Methoxy-4-methyl-2-pyrazol-1-yl-phenyl)-{(S)-2-[3-(2-trifluoromethoxy-phenyl)-[1,2,4]oxadiazol-5-yl]-pyrrolidin-1-yl}-methanone;

[5-Fluoro-2-(2H-pyrazol-3-yl)-phenyl]-{(S)-2-[3-(2-trifluoromethoxy-phenyl)-[1,2,4]oxadiazol-5-yl]-pyrrolidin-1-yl}-methanone;

(3,5-Dimethyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(2-Oxazol-2-yl-phenyl)-{(S)-2-[3-(2-trifluoromethoxy-phenyl)-[1,2,4]oxadiazol-5-yl]-pyrrolidin-1-yl}-methanone;

(4-Chloro-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

(4,5-Dimethyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone;

(5-Methoxy-4-methyl-2-[1,2,3]triazol-2-yl-phenyl)-{(S)-2-[3-(2-trifluoromethyl-phenyl)-[1,2,4]oxadiazol-5-yl]-pyrrolidin-1-yl}-methanone;

(5-Chloro-2-[1,2,3]triazol-2-yl-phenyl)-{(S)-2-[3-(2-difluoromethoxy-phenyl)-[1,2,4]oxadiazol-5-yl]-pyrrolidin-1-yl}-methanone;

{(S)-2-[3-(2-Difluoromethoxy-phenyl)-[1,2,4]oxadiazol-5-yl]-pyrrolidin-1-yl}-(4-methyl-2-[1,2,3]triazol-2-yl-phenyl)-methanone;

{(S)-2-[3-(2-Difluoromethoxy-phenyl)-[1,2,4]oxadiazol-5-yl]-pyrrolidin-1-yl}-[3-fluoro-2-(2H-pyrazol-3-yl)-phenyl]-methanone;

{(S)-2-[3-(2-Difluoromethoxy-phenyl)-[1,2,4]oxadiazol-5-yl]-pyrrolidin-1-yl}-(5-methyl-2-pyridin-2-yl-phenyl)-methanone;

(3,5-Dimethyl-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(2-[1,2,3]triazol-2-yl-phenyl)-methanone;

(5-Chloro-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(4-methyl-2-[1,2,3]triazol-2-yl-phenyl)-methanone;

{(S)-2-[3-(3-Fluoro-2-methoxy-phenyl)-[1,2,4]oxadiazol-5-yl]-pyrrolidin-1-yl}-(5-methoxy-2-[1,2,3]triazol-2-yl-phenyl)-methanone;

{(S)-2-[3-(3-Fluoro-2-methoxy-phenyl)-[1,2,4]oxadiazol-5-yl]-pyrrolidin-1-yl}-(5-fluoro-2-[1,2,3]triazol-2-yl-phenyl)-methanone;

{(S)-2-[3-(3-Fluoro-2-methoxy-phenyl)-[1,2,4]oxadiazol-5-yl]-pyrrolidin-1-yl}-[3-fluoro-2-(2H-pyrazol-3-yl)-phenyl]-methanone;

{(S)-2-[3-(3-Fluoro-2-methoxy-phenyl)-[1,2,4]oxadiazol-5-yl]-pyrrolidin-1-yl}-(5-methyl-2-pyridin-2-yl-phenyl)-methanone;

(4-Chloro-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(2-[1,2,3]triazol-2-yl-4-trifluoromethyl-phenyl)-methanone;

{(S)-2-[3-(3-Fluoro-2-methoxy-phenyl)-[1,2,4]oxadiazol-5-yl]-pyrrolidin-1-yl}-(4-fluoro-5-methoxy-2-[1,2,3]triazol-2-yl-phenyl)-methanone;

(4,5-Dimethoxy-2-[1,2,3]triazol-2-yl-phenyl)-{(S)-2-[3-(3-fluoro-2-methoxy-phenyl)-[1,2,4]oxadiazol-5-yl]-pyrrolidin-1-yl}-methanone;

(3,5-Dimethyl-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-pyridin-3-yl)-[1,2,4]oxadiazol-5-yl]-pyrrolidin-1-yl}-(4-methyl-2-[1,2,3]triazol-2-yl-phenyl)-methanone;

{(S)-2-[3-(2-Ethoxy-pyridin-3-yl)-[1,2,4]oxadiazol-5-yl]-pyrrolidin-1-yl}-(6-methyl-3-[1,2,3]triazol-2-yl-pyridin-2-yl)-methanone;

{(S)-2-[3-(2-Ethoxy-pyridin-3-yl)-[1,2,4]oxadiazol-5-yl]-pyrrolidin-1-yl}-[3-fluoro-2-(2H-pyrazol-3-yl)-phenyl]-methanone;

{(S)-2-[3-(2-Ethoxy-pyridin-3-yl)-[1,2,4]oxadiazol-5-yl]-pyrrolidin-1-yl}-(5-methoxy-2-[1,2,3]triazol-2-yl-phenyl)-methanone;

(4-Chloro-2-[1,2,3]triazol-2-yl-phenyl)-{(S)-2-[3-(2-ethoxy-pyridin-3-yl)-[1,2,4]oxadiazol-5-yl]-pyrrolidin-1-yl}-methanone;

{(S)-2-[3-(2-Ethoxy-pyridin-3-yl)-[1,2,4]oxadiazol-5-yl]-pyrrolidin-1-yl}-(4-fluoro-5-methoxy-2-[1,2,3]triazol-2-yl-phenyl)-methanone;

(5-Methoxy-4-methyl-2-[1,2,3]triazol-2-yl-phenyl)-{(S)-2-[3-(2-methoxy-phenyl)-[1,2,4]oxadiazol-5-yl]-pyrrolidin-1-yl}-methanone;

{(S)-2-[3-(2-Chloro-phenyl)-[1,2,4]oxadiazol-5-yl]-pyrrolidin-1-yl}-(4,5-dimethyl-2-[1,2,3]triazol-2-yl-phenyl)-methanone;

{(S)-2-[3-(2-Chloro-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(2-[1,2,3]triazol-2-yl-phenyl)-methanone;

(5-Chloro-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

{(S)-2-[3-(3-Fluoro-2-methyl-phenyl)-[1,2,4]oxadiazol-5-yl]-pyrrolidin-1-yl}-(4-methyl-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(5-methoxy-4-methyl-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(5-methoxy-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-(5-fluoro-2-[1,2,3]triazol-2-yl-phenyl)-methanone;

{(S)-2-[3-(3-Fluoro-2-methyl-phenyl)-[1,2,4]oxadiazol-5-yl]-pyrrolidin-1-yl}-[3-fluoro-2-(2H-pyrazol-3-yl)-phenyl]-methanone;

{(S)-2-[3-(2-Ethoxy-phenyl)-[1,2,4]oxadiazol-5-yl]-pyrrolidin-1-yl}-[3-fluoro-2-(2H-pyrazol-3-yl)-phenyl]-methanone;

{(S)-2-[3-(3,4-Dimethyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(2,4-Dimethyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(2,5-Dimethyl-phenyl)-[1,2,4]oxadiazol-5-yl]-pyrrolidin-1-yl}-(5-methyl-2-[1,2,3]triazol-2-yl-phenyl)-methanone;

{(S)-2-[3-(3-Chloro-2-methyl-phenyl)-[1,2,4]oxadiazol-5-yl]-pyrrolidin-1-yl}-(5-methoxy-4-methyl-2-pyrimidin-2-yl-phenyl)-methanone;

(5-Methyl-2-[1,2,3]triazol-2-yl-phenyl)-{(S)-2-[3-(3-trifluoromethoxy-phenyl)-[1,2,4]oxadiazol-5-yl]-pyrrolidin-1-yl}-methanone;

{(S)-2-[3-(3-Chloro-2-methyl-phenyl)-[1,2,4]oxadiazol-5-yl]-pyrrolidin-1-yl}-(5-methyl-2-pyrimidin-2-yl-phenyl)-methanone;

{(S)-2-[5-(2,3-Dihydro-benzofuran-7-yl)-[1,2,4]oxadiazol-3-yl]-pyrrolidin-1-yl}-(5-methyl-2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(3-Chloro-2-methyl-phenyl)-[1,2,4]oxadiazol-3-yl]-pyrrolidin-1-yl}-(4-fluoro-5-methoxy-2-[1,2,3]triazol-2-yl-phenyl)-methanone;

{(S)-2-[5-(2-Ethoxy-3-fluoro-phenyl)-[1,2,4]oxadiazol-3-yl]-pyrrolidin-1-yl}-(4-fluoro-5-methoxy-2-[1,2,3]triazol-2-yl-phenyl)-methanone;

{(S)-2-[5-(2-Ethoxy-pyridin-3-yl)-[1,2,4]oxadiazol-3-yl]-pyrrolidin-1-yl}-(4-fluoro-5-methoxy-2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(2-[1,2,3]triazol-2-yl-phenyl)-methanone;

{(S)-2-[5-(3-Fluoro-2-methoxy-phenyl)-[1,2,4]oxadiazol-3-yl]-pyrrolidin-1-yl}-(2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(3-Fluoro-2-methyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

{(S)-2-[3-(2,3-Dimethyl-phenyl)-isoxazol-5-yl]-pyrrolidin-1-yl}-(5-methyl-2-[,2,3]triazol-2-yl-phenyl)-methanone;

{(S)-2-[3-(3,5-Dimethyl-phenyl)-isoxazol-5-yl]-pyrrolidin-1-yl}-(5-methyl-2-[,2,3]triazol-2-yl-phenyl)-methanone;

{(S)-2-[3-(2-Methoxy-pyridin-3-yl)-isoxazol-5-yl]-pyrrolidin-1-yl}-(5-methyl-2-[1,2,3]triazol-2-yl-phenyl)-methanone;

{(S)-2-[3-(2-Ethoxy-pyridin-3-yl)-isoxazol-5-yl]-pyrrolidin-1-yl}-(5-methyl-2-[1,2,3]triazol-2-yl-phenyl)-methanone;

{(S)-2-[3-(3-Fluoro-2-methoxy-phenyl)-isoxazol-5-yl]-pyrrolidin-1-yl}-(5-methyl-2-[1,2,3]triazol-2-yl-phenyl)-methanone;

{(S)-2-[5-(3-Chloro-2-methyl-phenyl)-[1,3,4]oxadiazol-2-yl]-pyrrolidin-1-yl}-(5-methyl-2-[1,2,3]triazol-2-yl-phenyl)-methanone;

[5-(3-Fluoro-phenyl)-2-methyl-thiazol-4-yl]-{(S)-2-[5-(2-trifluoromethoxy-phenyl)-[1,3,4]oxadiazol-2-yl]-pyrrolidin-1-yl}-methanone;

{(S)-2-[5-(3-Chloro-2-methyl-phenyl)-[1,3,4]oxadiazol-2-yl]-pyrrolidin-1-yl}-(5-methoxy-4-methyl-2-[1,2,3]triazol-2-yl-phenyl)-methanone;

(4-Chloro-5-methoxy-2-[1,2,3]triazol-2-yl-phenyl)-{(S)-2-[5-(3-chloro-2-methyl-phenyl)-[1,3,4]oxadiazol-2-yl]-pyrrolidin-1-yl}-methanone;

(4-Chloro-5-methoxy-2-[1,2,3]triazol-2-yl-phenyl)-{(S)-2-[3-(3-chloro-2-methyl-phenyl)-[1,2,4]oxadiazol-5-yl]-pyrrolidin-1-yl}-methanone;

{(S)-2-[3-(3-Fluoro-2-methoxy-phenyl)-[1,2,4]oxadiazol-5-yl]-pyrrolidin-1-yl}-(5-methoxy-4-methyl-2-pyrimidin-2-yl-phenyl)-methanone;

{(S)-2-[3-(2-Ethoxy-pyridin-3-yl)-[1,2,4]oxadiazol-5-yl]-pyrrolidin-1-yl}-(5-methoxy-4-methyl-2-pyrimidin-2-yl-phenyl)-methanone;

(4-Fluoro-5-methoxy-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

{(S)-2-[5-(3-Fluoro-2-methoxy-phenyl)-[1,2,4]oxadiazol-3-yl]-pyrrolidin-1-yl}-(4-fluoro-5-methoxy-2-[1,2,3]triazol-2-yl-phenyl)-methanone;

(4-Chloro-5-methoxy-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(5-Chloro-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;

(4-Chloro-2-[1,2,3]triazol-2-yl-phenyl)-{(S)-2-[5-(3-fluoro-2-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

(5-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

{(S)-2-[5-(3-Chloro-2-methyl-phenyl)-4H-[1,2,4]triazol-3-yl]-pyrrolidin-1-yl}-(5-methyl-2-[1,2,3]triazol-2-yl-phenyl)-methanone;

{(S)-2-[5-(3-Fluoro-2-methyl-phenyl)-4H-[1,2,4]triazol-3-yl]-pyrrolidin-1-yl}-(5-methyl-2-[1,2,3]triazol-2-yl-phenyl)-methanone;

{(S)-2-[5-(2-Ethoxy-pyridin-3-yl)-4H-[1,2,4]triazol-3-yl]-pyrrolidin-1-yl}-(5-methyl-2-[1,2,3]triazol-2-yl-phenyl)-methanone;

{(S)-2-[5-(2,3-Dimethyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2,5-Dimethyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2,3-Dimethyl-phenyl)-[1,2,4]oxadiazol-3-yl]-pyrrolidin-1-yl}-(4-methyl-2-[1,2,3]triazol-2-yl-phenyl)-methanone;

{(S)-2-[5-(2,5-Dimethyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(2,3-dimethyl-phenyl)-[1 1,2,4]oxadiazol-3-yl]-pyrrolidin-1-yl}-methanone;

(5-Chloro-2-[1,2,3]triazol-2-yl-phenyl)-{(S)-2-[5-(2,5-dimethyl-phenyl)-[1 1,2,4]oxadiazol-3-yl]-pyrrolidin-1-yl}-methanone;

(4-Chloro-2-[1,2,3]triazol-2-yl-phenyl)-{(S)-2-[5-(2,3-dimethyl-phenyl)-[1 1,2,4]oxadiazol-3-yl]-pyrrolidin-1-yl}-methanone;

(4-Chloro-2-[1,2,3]triazol-2-yl-phenyl)-{(S)-2-[5-(2,5-dimethyl-phenyl)-[1,2,4]oxadiazol-3-yl]-pyrrolidin-1-yl}-methanone;

{(S)-2-[5-(2,5-Dimethyl-phenyl)-[1,2,4]oxadiazol-3-yl]-pyrrolidin-1-yl}-(4,5-dimethyl-2-[1,2,3]triazol-2-yl-phenyl)-methanone;

{(S)-2-[5-(5-Methoxy-2-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(2-Methoxy-5-methyl-phenyl)-[1,2,4]oxadiazol-3-yl]-pyrrolidin-1-yl}-(5-methyl-2-[1,2,3]triazol-2-yl-phenyl)-methanone;

{(S)-2-[5-(5-Methoxy-2-methyl-phenyl)-[1,2,4]oxadiazol-3-yl]-pyrrolidin-1-yl}-(4-methyl-2-[1,2,3]triazol-2-yl-phenyl)-methanone;

{(S)-2-[5-(2-Methoxy-5-methyl-phenyl)-[1,2,4]oxadiazol-3-yl]-pyrrolidin-1-yl}-(4-methyl-2-[1,2,3]triazol-2-yl-phenyl)-methanone;

(5-Chloro-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

(5-Chloro-2-[1,2,3]triazol-2-yl-phenyl)-{(S)-2-[5-(5-methoxy-2-methyl-phenyl)-1 [1,2,4]oxadiazol-3-yl]-pyrrolidin-1-yl}-methanone;

(5-Chloro-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(3-methoxy-5-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone;

(4-Chloro-2-[1,2,3]triazol-2-yl-phenyl)-{(S)-2-[5-(2-methoxy-5-methyl-phenyl)-[1,2,4]oxadiazol-3-yl]-pyrrolidin-1-yl}-methanone;

{(S)-2-[5-(5-Methoxy-2-methyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(2-Methoxy-5-methyl-phenyl)-[1,2,4]oxadiazol-3-yl]-pyrrolidin-1-yl}-(5-methoxy-4-methyl-2-[1,2,3]triazol-2-yl-phenyl)-methanone;

(4-Chloro-5-methoxy-2-[1,2,3]triazol-2-yl-phenyl)-{(S)-2-[3-(3-fluoro-2-methyl-phenyl)-[1,2,4]oxadiazol-5-yl]-pyrrolidin-1-yl}-methanone;

(4-Chloro-5-methoxy-2-[1,2,3]triazol-2-yl-phenyl)-{(S)-2-[5-(5-methoxy-2-methyl-phenyl)-[1,2,4]oxadiazol-3-yl]-pyrrolidin-1-yl}-methanone;

(4-Chloro-5-methoxy-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone;

(4,5-Dimethyl-2-[1,2,3]triazol-2-yl-phenyl)-{(S)-2-[5-(3-methoxy-2-methyl-phenyl)-[1,2,4]oxadiazol-3-yl]-pyrrolidin-1-yl}-methanone;

{(S)-2-[5-(3-Chloro-2-methoxy-phenyl)-[1,2,4]oxadiazol-3-yl]-pyrrolidin-1-yl}-(5-chloro-2-[1,2,3]triazol-2-yl-phenyl)-methanone;

{(S)-2-[5-(3-Methoxy-2-methyl-phenyl)-[1,2,4]oxadiazol-3-yl]-pyrrolidin-1-yl}-(5-methoxy-4-methyl-2-[1,2,3]triazol-2-yl-phenyl)-methanone;

{(S)-2-[5-(3-Methoxy-2-methyl-phenyl)-[1,2,4]oxadiazol-3-yl]-pyrrolidin-1-yl}-(5-methyl-2-[1,2,3]triazol-2-yl-phenyl)-methanone;

(2-[1,2,3]Triazol-2-yl-phenyl)-{(S)-2-[5-(2-trifluoromethoxy-phenyl)-4H-[1,2,4]triazol-3-yl]-pyrrolidin-1-yl}-methanone;

(5-Chloro-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;

(4-Chloro-5-methoxy-2-[1,2,3]triazol-2-yl-phenyl)-{(S)-2-[5-(2-methoxy-phenyl)-4H-[1,2,4]triazol-3-yl]-pyrrolidin-1-yl}-methanone;

(5-Methoxy-4-methyl-2-[1,2,3]triazol-2-yl-phenyl)-{(S)-2-[5-(2-methoxy-phenyl)-4H-[1,2,4]triazol-3-yl]-pyrrolidin-1-yl}-methanone;

(4-Chloro-2-[1,2,3]triazol-2-yl-phenyl)-{(S)-2-[5-(2-methoxy-phenyl)-4H-[1,2,4]triazol-3-yl]-pyrrolidin-1-yl}-methanone;

{(S)-2-[5-(3-Fluoro-2-methoxy-phenyl)-4H-[1,2,4]triazol-3-yl]-pyrrolidin-1-yl}-(5-methoxy-4-methyl-2-[1,2,3]triazol-2-yl-phenyl)-methanone;

{(S)-2-[5-(3-Fluoro-2-methoxy-phenyl)-4H-[1,2,4]triazol-3-yl]-pyrrolidin-1-yl}-(4-methyl-2-[1,2,3]triazol-2-yl-phenyl)-methanone;

{(S)-2-[5-(3-Chloro-2-methoxy-phenyl)-4H-[1,2,4]triazol-3-yl]-pyrrolidin-1-yl}-(5-methyl-2-[1,2,3]triazol-2-yl-phenyl)-methanone;

{(S)-2-[5-(3-Chloro-2-methoxy-phenyl)-4H-[1,2,4]triazol-3-yl]-pyrrolidin-1-yl}-(4-methyl-2-[1,2,3]triazol-2-yl-phenyl)-methanone;

{(S)-2-[5-(3-Chloro-2-methoxy-phenyl)-4H-[1,2,4]triazol-3-yl]-pyrrolidin-1-yl}-(5-methoxy-4-methyl-2-[1,2,3]triazol-2-yl-phenyl)-methanone;

{(S)-2-[5-(4-Chloro-6-methoxy-pyridin-2-yl)-[1,2,4]oxadiazol-3-yl]-pyrrolidin-1-yl}-(5-methyl-2-[1,2,3]triazol-2-yl-phenyl)-methanone;

{(S)-2-[5-(3-Methoxy-phenyl)-1H-imidazol-2-yl]-pyrrolidin-1-yl}-(5-methyl-2-[1,2,3]triazol-2-yl-phenyl)-methanone;

(5-Methyl-2-[1,2,3]triazol-2-yl-phenyl)-[(S)-2-(5-phenyl-isoxazol-3-yl)-pyrrolidin-1-yl]-methanone;

(5-Methoxy-4-methyl-2-[1,2,3]triazol-2-yl-phenyl)-[(S)-2-(5-phenyl-isoxazol-3-yl)-pyrrolidin-1-yl]-methanone;

(4-Chloro-5-methoxy-2-[1,2,3]triazol-2-yl-phenyl)-{(S)-2-[5-(2-trifluoromethoxy-phenyl)-isoxazol-3-yl]-pyrrolidin-1-yl}-methanone;

{(S)-2-[3-(2-Cyclobutoxy-pyridin-3-yl)-[1,2,4]oxadiazol-5-yl]-pyrrolidin-1-yl}-(5-methyl-2-[1,2,3]triazol-2-yl-phenyl)-methanone;

(2-Fluoro-3-methoxy-6-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;

{(S)-2-[5-(2-Methoxy-phenyl)-4H-[1,2,4]triazol-3-yl]-pyrrolidin-1-yl}-(5-methyl-2-[1,2,3]triazol-2-yl-phenyl)-methanone;

(4,5-Dimethyl-2-[1,2,3]triazol-2-yl-phenyl)-{(S)-2-[5-(2-methoxy-phenyl)-4H-[1,2,4]triazol-3-yl]-pyrrolidin-1-yl}-methanone;

{(S)-2-[5-(2-Methoxy-phenyl)-4H-[1,2,4]triazol-3-yl]-pyrrolidin-1-yl}-(4-methyl-2-[1,2,3]triazol-2-yl-phenyl)-methanone; and (5-Methyl-2-[1,2,3]triazol-2-yl-phenyl)-[(S)-2-(1-phenyl-1H-[1,2,4]triazol-3-yl)-pyrrolidin-1-yl]-methanone;

or a pharmaceutically acceptable salt thereof.

12. The compound according to claim 1 selected from the group consisting of:

(5-Methyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;

4-Methyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;

(4-Chloro-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;

(5-Chloro-4-methyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;

(4,5-Dimethyl-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;

(5-Chloro-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;

{(S)-2-[5-(3-Chloro-2-methyl-phenyl)-4H-[1,2,4]triazol-3-yl]-2-methyl-pyrrolidin-1-yl}-(4-methyl-2-[1,2,3]triazol-2-yl-phenyl)-methanone;

{(S)-2-[5-(3-Chloro-2-methyl-phenyl)-4H-[1,2,4]triazol-3-yl]-2-methyl-pyrrolidin-1-yl}-(5-chloro-4-methyl-2-[1,2,3]triazol-2-yl-phenyl)-methanone;

{(S)-2-[5-(3-Chloro-2-methyl-phenyl)-4H-[1,2,4]triazol-3-yl]-2-methyl-pyrrolidin-1-yl}-(4,5-dimethyl-2-[1,2,3]triazol-2-yl-phenyl)-methanone; and {(S)-2-[5-(3-Chloro-2-methyl-phenyl)-4H-[1,2,4]triazol-3-yl]-2-methyl-pyrrolidin-1-yl}-(4-chloro-2-[1,2,3]triazol-2-yl-phenyl)-methanone;

{(S)-2-[5-(3-Chloro-2-methyl-phenyl)-4H-[1,2,4]triazol-3-yl]-2-methyl-pyrrolidin-1-yl}-(5-chloro-2-[1,2,3]triazol-2-yl-phenyl)-methanone;

(5-Methyl-biphenyl-2-yl)-{(S)-2-methyl-2-[5-(2-trifluoromethoxy-phenyl)-4H-[1,2,4]triazol-3-yl]-pyrrolidin-1-yl}-methanone; and (4-Methyl-biphenyl-2-yl)-{(S)-2-methyl-2-[5-(2-trifluoromethoxy-phenyl)-4H-[1,2,4]triazol-3-yl]-pyrrolidin-1-yl}-methanone;

or a pharmaceutically acceptable salt thereof.

13. A pharmaceutical composition comprising, as active principle, one or more compounds according to claim 1, or a pharmaceutically acceptable salt thereof, and at least one therapeutically inert excipient.

14. A method of treatment of diseases or disorders relating to orexinergic disorders selected from sleep disorders, anxiety disorders, addiction disorders, cognitive dysfunctions, mood disorders, or appetite disorders; comprising administering to a patient a pharmaceutically active amount of the compound as defined in claim 1, or a pharmaceutically acceptable salt thereof.

15. The compound according to claim 3; wherein the group

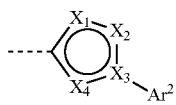

represents a group independently selected from the following groups A) to H):

A): [1,2,4]oxadiazol-3,5-diyl groups selected from the groups:

A1)

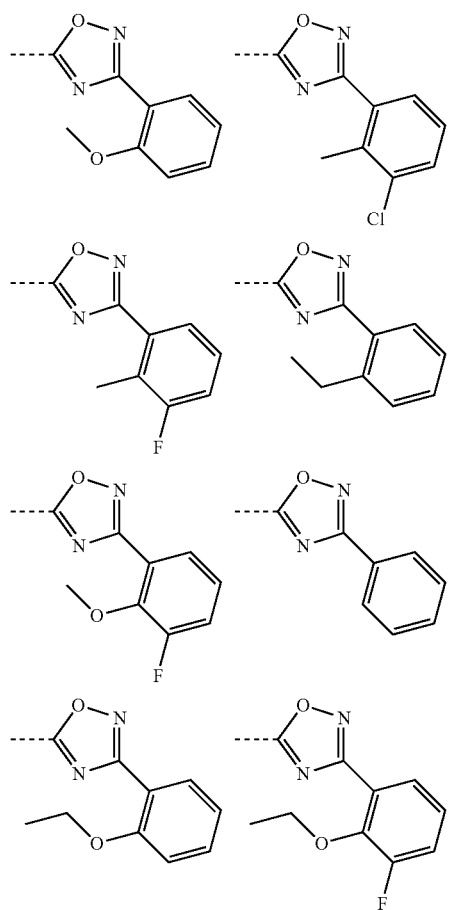

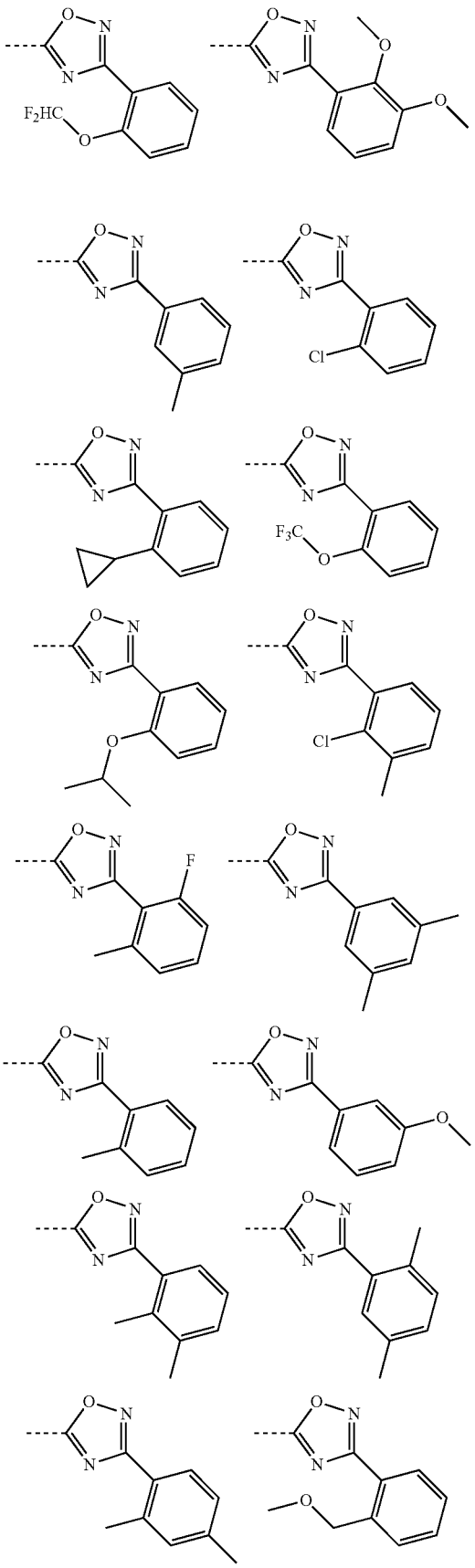

267
-continued
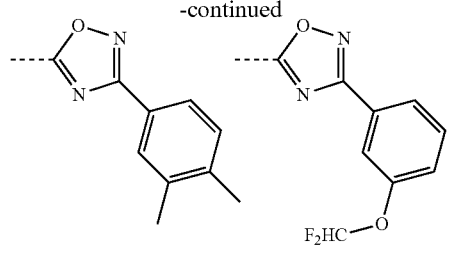
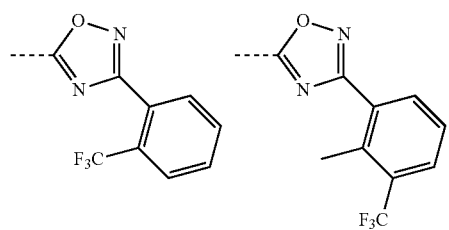
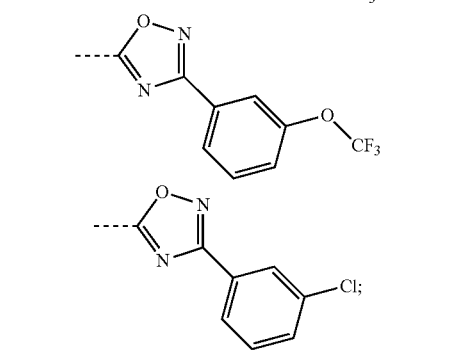
A2)
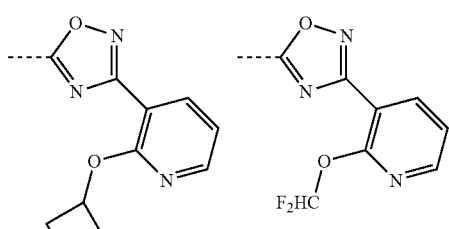
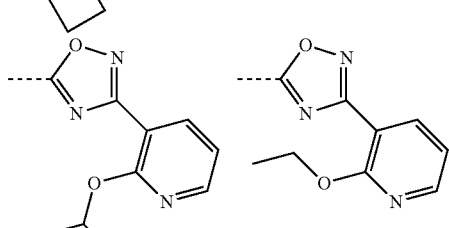
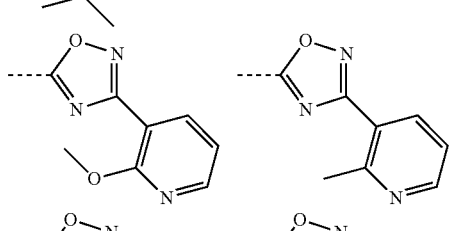
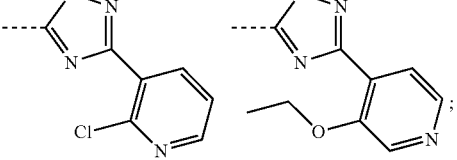
268
-continued
A3)
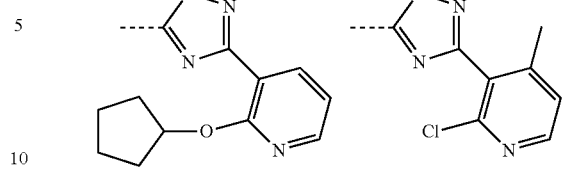
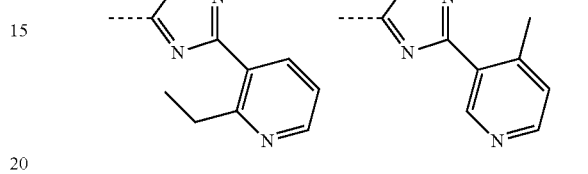
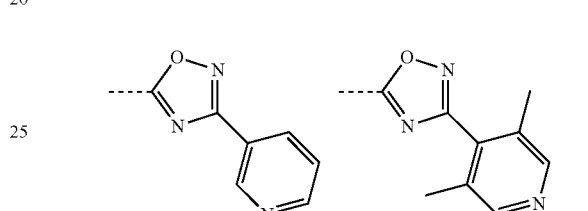
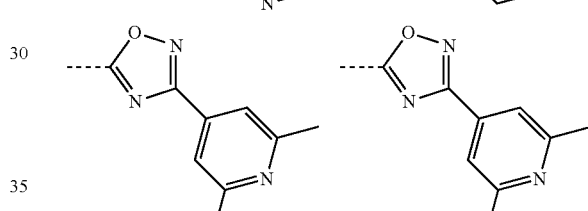
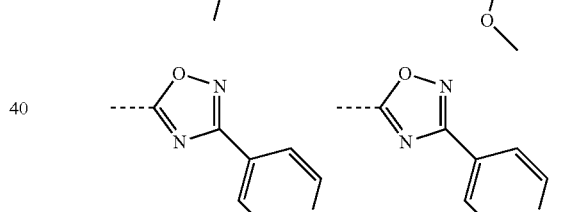
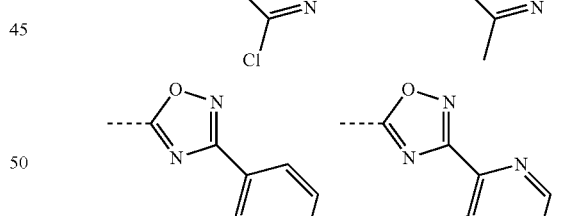
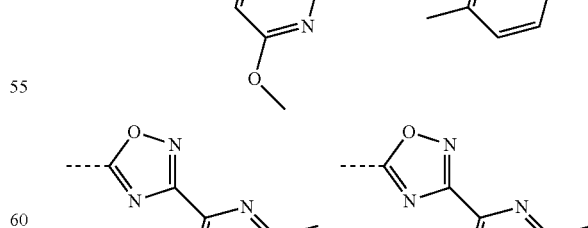
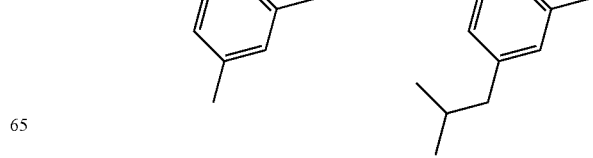

-continued
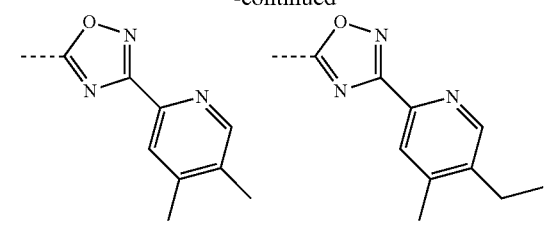
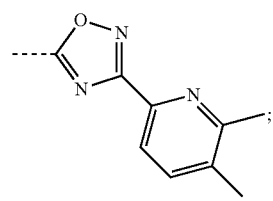
A4)
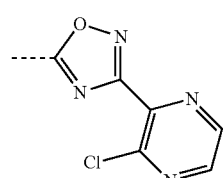
A5)
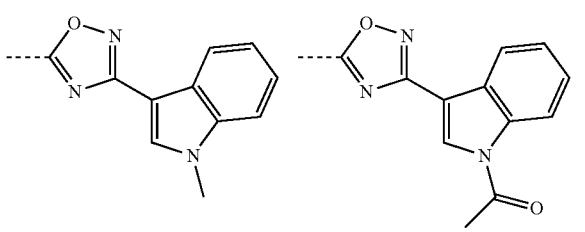
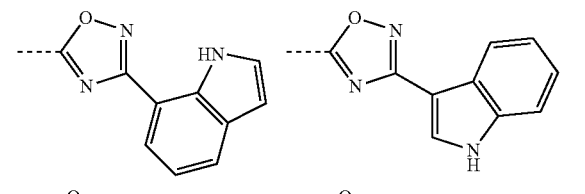
A6)
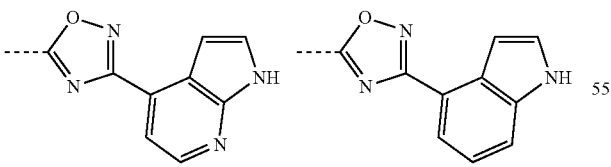
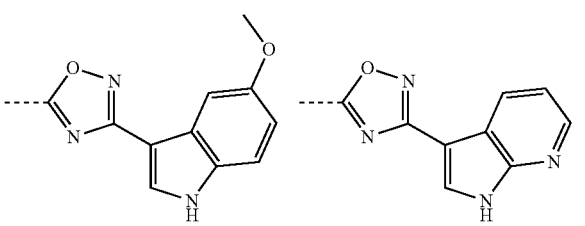
-continued
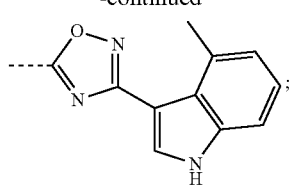
A7)
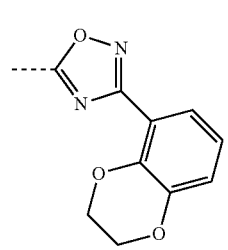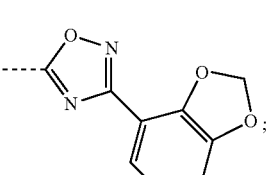
A8)
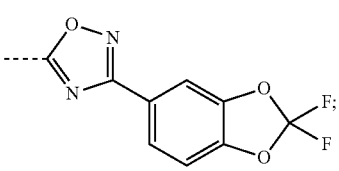
B): [1,2,4]oxadiazol-3,5-diyl groups selected from the groups:
B1)
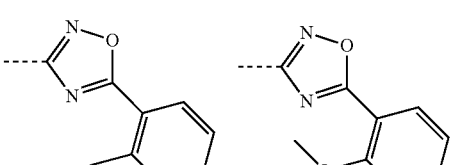
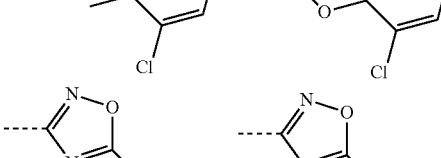
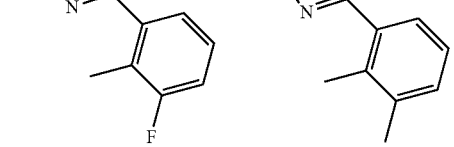
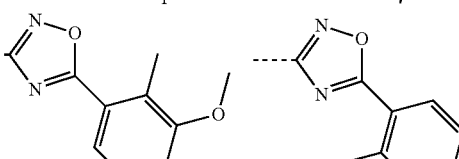
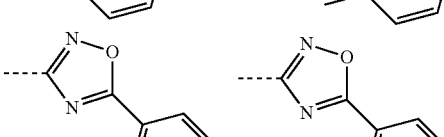
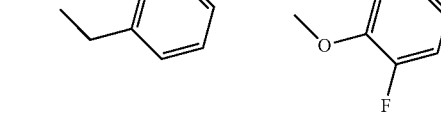

-continued
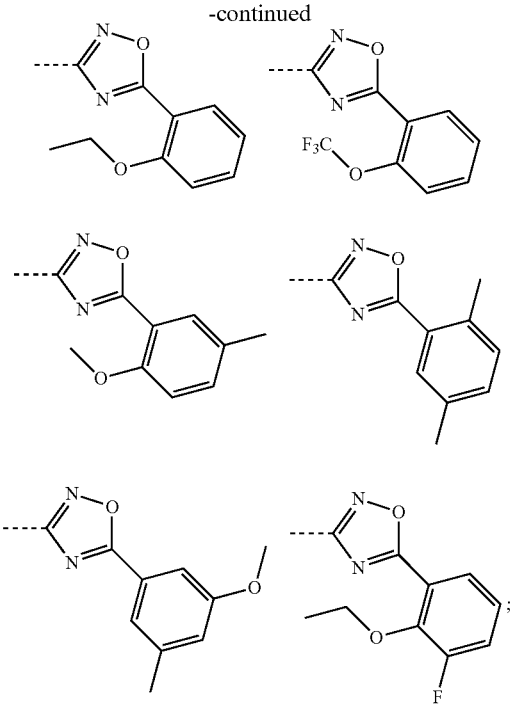
B2)
B3)
C): oxazol-2,4-diyl groups selected from:
D): oxazol-2,5-diyl groups selected from:
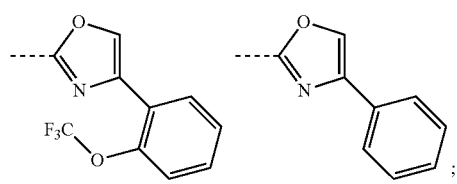
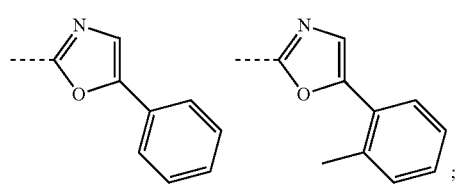
E): isoxazol-3,5-diyl groups selected from the groups:
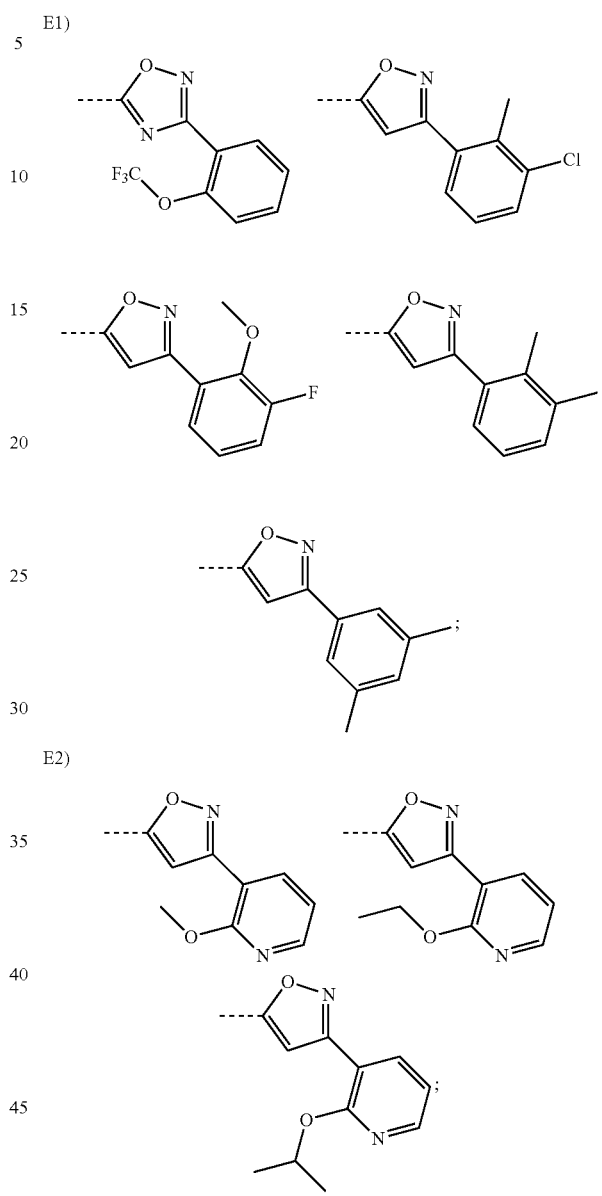

F) [1,2,4]triazol-3,5-diyl groups selected from the groups:
F1)
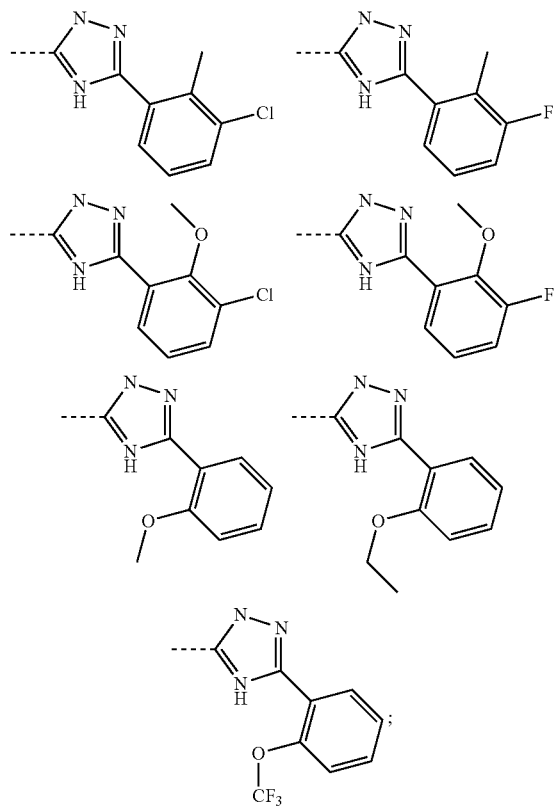
F2)
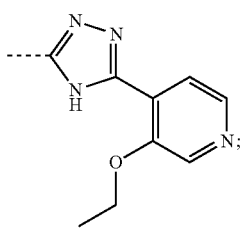
F3)
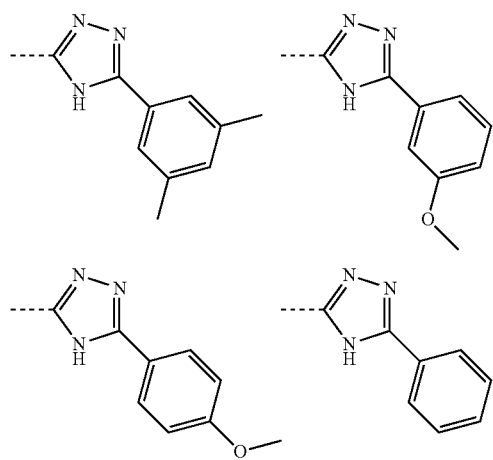
-continued
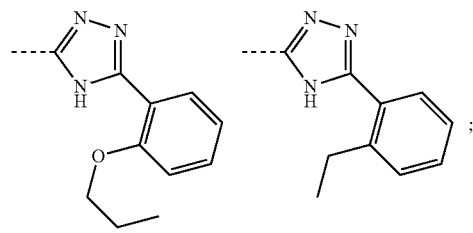
G): imidazol-2,4-diyl groups selected from the groups:
G1)
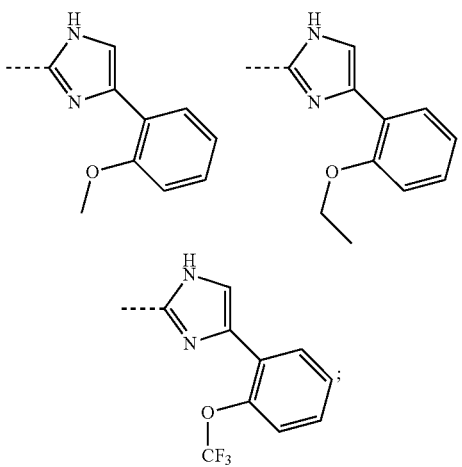
G2)
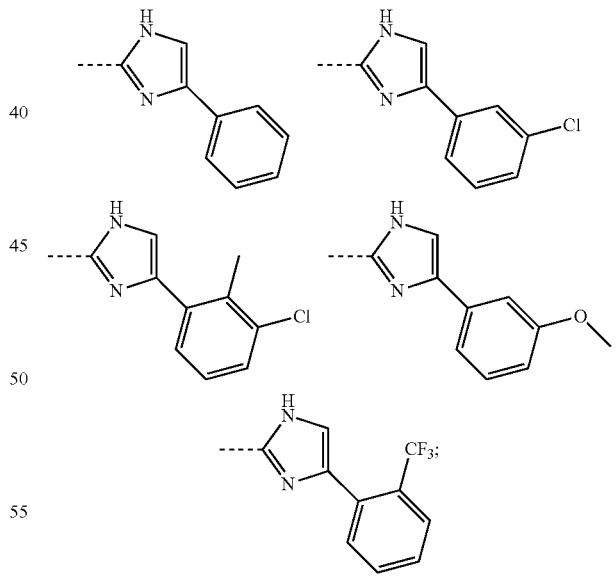
G3)
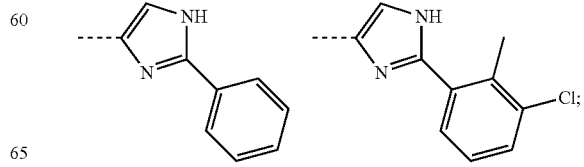

H): 1H-[1,2,4]triazol-1,3-diyl groups selected from:
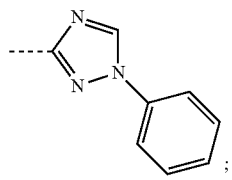
or a pharmaceutically acceptable salt thereof.
16. The compound according to claim 7; wherein the group
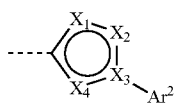
represents a group independently selected from the following groups A) to H):
A): [1,2,4]oxadiazol-3,5-diyl groups selected from the groups:
A1)
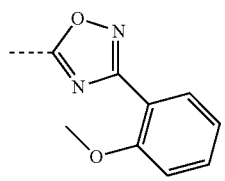 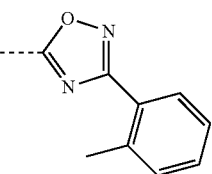
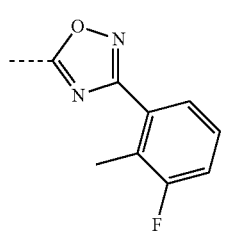 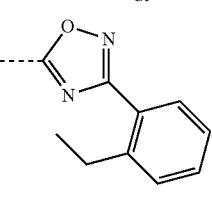
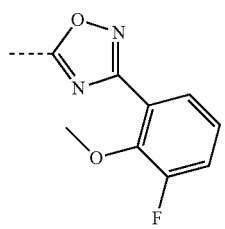 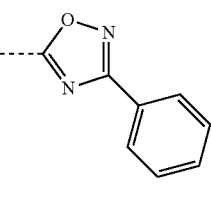
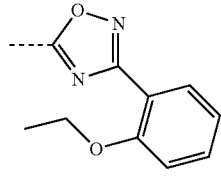 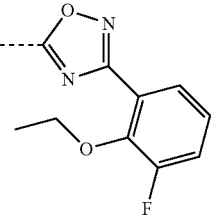
-continued
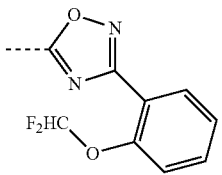 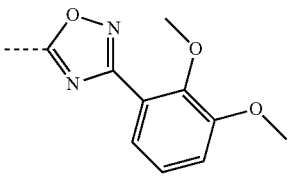
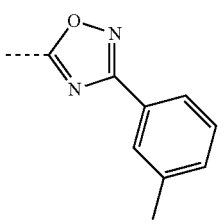 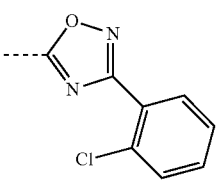
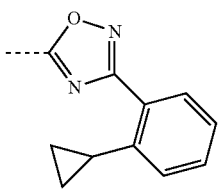 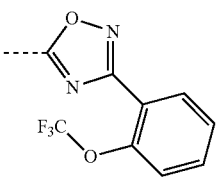
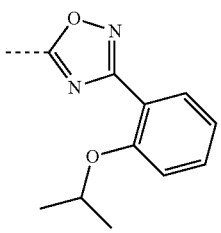 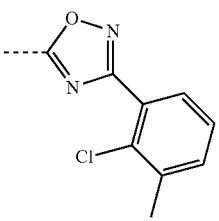
 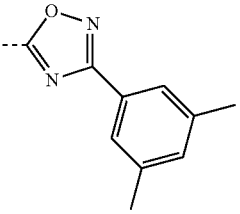
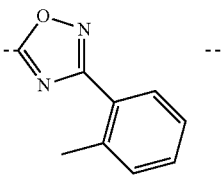 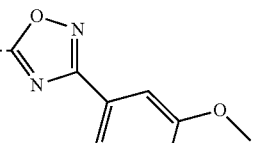
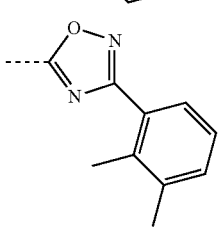 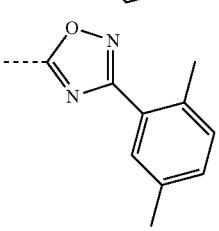
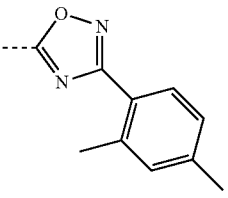 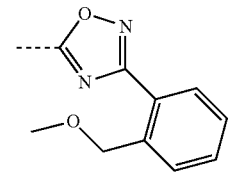

-continued
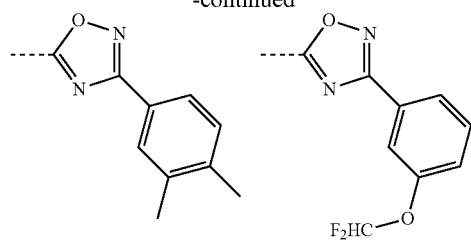
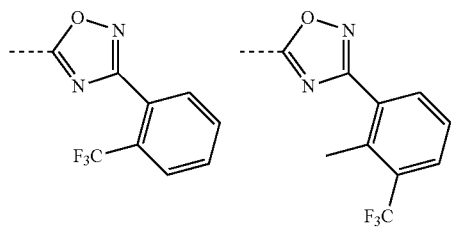
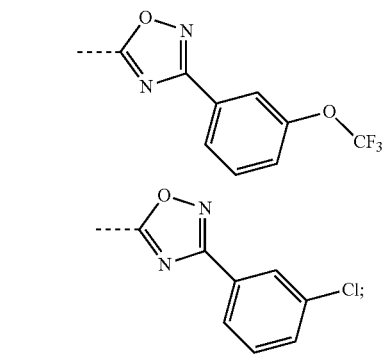
A2)
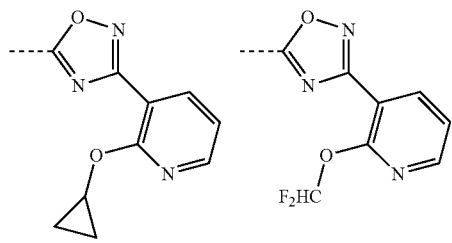
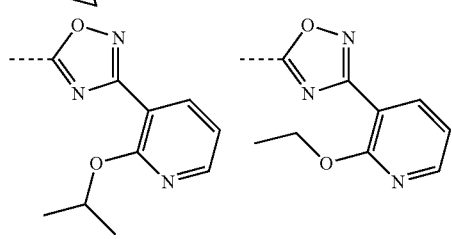
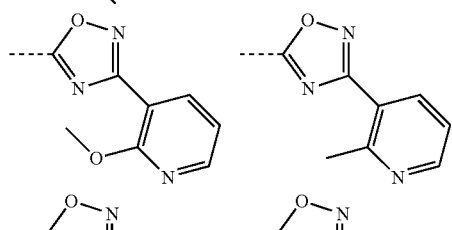
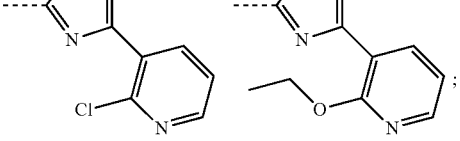
-continued
A3)
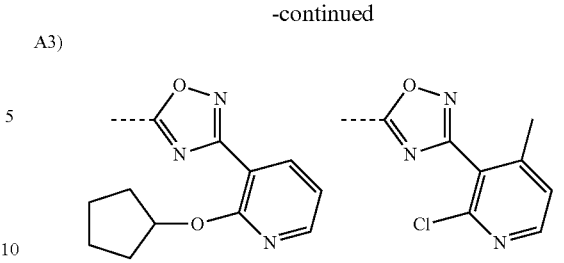
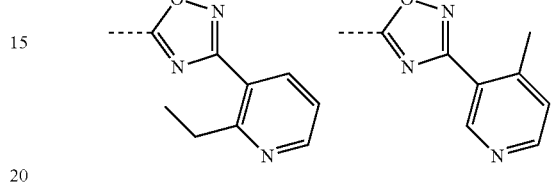
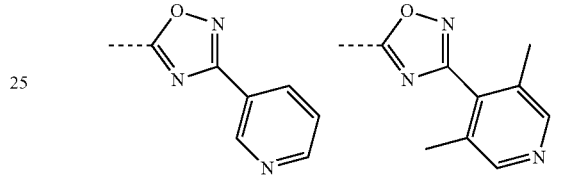
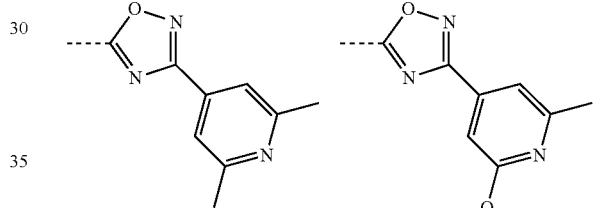
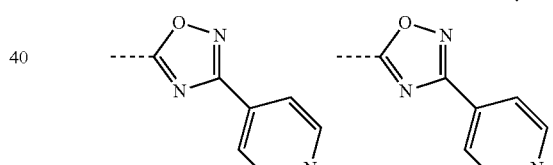
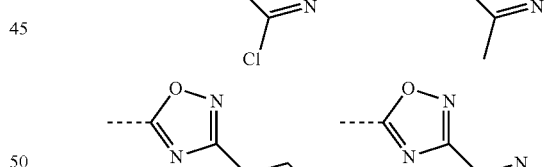
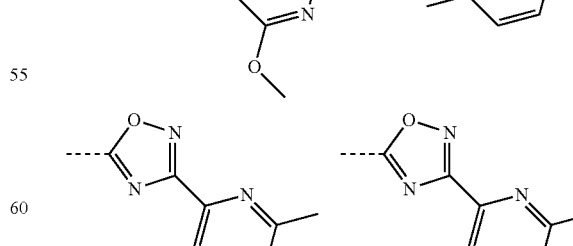
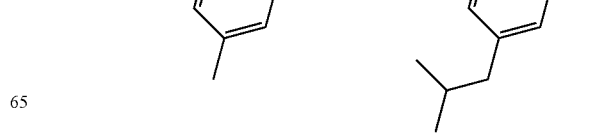

-continued
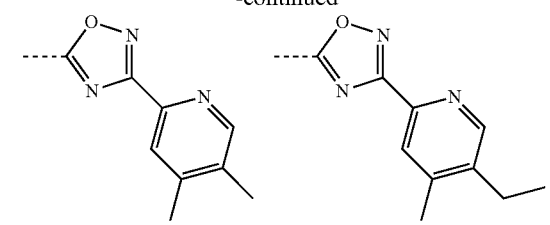
A4)
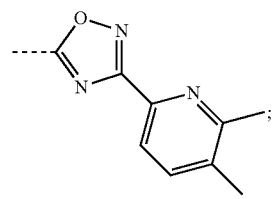
A5)
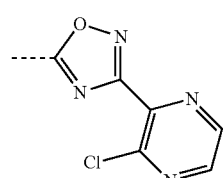
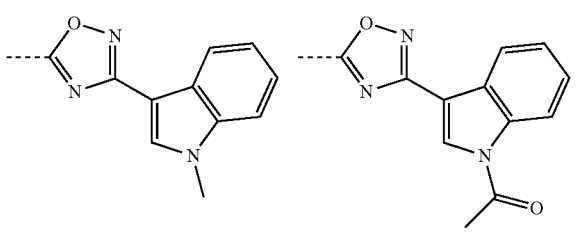
A6)
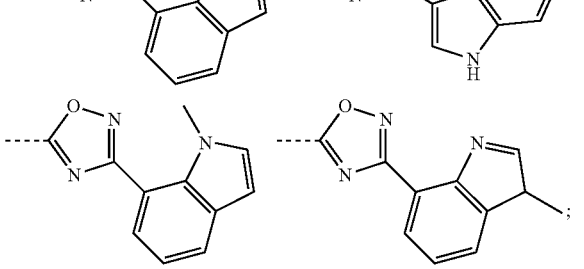
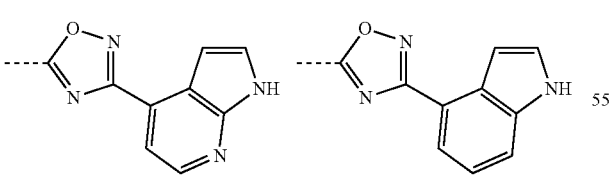
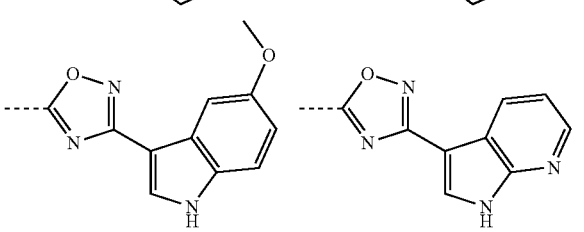
-continued
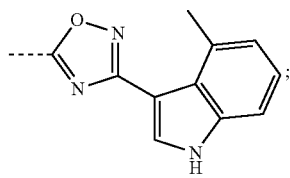
A7)
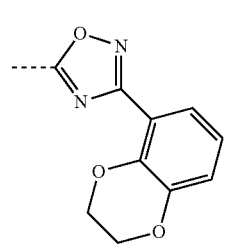 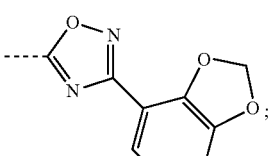
A8)
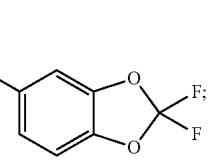
B): [1,2,4]oxadiazol-3,5-diyl groups selected from the groups:
B1)
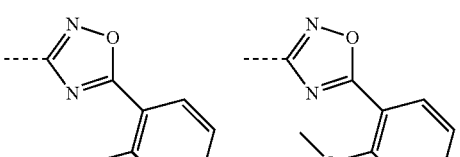
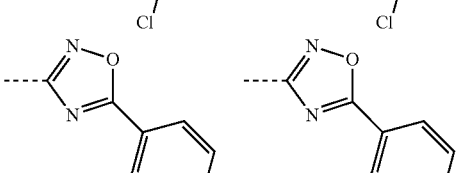
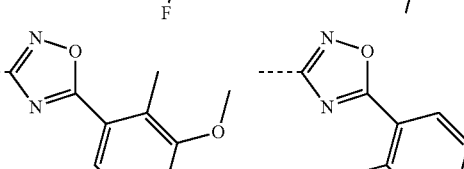
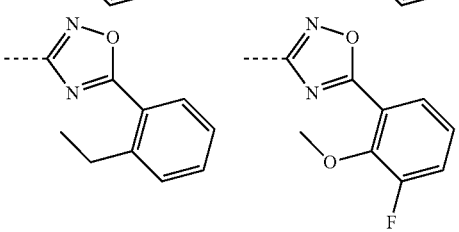

-continued
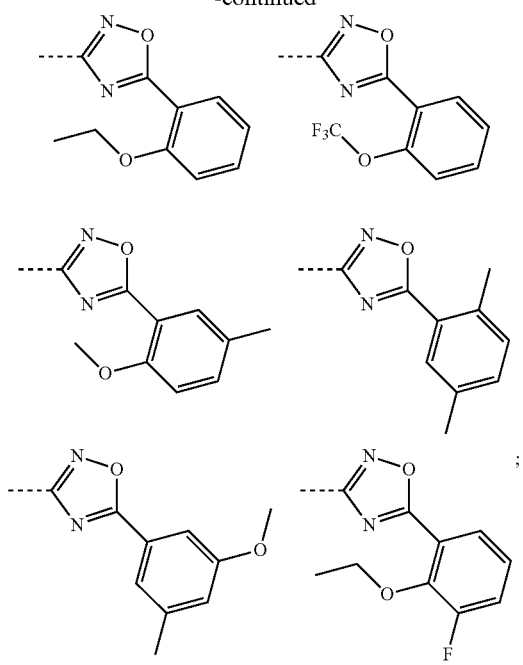
B2)
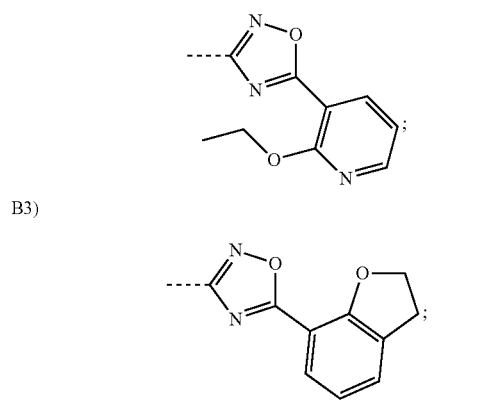
B3)
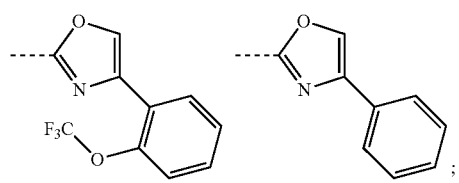
C): oxazol-2,4-diyl groups selected from:
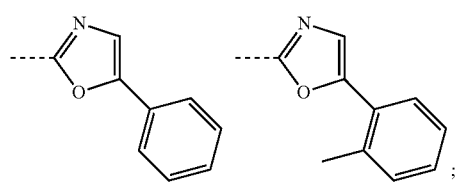
D): oxazol-2,5-diyl groups selected from:
E): isoxazol-3,5-diyl groups selected from the groups:
E1)
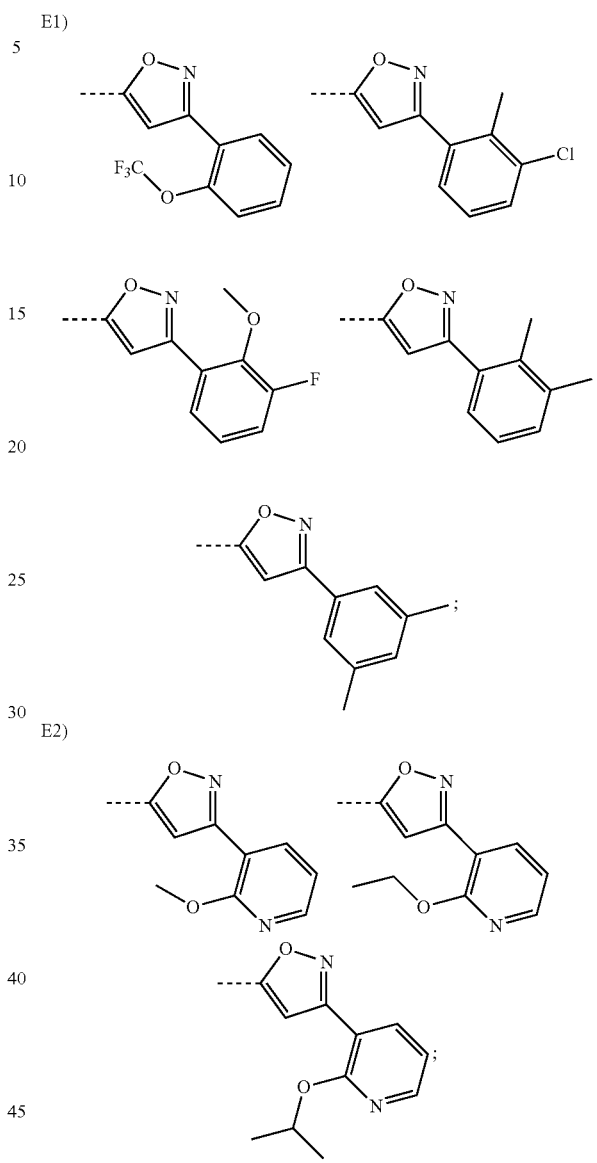
E2)
E3)
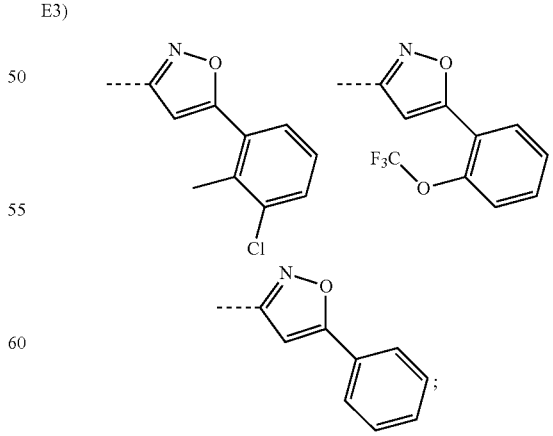
F): [1,2,4]triazol-3,5-diyl groups selected from the groups:

F1)
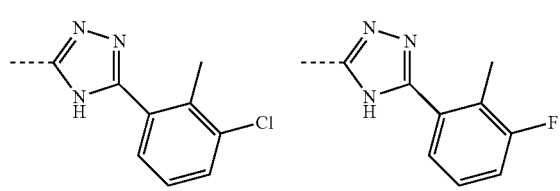
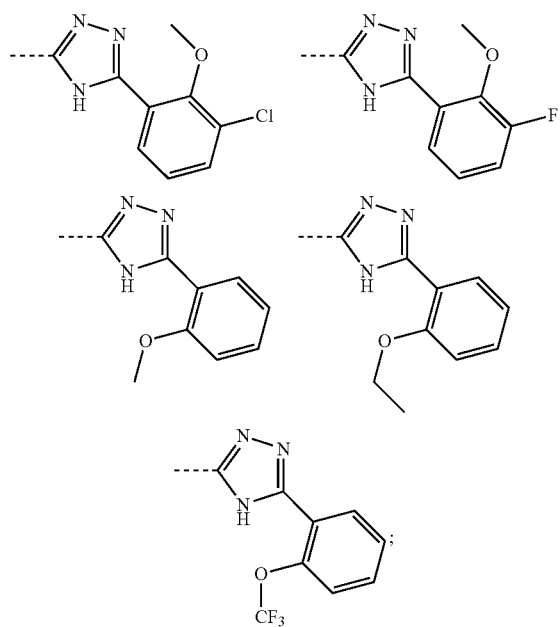
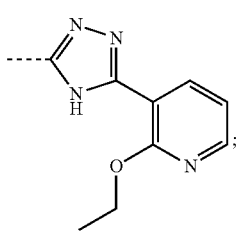
F2)
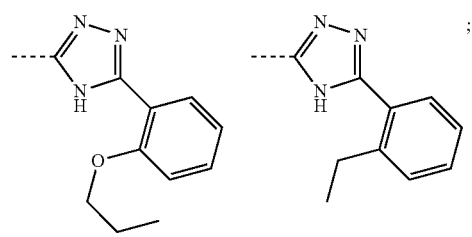
G): imidazol-2,4-diyl groups selected from the groups:
G1)
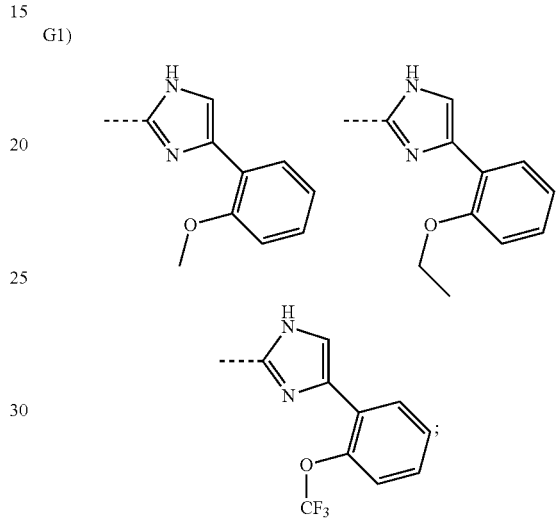
G2)
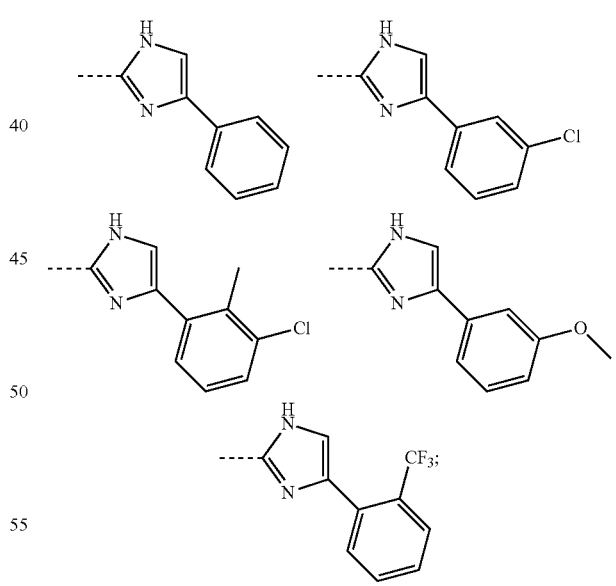
F3)
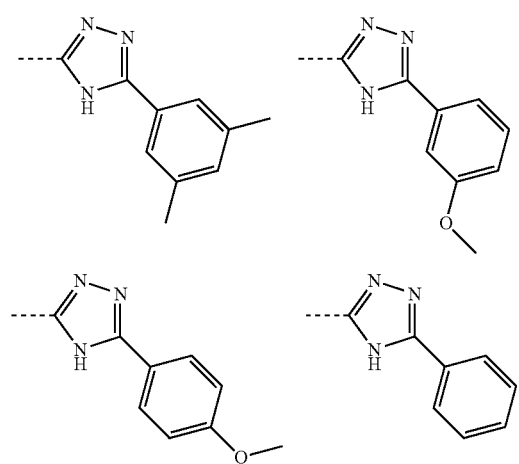
G3)
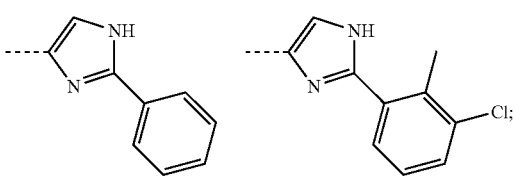

H): 1H-[1,2,4]triazol-1,3-diyl groups selected from:

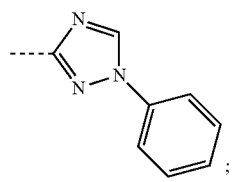

or a pharmaceutically acceptable salt thereof.

17. The compound according to claim 1 selected from the group consisting of:
   (5-Methoxy-4-methyl-2-[1,2,3]triazol-2-yl-phenyl)-{(S)-2-[5-(2-trifluoromethoxy-phenyl)-[1,2,4]oxadiazol-3-yl]-pyrrolidin-1-yl}-methanone;
   (5-Methoxy-4-methyl-2-[1,2,3]triazol-2-yl-phenyl)-{(S)-2-[3-(2-trifluoromethoxy-phenyl)-[1,2,4]oxadiazol-5-yl]-pyrrolidin-1-yl}-methanone;
   {(S)-2-[3-(3-Chloro-2-methyl-phenyl)-[1,2,4]oxadiazol-5-yl]-pyrrolidin-1-yl}-(4,5-dimethyl-2-[1,2,3]triazol-2-yl-phenyl)-methanone;
   {(S)-2-[3-(3-Fluoro-2-methoxy-phenyl)-[1,2,4]oxadiazol-5-yl]-pyrrolidin-1-yl}-(5-methoxy-4-methyl-2-pyrimidin-2-yl-phenyl)-methanone;
   (4-Methyl-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone;
   (4-Chloro-2-[1,2,3]triazol-2-yl-phenyl)-{(S)-2-[5-(2-trifluoromethoxy-phenyl)-4H-[1,2,4]triazol-3-yl]-pyrrolidin-1-yl}-methanone; and
   (4-Chloro-2-[1,2,3]triazol-2-yl-phenyl)-{(S)-2-methyl-2-[5-(2-trifluoromethoxy-phenyl)-4H-[1,2,4]triazol-3-yl]-pyrrolidin-1-yl}-methanone;
   or a pharmaceutically acceptable salt thereof.

18. A method of treatment of diseases or disorders relating to orexinergic disorders selected from sleep disorders, anxiety disorders, addiction disorders, cognitive dysfunctions, mood disorders, or appetite disorders; comprising administering to a patient a pharmaceutically active amount of the compound as defined in claim 11, or a pharmaceutically acceptable salt thereof.

19. A method of treatment of diseases or disorders relating to orexinergic disorders selected from sleep disorders, anxiety disorders, addiction disorders, cognitive dysfunctions, mood disorders, or appetite disorders; comprising administering to a patient a pharmaceutically active amount of the compound as defined in claim 12, or a pharmaceutically acceptable salt thereof.

20. A method of treatment of diseases or disorders relating to orexinergic disorders selected from sleep disorders, anxiety disorders, addiction disorders, cognitive dysfunctions, mood disorders, or appetite disorders; comprising administering to a patient a pharmaceutically active amount of the compound as defined in claim 16, or a pharmaceutically acceptable salt thereof.

21. A method of treatment of diseases or disorders relating to orexinergic disorders selected from sleep disorders, anxiety disorders, addiction disorders, cognitive dysfunctions, mood disorders, or appetite disorders; comprising administering to a patient a pharmaceutically active amount of the compound as defined in claim 17, or a pharmaceutically acceptable salt thereof.

* * * * *

UNITED STATES PATENT AND TRADEMARK OFFICE
CERTIFICATE OF CORRECTION

Page 1 of 3

PATENT NO. : 9,493,446 B2
APPLICATION NO. : 14/434997
DATED : November 15, 2016
INVENTOR(S) : Bolli et al.

It is certified that error appears in the above-identified patent and that said Letters Patent is hereby corrected as shown below:

In the Specification

Column 34, Line 50-55: "  " should be "  ";

Column 35, Line 10-15: "  " should be "  ";

In the Claims

Column 234, Line 36 (Claim 1): "mew" should be "meta";

Signed and Sealed this
Ninth Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 9,493,446 B2

Column 237, Line 55-60 (Claim 7): " 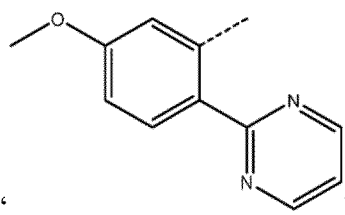 " should be
" 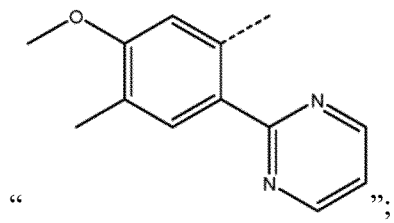 ";

Column 241, Line 40-45 (Claim 10): " 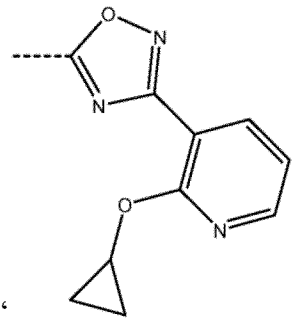 " should be " 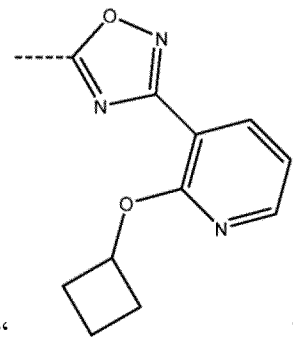 ";

Column 241, Line 60-65 (Claim 10): " 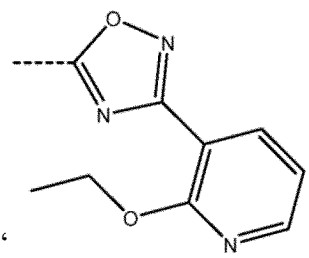 " should be
" 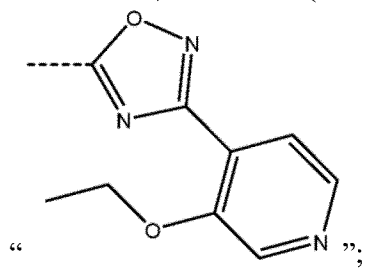 ";

CERTIFICATE OF CORRECTION (continued)　　　　　　　　　　　　Page 3 of 3
U.S. Pat. No. 9,493,446 B2

Column 277, Line 40-45 (Claim 16): " 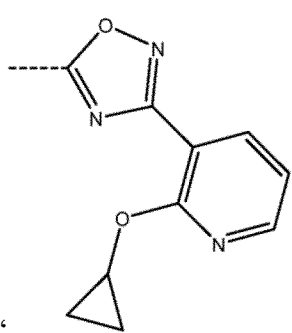 " should be " 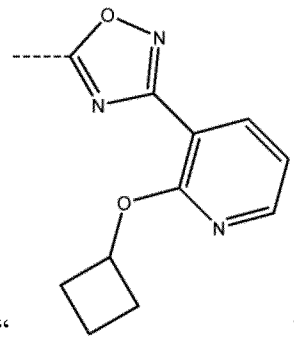 ";

Column 277, Line 60-65 (Claim 16): " 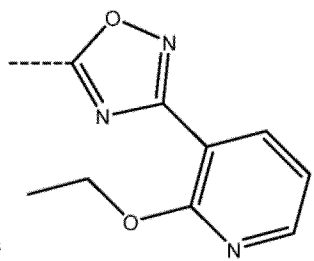 " should be " 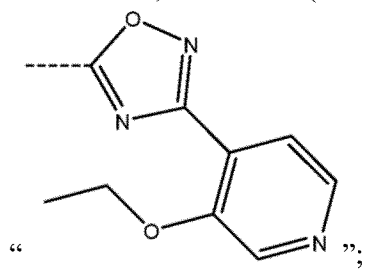 ";

Column 279, Line 45-50 (Claim 16): " 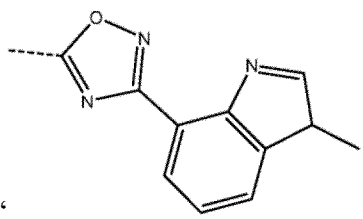 " should be " 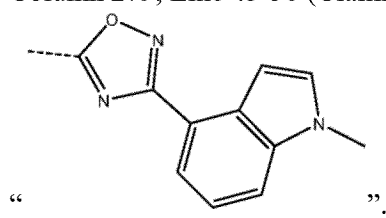 ".